United States Patent
Sasaki et al.

(10) Patent No.: US 10,723,703 B2
(45) Date of Patent: Jul. 28, 2020

(54) PYRAZOLE COMPOUND

(71) Applicant: Sumitomo Dainippon Pharma Co., Ltd., Osaka (JP)

(72) Inventors: Izumi Sasaki, Chuo-ku (JP); Tomohiro Toyoda, Suita (JP); Hidefumi Yoshinaga, Osaka (JP); Itaru Natsutani, Suita (JP); Yoko Takahashi, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 16/193,232

(22) Filed: Nov. 16, 2018

(65) Prior Publication Data

US 2019/0084938 A1    Mar. 21, 2019

Related U.S. Application Data

(60) Continuation of application No. 15/990,026, filed on May 25, 2018, now Pat. No. 10,183,913, which is a continuation of application No. 15/491,130, filed on Apr. 19, 2017, now Pat. No. 10,087,146, which is a division of application No. 14/324,509, filed on Jul. 7, 2014, now Pat. No. 9,663,472, which is a division of application No. 14/041,246, filed on Sep. 30, 2013, now Pat. No. 8,809,383, which is a division of application No. 13/810,030, filed as application No. PCT/JP2011/066091 on Jul. 14, 2011, now Pat. No. 8,569,353.

(30) Foreign Application Priority Data

Jul. 15, 2010  (JP) .................... 2010-160705

(51) Int. Cl.
| C07D 231/20 | (2006.01) |
| C07D 231/44 | (2006.01) |
| C07D 493/08 | (2006.01) |
| C07D 231/22 | (2006.01) |
| C07D 231/38 | (2006.01) |
| C07D 231/18 | (2006.01) |
| C07D 405/06 | (2006.01) |

(52) U.S. Cl.
CPC ......... *C07D 231/20* (2013.01); *C07D 231/18* (2013.01); *C07D 231/22* (2013.01); *C07D 231/38* (2013.01); *C07D 231/44* (2013.01); *C07D 405/06* (2013.01); *C07D 493/08* (2013.01)

(58) Field of Classification Search
None
See application file for complete search history.

(56) References Cited

U.S. PATENT DOCUMENTS

| 6,538,015 | B1 | 3/2003 | Dymock et al. |
| 2004/0192666 | A1 | 9/2004 | Dunn |
| 2006/0111412 | A1 | 5/2006 | Shipps, Jr. et al. |
| 2006/0264419 | A1 | 11/2006 | Schiemann et al. |
| 2007/0010531 | A1 | 1/2007 | Schadt et al. |
| 2007/0049604 | A1 | 3/2007 | Nam et al. |
| 2008/0312253 | A1 | 12/2008 | Nam et al. |
| 2009/0275617 | A1 | 11/2009 | Ito et al. |
| 2010/0075964 | A1 | 3/2010 | Busch et al. |

(Continued)

FOREIGN PATENT DOCUMENTS

| EP | 1 304 325 | 4/2003 |
| EP | 1 884 513 | 2/2008 |

(Continued)

OTHER PUBLICATIONS

International Search Report dated Aug. 16, 2011 in International (PCT) Application No. PCT/JP2011/066091.

(Continued)

*Primary Examiner* — Kamal A Saeed
(74) *Attorney, Agent, or Firm* — Wenderoth, Lind & Ponack, L.L.P.

(57) ABSTRACT

The present invention relates to a novel serotonin reuptake inhibitor which also exhibits 5-HT$_{2C}$ antagonistic action (antidepressive and anxiolytic effects), in particular, 5-HT$_{2C}$ inverse agonistic action comprising Compound (1):

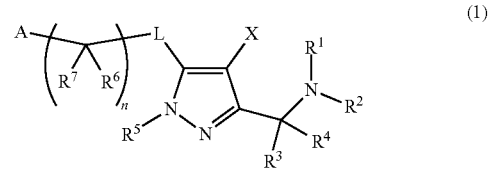

(1)

or a pharmaceutically acceptable salt thereof
wherein $R^1$, $R^2$, $R^3$ and $R^4$ are independently hydrogen or $C_{1-6}$ alkyl etc.; $R^5$ is $C_{4-7}$ alkyl or —$(CR^8R^9)_r$-E; $R^6$, $R^7$, $R^8$ and $R^9$ are independently hydrogen, fluorine or $C_{1-6}$ alkyl; A is $C_{6-10}$ aryl or heteroaryl etc.; r is 1, 2, 3 or 4; E is $C_{3-8}$ cycloalkyl or $C_{6-10}$ aryl etc.; L is oxygen, sulfur or —$NR^{10}$—; n is 1, 2 or 3; $R^{10}$ is hydrogen or $C_{1-6}$ alkyl etc.; and X is hydrogen or halogen etc.

2 Claims, No Drawings

(56) References Cited

U.S. PATENT DOCUMENTS

2010/0210696 A1    8/2010   Nishida et al.
2013/0040950 A1    2/2013   Short et al.

FOREIGN PATENT DOCUMENTS

| | | |
|---|---|---|
| JP | 2004-532276 | 10/2004 |
| JP | 2006-515339 | 5/2006 |
| JP | 2006-522035 | 9/2006 |
| JP | 2008-518920 | 6/2008 |
| WO | 02/100853 | 12/2002 |
| WO | 03/031435 | 4/2003 |
| WO | 03/057673 | 7/2003 |
| WO | 2004/074257 | 9/2004 |
| WO | 2004/089931 | 10/2004 |
| WO | 2004/089932 | 10/2004 |
| WO | 2007/002559 | 1/2007 |
| WO | 2007/037513 | 4/2007 |
| WO | 2009/004171 | 1/2009 |
| WO | 2009/041447 | 4/2009 |
| WO | 2011/126903 | 10/2011 |

OTHER PUBLICATIONS

Written Opinion dated Aug. 16, 2011 in International (PCT) Application No. PCT/JP2011/066091.

Kaye et al., "Double-Blind Placebo-Controlled Administration of Fluoxetine in Restricting- and Restricting-Purging-Type Anorexia Nervosa", Biol Psychiatry, vol. 49, pp. 644-652 (2001).

McGregor et al., "Symptoms and sleep patterns during inpatient treatment of methamphetamine withdrawal: A comparison of mirtazapine and modafinil with treatment as usual", Journal of Substance Abuse Treatment, vol. 35, pp. 334-342.

PYRAZOLE COMPOUND

TECHNICAL FIELD

The present invention relates to a medicament comprising a novel pyrazole derivative or a pharmaceutically acceptable salt thereof as an active ingredient. In detail, the present invention relates to a medicament for treating depression, anxiety and the like or preventing a relapse thereof, which has $5\text{-HT}_{2C}$ antagonistic action, in particular, $5\text{-HT}_{2C}$ inverse agonistic action, and serotonin reuptake inhibitory action.

BACKGROUND ART

Depression is a chronic disease which can affect people of all ages. Amongst currently-used various antidepressants, the most successful one is a selective serotonin reuptake inhibitor (hereinafter, optionally abbreviated as "SSRI"). SSRIs have a higher serotonin reuptake inhibitory action than dopamine or noradrenaline reuptake inhibitory action. SSRIs include, for example, fluvoxamine, citalopram, sertraline and paroxetine, which play the main role in the drug treatment for depression.

Such SSRIs have lower side effects, compared with a tricyclic antidepressant (hereinafter, optionally abbreviated as "TCA") which is known as a conventional antidepressant, and thus SSRIs are widely used as a highly safe antidepressant. On the other hand, some problems in SSRIs are also indicated. The problems include, for example, that it takes a long term of 3 to 8 weeks to exert enough antidepressive action; gastrointestinal symptom such as nausea, vomiting, and diarrhea, and so-called activation syndrome such as initiation or exacerbation in anxiety symptom and restlessness appear as side effects, in particular, early after a SSRI is administered; and the remission rate of the treatment with a SSRI alone is about ⅓, which is not enough for the therapeutic effect. Namely, SSRIs show slow and insufficient onset of the antidepressive action, but the side effects appear promptly. Hence, the compliance thereof is often adversely affected early after a SSRI is administered. Furthermore, SSRIs have a problem for increasing a risk for suicide early after the administration, since the onset of the antidepressive action is slow and then a patient recovers its initiative before the patient experiences enough improvement in its depressive symptom. Accordingly, it has been desired to develop a new antidepressant whose onset of the antidepressive action is prompt and whose antidepressive action is potent.

It is known that a serotonin 2C (hereinafter, optionally abbreviated as "$5\text{-HT}_{2C}$") ligand can affect the release of serotonin and dopamine in a rat cerebral cortex (e.g., Neuropsychopharmacology, (2004), 29, 1782-1789 (5-HT), Synapse, (2000), 36, 205-221(DA)). The mechanism of controlling the release of a monoamine such as serotonin and dopamine by $5\text{-HT}_{2C}$ receptor is thought as mentioned below. Serotonin neuron and dopamine neuron are suppressively controlled by GABA (gamma-aminobutyric acid) neuron in dorsal raphe nucleus and ventral tegmental area which are each nucleus of origin, respectively. There are $5\text{-HT}_{2C}$ receptors on the GABA neuron. When the receptors are stimulated, the GABA release is promoted to inhibit serotonin neuron and dopamine neuron. Namely, when $5\text{-HT}_{2C}$ receptors are inhibited, it is thought that the GABA release is suppressed in nucleus of origin to promote the release of a monoamine such as serotonin and dopamine in prefrontal cortexes or hippocampi which are projection targets of each neuron. In addition, it has been reported that compounds having the inverse agonistic action for $5\text{-HT}_{2C}$ receptor exhibit more potent promoting action of the monoamine release than compounds having only the inhibitory action thereof (e.g., The Journal of Neuroscience, (2004), 24, 3235-3241).

It has been reported that a combination of a SSRI and a $5\text{-HT}_{2C}$ antagonist/inverse agonist can early increase the serotonin level in rat prefrontal cortexes compared with the case of a SSRI alone (e.g., Neuropsychopharmacology, (2004), 29, 1782-1789). Accordingly, a compound having both the serotonin reuptake inhibitory action and the $5\text{-HT}_{2C}$ antagonistic/inverse agonistic action is expected to exhibit the antidepressive action for a patient suffering from depression at an early stage.

On the other hand, as a trial to increase the antidepressive action, it has been reported that a combination therapy of a SSRI and a mood-stabilizing drug such as lithium carbonate and tri-iodotyrosine, as well as a combination therapy of a conventional antidepressant having the serotonin reuptake inhibitory action such as a TCA and a SSRI, and a dopamine agonist such as bromocriptine are effective for a patient suffering from depression who is resistant to the monotherapy of a SSRI (e.g., Biol psychiatry (1996), 40, 152). Accordingly, the activation of both serotonin neuron and dopamine neuron is expected to exhibit a potent antidepressive action for a patient suffering from wide range depression.

A SSRI in clinical practice is useful as an anxiolytic drug, but it takes several weeks for the onset of its therapeutic effect as is the case in the therapy of depression, which is a problem. In addition, it has been reported that a $5\text{-HT}_{2C}$ antagonist or inverse agonist also exhibits the anxiolytic action in a variety of anxious animal models (e.g., British Journal of Pharmacology, (1996), 117, 427-434, European Journal of Pharmacology, (2006) 553, 171-184). Accordingly, a compound having both serotonin reuptake inhibitory action and $5\text{-HT}_{2C}$ antagonistic/inverse agonistic action is expected to exhibit a potent anxiolytic action.

Amongst patients suffering from depression, it is known that the rate of patients suffering from depression who are accompanied with anxiety symptom is high, and additionally the depression symptom accompanied with anxiety symptom is apt to be protracted, thus patients suffering from depression who are accompanied with anxiety symptom are apt to be resistant to the therapy with a SSRI (e.g., Psychological Medicine, (2004), 34, 1299-1308). Accordingly, an antidepressant having a potent anxiolytic action is thought to be very useful in the depression therapy.

From the above-mentioned viewpoint, a compound having both the serotonin reuptake inhibitory action and the $5\text{-HT}_{2C}$ antagonistic action, in particular, the $5\text{-HT}_{2C}$ inverse agonistic action can activate both serotonin neuron and dopamine neuron by increasing the amount of serotonin released by the serotonin reuptake inhibitory action and indirectly increasing the amount of dopamine released by the $5\text{-HT}_{2C}$ antagonistic action. Accordingly, such compound is expected to be a new antidepressant useful for a patient suffering from wide range depression, which exhibits prompt onset of its action and has a potent antidepressive action and anxiolytic action. It has been desired to develop a new medicament comprising such a new compound. For example, US 2007/0105843 A discloses a combination of a medicament having the serotonin reuptake inhibitory action and a medicament having the $5\text{-HT}_{2C}$ antagonistic action and use of a compound having both the serotonin reuptake inhibitory action and the $5\text{-HT}_{2C}$ antagonistic action as an antidepressant or an anxiolytic drug, but does not specifically disclose any compounds having both the serotonin reuptake inhibitory action and the 5-HT$_{2C}$ antagonistic action, in particular, 5-HT$_{2C}$ inverse agonistic action.

For example, Patent References 1 to 5 as mentioned below report a compound wherein an aminomethyl group is attached at the 3-position of the pyrazole ring.

Patent Reference 1 discloses, for example, a 3-aminomethylpyrazole derivative of the following formula P-1. However, the structure thereof differ from that of the present compound in that the compound of Patent Reference 1 has an isopropyl group and a substituted phenoxy group as a substituent at 1- and 5-position of the pyrazole ring, respectively. In addition, Patent Reference 1 is directed to a HIV reverse transcriptase inhibitor, but neither discloses nor suggests serotonin reuptake action, 5-HT$_{2C}$ antagonistic action or 5-HT$_{2C}$ inverse agonistic action.

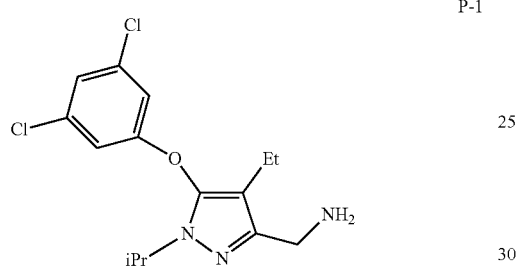

P-1

Patent Reference 2 discloses, for example, a 3-aminomethylpyrazole derivative of the following formula P-2. However, the structure thereof differ from that of the present compound in that the compound of Patent Reference 2 has a isopropyl group, a pyridylmethyl group, and a substituted phenylthio group as a substituent at 1-, 4- and 5-position of the pyrazole ring, respectively. In addition, Patent Reference 2 is directed to a HIV reverse transcriptase inhibitor, but neither discloses nor suggests serotonin reuptake action, 5-HT$_{2C}$ antagonistic action or 5-HT$_{2C}$ inverse agonistic action.

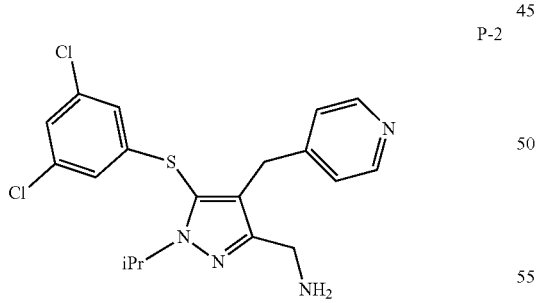

P-2

Patent Reference 3 discloses, for example, a 3-aminomethylpyrazole derivative of the following formula P-3. However, the structure thereof differ from that of the present compound in that the compound of Patent Reference 3 has a cyclopropyl group and a substituted phenyl group as a substituent at 1- and 5-position of the pyrazole ring, respectively. In addition, Patent Reference 3 is directed to a nociceptin inhibitor, but neither discloses nor suggests serotonin reuptake action, 5-HT$_{2C}$ antagonistic action or 5-HT$_{2C}$ inverse agonistic action.

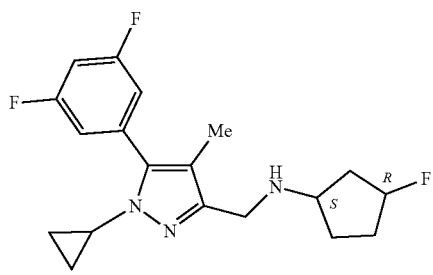

P-3

Patent Reference 4 discloses, for example, a 3-aminomethylpyrazole derivative of the following formula P-4. However, the structure thereof differ from that of the present compound in that the compound of Patent Reference 4 has a substituted phenyl group as a substituent at 5-position of the pyrazole ring. In addition, Patent Reference 4 discloses the pyrazole derivative as a synthetic intermediate, but neither discloses nor suggests serotonin reuptake action, 5-HT$_{2C}$ antagonistic action or 5-HT$_{2C}$ inverse agonistic action.

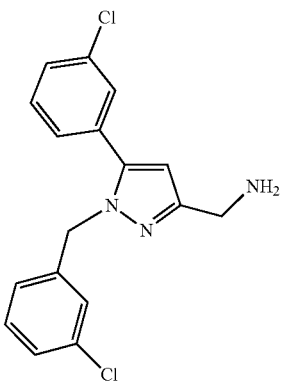

P-4

Patent Reference 5 and Patent Reference 6 disclose, for example, a 3-piperazinylmethylpyrazole derivative of the following formula P-5. However, the structure thereof differ from that of the present compound in that the compound of Patent References 5 and 6 have a biphenyl group and a substituted phenyl group as a substituent at 1- and 5-position of the pyrazole ring, respectively. In addition, Patent Reference 6 discloses that the pyrazole derivative has both 5-HT$_{2C}$ antagonistic action and 5-HT$_{2A}$ antagonistic action, but neither discloses nor suggests serotonin reuptake action.

P-5

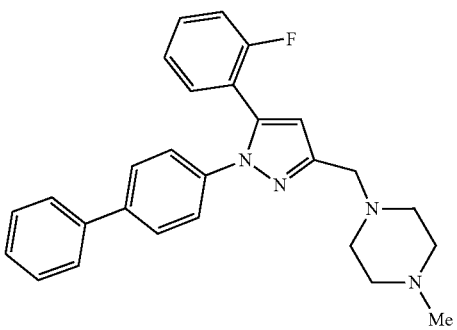

PRIOR ART DOCUMENTS

Patent Reference

[Patent Reference 1] WO 2004/074257
[Patent Reference 2] WO 2002/100853
[Patent Reference 3] WO 2007/037513
[Patent Reference 4] WO 2009/004171
[Patent Reference 5] WO 2003/031435
[Patent Reference 6] WO 2004/089931

SUMMARY OF INVENTION

Technical Problem

The purpose of the present invention is to provide a new serotonin reuptake inhibitor having 5-HT$_{2C}$ antagonistic action, in particular, 5-HT$_{2C}$ inverse agonistic action, which is useful as a medicament for treating depression or anxiety (anxiety disorder), or preventing a relapse thereof.

Solution to Problem

The present inventors have extensively studied to solve the above problem and then have found that a compound having a pyrazole structure or a pharmaceutically acceptable salt thereof has both 5-HT$_{2C}$ antagonistic action (in particular, 5-HT$_{2C}$ inverse agonistic action) and serotonin reuptake inhibitory action, which is useful as a medicament for treating depression or anxiety, or preventing a relapse thereof. Based upon the new findings, the present invention has been completed. The present invention relates to the following inventions.

[1] A compound of Formula (1):

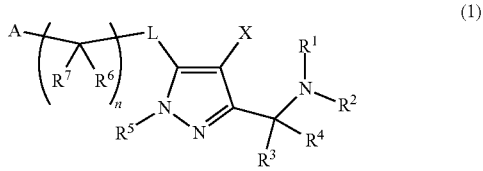

(1)

[hereinafter, optionally referred to as "the compound of Formula (1)" or "Compound (1)"]
or a pharmaceutically acceptable salt thereof wherein
R$^1$ and R$^2$ are independently selected from the group consisting of hydrogen atom, a C$_{1-6}$ alkyl group and a C$_{3-8}$ cycloalkyl group, R$^3$ and R$^4$ are independently selected from the group consisting of hydrogen atom and a C$_{1-6}$ alkyl group,
R$^5$ is an optionally-substituted C$_{4-7}$ alkyl group or —(C$^8$R$^9$)$_r$-E,
R$^6$, R$^7$, R$^8$ and R$^9$ are independently selected from the group consisting of hydrogen atom, fluorine atom and an optionally-substituted C$_{1-6}$ alkyl group,
A is an optionally-substituted C$_{6-10}$ aryl group or an optionally-substituted 5- to 10-membered heteroaryl group,
r is 1, 2, 3 or 4,
E is an optionally-substituted C$_{3-8}$ cycloalkyl group, an optionally-substituted C$_{4-8}$ cycloalkenyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted C$_{6-10}$ aryl group or an optionally-substituted 5- to 10-membered heteroaryl group,
L is oxygen atom, sulfur atom or —NR$^{10}$—,
n is 1, 2 or 3,
R$^{10}$ is hydrogen atom, a C$_{1-6}$ alkyl group or a C$_{3-8}$ cycloalkyl group, and
X is hydrogen atom, a C$_{1-6}$ alkyl group optionally-substituted with fluorine atom or a halogen atom.

[2] The compound of [1] or a pharmaceutically acceptable salt thereof wherein
R$^1$, R$^2$ and R$^3$ are independently selected from the group consisting of hydrogen atom and methyl group, and
R$^4$ is hydrogen atom.

[3] The compound of [1] or [2] or a pharmaceutically acceptable salt thereof wherein A is an optionally-substituted C$_{6-10}$ aryl group.

[4] The compound of any one of [1] to [3] or a pharmaceutically acceptable salt thereof wherein X is hydrogen atom.

[5] The compound of any one of [1] to [4] or a pharmaceutically acceptable salt thereof wherein L is oxygen atom.

[6] The compound of any one of [1] to [5] or a pharmaceutically acceptable salt thereof wherein n is 1.

[7] The compound of any one of [1] to [6] or a pharmaceutically acceptable salt thereof wherein
R$^1$, R$^3$ and R$^4$ are hydrogen atom, and
R$^2$ is methyl group.

[8] The compound of any one of [1] to [7] or a pharmaceutically acceptable salt thereof wherein R$^6$, R$^7$, R$^8$ and R$^9$ are hydrogen atom.

[9] The compound of any one of [1] to [8] or a pharmaceutically acceptable salt thereof wherein E is an optionally-substituted C$_{3-8}$ cycloalkyl group, an optionally-substituted 5- to 10-membered saturated heterocyclic group which comprises 1 to 3 oxygen atoms as a constituent atom of the ring, or an optionally-substituted phenyl group.

[10] The compound of any one of [1] to [9] or a pharmaceutically acceptable salt thereof wherein E is an optionally-substituted C$_{3-8}$ cycloalkyl group.

[11] The compound of any one of [1] to [10] or a pharmaceutically acceptable salt thereof wherein r is 1 or 2.

[12] The compound of any one of [1] to [8] or a pharmaceutically acceptable salt thereof wherein R$^5$ is an optionally-substituted C$_{4-7}$ alkyl group.

[13] The compound of [1] wherein the compound of Formula (1) is any one of the following compounds, or a pharmaceutically acceptable salt thereof:
1-[5-(benzyloxy)-1-(cyclohexylmethyl)-1H-pyrazol-3-yl]-N-methylmethanamine; Example 5
1-{1-(cyclohexylmethyl)-5-[(2-fluorobenzyl)oxy]-1H-pyrazol-3-yl}-N-methylmethanamine; Example 20

1-{1-(cyclohexylmethyl)-5-[(3-fluorobenzyl)oxy]-1H-pyrazol-3-yl}-N-methylmethanamine; Example 21
1-{1-(cyclohexylmethyl)-5-[(4-fluorobenzyl)oxy]-1H-pyrazol-3-yl}-N-methylmethanamine; Example 22
1-{5-[(2-chlorobenzyl)oxy]-1-(cyclohexylmethyl)-1H-pyrazol-3-yl}-N-methylmethanamine; Example 23
1-{5-[(3-chlorobenzyl)oxy]-1-(cyclohexylmethyl)-1H-pyrazol-3-yl}-N-methylmethanamine; Example 24
1-{1-(cyclohexylmethyl)-5-[(2-methylbenzyl)oxy]-1H-pyrazol-3-yl}-N-methylmethanamine; Example 26
1-{1-(cyclohexylmethyl)-5-[(3-methylbenzyl)oxy]-1H-pyrazol-3-yl}-N-methylmethanamine; Example 27
1-{1-(cyclohexylmethyl)-5-[(2,4-difluorobenzyl)oxy]-1H-pyrazol-3-yl}-N-methylmethanamine; Example 29
1-{5-[(2-chloro-4-fluorobenzyl)oxy]-1-(cyclohexylmethyl)-1H-pyrazol-3-yl}-N-methylmethanamine; Example 30
1-{1-(cyclohexylmethyl)-5-[(4-fluoro-2-methylbenzyl)oxy]-1H-pyrazol-3-yl}-N-methylmethanamine; Example 31
1-{1-(cyclohexylmethyl)-5-[(2,5-difluorobenzyl)oxy]-1H-pyrazol-3-yl}-N-methylmethanamine; Example 33
1-{5-[(5-chloro-2-fluorobenzyl)oxy]-1-(cyclohexylmethyl)-1H-pyrazol-3-yl}-N-methylmethanamine; Example 34
1-{1-(cyclohexylmethyl)-5-[(2-fluoro-5-methylbenzyl)oxy]-1H-pyrazol-3-yl}-N-methylmethanamine; Example 35
1-{5-[(2-chloro-5-fluorobenzyl)oxy]-1-(cyclohexylmethyl)-1H-pyrazol-3-yl}-N-methylmethanamine; Example 37
1-{1-(cyclohexylmethyl)-5-[(2,5-dichlorobenzyl)oxy]-1H-pyrazol-3-yl}-N-methylmethanamine; Example 38
1-{5-[(2-chloro-5-methylbenzyl)oxy]-1-(cyclohexylmethyl)-1H-pyrazol-3-yl}-N-methylmethanamine; Example 39
1-[5-(benzyloxy)-1-(cyclopentylmethyl)-1H-pyrazol-3-yl]-N-methylmethanamine; Example 4
1-{1-(cyclopentylmethyl)-5-[(2-fluorobenzyl)oxy]-1H-pyrazol-3-yl}-N-methylmethanamine; Example 135
1-{1-(cyclopentylmethyl)-5-[(3-fluorobenzyl)oxy]-1H-pyrazol-3-yl}-N-methylmethanamine; Example 136
1-{1-(cyclopentylmethyl)-5-[(4-fluorobenzyl)oxy]-1H-pyrazol-3-yl}-N-methylmethanamine; Example 137
1-{5-[(2-chlorobenzyl)oxy]-1-(cyclopentylmethyl)-1H-pyrazol-3-yl}-N-methylmethanamine; Example 138
1-{5-[(3-chlorobenzyl)oxy]-1-(cyclopentylmethyl)-1H-pyrazol-3-yl}-N-methylmethanamine; Example 139
1-{1-(cyclopentylmethyl)-5-[(2-methylbenzyl)oxy]-1H-pyrazol-3-yl}-N-methylmethanamine; Example 141
1-{1-(cyclopentylmethyl)-5-[(3-methylbenzyl)oxy]-1H-pyrazol-3-yl}-N-methylmethanamine; Example 142
1-{1-(cyclopentylmethyl)-5-[(2,4-difluorobenzyl)oxy]-1H-pyrazol-3-yl}-N-methylmethanamine; Example 144
1-{5-[(2-chloro-4-fluorobenzyl)oxy]-1-(cyclopentylmethyl)-1H-pyrazol-3-yl}-N-methylmethanamine; Example 145
1-{1-(cyclopentylmethyl)-5-[(4-fluoro-2-methylbenzyl)oxy]-1H-pyrazol-3-yl}-N-methylmethanamine; Example 146
1-{1-(cyclopentylmethyl)-5-[(2,5-difluorobenzyl)oxy]-1H-pyrazol-3-yl}-N-methylmethanamine; Example 147
1-{5-[(5-chloro-2-fluorobenzyl)oxy]-1-(cyclopentylmethyl)-1H-pyrazol-3-yl}-N-methylmethanamine; Example 148
1-{1-(cyclopentylmethyl)-5-[(2-fluoro-5-methylbenzyl)oxy]-1H-pyrazol-3-yl}-N-methylmethanamine; Example 149
1-{5-[(2-chloro-5-fluorobenzyl)oxy]-1-(cyclopentylmethyl)-1H-pyrazol-3-yl}-N-methylmethanamine; Example 150
1-{1-(cyclopentylmethyl)-5-[(2,5-dichloro benzyl)oxy]-1H-pyrazol-3-yl}-N-methylmethanamine; Example 151
1-{5-[(2-chloro-5-methylbenzyl)oxy]-1-(cyclopentylmethyl)-1H-pyrazol-3-yl}-N-methylmethanamine; Example 152
1-[5-(benzyloxy)-1-(3,3-dimethylbutyl)-1H-pyrazol-3-yl]-N-methylmethanamine; Example 264
1-{5-[(3-chlorobenzyl)oxy]-1-(3,3-dimethylbutyl)-1H-pyrazol-3-yl}-N-methylmethanamine; Example 265
1-{5-[(2,5-difluorobenzyl)oxy]-1-(3,3-dimethylbutyl)-1H-pyrazol-3-yl}-N-methylmethanamine; Example 266
1-{5-[(5-chloro-2-fluorobenzyl)oxy]-1-(3,3-dimethylbutyl)-1H-pyrazol-3-yl}-N-methylmethanamine; Example 267
1-[5-(benzyloxy)-1-(3-methylbutyl)-1H-pyrazol-3-yl]-N-methylmethanamine; Example 268
1-{5-[(2,5-difluorobenzyl)oxy]-1-(3-methylbutyl)-1H-pyrazol-3-yl}-N-methylmethanamine; Example 269
1-{5-[(5-chloro-2-fluorobenzyl)oxy]-1-(3-methylbutyl)-1H-pyrazol-3-yl}-N-methylmethanamine; Example 270
1-{5-[(2,5-difluorobenzyl)oxy]-1-(3-methoxy-3-methyl-butyl)-1H-pyrazol-3-yl}-N-methylmethanamine; Example 274
1-{5-[(5-chloro-2-fluorobenzyl)oxy]-1-(3-methoxy-3-methylbutyl)-1H-pyrazol-3-yl}-N-methylmethanamine; Example 275
1-{1-(cyclopentylmethyl)-5-[(2,4,5-trifluorobenzyl)-oxy]-1H-pyrazol-3-yl}-N-methylmethanamine; Example 280
1-{1-(cyclohexylmethyl)-5-[(2,4,5-trifluorobenzyl)-oxy]-1H-pyrazol-3-yl}-N-methylmethanamine;
1-{1-(2-cyclopentylethyl)-5-[(2,5-difluorobenzyl)oxy]-1H-pyrazol-3-yl}-N-methylethanamine; Example 315
N-methyl-1-{1-(3-methylbutyl)-5-[(2,4,5-trifluoro-benzyl)oxy]-1H-pyrazol-3-yl}methanamine; Example 283
1-{1-(3,3-dimethylbutyl)-5-[(2,4,5-trifluorobenzyl)-oxy]-1H-pyrazol-3-yl}-N-methylmethanamine; Example 284
1-{1-(4-fluorobenzyl)-5-[(2-fluorobenzyl)oxy]-1H-pyrazol-3-yl}-N-methylmethanamine; Example 218
1-{5-[(2,5-difluorobenzyl)oxy]-1-(4-fluorobenzyl)-1H-pyrazol-3-yl}-N-methylmethanamine; Example 219
1-{1-(4-fluorobenzyl)-5-[(2,4,5-trifluorobenzyl)oxy]-1H-pyrazol-3-yl}-N-methylmethanamine;
1-{5-[(2-fluorobenzyl)oxy]-1-(4-methylbenzyl)-1H-pyrazol-3-yl}-N-methylmethanamine; Example 228
1-{5-[(2,5-difluorobenzyl)oxy]-1-(4-methylbenzyl)-1H-pyrazol-3-yl}-N-methylmethanamine; Example 230
N-methyl-1-{1-(4-methylbenzyl)-5-[(2,4,5-trifluoro-benzyl)oxy]-1H-pyrazol-3-yl}methanamine; Example 286
1-{5-[(2,5-difluorobenzyl)oxy]-1-(4-methoxybenzyl)-1H-pyrazol-3-yl}-N-methylmethanamine; no Examples
1-{1-(4-methoxybenzyl)-5-[(2,4,5-trifluorobenzyl)oxy]-1H-pyrazol-3-yl}-N-methylmethanamine; Example 285
1-{5-[(5-chloro-2-fluorobenzyl)oxy]-1-(cyclopropyl-methyl)-1H-pyrazol-3-yl}-N-methylmethanamine; Example 131
1-{5-[(4-fluorobenzyl)oxy]-1-(2-methylpropyl)-1H-pyrazol-3-yl}-N-methylmethanamine; Example 369
1-{5-[(5-chloro-2-fluorobenzyl)oxy]-1-(2-methyl-propyl)-1H-pyrazol-3-yl}-N-methylmethanamine; Example 256
1-{1-(2,2-dimethylpropyl)-5-[(4-fluorobenzyl)oxy]-1H-pyrazol-3-yl}-N-methylmethanamine; Example 375

1-{5-[(2,5-difluorobenzyl)oxy]-1-(2,2-dimethylpropyl)-1H-pyrazol-3-yl}-N-methylmethanamine; Example 258

1-{5-[(5-chloro-2-fluorobenzyl)oxy]-1-(2,2-dimethyl-propyl)-1H-pyrazol-3-yl}-N-methylmethanamine; Example 259

1-{5-[(2-fluorobenzyl)oxy]-1-(3-methylbutyl)-1H-pyrazol-3-yl}-N-methylmethanamine; Example 381

1-{5-[(4-fluorobenzyl)oxy]-1-(3-methylbutyl)-1H-pyrazol-3-yl}-N-methylmethanamine; Example 383

1-(5-[(4-fluorobenzyl)oxy]-1-{[1-(trifluoromethyl)-cyclopentyl]methyl}-1H-pyrazol-3-yl)-N-methylmethanamine; Example 446

1-(5-[(2,5-difluorobenzyl)oxy]-1-{[1-(trifluoro-methyl)cyclopentyl]methyl}-1H-pyrazol-3-yl)-N-methylmethanamine; Example 447

1-(5-[(5-chloro-2-fluorobenzyl)oxy]-1-{[1-(trifluoromethyl)cyclopentyl]methyl}-1H-pyrazol-3-yl)-N-methylmethanamine; Example 448

(−)-1-{5-[(5-chloro-2-fluorobenzyl)oxy]-1-(tetrahydro-2H-pyran-2-ylmethyl)-1H-pyrazol-3-yl}-N-methylmethanamine; Example 474

(+)-1-{5-[(5-chloro-2-fluorobenzyl)oxy]-1-(tetrahydro-2H-pyran-2-ylmethyl)-1H-pyrazol-3-yl}-N-methylmethanamine; Example 475

(−)-1-{1-(2-cyclopentylethyl)-5-[(2,5-difluorobenzyl)-oxy]-1H-pyrazol-3-yl}-N-methylethanamine; Example 476

(+)-1-{1-(2-cyclopentylethyl)-5-[(2,5-difluorobenzyl)-oxy]-1H-pyrazol-3-yl}-N-methylethanamine; Example 477

1-{5-[(2,5-difluorobenzyl)oxy]-1-(3-fluoro-3-methyl-butyl)-1H-pyrazol-3-yl}-N-methylmethanamine; Example 481 or, 1-{5-[(5-chloro-2-fluorobenzyl)oxy]-1-(3-fluoro-3-methylbutyl)-1H-pyrazol-3-yl}-N-methylmethanamine; Example 482.

[14] A medicament comprising the compound of any one of [1] to [13] or a pharmaceutically acceptable salt thereof as an active ingredient.

[15] The medicament of [14] which is used for treating depression or anxiety, or preventing a relapse thereof.

[16] A serotonin reuptake inhibitor comprising the compound of any one of [1] to [13] or a pharmaceutically acceptable salt thereof as an active ingredient.

[17] A pharmaceutical composition comprising the compound of any one of [1] to [13] or a pharmaceutically acceptable salt thereof, and a pharmaceutically acceptable carrier.

Effect of Invention

The present invention can provide a serotonin reuptake inhibitor having 5-$HT_{2C}$ antagonistic action, in particular 5-$HT_{2C}$ inverse agonistic action, which comprises a pyrazole derivative or a pharmaceutically acceptable salt thereof as an active ingredient. The serotonin reuptake inhibitor of the present invention exhibits antidepressive and anxiolytic effects, and is thus useful as a medicament for treating depression and anxiety or preventing a relapse thereof.

DESCRIPTION OF EMBODIMENTS

Throughout the description, for example, $C_{1-6}$, $C_{1-4}$, and $C_6$ indicate that the number of carbon atom is 1 to 6, 1 to 4, and 6, respectively. As used herein, a similar definition of carbon having a different subscript number is also meant in the same manner.

The "halogen atom" used herein includes fluorine atom, chlorine atom, bromine atom and iodine atom.

The "$C_{1-6}$ alkyl group" used herein means a straight- or branched-chain saturated aliphatic hydrocarbon group having 1 to 6 carbon atoms, and specifically includes methyl group, ethyl group, propyl group, n-butyl group, n-pentyl group, n-hexyl group, isopropyl group, sec-butyl group, isobutyl group, tert-butyl group, 1-methylbutyl group, 2-methylbutyl group, 3-methylbutyl group, 1-ethylpropyl group and the like. The $C_{1-6}$ alkyl group includes preferably a $C_{1-4}$ alkyl group, more preferably a $C_{1-3}$ alkyl group.

The "$C_{4-7}$ alkyl group" used herein means a straight- or branched-chain saturated aliphatic hydrocarbon group having 4 to 7 carbon atoms, and specifically includes n-butyl group, n-pentyl group, n-hexyl group, n-heptyl group, 1-ethylpropyl group, 1,1-dimethylpropyl group, 1-methyl-1-ethylpropyl group, 1,1-diethylpropyl group, 2,2-dimethylpropyl group, sec-butyl group, isobutyl group, tert-butyl group, 1-methylbutyl group, 2-methylbutyl group, 3-methylbutyl group, 2-ethylbutyl group, 2,2-dimethylbutyl group, 3,3-dimethylbutyl group, 2-methyl-2-ethylbutyl group and the like. The $C_{4-7}$ alkyl group includes preferably a $C_{4-6}$ alkyl group, and specifically includes isobutyl group, 2,2-dimethylpropyl group, 3-methylbutyl group, 3,3-dimethylbutyl group and 2-ethylbutyl group.

The "$C_{6-10}$ aryl group" used herein means a monocyclic or bicyclic aromatic hydrocarbon ring group having 6 to 10 carbon atoms, and includes preferably a $C_6$ or $C_{10}$ aryl group. The $C_{6-10}$ aryl group specifically includes phenyl group, 1- and 2-naphthyl group, and the like.

The "5- to 10-membered heteroaryl group" means a 5- to 10-membered monocyclic or bicyclic aromatic heterocyclic group comprising 1 to 3 heteroatoms independently selected from the group consisting of nitrogen atom, oxygen atom and sulfur atom, wherein the position of the heteroatom in the heteroaryl group and the bonding position of the heteroaryl group are not limited as long as they are chemically stable. The 5- to 10-membered heteroaryl group specifically includes furyl group, thienyl group, pyrrolyl group, oxazolyl group, isoxazolyl group, thiazolyl group, isothiazolyl group, imidazolyl group, pyrazolyl group, furazanyl group, oxadiazolyl group, triazolyl group, tetrazolyl group, pyridyl group, pyrimidinyl group, pyridazinyl group, pyrazinyl group, indolyl group, quinolyl group, isoquinolyl group, quinazolinyl group, imidazo[2,1-b] [1,3]thiazolyl group, benzofuryl group, indolizinyl group, indazolyl group and the like; preferably 5- and 6-membered monocyclic heteroaryl group and 9- and 10-membered bicyclic heteroaryl group. The 5- to 10-membered heteroaryl group also includes an N-oxide form thereof wherein the nitrogen atom of the heteroaryl group is oxidized.

Furthermore, the $C_{6-10}$ aryl group and the 5- to 10-membered heteroaryl group may each form a condensed ring with a $C_{3-8}$ cycloalkyl, $C_{4-8}$ cycloalkenyl or 5- to 10-membered saturated heterocyclic group. In this case, the $C_{6-10}$ aryl group forming a condensed ring specifically includes the following formulae:

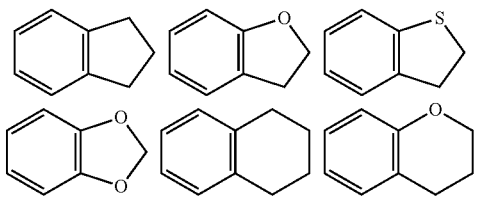

-continued

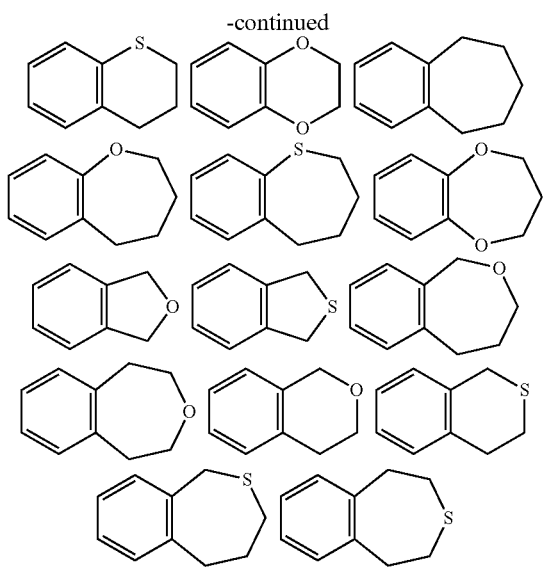

wherein the bonding position of the benzene ring is not limited as long as it is chemically stable.

Furthermore, the 5- to 10-membered heteroaryl group forming a condensed ring specifically includes the following formulae:

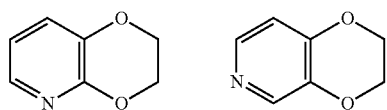 [SMILES: c1cnc2c(c1)OCCO2 ; c1cc2c(cn1)OCCO2]

wherein the bonding position of the pyridine ring is not limited as long as it is chemically stable.

The condensed ring may have the below-mentioned substituent which is shown as a substituent for each of the rings forming the condensed ring.

The "$C_{3-8}$ cycloalkyl group" used herein means a monocyclic or bicyclic saturated aliphatic hydrocarbon ring group having 3 to 8 carbon atoms; and specifically includes cyclopropyl group, cyclobutyl group, cyclopentyl group, cyclohexyl group, cycloheptyl group, cyclooctyl group, bicyclo[2,2,1]heptyl group, bicyclo[3,2,0]heptyl group, and the like. The $C_{3-8}$ cycloalkyl group includes preferably a monocyclic $C_{3-6}$ cycloalkyl group.

The "$C_{4-8}$ cycloalkenyl group" used herein means a monocyclic or bicyclic unsaturated aliphatic hydrocarbon ring group having 4 to 8 carbon atoms with 1 or 2 double bonds, and specifically includes cyclobutenyl group, cyclopentenyl group, cyclohexenyl group, and cycloheptenyl group. The position of the double bond in the ring is not limited. The cycloalkenyl group includes preferably $C_5$ and $C_6$ cycloalkenyl groups.

The "5- to 10-membered saturated heterocyclic group which comprises 1 to 3 heteroatoms independently selected from the group consisting of oxygen atom and sulfur atom as a constituent atom of the ring" used herein means a 5- to 10-membered monocyclic or bicyclic saturated aliphatic heterocyclic group comprising 1 to 3 heteroatoms independently selected from the group consisting of oxygen atom and sulfur atom, wherein the position of the heteroatom in the heteroaryl group and the bonding position of the heteroaryl group are not limited as long as they are chemically stable. The saturated heterocyclic group includes preferably 5- to 8-membered saturated heterocyclic groups, more preferably 5- and 6-membered saturated heterocyclic groups. The 5- to 10-membered saturated heterocyclic group specifically includes tetrahydrofuryl group, tetrahydro-2H-pyranyl group, 1,4-dioxanyl group, tetrahydrothienyl group, tetrahydro-2H-thiopyranyl group, and bicyclic groups of the following formulae:

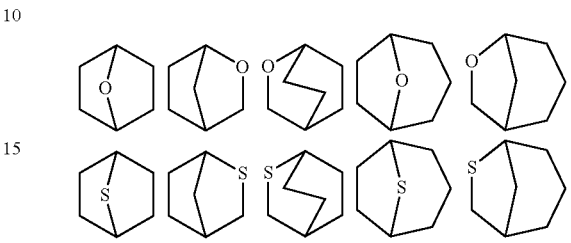

wherein the bonding position of the ring is not limited as long as it is chemically stable. The 5- to 10-membered saturated heterocyclic group is preferably a saturated heterocyclic group comprising 1 or 2 oxygen atoms in the ring, and includes, for example, tetrahydrofuryl group, tetrahydro-2H-pyranyl group, 1,4-dioxanyl group, 7-oxabicyclo[2,2,1]heptyl group, and 2-oxabicyclo[2,2,2]octyl group.

The $C_{3-8}$ cycloalkyl group, $C_{4-8}$ cycloalkenyl group and 5- to 10-membered saturated heterocyclic group may each form a condensed ring with a $C_{6-10}$ aryl or 5- to 10-membered heteroaryl. The condensed ring specifically includes the following formulae:

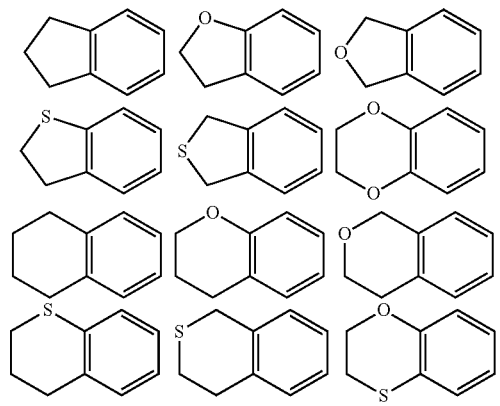

wherein the bonding position of the $C_{3-8}$ cycloalkyl group, $C_{4-8}$ cycloalkenyl group and 5- to 10-membered saturated heterocyclic group is not limited as long as it is chemically stable. The condensed ring may have the below-mentioned substituent which is shown as a substituent for each of the rings forming the condensed ring.

The substituents of the "optionally-substituted $C_{6-10}$ aryl group" and "optionally-substituted 5- to 10-membered heteroaryl group" includes, for example, a halogen atom, a $C_{1-6}$ alkyl group optionally substituted with fluorine atom, a $C_{1-6}$ alkyloxy group optionally substituted with fluorine atom, hydroxy group, a $C_{1-6}$ alkylthio group, a $C_{6-10}$ aryloxy group, a $C_{6-10}$ arylthio group, cyano group, —$CO_2R^{11}$, —$SO_2R^{11}$, —$NR^{10}SO_2R^{11}$, —$OSO_2R^{11}$, —$COR^{12}$, —$SO_2NR^{12}R^{13}$, —$CONR^{12}R^{13}$, —$NR^{12}R^{13}$, —$NR^{10}CONR^{12}R^{13}$, —$NR^{10}COR^{12}$, —$CR^{12}$=$N(OR^{11})$—, oxime group, a $C_{3-8}$ cycloalkyl group, a $C_{6-10}$ aryl group, and a 5- to 10-membered heteroaryl group (wherein $R^{10}$ is the same as defined in the above [1], $R^{11}$ is a $C_{1-6}$ alkyl group, a $C_{3-8}$ cycloalkyl group, an aryl group or a heteroaryl group, and $R^{12}$ and $R^{13}$ are independently selected from the group consisting of hydrogen atom, a $C_{1-6}$ alkyl group, a $C_{3-8}$ cycloalkyl group, an aryl group and a heteroaryl group; and the aryl, heteroaryl, aryloxy and arylthio groups in $R^{11}$, $R^{12}$ and $R^{13}$ may be each further substituted with halogen atom, a $C_{1-6}$ alkyl group, hydroxy group or a $C_{1-6}$ alkyloxy group). The substituents include preferably a halogen atom, a $C_{1-6}$ alkyl group optionally substituted with fluorine atom, a $C_{1-6}$ alkyloxy group optionally substituted with fluorine atom, hydroxy group, a $C_{1-6}$ alkylthio group and cyano group; and more preferably fluorine atom, chlorine atom, bromine atom, methyl group, ethyl group, isopropyl group, trifluoromethyl group, methoxy group, ethoxy group, isopropoxy group, trifluoromethoxy group, difluoromethoxy group, and cyano group. As used herein, one or more of the same or different substituents may exist at any position as long as the substitution is possible.

The substituents of the "optionally-substituted $C_{1-6}$ alkyl group" and "optionally-substituted $C_{4-7}$ alkyl group" include, for example, fluorine atom, hydroxy group, and a $C_{1-6}$ alkyloxy group optionally substituted with fluorine atom. As used herein, one or more of the same or different substituents may exist at any position as long as the substitution is possible.

The substituents of the "optionally-substituted $C_{3-8}$ cycloalkyl group", "optionally-substituted. $C_{4-8}$ cycloalkenyl group" and "optionally-substituted 5- to 10-membered saturated heterocyclic group" include, for example, fluorine atom, a $C_{1-6}$ alkyl group optionally substituted with fluorine atom, hydroxy group, and a $C_{1-6}$ alkyloxy group optionally substituted with fluorine atom. As used herein, one or more of the same or different substituents may exist at any position as long as the substitution is possible.

The "$C_{1-6}$ alkyloxy group" used herein means an oxy group substituted with the above-defined "$C_{1-6}$ alkyl group", and specifically includes methoxy group, ethoxy group, propoxy group, isopropoxy group, 1-methylethoxy group, n-butoxy group, sec-butoxy group, tert-butoxy group, 1-methylpropoxy group, 2-methylpropoxy group, 1,1-dimethylethoxy group, pentyloxy group, and hexyloxy group. The $C_{1-6}$ alkyloxy group includes preferably a $C_{1-4}$ alkyloxy group, and includes, for example, methoxy group, ethoxy group and isopropoxy group.

The "$C_{1-6}$ alkylthio group" used herein means a thio group substituted with the above-defined "$C_{1-6}$ alkyl group" and includes, for example, methylthio group, ethylthio group, propylthio group, 1-methylethylthio group, butylthio group, 1-methylpropylthio group, 2-methylpropylthio group, 1,1-dimethylethylthio group, pentylthio group, and hexylthio group. The $C_{1-6}$ alkylthio group includes preferably a $C_{1-4}$ alkylthio group.

The "—$CONR^{12}R^{13}$" used herein includes, for example, carbamoyl group, methylcarbamoyl group, ethylcarbamoyl group, propylcarbamoyl group, isopropylcarbamoyl group, dimethylcarbamoyl group, diethylcarbamoyl group, and methylethylcarbamoyl group.

The "—$CO_2R^{11}$" used herein includes, for example, methoxycarbonyl group, ethoxycarbonyl group, propoxycarbonyl group, butoxycarbonyl group, and tert-butoxycarbonyl group.

The "—$COR^{12}$" used herein includes, for example, acetyl group, propionyl group, butyryl group, isobutyryl group, valeryl group, isovaleryl group, pivaloyl group, pentanoyl group, isopentanoyl group, neopentanoyl group, and hexanoyl group.

The "—$SO_2R^{11}$" used herein includes, for example, methylsulfonyl group, ethylsulfonyl group, propylsulfonyl group, butylsulfonyl group, and tert-butylsulfonyl group.

The "—$NR^{10}SO_2R^{11}$" used herein includes, for example, methylsulfonylamide group, ethylsulfonylamide group, propylsulfonylamide group, butylsulfonylamide group, and tert-butylsulfonylamide group.

The "—$NR^{10}CONR^{12}R^{13}$" used herein includes, for example, methylureido group, ethylureido group, and propylureido group.

The "—$NR^{12}R^{13}$" used herein includes, for example, amino group, methylamino group, ethylamino group, propylamino group, dimethylamino group, diethylamino group, and methylethylamino group.

The "—$NR^{10}COR^{12}$" used herein includes, for example, acetylamino group, ethylcarbonylamino group, propyl-carbonylamino group, isopropylcarbonylamino group, butylcarbonylamino group, isobutylcarbonylamino group, benzoylamino group, and 1- and 2-naphthoylamino group.

The "—$OSO_2R^{11}$" used herein includes, for example, methylsulfonyloxy group, ethylsulfonyloxy group, propylsulfonyloxy group, butylsulfonyloxy group, and tert-butylsulfonyloxy group.

The "—$SO_2NR^{12}R^{13}$" used herein includes, for example, methylaminosulfonyl group, ethylaminosulfonyl group, propylaminosulfonyl group, butylaminosulfonyl group, and tert-butylaminosulfonyl group.

The "—$CR^{12}=N(OR^{11})$—" used herein includes, for example, N-hydroxyiminoethyl group, N-hydroxy-1-iminopropyl group, N-methoxyiminoethyl group, N-methoxy-1-iminopropyl group, N-ethoxyiminoethyl group, and N-ethoxy-1-iminopropyl group.

Among the present compound represented as Formula (1), the substituents thereof are preferably as follows.

$R^1$ and $R^2$ are independently selected from the group consisting of hydrogen atom, a $C_{1-6}$ alkyl group and a $C_{3-8}$ cycloalkyl group; preferably hydrogen atom and a $C_{1-3}$ alkyl group; more preferably either of $R^1$ and $R^2$ is hydrogen atom, and the other is a $C_{1-3}$ alkyl group.

$R^1$ and $R^2$ specifically include hydrogen atom, methyl group, ethyl group, propyl group, isopropyl group and cyclopropyl group; preferably either of $R^1$ and $R^2$ is hydrogen atom, and the other is methyl group.

$R^3$ and $R^4$ are independently selected from the group consisting of hydrogen atom and a $C_{1-6}$ alkyl group, preferably hydrogen atom and a $C_{1-3}$ alkyl group.

$R^3$ and $R^4$ specifically include hydrogen atom, methyl group and ethyl group; preferably both of $R^3$ and $R^4$ are hydrogen atom.

$R^5$ is an optionally-substituted $C_{4-7}$ alkyl group or —$(CR^8R^9)_r$-E.

The $C_{4-7}$ alkyl group of $R^5$ specifically includes n-butyl group, n-pentyl group, n-hexyl group, n-heptyl group, 1-ethylpropyl group, 1,1-dimethylpropyl group, 1-methyl-1-ethylpropyl group, 1,1-diethylpropyl group, 2,2-dimethylpropyl group, sec-butyl group, isobutyl group, tert-butyl group, 1-methylbutyl group, 2-methylbutyl group, 3-methylbutyl group, 2-ethylbutyl group, 2,2-dimethylbutyl group, 3,3-dimethylbutyl group, 2-methyl-2-ethylbutyl group and the like; preferably isobutyl group, 2,2-dimethylpropyl group, 3-methylbutyl group, 3,3-dimethylbutyl group and 2-ethylbutyl group.

$R^8$ and $R^9$ are independently selected from the group consisting of hydrogen atom, fluorine atom and an optionally-substituted $C_{1-6}$ alkyl group; preferably hydrogen atom and a $C_{1-3}$ alkyl group; more preferably both of $R^8$ and $R^9$ are hydrogen atom. $R^8$ and $R^9$ specifically include hydrogen atom, methyl group, ethyl group, and hydroxymethyl group.

r is 1, 2, 3 or 4; preferably 1, 2 or 3; more preferably 11 or 2; even more preferably 1.

E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted $C_{6-10}$ aryl group or an optionally-substituted 5- to 10-membered heteroaryl group; preferably an optionally-substituted $C_{3-8}$ cycloalkyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted $C_{6-10}$ aryl group or an optionally-substituted 5- to 10-membered heteroaryl group; more preferably an optionally-substituted $C_{3-8}$ cycloalkyl group, an optionally-substituted 5- to 10-membered saturated heterocyclic group which comprises 1 to 3 heteroatoms independently selected from the group consisting of oxygen atom and sulfur atom as a constituent atom of the ring, or an optionally-substituted $C_{6-10}$ aryl group; even more preferably an optionally-substituted $C_{3-8}$ cycloalkyl group or an optionally-substituted $C_{6-10}$ aryl group.

The substituents of the $C_{6-10}$ aryl group and 5- to 10-membered heteroaryl group in E include, for example, (i) halogen atoms such as fluorine atom and chlorine atom, (ii) $C_{1-6}$ alkyl groups such as methyl group, ethyl group, and propyl group, (iii) $C_{1-6}$ alkyloxy groups such as methoxy group, ethoxy group, and isopropoxy group, (iv) $C_{1-6}$ alkylthio groups such as methylthio group and ethylthio group, (v) cyano group, (vi) trifluoromethyl group, (vii) trifluoromethoxy group, (viii) hydroxy group, and (ix) difluoromethoxy group; preferably fluorine atom, chlorine atom, methyl group, and methoxy group. As used herein, one or more of the same or different substituents may exist at any position as long as the substitution is possible.

E specifically includes phenyl group (preferably substituted at the 4-position), cyclopropyl group, cyclobutyl group, cyclopentyl group, cyclohexyl group, cycloheptyl group, tetrahydrofuryl group, tetrahydro-2H-pyranyl group, 1,4-dioxanyl group, tetrahydrothienyl group, tetrahydro-2H-thiopyranyl group, and bicyclic groups of the following formulae:

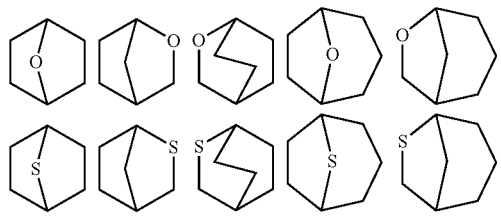

wherein the bonding position of the bicyclic ring is not limited as long as it is chemically stable, in which the above-listed groups may be optionally substituted with a substituent selected from the group consisting of halogen atom, cyano group, an optionally-substituted $C_{1-6}$ alkyl group and an optionally-substituted $C_{1-6}$ alkyloxy group. E includes preferably phenyl group, 4-fluorophenyl group, 4-chlorophenyl group, 4-methylphenyl group, 4-ethylphenyl group, 4-methoxyphenyl group, 4-ethoxyphenyl group, 4-isopropoxyphenyl group, 4-trifluoromethylphenyl group, cyclopropyl group, cyclobutyl group, cyclopentyl group, cyclohexyl group, and groups of the following formulae:

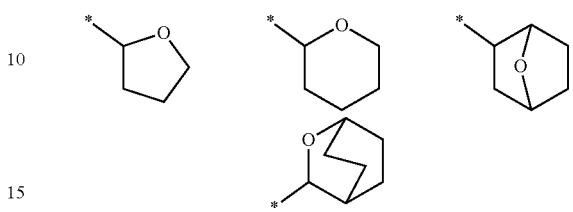

wherein * is a bonding position.

$R^6$ and $R^7$ are independently selected from the group consisting of hydrogen atom, fluorine atom and an optionally-substituted $C_{1-6}$ alkyl group; preferably hydrogen atom and fluorine atom; more preferably both of $R^6$ and $R^7$ are hydrogen atom. $R^6$ and $R^7$ specifically include hydrogen atom, fluorine atom, and methyl group.

A is an optionally-substituted $C_{6-10}$ aryl group or an optionally-substituted 5- to 10-membered heteroaryl group; preferably an optionally-substituted $C_{6-10}$ aryl group. The optionally-substituted $C_{6-10}$ aryl group is preferably an optionally-substituted $C_6$ or $C_{10}$ aryl group, more preferably an optionally-substituted $C_6$ aryl group. The optionally-substituted 5- to 10-membered heteroaryl group is preferably an optionally-substituted 5- or 6-, or 9- or 10-membered heteroaryl group; more preferably an optionally-substituted 5- or 6-membered heteroaryl group.

Specific examples of A include preferably an optionally-substituted phenyl group and an optionally-substituted 1- and 2-naphthyl group; more preferably an optionally-substituted phenyl group.

The substituents of the optionally-substituted $C_{6-10}$ aryl group, optionally-substituted 5- to 10-membered heteroaryl group, optionally-substituted phenyl group and optionally-substituted 1- or 2-naphthyl group in A include, for example, (i) a halogen atom such as fluorine atom and chlorine atom, (ii) a $C_{1-6}$ alkyl group optionally substituted with fluorine atom such as methyl group, ethyl group, propyl group, and trifluoromethyl group, (iii) a $C_{1-6}$ alkyloxy group optionally substituted with fluorine atom such as methoxy group, ethoxy group, isopropoxy group, and trifluoromethoxy group, (iv) a $C_{1-6}$ alkylthio group such as methylthio group and ethylthio group, (v) cyano group, and (vi) hydroxy group; preferably fluorine atom, chlorine atom, methyl group and methoxy group; more preferably fluorine atom and chlorine atom. As used herein, one or more of the same or different substituents may exist at any position as long as the substitution is possible. In addition, the $C_6$-10 aryl group and the 5- to 10-membered heteroaryl group may form a fused ring with a $C_{3-8}$ cycloalkyl, $C_{4-8}$ cycloalkenyl or 5- to 10-membered saturated heterocyclic group.

The optionally-substituted phenyl group includes, for example, the following formulae:

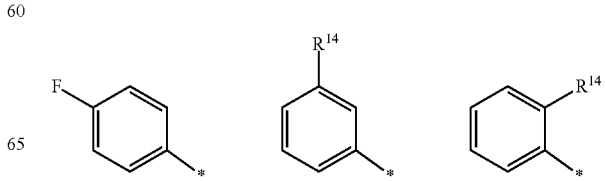

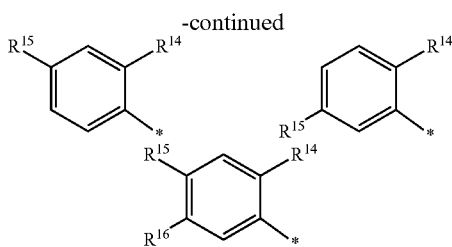

wherein $R^{14}$, $R^{15}$ and $R^{16}$ are independently selected from the group consisting of a halogen atom, a $C_{1-6}$ alkyl group optionally substituted with fluorine atom, a $C_{1-6}$ alkyloxy group optionally substituted with fluorine atom, and cyano group, and

* is a bonding position.

L is oxygen atom, sulfur atom or —$NR^{10}$—; preferably oxygen atom or sulfur atom; more preferably oxygen atom.

$R^{10}$ is hydrogen atom, a $C_{1-6}$ alkyl group or a $C_{3-8}$ cycloalkyl group; preferably hydrogen atom or a $C_{1-6}$ alkyl group; more preferably hydrogen atom or a $C_{1-3}$ alkyl group.

$R^{10}$ specifically includes hydrogen atom, methyl group, ethyl group, n-propyl group, butyl group, pentyl group, hexyl group, cyclopropyl group, cyclobutyl group, cyclopentyl group and cyclohexyl group; preferably hydrogen atom and methyl group.

X is hydrogen atom, a $C_{1-6}$ alkyl group optionally substituted with fluorine atom or a halogen atom, and includes, for example, hydrogen atom, fluorine atom, chlorine atom and methyl group. X is preferably hydrogen atom or a halogen atom, more preferably hydrogen atom.

n is 1, 2 or 3; preferably 1 or 2; more preferably 1.

The present compounds include preferably the following compounds or pharmaceutically acceptable salts thereof.

In one preferred embodiment, the present compound includes a compound wherein $R^1$ and $R^2$ are independently selected from the group consisting of hydrogen atom and a $C_{1-6}$ alkyl group, $R^3$ and $R^4$ are independently selected from the group consisting of hydrogen atom and methyl group, $R^5$ is an optionally-substituted $C_{4-7}$ alkyl group or —$(CR^8R^9)_r$-E, $R^6$ and $R^7$ are hydrogen atom, $R^8$ and $R^9$ are independently selected from the group consisting of hydrogen atom, fluorine atom and an optionally-substituted $C_{1-6}$ alkyl group, A is an optionally-substituted $C_{6-10}$ aryl group or an optionally-substituted 5- to 10-membered heteroaryl group, r is 1 or 2, E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted $C_{6-10}$ aryl group or an optionally-substituted 5- to 10-membered heteroaryl group, L is oxygen atom or sulfur atom, n is 1, and X is hydrogen atom, a $C_{1-6}$ alkyl group optionally substituted with fluorine atom or a halogen atom.

Preferably, the present compound includes a compound wherein $R^1$ and $R^2$ are independently selected from the group consisting of hydrogen atom and a $C_{1-6}$ alkyl group, $R^3$ and $R^4$ are hydrogen atom, $R^5$ is an optionally-substituted $C_{4-7}$ alkyl group or —$(CR^8R^9)_r$-E, $R^6$ and $R^7$ are hydrogen atom, $R^8$ and $R^9$ are independently selected from the group consisting of hydrogen atom, fluorine atom and an optionally-substituted $C_{1-6}$ alkyl group, A is an optionally-substituted $C_{6-10}$ aryl group, r is 1 or 2, E is an optionally-substituted $C_{3-8}$ cycloalkyl group, an optionally-substituted 5- to 10-membered saturated heterocyclic group which comprises 1 to 3 oxygen atoms as a constituent atom of the ring, or an optionally-substituted $C_{6-10}$ aryl group, L is oxygen atom, n is 1, and X is hydrogen atom.

More preferably, the present compound includes a compound wherein either of $R^1$ and $R^2$ is hydrogen atom, and the other is a $C_{1-6}$ alkyl group (preferably methyl group), $R^5$ is an optionally-substituted $C_{4-7}$ alkyl group (preferably isobutyl group, 2,2-dimethylpropyl group, 3-methylbutyl group, 3,3-dimethylbutyl group or 2-ethylbutyl group) or —$CH_2$-E, $R^3$, $R^4$, $R^6$, and $R^7$ are hydrogen atom, A is an optionally-substituted $C_{6-10}$ aryl group (preferably phenyl group or naphthyl group), r is 1, E is an optionally-substituted $C_{3-8}$ cycloalkyl group (preferably cyclopropyl group, cyclobutyl group, cyclopentyl group, or cyclohexyl group) or an optionally-substituted $C_{6-10}$ aryl group (preferably phenyl group or naphthyl group), L is oxygen atom, n is 1, and X is hydrogen atom.

In another embodiment, the present compound includes preferably the following compounds or pharmaceutically acceptable salts thereof:

1-[5-(benzyloxy)-1-(cyclohexylmethyl)-1H-pyrazol-3-yl]-N-methylmethanamine; Example 5

1-{1-(cyclohexylmethyl)-5-[(2-fluorobenzyl)oxy]-1H-pyrazol-3-yl}-N-methylmethanamine; Example 20

1-{1-(cyclohexylmethyl)-5-[(3-fluorobenzyl)oxy]-1H-pyrazol-3-yl}-N-methylmethanamine; Example 21

1-{1-(cyclohexylmethyl)-5-[(4-fluorobenzyl)oxy]-1H-pyrazol-3-yl}-N-methylmethanamine; Example 22

1-{5-[(2-chlorobenzyl)oxy]-1-(cyclohexylmethyl)-1H-pyrazol-3-yl}-N-methylmethanamine; Example 23

1-{5-[(3-chlorobenzyl)oxy]-1-(cyclohexylmethyl)-1H-pyrazol-3-yl}-N-methylmethanamine; Example 24

1-{1-(cyclohexylmethyl)-5-[(2-methylbenzyl)oxy]-1H-pyrazol-3-yl}-N-methylmethanamine; Example 26

1-{1-(cyclohexylmethyl)-5-[(3-methylbenzyl)oxy]-1H-pyrazol-3-yl}-N-methylmethanamine; Example 27

1-{1-(cyclohexylmethyl)-5-[(2,4-difluorobenzyl)oxy]-1H-pyrazol-3-yl}-N-methylmethanamine; Example 29

1-{5-[(2-chloro-4-fluorobenzyl)oxy]-1-(cyclohexylmethyl)-1H-pyrazol-3-yl}-N-methylmethanamine; Example 30

1-{1-(cyclohexylmethyl)-5-[(4-fluoro-2-methylbenzyl)oxy]-1H-pyrazol-3-yl}-N-methylmethanamine; Example 31

1-{1-(cyclohexylmethyl)-5-[(2,5-difluorobenzyl)oxy]-1H-pyrazol-3-yl}-N-methylmethanamine; Example 33

1-{5-[(5-chloro-2-fluorobenzyl)oxy]-1-(cyclohexylmethyl)-1H-pyrazol-3-yl}-N-methylmethanamine; Example 34
1-{1-(cyclohexylmethyl)-5-[(2-fluoro-5-methylbenzyl)oxy]-1H-pyrazol-3-yl}-N-methylmethanamine; Example 35
1-{5-[(2-chloro-5-fluorobenzyl)oxy]-1-(cyclohexylmethyl)-1H-pyrazol-3-yl}-N-methylmethanamine; Example 37
1-{1-(cyclohexylmethyl)-5-[(2,5-dichlorobenzyl)oxy]-1H-pyrazol-3-yl}-N-methylmethanamine; Example 38
1-{5-[(2-chloro-5-methylbenzyl)oxy]-1-(cyclohexylmethyl)-1H-pyrazol-3-yl}-N-methylmethanamine; Example 39
1-[5-(benzyloxy)-1-(cyclopentylmethyl)-1H-pyrazol-3-yl]-N-methylmethanamine; Example 4
1-{1-(cyclopentylmethyl)-5-[(2-fluorobenzyl)oxy]-1H-pyrazol-3-yl}-N-methylmethanamine; Example 135
1-{1-(cyclopentylmethyl)-5-[(3-fluorobenzyl)oxy]-1H-pyrazol-3-yl}-N-methylmethanamine; Example 136
1-{1-(cyclopentylmethyl)-5-[(4-fluorobenzyl)oxy]-1H-pyrazol-3-yl}-N-methylmethanamine; Example 137
1-{5-[(2-chlorobenzyl)oxy]-1-(cyclopentylmethyl)-1H-pyrazol-3-yl}-N-methylmethanamine; Example 138
1-{5-[(3-chlorobenzyl)oxy]-1-(cyclopentylmethyl)-1H-pyrazol-3-yl}-N-methylmethanamine; Example 139
1-{1-(cyclopentylmethyl)-5-[(2-methylbenzyl)oxy]-1H-pyrazol-3-yl}-N-methylmethanamine; Example 141
1-{1-(cyclopentylmethyl)-5-[(3-methylbenzyl)oxy]-1H-pyrazol-3-yl}-N-methylmethanamine; Example 142
1-{1-(cyclopentylmethyl)-5-[(2,4-difluorobenzyl)oxy]-1H-pyrazol-3-yl}-N-methylmethanamine; Example 144
1-{5-[(2-chloro-4-fluorobenzyl)oxy]-1-(cyclopentylmethyl)-1H-pyrazol-3-yl}-N-methylmethanamine; Example 145
1-{1-(cyclopentylmethyl)-5-[(4-fluoro-2-methylbenzyl)oxy]-1H-pyrazol-3-yl}-N-methylmethanamine; Example 146
1-{1-(cyclopentylmethyl)-5-[(2,5-difluorobenzyl)oxy]-1H-pyrazol-3-yl}-N-methylmethanamine; Example 147
1-{5-[(5-chloro-2-fluorobenzyl)oxy]-1-(cyclopentylmethyl)-1H-pyrazol-3-yl}-N-methylmethanamine; Example 148
1-{1-(cyclopentylmethyl)-5-[(2-fluoro-5-methylbenzyl)oxy]-1H-pyrazol-3-yl}-N-methylmethanamine; Example 149
1-{5-[(2-chloro-5-fluorobenzyl)oxy]-1-(cyclopentylmethyl)-1H-pyrazol-3-yl}-N-methylmethanamine; Example 150
l-{1-(cyclopentylmethyl)-5-[(2,5-dichlorobenzyl)oxy]-1H-pyrazol-3-yl}-N-methylmethanamine; Example 151
1-{5-[(2-chloro-5-methylbenzyl)oxy]-1-(cyclopentylmethyl)-1H-pyrazol-3-yl}-N-methylmethanamine; Example 152
1-[5-(benzyloxy)-1-(3,3-dimethylbutyl)-1H-pyrazol-3-yl]-N-methylmethanamine; Example 264
1-{5-[(3-chlorobenzyl)oxy]-1-(3,3-dimethylbutyl)-1H-pyrazol-3-yl}-N-methylmethanamine; Example 265
1-{5-[(2,5-difluorobenzyl)oxy]-1-(3,3-dimethylbutyl)-1H-pyrazol-3-yl}-N-methylmethanamine; Example 266
1-{5-[(5-chloro-2-fluorobenzyl)oxy]-1-(3,3-dimethylbutyl)-1H-pyrazol-3-yl}-N-methylmethanamine; Example 267
1-[5-(benzyloxy)-1-(3-methylbutyl)-1H-pyrazol-3-yl]-N-methylmethanamine; Example 268
1-{5-[(2,5-difluorobenzyl)oxy]-1-(3-methylbutyl)-1H-pyrazol-3-yl}-N-methylmethanamine; Example 269
1-{5-[(5-chloro-2-fluorobenzyl)oxy]-1-(3-methylbutyl)-1H-pyrazol-3-yl}-N-methylmethanamine; Example 270
1-{5-[(2,5-difluorobenzyl)oxy]-1-(3-methoxy-3-methyl-butyl)-1H-pyrazol-3-yl}-N-methylmethanamine; Example 274
1-{5-[(5-chloro-2-fluorobenzyl)oxy]-1-(3-methoxy-3-methylbutyl)-1H-pyrazol-3-yl}-N-methylmethanamine; Example 275
1-{1-(cyclopentylmethyl)-5-[(2,4,5-trifluorobenzyl)-oxy]-1H-pyrazol-3-yl}-N-methylmethanamine; Example 280
l-{1-(cyclohexylmethyl)-5-[(2,4,5-trifluorobenzyl)-oxy]-1H-pyrazol-3-yl}-N-methylmethanamine;
1-{1-(2-cyclopentylethyl)-5-[(2,5-difluorobenzyl)oxy]-1H-pyrazol-3-yl}-N-methylethanamine; Example 315
N-methyl-1-{1-(3-methylbutyl)-5-[(2,4,5-trifluoro-benzyl)oxy]-1H-pyrazol-3-yl}methanamine; Example 283
1-{1-(3,3-dimethylbutyl)-5-[(2,4,5-trifluorobenzyl)-oxy]-1H-pyrazol-3-yl}-N-methylmethanamine; Example 284
1-{1-(4-fluorobenzyl)-5-[(2-fluorobenzyl)oxy]-1H-pyrazol-3-yl}-N-methylmethanamine; Example 218
1-{5-[(2,5-difluorobenzyl)oxy]-1-(4-fluorobenzyl)-1H-pyrazol-3-yl}-N-methylmethanamine; Example 219
1-{1-(4-fluorobenzyl)-5-[(2,4,5-trifluorobenzyl)oxy]-1H-pyrazol-3-yl}-N-methylmethanamine;
1-{5-[(2-fluorobenzyl)oxy]-1-(4-methylbenzyl)-1H-pyrazol-3-yl}-N-methylmethanamine; Example 228
1-{5-[(2,5-difluorobenzyl)oxy]-1-(4-methylbenzyl)-1H-pyrazol-3-yl}-N-methylmethanamine; Example 230
N-methyl-1-{1-(4-methylbenzyl)-5-[(2,4,5-trifluoro-benzyl)oxy]-1H-pyrazol-3-yl}methanamine; Example 286
1-{5-[(2,5-difluorobenzyl)oxy]-1-(4-methoxybenzyl)-1H-pyrazol-3-yl}-N-methylmethanamine; no Example
1-{1-(4-methoxybenzyl)-5-[(2,4,5-trifluorobenzyl)oxy]-1H-pyrazol-3-yl}-N-methylmethanamine; Example 285
1-{5-[(5-chloro-2-fluorobenzyl)oxy]-1-(cyclopropylmethyl)-1H-pyrazol-3-yl}-N-methylmethanamine; Example 131
l-{5-[(4-fluorobenzyl)oxy]-1-(2-methylpropyl)-1H-pyrazol-3-yl}-N-methylmethanamine; Example 369
1-{5-[(5-chloro-2-fluorobenzyl)oxy]-1-(2-methyl-propyl)-1H-pyrazol-3-yl}-N-methylmethanamine; Example 256
1-{1-(2,2-dimethylpropyl)-5-[(4-fluorobenzyl)oxy]-1H-pyrazol-3-yl}-N-methylmethanamine; Example 375
1-{5-[(2,5-difluorobenzyl)oxy]-1-(2,2-dimethylpropyl)-1H-pyrazol-3-yl}-N-methylmethanamine; Example 258
1-{5-[(5-chloro-2-fluorobenzyl)oxy]-1-(2,2-dimethyl-propyl)-1H-pyrazol-3-yl}-N-methylmethanamine; Example 259
1-{5-[(2-fluorobenzyl)oxy]-1-(3-methylbutyl)-1H-pyrazol-3-yl}-N-methylmethanamine; Example 381
1-{5-[(4-fluorobenzyl)oxy]-1-(3-methylbutyl)-1H-pyrazol-3-yl}-N-methylmethanamine; Example 383
1-(5-[(4-fluorobenzyl)oxy]-1-{[1-(trifluoromethyl)-cyclopentyl]methyl}-1H-pyrazol-3-yl)-N-methylmethanamine; Example 446
1-(5-[(2,5-difluorobenzyl)oxy]-1-{[1-(trifluoro-methyl)-cyclopentyl]methyl}-1H-pyrazol-3-yl)-N-methylmethanamine; Example 447
1-(5-[(5-chloro-2-fluorobenzyl)oxy]-1-{[1-(trifluoromethyl)cyclopentyl]methyl}-1H-pyrazol-3-yl)-N-methylmethanamine; Example 448
(−)-1-{5-[(5-chloro-2-fluorobenzyl)oxy]-1-(tetrahydro-2H-pyran-2-ylmethyl)-1H-pyrazol-3-yl}-N-methylmethanamine; Example 474
(+)-1-{5-[(5-chloro-2-fluorobenzyl)oxy]-1-(tetrahydro-2H-pyran-2-ylmethyl)-1H-pyrazol-3-yl}-N-methylmethanamine; Example 475

(−)-1-{1-(2-cyclopentylethyl)-5-[(2,5-difluorobenzyl)-oxy]-1H-pyrazol-3-yl}-N-methylethanamine; Example 476
(+)-1-{1-(2-cyclopentylethyl)-5-[(2,5-difluorobenzyl)-oxy]-1H-pyrazol-3-yl}-N-methylethanamine; Example 477
1-{5-[(2,5-difluorobenzyl)oxy]-1-(3-fluoro-3-methyl-butyl)-1H-pyrazol-3-yl}-N-methylmethanamine; Example 481 and,
1-{5-[(5-chloro-2-fluorobenzyl)oxy]-1-(3-fluoro-3-methyl-butyl)-1H-pyrazol-3-yl}-N-methylmethanamine; Example 482.

Processes of Compound (1)

Hereinafter, processes of Compound (1) are explained.

The pyrazole compounds of the present invention can be prepared from well-known compounds in the art, by using the following processes or processes similar thereto and also optionally combining synthetic processes known to a person skilled in the art. The starting compounds used herein may be well-known compounds in the art, or may be prepared by using the following processes in Examples or processes similar thereto and also optionally combining synthetic processes known to a person skilled in the art.

Process 1

Among Compound (1), the compound wherein $R^2$ and X are hydrogen atom [i.e. Compound (A-4) or a salt thereof can be prepared by, for example, the following process:

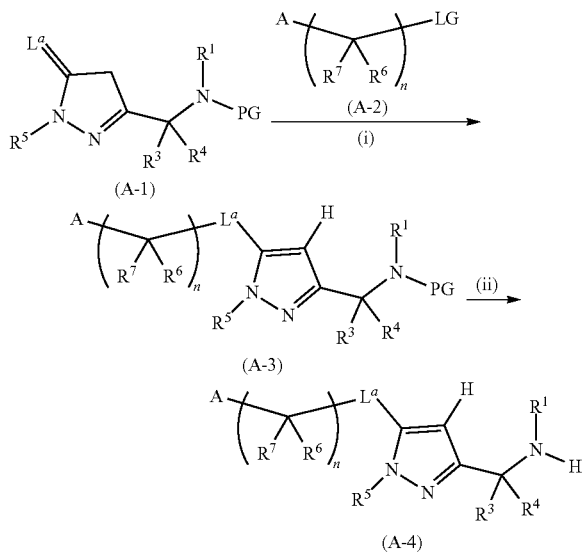

wherein $R^1$, $R^3$, $R^4$, $R^5$, $R^6$, $R^7$, A and n are the same as defined in the above [1], $L^a$ is oxygen atom or sulfur atom, LG is a leaving group including, for example, iodine atom, bromine atom, chlorine atom, and substituted sulfonyloxy groups such as p-toluenesulfonyloxy group, benzenesulfonyloxy group and methanesulfonyloxy group, and PG is a protecting group on amino group including, for example, tert-butoxycarbonyl group and benzyloxycarbonyl group.

Step (i)

Compound (A-3) or a salt thereof can be obtained by reacting Compound (A-1) or a salt thereof with Compound (A-2). The reaction can be carried out by reacting the compounds in the presence or absence of a base and/or a phase-transfer catalyst in a suitable inert-solvent at a temperature of about −20° C. to the boiling point of the solvent for 10 minutes to 48 hours.

The base used herein includes, for example, organic bases such as triethylamine and pyridine; inorganic bases such as sodium carbonate, potassium carbonate, cesium carbonate, sodium hydride, potassium hydroxide, silver oxide and silver carbonate; and metal alkoxides such as potassium tert-butoxide. The phase transfer catalyst used herein includes, for example, tetrabutylammonium hydrogen sulfate. The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF), N-methyl-2-pyrrolidone (NMP) and acetonitrile; and mixed solvents thereof. Preferably, the solvent includes N,N-dimethylformamide (DMF), N-methyl-2-pyrrolidone (NMP) and acetonitrile. The leaving group (LG) used herein includes preferably halogen atoms such as chlorine atom, bromine atom and iodine atom, and substituted sulfonyloxy groups such as p-toluenesulfonyloxy group, benzenesulfonyloxy group and methanesulfonyloxy group; and more preferably halogen atoms such as chlorine atom, bromine atom and iodine atom.

Step (ii)

The protecting group (PG) on the amino group of Compound (A-3) can be deprotected by a suitable method to give the desired Compound (A-4). In case that the protecting group (PG) on the amino group is Boc group, the deprotection can be carried out by treating Compound (A-3) in a suitable inert-solvent at a temperature of about −20° C. to the boiling point of the solvent with inorganic acids (e.g. hydrochloric acid and sulfuric acid) or organic acids (e.g. trifluoroacetic acid). The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF) and N-methyl-2-pyrrolidone (NMP); and mixed solvents thereof.

In case that PG is benzyloxycarbonyl group, the deprotection can be carried out by a hydrogenation reaction in a suitable inert-solvent at a temperature of about −20° C. to the boiling point of the solvent with palladium catalysts (e.g. palladium carbon and palladium hydroxide) The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF) and N-methyl-2-pyrrolidone (NMP); and mixed solvents thereof.

Process 2

Among Compound (1), the compound wherein L is amino group, and $R^2$ and X are hydrogen atom [i.e. Compound (A-9)] or a salt thereof can be prepared by, for example, the following process:

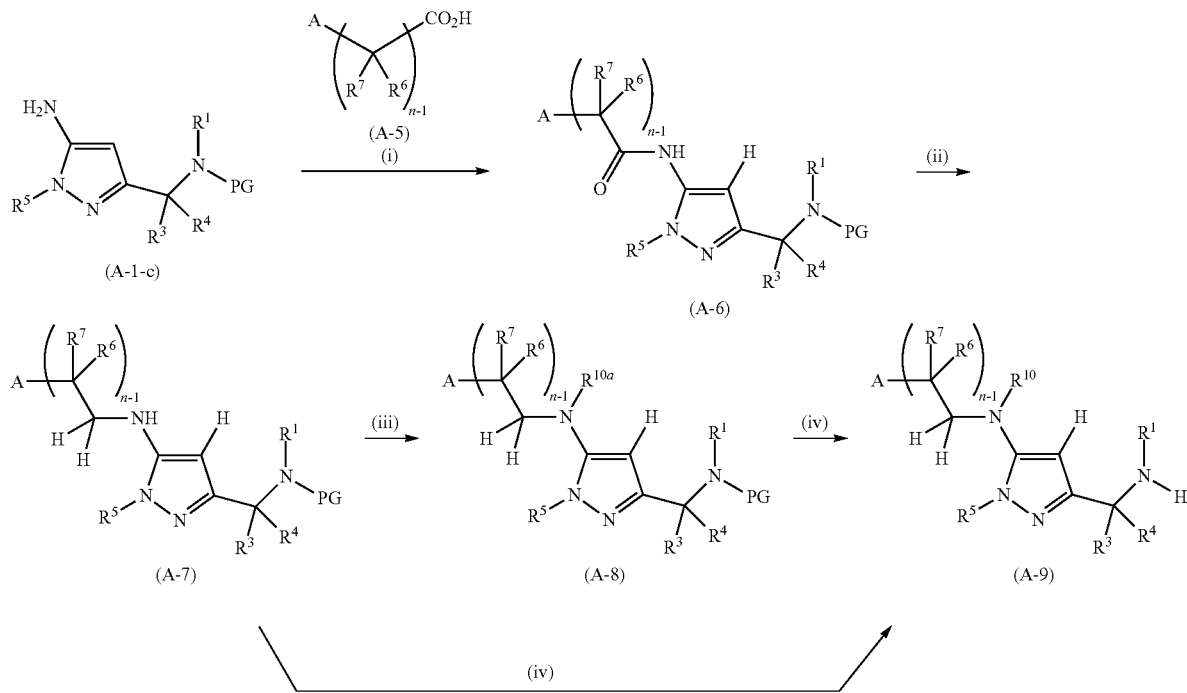

wherein

R$^1$, R$^3$, R$^4$, R$^5$, R$^6$, R$^7$, R$^{10}$, A, PG and n are as defined above, and R$^{10a}$ is a C$_{1-6}$ alkyl group.

Step (i)

Compound (A-6) can be obtained by reacting Compound (A-1-c) or a salt thereof and Compound (A-5) or a salt thereof to form an amide bond. In the reaction of forming the amide bond, the carboxyl group of Compound (A-5) can be activated by acid chloride methods using thionyl chloride, oxalyl chloride and the like or mixed acid anhydride methods using chlorocarbonates or pivaloyl chloride, or activated by condensing agents such as dicyclohexylcarbodiimide (DCC), 1-ethyl-3-(3-dimethyl-aminopropyl)carbodiimide (EDC or WSC) and 1,1'-carbonyldiimidazole (CDI), and then the Compound (A-5) can be reacted with Compound (A-1-c).

Step (ii)

Compound (A-7) can be obtained by reacting Compound (A-6) in a suitable inert-solvent at a temperature of about −20° C. to the boiling point of the solvent with a suitable reducing agent for 10 minutes to 48 hours. The suitable reducing agent used herein includes, for example, lithium aluminum hydride and diborane. The suitable inert-solvent used herein includes, for example, aromatic hydrocarbons such as benzene and toluene; and ether type solvents such as diethyl ether, tetrahydrofuran (THF) and 1,4-dioxane.

Step (iii)

Compound (A-8) can be obtained by an alkylation reaction of Compound (A-7) in a suitable inert-solvent at a temperature of about −20° C. to the boiling point of the solvent in the presence of a suitable base with an alkyl halide corresponding to R$^{10a}$. The suitable inert-solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF), N-methyl-2-pyrrolidone (NMP) and acetonitrile; and mixed solvents thereof. The suitable base used herein includes, for example, inorganic bases such as potassium carbonate, sodium carbonate, cesium carbonate, sodium hydride and potassium hydride; and metal alkoxides such as potassium tert-butoxide.

Step (iv)

The desired Compound (A-9) can be obtained by deprotecting the amino group of Compound (A-7) or Compound (A-8) in the same manner as in Step (ii) of Process 1.

Process 3

Among Compound (1), Compound (A-12) or a salt thereof can be prepared by the following process:

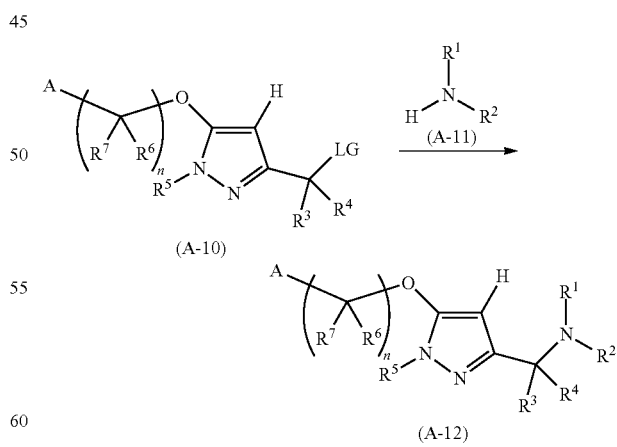

wherein R$^1$, R$^2$, R$^3$, R$^4$, R$^5$, R$^6$, R$^7$, A, n and LG are as defined above.

Compound (A-12) or a salt thereof can be obtained by reacting Compound (A-10) or a salt thereof with Compound (A-11) or a salt thereof. The reaction can be carried out in the presence or absence of a base and/or a phase transfer catalyst in a suitable inert-solvent at a temperature of about −20° C. to the boiling point of the solvent for 10 minutes to 48 hours. The base used herein includes, for example, organic bases such as triethylamine and pyridine; inorganic bases such as sodium carbonate, potassium carbonate, cesium carbonate, sodium hydride and potassium hydroxide; and metal alkoxides such as sodium methoxide and potassium tert-butoxide. The phase transfer catalyst used herein includes, for example, tetrabutylammonium hydrogen sulfate. The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF), N-methyl-2-pyrrolidone (NMP) and acetonitrile; and mixed solvents thereof. The leaving group (LG) used herein includes preferably halogen atoms such as chlorine atom, bromine atom and iodine atom, and substituted sulfonyloxy groups such as p-toluenesulfonyloxy group, benzenesulfonyloxy group and methanesulfonyloxy group.

Process 4

Among Compound (1), the compound wherein $R^3$, $R^4$ and X are hydrogen atom [i.e. Compound (A-15)] or a salt thereof can be prepared by, for example, the following process:

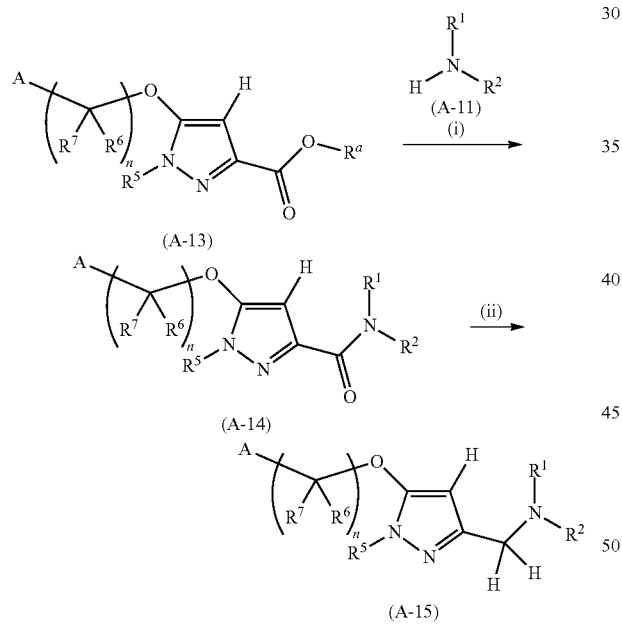

wherein
$R^1$, $R^2$, $R^5$, $R^6$, $R^7$, A and n are as defined above, and
$R^a$ is hydrogen atom or a $C_{1-6}$ alkyl group.

Step (i)

Compound (A-14) or a salt thereof can be obtained by reacting Compound (A-13) or a salt thereof and Compound (A-11) or a salt thereof to combine them via an amide bond. In the reaction of forming the amide bond when $R^a$ is hydrogen atom, the carboxyl group of Compound (A-13) can be activated by acid chloride methods using thionyl chloride, oxalyl chloride and the like or mixed acid anhydride methods using chlorocarbonates or pivaloyl chloride, or activated by condensing agents such as dicyclohexylcarbodiimide (DCC), 1-ethyl-3-(3-dimethylamino-propyl)carbodiimide (EDC or WSC) and 1,1'-carbonyldiimidazole (CDI), and then the Compound (A-13) can be reacted with Compound (A-11). When $R^a$ is a $C_{1-6}$ alkyl group, the reaction of forming the amide bond can be carried out by reacting Compound (A-13) and Compound (A-11) or a salt thereof in the presence or absence of a suitable acid or base in a suitable inert-solvent or in the absence of a solvent at a temperature of about −20° C. to the boiling point of the solvent for 10 minutes to 48 hours. The suitable base used herein includes, for example, organic bases such as triethylamine and pyridine; inorganic bases such as sodium carbonate, potassium carbonate, cesium carbonate, sodium hydride and potassium hydroxide. The suitable acid used herein includes organic acids such as p-toluenesulfonic acid, acetic acid, and trifluoroacetic acid; inorganic acids such as hydrochloric acid and sulfuric acid; and Lewis acids such as aluminum chloride. The suitable inert-solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF) and N-methyl-2-pyrrolidone (NMP); and mixed solvents thereof.

Step (ii)

The step can be carried out by reacting Compound (A-14) with a suitable reducing agent in a suitable inert-solvent at a temperature of about −78° C. to the boiling point of the solvent for 10 minutes to 48 hours. The suitable reducing agent used herein includes, for example, lithium aluminum hydride and diborane. The suitable inert-solvent used herein includes, for example, aromatic hydrocarbons such as benzene and toluene; and ether type solvents such as diethyl ether, tetrahydrofuran (THF) and 1,4-dioxane.

Process 5

Among Compound (1), the compound wherein $R^3$ and X are hydrogen atom [i.e. Compound (A-17)] or a salt thereof can be prepared by, for example, the following process:

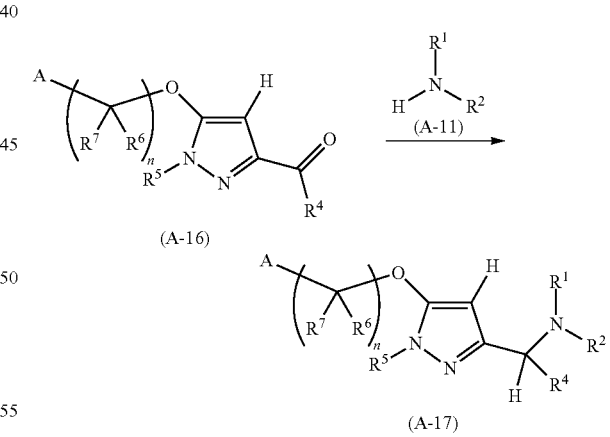

wherein $R^1$, $R^2$, $R^4$, $R^5$, $R^6$, $R^7$, A and n are as defined above.

The desired Compound (A-17) or a salt thereof can be obtained by reacting Compound (A-16) and Compound (A-11) or a salt thereof in a suitable inert-solvent in the presence or absence of a suitable acid at a temperature of about −78° C. to the boiling point of the solvent with a suitable reducing agent under reductive amination conditions. The inert solvent used herein includes, for example, aromatic hydrocarbons such as benzene and toluene; ether type solvents such as diethyl ether, tetrahydrofuran (THF)

and 1,4-dioxane; lower alcohols such as methanol, ethanol and isopropanol; aprotic polar solvents such as N,N-dimethylformamide (DMF), N-methyl-2-pyrrolidone (NMP) and acetonitrile; acetic acid; water; and mixed solvents thereof. The suitable acid used herein includes inorganic acids such as phosphoric acid, hydrochloric acid and sulfuric acid; and organic acids such as acetic acid and trifluoroacetic acid. The reducing agent used herein includes, for example, sodium cyanoborohydride, sodium triacetoxyborohydride and sodium borohydride. Compound (A-16) and Compound (A-11) or a salt thereof may be reacted by simply mixing them, or stepwise by firstly forming an imine thereof and then reducing it.

Process 6

Among Compound (1), the compound wherein the 4-position of the pyrazole ring is substituted with a halogen atom [i.e. Compound (A-20)] or a salt thereof can be prepared by, for example, the following process:

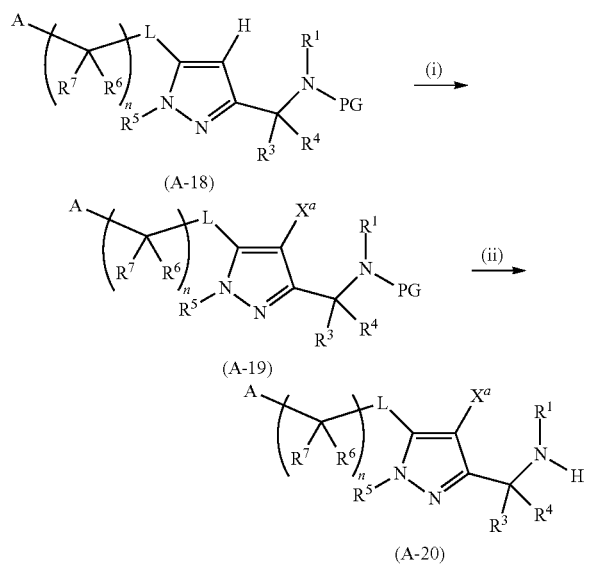

wherein $R^1$, $R^3$, $R^4$, $R^5$, $R^6$, $R^7$, A, L, n and PG are as defined above, and $X^a$ is a halogen atom such as fluorine atom, chlorine atom and bromine atom.

Step (i)

Compound (A-19) can be obtained by reacting Compound (A-18) in a suitable inert-solvent at a temperature of about −78° C. to the boiling point of the solvent with a suitable halogenating-agent. The suitable inert-solvent used herein includes lower alcohols such as methanol, ethanol and isopropanol; and aprotic polar solvents such as N,N-dimethylformamide (DMF) and N-methyl-2-pyrrolidone (NMP). The suitable halogenating-agent used herein includes N-chlorosuccinimide (NCS) when $X^a$ is chlorine atom, N-bromosuccinimide (NBS) and 5,5-dimethyl-1,3-dibromo-hydantoin when $X^a$ is bromine atom, N-iodosuccinimide (NIS) when $X^a$ is iodine atom, and 1-chloromethyl-4-fluoro-1,4-diazoniabicyclo[2.2.2]-octane bis (tetrafluoroborate) [Selectfluor (trademark)] when $X^a$ is fluorine atom.

Step (ii)

The desired Compound (A-20) can be obtained by deprotecting the amino group in the same manner as in Step (ii) of Process 1.

Process 7

Among Compound (1), the compound wherein the 4-position of the pyrazole ring is substituted with an alkyl group [i.e. Compound (A-23)] or a salt thereof can be prepared by, for example, the following process:

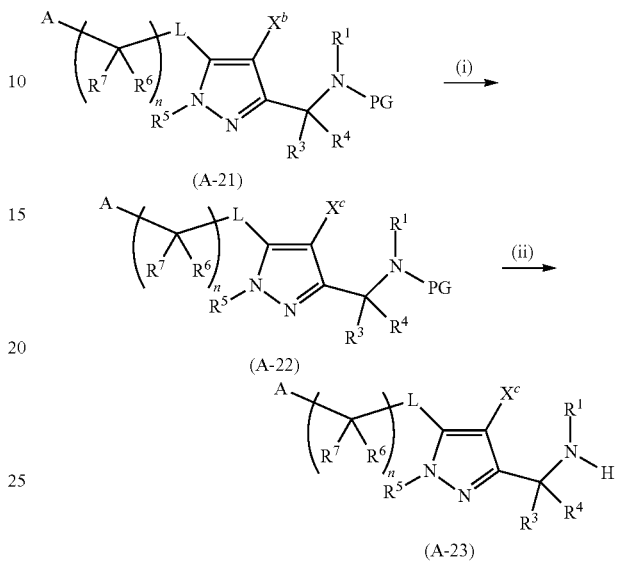

wherein $R^1$, $R^3$, $R^4$, $R^5$, $R^6$, $R^7$, A, L, n and PG are as defined above, $X^b$ is chlorine atom, bromine atom or iodine atom, and $X^c$ is a $C_{1-6}$ alkyl group optionally substituted with fluorine atom such as methyl group and trifluoromethyl group.

Step (i)

In case that $X^c$ is methyl group, Compound (A-22) can be obtained by reacting Compound (A-21) in a suitable inert-solvent at a temperature of about −78° C. to the boiling point of the solvent in the presence of zerovalent palladium catalysts [e.g. tetrakis triphenylphosphine palladium (0), bis(dibenzylideneacetone)palladium (0) and bis(tri-tert-butylphosphine)palladium (0)] with alkyl-boronic acids (e.g. methylboronic acid), alkylaluminums (e.g. trimethylaluminum) or alkylzinc reagents (e.g. methyl zinc chloride). In case that $X^c$ is trifluoromethyl group, Compound (A-22) can be obtained according to the methods disclosed in, for example, J. Fluorine. Chem. 2007, 128 (10), 1318. and Eur. J. Org. Chem. 1998, (2), 335. In specific, Compound (A-21) can be obtained by reacting in the presence of monovalent cuprate [e.g. copper iodide (I)] with methyl trifluoroacetate or sodium trifluoroacetate.

Step (ii)

The desired Compound (A-23) can be obtained by deprotecting the amino group in the same manner as in Step (ii) of Process 1.

Process 8 (Introduction of a Substituent in Amino Group)

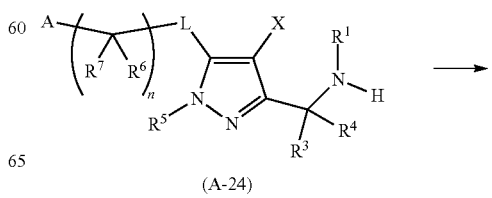

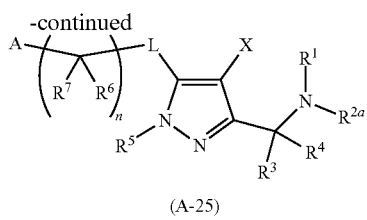

(A-25)

wherein $R^1$, $R^3$, $R^4$, $R^5$, $R^6$, $R^7$, A, L, X and n are as defined above, and $R^{2a}$ is a $C_{1-6}$ alkyl group or a $C_{3-8}$ cycloalkyl group.

Compound (A-25) can be prepared by reacting Compound (A-24) with an alkylating agent, aldehyde, ketone, carboxylic acid or ester corresponding to $R^{2a}$ in the same manner as in Processes 3 to 5.

Process 9

Compound (A-1) in Process 1 wherein $L^3$ is oxygen atom [i.e. Compound (A-1-a)] or $L^a$ is sulfur atom [i.e. Compound (A-1-b)] can be prepared by the following process:

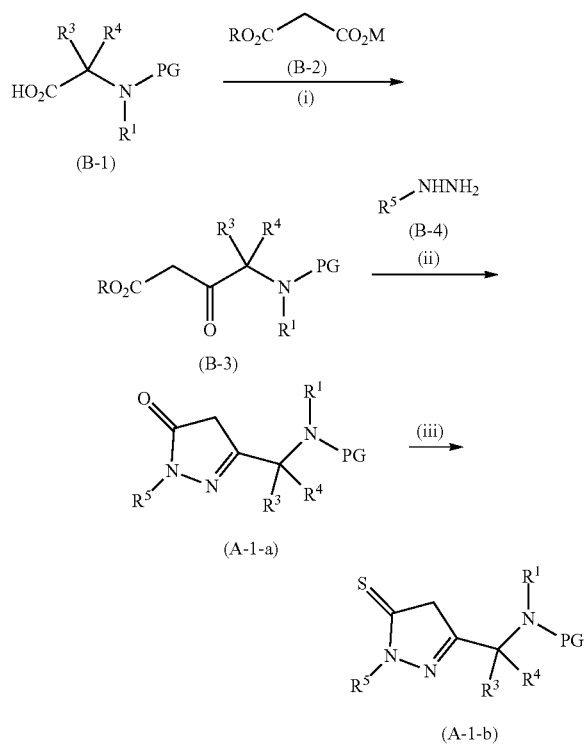

wherein $R^1$, $R^3$, $R^4$, $R^5$ and PG are as defined above,

M is alkali metals such as sodium and potassium, or alkaline earth metals such as magnesium and calcium, and R is a $C_{1-6}$ alkyl group.

Steps (i) to (ii)

Compound (B-3) can be prepared from Compound (B-1) and Compound (B-2) or a salt thereof in the same manner as disclosed in, for example, Tetrahedron, 60(2004), 1731-1848). In specific, Compound (B-3) can be obtained by activating Compound (B-1) in a suitable inert-solvent at a temperature of about −20° C. to 30° C. with carbonyldiimidazole (CDI); and then reacting the Compound (B-1) in the presence of a suitable acid or base at a temperature of about −20° C. to the boiling point of the solvent with Compound (B-2). The suitable inert solvent used herein includes, for example, aromatic hydrocarbons such as benzene and toluene; ether type solvents such as diethyl ether, tetrahydrofuran (THF) and 1,4-dioxane; and mixed solvents thereof. The suitable acid used herein includes magnesium chloride. Compound (A-1-a) can be prepared by reacting Compound (B-3) and Compound (B-4) in the presence of a suitable acid or base in a suitable inert solvent or in the absence of a solvent at a temperature of about −20° C. to the boiling point of the solvent for 10 minutes to 48 hours. The suitable base used herein includes, for example, organic bases such as triethylamine and pyridine; metal alkoxides such as potassium tert-butoxide; and inorganic bases such as sodium carbonate, potassium carbonate and cesium carbonate. The suitable acid used herein includes organic acids such as p-toluenesulfonic acid, methanesulfonic acid, acetic acid and trifluoroacetic acid; and inorganic acids such as hydrochloric acid, sulfuric acid and phosphoric acid. The suitable inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF) and N-methyl-2-pyrrolidone (NMP); and mixed solvents thereof.

Step (iii)

Compound (A-1-b) can be prepared by reacting Compound (A-1-a) in a suitable inert-solvent or in the absence of a solvent at a temperature of about −20° C. to the boiling point of the solvent with Lawesson's reagent. The suitable inert-solvent used herein includes, for example, aromatic hydrocarbons such as benzene and toluene; and ether type solvents such as diethyl ether, tetrahydrofuran (THF) and 1,4-dioxane.

Process 10

On the basis of the process disclosed in Journal of Heterocyclic Chemistry, 2009, 39, Compound (A-1-c) in Process 2 can be prepared by the following process:

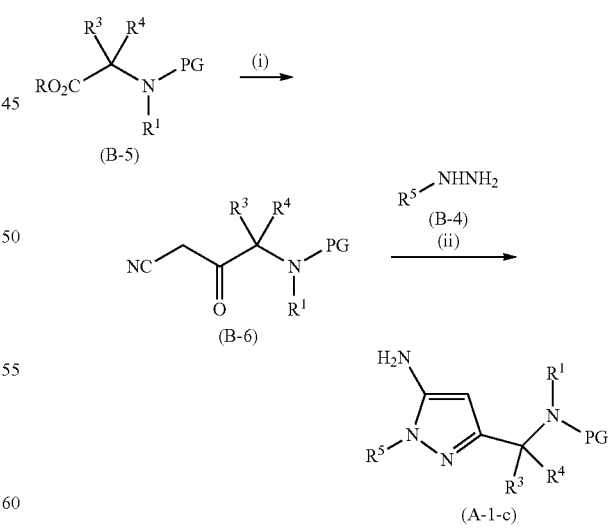

wherein $R^1$, $R^3$, $R^4$, $R^5$, PG and R are as defined above.

Step (i)

Compound (B-6) can be obtained by reacting Compound (B-5) in a suitable inert-solvent at a temperature of about −78° C. to the boiling point of the solvent with an anion generated by reacting acetonitrile with a suitable base. The suitable inert-solvent used herein includes, for example, aromatic hydrocarbons such as benzene and toluene; and ether type solvents such as diethyl ether, tetrahydrofuran (THF) and 1,4-dioxane. The suitable base used herein includes, for example, inorganic bases such as sodium hydride and potassium hydroxide, and metal alkoxides such as sodium methoxide and potassium tert-butoxide.

Step (ii)

Compound (A-1-c) can be obtained by reacting Compound (B-6) and Compound (B-4) in the same manner as in Step (ii) of Process 9.

Process 11

Compound (A-10), Compound (A-13) and Compound (A-16) in Processes 3 to 5 can be prepared by the following process:

or in the absence of a solvent, at a temperature of about −20° C. to the boiling point of the solvent with Compound (B-4) for 10 minutes to 48 hours. The suitable base used herein includes, for example, amines such as triethylamine and pyridine; and inorganic bases such as sodium carbonate, potassium carbonate and cesium carbonate. The suitable acid used herein includes organic acids such as p-toluenesulfonic acid, methanesulfonic acid, acetic acid and trifluoroacetic acid; and inorganic acids such as hydrochloric acid, sulfuric acid and phosphoric acid. The suitable inert-solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF) and N-methyl-2-pyrrolidone (NMP); and mixed solvents thereof.

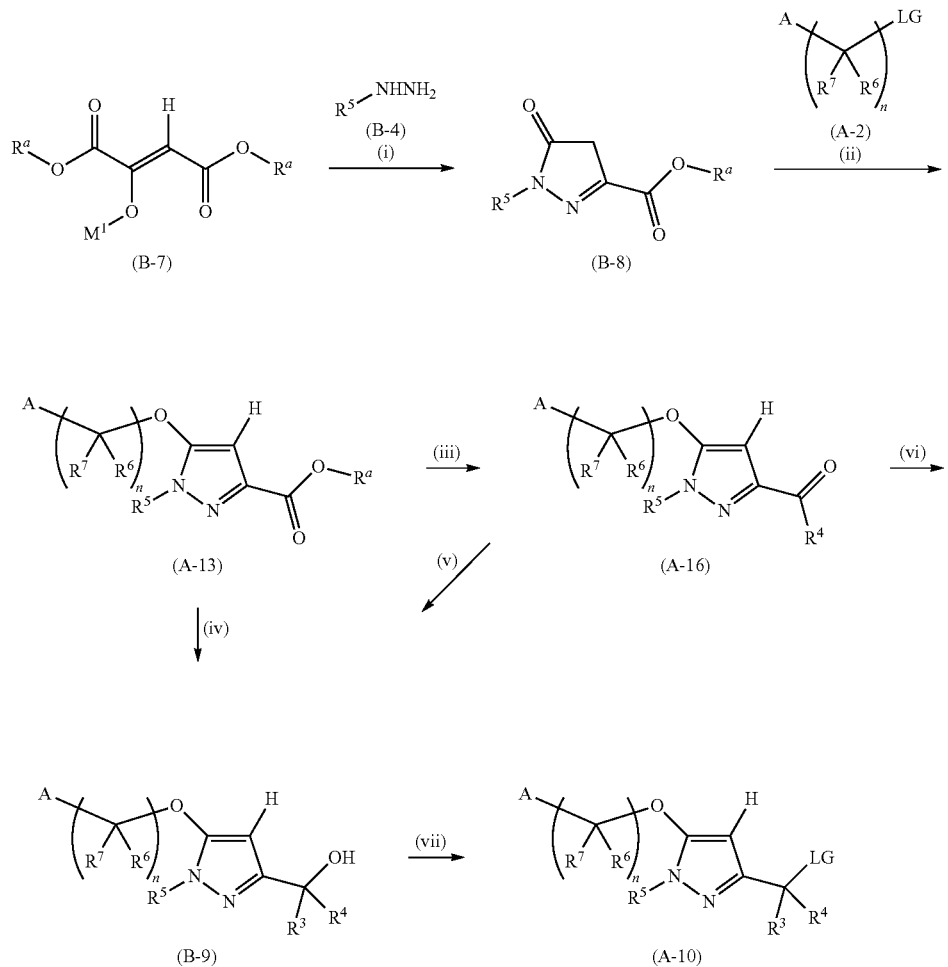

wherein $R^3$, $R^4$, $R^5$, $R^6$, $R^7$, LG, n, A and $R^a$ are as defined above, and $M^1$ is hydrogen atom, an alkali metal such as sodium and potassium, or an alkaline earth metal such as magnesium and calcium.

Step (i)

On the basis of the process disclosed in Bioorganic & Medicinal Chemistry Letters, 17 (2007), 5567, Compound (B-8) can be prepared by reacting Compound (B-7) in the presence of a suitable acid or base, in a suitable inert-solvent Step (ii)

Compound (A-13) can be obtained by reacting Compound (B-8) and Compound (A-2) in the same manner as in Step (i) of Process 1.

Steps (iii) to (vii)

Compound (A-13) can be, if necessary, converted to Compound (A-10) or Compound (A-16) by general processes typically used in the art (see, for example, Comprehensive Organic Transformations, R. C. Larock, 1989).

Process 12

Among Compound (1), Compound (A-12-a) or a salt thereof can be prepared by the following process:

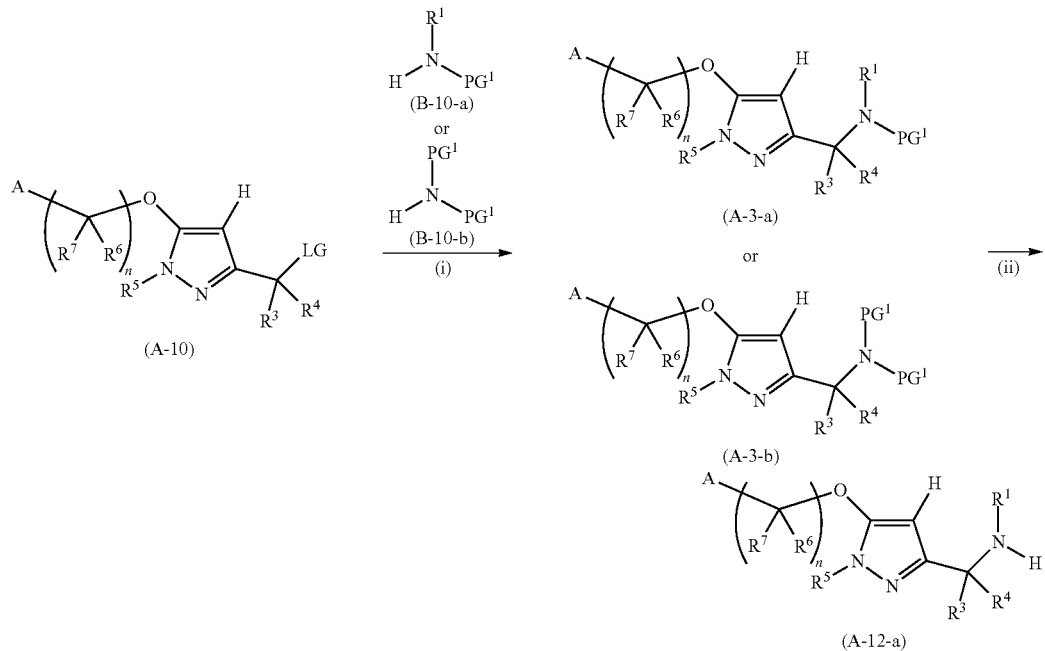

wherein

R¹, R³, R⁴, R⁵, R⁶, R⁷, LG, n, and A are as defined above, and

PG¹ is a protecting group on the amino group such as tert-butoxycarbonyl group and benzyloxycarbonyl group, or the two PG¹ groups attached to the same nitrogen atom may be combined with the nitrogen atom to form a ring such as phthalic imide and succinimide.

Step (i)

Compound (A-3-a) or Compound (A-3-b), or a salt thereof can be obtained by reacting Compound (A-10) or a salt thereof with Compound (B-10-a) or Compound (B-10-b), or a salt thereof. The reaction can be carried out in the presence or absence of a base and/or phase transfer catalyst, in a suitable inert-solvent, at a temperature of about −20° C. to the boiling point of the solvent for 10 minutes to 48 hours. The base used herein includes, for example, organic bases such as triethylamine and pyridine; inorganic bases such as sodium carbonate, potassium carbonate, cesium carbonate, sodium hydroxide, potassium hydroxide, sodium hydride and potassium hydroxide; and metal alkoxides such as sodium methoxide and potassium tert-butoxide. The phase transfer catalyst used herein includes, for example, tetrabutylammonium hydrogen sulfate. The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; aprotic polar solvents such as N,N-dimethylformamide (DMF), N-methyl-2-pyrrolidone (NMP) and acetonitrile; and mixed solvents thereof. The leaving group (LG) used herein includes preferably halogen atoms such as chlorine atom, bromine atom and iodine atom; and substituted sulfonyloxy groups such as p-toluenesulfonyloxy group, benzenesulfonyloxy group and methanesulfonyloxy group.

Step (ii)

The desired Compound (A-12-a) can be obtained by deprotecting the amino group in the same manner as in Step (ii) of Process 1. In case that the two PG¹ groups attached to the same nitrogen atom are combined with the nitrogen atom to form a ring of phthalic imide or succinimide, the step can be carried out by reacting the compound with an amino compound (e.g. hydrazine monohydrate and methylamine) in a suitable inert solvent or in the absence of a solvent at a temperature of about −20° C. to the boiling point of the solvent for 10 minutes to 48 hours. The inert solvent used herein includes, for example, aromatic hydrocarbons such as benzene and toluene; ether type solvents such as diethyl ether, tetrahydrofuran (THF) and 1,4-dioxane; lower alcohols such as methanol, ethanol and isopropanol; and mixed solvents thereof.

Unless otherwise noted, the starting materials and reagents used in the above processes are commercially available or can be prepared from well-known compounds by well-known methods. Furthermore, the functional group of the above-shown Compound (1) may be modified to prepare a different type of Compound (1). The modification of the functional group can be carried out according to general methods typically used in the art (e.g. see, Comprehensive Organic Transformations, R. C. Larock, 1989).

Among the above-shown processes, in case that functional groups other than the reactive site could react under the given reaction-condition or are not suitable to carry out the given process, the desired compound can be obtained by firstly protecting the functional groups with a suitable protecting group, and then carrying out the reaction and deprotecting the protecting group. The protecting group used herein includes typical protecting groups disclosed in, for example, Protective Groups in Organic Synthesis, T. W. Greene, John Wiley & Sons Inc., 1981. In specific, protecting groups on amine include, for example, ethoxycarbonyl, tert-butoxycarbonyl, benzyloxycarbonyl, acetyl, benzoyl and benzyl. Protecting groups on hydroxy group include, for example, trialkylsilyl, acetyl, benzoyl and benzyl. Protecting groups of ketone include, for example, dimethylacetal, 1,3-dioxane, 1,3-dioxolane, S,S'-dimethyldithioacetal, 1,3-dithiane, and oxime.

The protecting groups can be induced and deprotected according to methods typically-used in synthetic organic chemistry (e.g. see, the above-cited Protective Groups in Organic Synthesis) and other similar methods.

The intermediates and desired compounds in the above-shown processes can be isolated and purified according to purification methods which are typically used in synthetic organic chemistry such as neutralization, filtration, extraction, washing, drying, concentration, recrystallization, various chromatographies, and the like. Furthermore, the intermediates can be used for the subsequent reaction without specific purification.

Compound (1) or a pharmaceutically acceptable salt thereof may include tautomers thereof. The tautomers include, for example, the following formula:

In addition to the tautomers, the present invention also includes other possible isomers such as optical isomers, stereoisomers, regioisomers and rotamers, and mixtures thereof. For example, in case that optical isomers of Compound (1) exist, each optical isomer thereof is also included in Compound (1). The isomers can be isolated and purified by well-known synthetic and resolving methods such as chromatography and recrystallization.

Each optical isomer of Compound (1) can be resolved according to optical resolution methods which are well-known to a person skilled in the art. For example, according to typical methods, the resolution can be carried out by forming diastereomeric salts with an optically active acid, resolving the diastereomeric salts into two types, and then converting them into a free base. The optically active acid used herein includes, for example, monocarboxylic acids such as mandelic acid, N-benzyloxyalanine and lactic acid; dicarboxylic acids such as tartaric acid, o-diisopropylidene tartaric acid and malic acid; and sulfonic acids such as camphorsulfonic acid and bromo camphorsulfonic acid. The temperature used herein to form salts includes room temperature to the boiling point of the solvent.

Furthermore, Compound (1) includes compounds labeled with isotopes such as $^3$H, $^{14}$C, $^{35}$S and $^{125}$I, and also compounds wherein $^1$H is substituted with deuterium, i.e. $^2$H (D).

The pharmaceutically acceptable salts of Compound (1) are typically-used nontoxic salts including, for example, acid addition salts such as organic acid salts (e.g. acetate, propionate, trifluoroacetate, maleate, fumarate, citrate, succinate, tartrate, methanesulfonate, benzene-sulfonate, formate and toluenesulfonate) and inorganic acid salts (e.g. hydrochloride, hydrobromide, hydroiodide, sulfate, nitrate and phosphate); salts with amino acids such as arginine acid, aspartic acid and glutamic acid; metal salts such as alkali metal salts (e.g. sodium salt and potassium salt) and alkaline earth metal salts (e.g. calcium salt and magnesium salt); ammonium salts; and organic base salts (e.g. trimethylamine salt, triethylamine salt, pyridine salt, picoline salt, dicyclohexylamine salt and N,N'-dibenzylethylenediamine salt).

In case that Compound (1) is given in the form of a pharmaceutically acceptable salt, the pharmaceutically acceptable salt of Compound (1) can be obtained by directly purifying the product. On the other hand, in case that Compound (1) is given in a free form, the pharmaceutically acceptable salt of Compound (1) can be obtained by a typical method, i.e. dissolving or suspending the product in a suitable organic solvent, and then adding an acid or base thereto. For example, the salt can be formed by mixing the product with a pharmaceutically acceptable acid or alkali in a solvent such as water, methanol, ethanol, acetone, and the like.

Furthermore, Compound (1) and a pharmaceutically acceptable salt thereof may exist as a hydrate containing water or a solvate containing various solvents such as ethanol, and thus the hydrate and solvate thereof are also included in the present invention.

In case that Compound (1) or a pharmaceutically acceptable salt thereof is given as a crystal, crystalline polymorphisms may exist in the crystal, and thus the crystalline polymorphisms are also included in the present invention.

The present pyrazole-compound and a pharmaceutically acceptable salt thereof have human serotonin reuptake inhibitory action and 5-HT$_{2C}$ antagonistic action, in particular, inverse agonistic action. Thus, the compound and salt are useful as a medicament for treating diseases mediated by serotonin nervous system or preventing a relapse thereof. The diseases mediated by serotonin nervous system include, for example, depression and anxiety. Depression is included in mood disorder according to the classification of psychiatric disease. The mood disorder mainly includes depressive disorder and bipolar disorder. In more detail, a general depression includes, for example, (i) depressive disorders such as major depressive disorder, dysthymic disorder, and depressive disorders not otherwise specified, (ii) depression, and (iii) seasonal affective disorder. The present compound and salt thereof are useful as a medicament for treating the above-mentioned diseases or preventing a relapse thereof. Furthermore, the present compound and salt thereof are also useful as a medicament for treating (iv) major depressive episode in bipolar disorder, or preventing a relapse thereof. On the other hand, anxiety (anxiety disorder) mainly includes anxiety disorder and phobia. The present compound and salt thereof are useful as a medicament for treating anxiety (anxiety disorder) such as (v) panic disorder, obsessive-compulsive disorder, posttraumatic stress disorder, acute stress disorder, generalized anxiety disorder and anxiety disorder due to a general medical condition, (vi) anxiety disorder comprising substance-induced anxiety disorder, (vii) agoraphobia, (viii) social phobia, (ix) avoidant personality disorder, and (x) psychophysiological disorder, or preventing a relapse thereof. Furthermore, the present compound and salt thereof are also useful for treating symptoms of depression and anxiety associated with other diseases such as schizophrenia and dementia, or preventing a relapse thereof. Moreover, the present compound and salt thereof are also useful for treating memory impairments such as dementia, amnesia and age-related memory impairments; eating behavior disorder including neural anorexia and neural starvation; obesity; sleep disorder; schizophrenia; addiction to drugs such as alcohol, tobacco, nicotine, narcotic, psychostimulant and psychotropic drug; cluster headache; migraine; pain; Alzheimer's disease; chronic paroxysmal hemicrania; headache associated with vascular disorder; Parkinson's disease including dementia, depression and anxiety in Parkinson's disease, neuroleptic-induced Parkinson's syndrome, and tardive dyskinesia; endocrine abnormality such as hyperprolactinemia; vasospasm (in particular, in cerebrovascular system); hypertension; gastrointestinal disorder associated with motility and secretory change; and sexual dysfunction such as precocious ejaculation, or preventing a relapse thereof.

The dose of the present pyrazole-compound and a pharmaceutically acceptable salt thereof may vary depending on the age and condition of patients; and in general, when the patients are human beings, 0.1 mg to about 1,000 mg, preferably 1 mg to about 100 mg can be administered as a daily dose per the individual patient. The administration may be once or several times a day, and each administration may include 1, 2 or 3 doses.

In case that the present pyrazole-compound and a pharmaceutically acceptable salt thereof is used for treatment, they can be administered orally or parenterally [e.g. intravenously, subcutaneously, intramuscularly, intrathecally, topically, transrectally, percutaneously, nasally and pulmonarily (i.e. by lung)] as a pharmaceutical composition. Oral dosage forms include, for example, tablets, capsules, pills, granules, fine granules, powders, solutions, syrups and suspensions; and parenteral dosage forms include, for example, aqueous injections, non aqueous injections, suppositories, nasal preparations, transdermal preparations such as lotions, emulsion, ointments, creams, jellies, gels, adhesive skin patches (e.g. tapes, transdermal patches and poultices), topical powders, and the like. These formulations can be formulated according to conventionally well-known techniques, and they may comprise nontoxic and inactive carriers or excipients which are typically used in the field of formulation.

The pharmaceutically acceptable carriers used for formulation include substances typically used in the field of formulation which react with neither Compound (1) nor a pharmaceutically acceptable salt thereof. In specific, the pharmaceutical composition containing Compound (1) or a pharmaceutically acceptable salt thereof may further comprise carriers used for formulation such as excipients, binders, lubricants, stabilizers, disintegrants, buffers, solubilizers, tonicity agents, pH adjusters, surfactants, emulsifying agents, suspending agents, dispersants, suspension stabilizers, thickeners, viscosity modifiers, gelling agents, soothing agents, preservatives, plasticizers, transdermal-absorption promoters, antioxidants, humectants, antiseptics, flavors, and the like. Furthermore, the pharmaceutical composition may optionally comprise a mixture of two or more of the above-listed carriers used for formulation.

Solid formulations such as tablets can be formulated by mixing the active ingredient with, for example, pharmaceutically acceptable carriers or excipients typically used in the art (e.g. lactose, sucrose and corn starch), binders (e.g. crystalline cellulose, hydroxy-propylcellulose, polyvinylpyrrolidone and hydroxypropyl methylcellulose), disintegrants (e.g. carboxymethyl-cellulose sodium and sodium carboxymethyl starch), lubricants (e.g. stearic acid and magnesium stearate), and preservatives.

When administering parenterally, the active ingredient is dissolved or suspended in physiologically acceptable carriers such as water, saline, oil and aqueous glucose solution; and if necessary, adjuvants such as emulsifying agents, stabilizing agents, salts for regulating osmotic pressure and/or buffers may be added thereto.

In case that the present pyrazole-compound and a pharmaceutically acceptable salt thereof are applied to pharmaceutical use as mentioned above, they are generally administered in the form of a formulation mixed with the carriers used for formulation. Such a formulation can be prepared according to typical methods. For example, the pharmaceutical composition of the present invention may contain the present pyrazole-compound and a pharmaceutically acceptable salt thereof as an active ingredient in an amount of 0.05 wt % to 99 wt %, preferably 0.05 wt % to 80 wt %, more preferably 0.1 wt % to 70 wt %, even more preferably 0.1 wt % to 50 wt %. The formulation may comprise other ingredients which are efficacious for the treatment.

The formulation of the present compound may be, for example, tablets which can be formulated by mixing 20 mg of the compound of Example 1, 100 mg of lactose, 25 mg of crystalline cellulose and 1 mg of magnesium stearate, and then compressing the mixture.

For the purpose of enhancing efficacy, the present pyrazole-compound and a pharmaceutically acceptable salt thereof may be used in combination with medicaments (i.e. combined medicaments) such as antidepressants, anxiolytic drugs, antipsychotic drugs, dopamine receptor agonists, anti-Parkinson drugs, antiepileptic drugs, antiseizure drugs, analgesic drugs, hormone preparations, therapeutic drugs for migraine, adrenergic β receptor antagonists, therapeutic drugs for dementia and therapeutic drugs for mood disorder. Furthermore, for the purpose of reducing side effects, the present pyrazole-compound and a pharmaceutically acceptable salt thereof may be used in combination with medicaments (i.e. combined medicaments) such as antiemetic drugs, sleep-inducing drugs and anticonvulsants. The timing of administration of the present compound and the additional medicament is not limited, and thus they can be administered simultaneously or sequentially to the subject. Furthermore, the present compound and the additional medicament can be used as a drug combination. The dose of the combined medicament may vary, and can be determined on the basis of the amount used in clinical practice. The ratio of the present compound and combined medicament can be determined on the basis of, for example, the subject, administration route, disease, symptom, or combination of the drug. For example, when the subject is human beings, 0.01 to 1000 parts by volume of the combined medicament per part by volume of the present compound may be used.

EXAMPLE

Hereinafter, the present invention is illustrated in more detail by Reference examples, Examples and Tests, but the technical scope of the present invention should not be limited thereto. In addition, the compound names shown in the Reference Examples and Examples below do not necessarily follow the IUPAC nomenclature system.

The following abbreviations may be used in the Reference examples and Examples.

Me: Methyl
Et: Ethyl
n-Bu: Normal butyl
n-Pent: Normal pentyl
n-Hex: Normal hexyl
n-Hep: Normal heptyl
Boc: tert-Butoxycarbonyl
DMSO: Dimethylsulfoxide
THF: Tetrahydrofuran
DMF: N,N-dimethylformamide
CDI: 1,1'-Carbonyldiimidazole
Ms: Methanesulfonyl
Bn: Benzyl
TFA: Trifluoroacetic acid DBU: 1,8-Diazabicyclo[5.4.0]undec-7-ene
PTLC: Preparative thin layer chromatography
Obs MS [M+1]: Observed protonated-molecule Compounds were identified by proton nuclear magnetic resonance spectra ($^1$H-NMR spectra) and mass spectra (LC-MS). In the LC-MS analysis, the mass spectra of molecules protonated by electro spray ionization were observed.

Preparation of Pyrazol Compounds:

Reference Example 1 tert-Butyl {[1-(cyclopentylmethyl)-5-oxo-4,5-di-hydro-1H-pyrazol-3-yl]-methyl}methylcarbamate

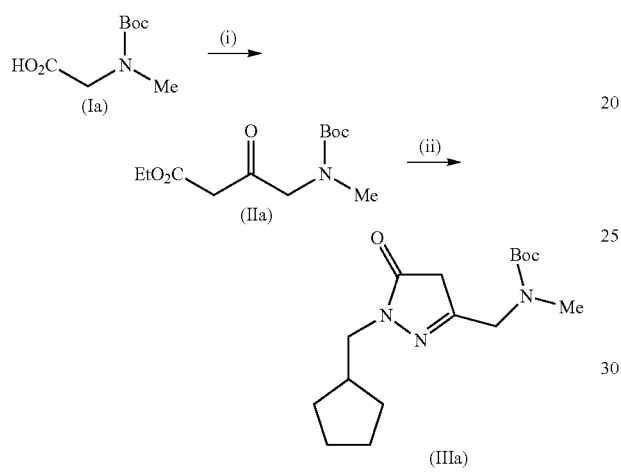

Step (i)

To a solution of Compound (Ia) (142 g, 0.75 mol) in THF (750 mL) was added CDI (134 g, 0.83 mol) in small portions at 21° C. to 23° C. over 15 minutes. The reaction mixture was stirred at room temperature for 1.5 hours, and then magnesium chloride (92.8 g, 0.98 mol) and potassium ethyl malonate (166 g, 0.98 mmol) were added thereto. The reaction mixture was stirred at 50° C. for 2 hours, cooled to room temperature, and water (1.5 L) was added thereto with cooling the reaction to keep the internal temperature below 25° C. The solution was extracted with toluene (2 L), and the combined organic layers were subsequently washed with 5% $K_2CO_3$ (1.5 L), water (×2, both 1.5 L), 5% $KHSO_4$ (×2, 1.5 L and 1.0 L) and water (1.5 L). The organic layer was dried over anhydrous $MgSO_4$, and the solvent was evaporated under reduced pressure to give Compound (IIa) (183 g, 91%) as a yellow-brown oil.

Step (ii)

A solution of (cyclopentylmethyl) hydrazine dihydrochloride (82.1 g, 0.43 mol) and triethylamine (108 g, 1.1 mol) in ethanol (855 mL) was stirred at 55° C. After the solution was homogeneous, the Compound (IIa) (108.5 g, 0.41 mol) was added thereto. The reaction mixture was stirred at 65° C. for about 1 hour and cooled to room temperature. To the mixture were added 5% $KHSO_4$ (584 g) and then water (876 mL). The ethanol was evaporated under reduced pressure until the total weight was 1567 g. The concentrated residue was extracted with ethyl acetate (×2, 1.4 L and 0.95 L), the combined organic layers were dried over anhydrous $MgSO_4$, and the solvent was evaporated under reduced pressure. To the concentrated residue was added ethyl acetate (332 mL), and the mixture was heated. After the solid was dissolved, the solution was cooled to 45° C. and seed crystals of Compound (IIIa) were added thereto. The mixture was stirred at 43° C. to 45° C. (internal temperature) for 1 hour, and n-hexane (332 mL) was added dropwise thereto over 45 minutes with keeping the internal temperature at 43° C. to 45° C. The mixture was stirred at the same condition for 1 hour, stirred with slowly cooling to 10° C. over 3 hours, and then stirred at 4° C. to 10° C. (internal temperature) for 1 hour. The resulting precipitate was collected by filtration and washed twice with a mixture of cooled n-hexane/ethyl acetate (1:1) (116 mL). The obtained powder was dried under reduced pressure to give Compound (IIIa) (92.5 g, 70%) as a white solid.

$^1$H-NMR (300 MHz, CDCl$_3$) δ: 1.20-1.75 (8H, m), 1.46 (9H, s), 2.23-2.35 (1H, m), 2.84 (3H, br s), 3.20 (2H, s), 3.55 (2H, d, J=7.5 Hz), 4.10 (2H, br s).

The following compounds of Reference Examples 2 to 30 were prepared in the same manner as in Reference Example 1.

Reference Example 2 tert-Butyl {[1-(cyclopropylmethyl)-5-oxo-4,5-di-hydro-1H-pyrazol-3-yl]-methyl}methylcarbamate

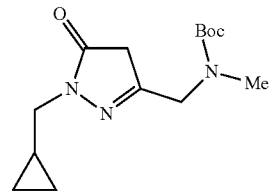 [SMILES: CN(CC1=NN(CC2CC2)C(=O)C1)C(=O)OC(C)(C)C]

$^1$H-NMR (300 MHz, CDCl$_3$) δ: 0.29-0.38 (2H, m), 0.49-0.55 (2H, m), 1.08-1.29 (1H, m), 1.47 (9H, s), 2.88 (3H, br s), 3.23 (2H, s), 3.51 (2H, d, J=7.0 Hz), 4.14 (2H, br s).

Reference Example 3 tert-Butyl {[1-(cyclobutylmethyl)-5-oxo-4,5-di-hydro-1H-pyrazol-3-yl]-methyl}methylcarbamate

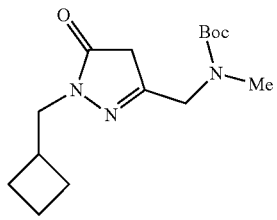 [SMILES: CN(CC1=NN(CC2CCC2)C(=O)C1)C(=O)OC(C)(C)C]

$^1$H-NMR (300 MHz, CDCl$_3$) δ: 1.47 (9H, s), 1.72-1.94 (4H, m), 1.98-2.09 (2H, m), 2.62-2.77 (1H, m), 2.86 (3H, br s), 3.21 (2H, s), 3.67 (2H, d, J=7.3 Hz), 4.11 (2H, br s).

Reference Example 4 tert-Butyl {[1-(cyclohexylmethyl)-5-oxo-4,5-dihydro-1H-pyrazol-3-yl]-methyl}methylcarbamate

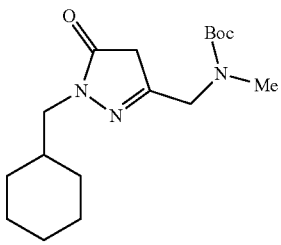 [SMILES: CN(CC1=NN(CC2CCCCC2)C(=O)C1)C(=O)OC(C)(C)C]

$^1$H-NMR (300 MHz, CDCl$_3$) δ: 0.87-1.06 (2H, m), 1.10-1.31 (4H, m), 1.47 (9H, s), 1.61-1.81 (5H, m), 3.12 (3H, s), 3.23 (2H, s), 3.48 (2H, d, J=7.0 Hz), 4.11 (2H, s).

Reference Example 5 tert-Butyl methyl{[5-oxo-1-(tetrahydro-2H-pyran-2-yl-methyl)-4,5-dihydro-1H-pyrazol-3-yl]methyl}carbamate

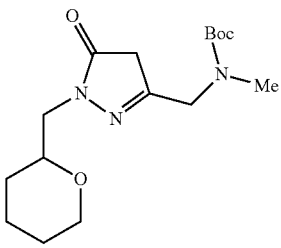 [SMILES: CN(CC1=NN(CC2CCCCO2)C(=O)C1)C(=O)OC(C)(C)C]

$^1$H-NMR (300 MHz, CDCl$_3$) δ: 1.21-1.72 (14H, m), 1.79-1.93 (1H, m), 2.86 (3H, brs), 3.24 (1H, s), 3.32-3.44 (1H, m), 3.52-3.67 (2H, m), 3.70-3.83 (1H, m), 3.94-4.31 (4H, m).

Reference Example 6 tert-Butyl {[1-(l-cyclopentylethyl)-5-oxo-4,5-dihydro-1H-pyrazol-3-yl]-methyl}methylcarbamate

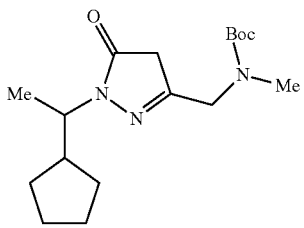 [SMILES: CC(C1CCCC1)N1N=C(CN(C)C(=O)OC(C)(C)C)CC1=O]

$^1$H-NMR (300 MHz, CDCl$_3$) δ: 1.10-1.23 (3H, m), 1.25 (3H, d, J=6.6 Hz), 1.37-1.66 (13H, m), 1.72-1.83 (1H, m), 2.16 (1H, tdd, J=16.9, 7.7, 2.1 Hz), 2.83 (3H, br s), 3.20 (2H, s), 3.90-4.00 (1H, m), 4.03-4.17 (2H, m).

Reference Example 7 tert-Butyl {[1-(1-cyclohexylethyl)-5-oxo-4,5-dihydro-1H-pyrazol-3-yl]-methyl}methylcarbamate

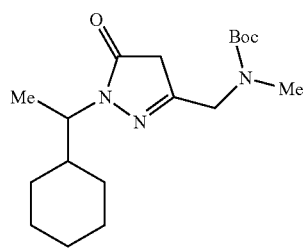 [SMILES: CC(C1CCCCC1)N1N=C(CN(C)C(=O)OC(C)(C)C)CC1=O]

$^1$H-NMR (300 MHz, CDCl$_3$) δ: 0.88-1.06 (2H, m), 1.07-1.23 (4H, m), 1.26 (3H, d, J=6.8 Hz), 1.47 (9H, s), 1.52-1.88 (5H, m), 2.86 (3H, s), 3.23 (2H, s), 3.89-4.00 (1H, m), 4.11 (2H, s).

Reference Example 8 tert-Butyl {[1-(1-cyclohexylpropyl)-5-oxo-4,5-dihydro-1H-pyrazol-3-yl]-methyl}methylcarbamate

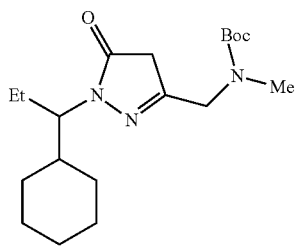 [SMILES: CCC(C1CCCCC1)N1N=C(CN(C)C(=O)OC(C)(C)C)CC1=O]

$^1$H-NMR (300 MHz, CDCl$_3$) δ: 0.78 (3H, t, J=7.3 Hz), 0.88-1.26 (5H, m), 1.47 (9H, s), 1.55-1.88 (8H), 2.85 (3H, s), 3.26 (2H, s), 3.73 (1H, m), 4.12 (2H, s).

Reference Example 9 tert-Butyl {[1-(bicyclo[2.2.1]hept-2-ylmethyl)-5-oxo-4,5-dihydro-1H-pyrazol-3-yl]methyl}methylcarbamate

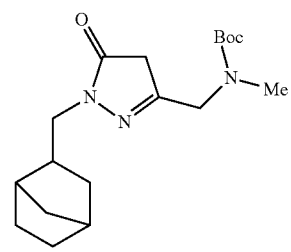 [SMILES: CN(CC1=NN(CC2CC3CCC2C3)C(=O)C1)C(=O)OC(C)(C)C]

$^1$H-NMR (300 MHz, CDCl$_3$) δ: 1.07-1.20 (4H, m), 1.31-1.55 (13H, m), 1.87-1.96 (1H, m), 2.03-2.07 (1H, m), 2.22-2.26 (1H, m), 2.87 (3H, br s), 3.22 (2H, br s), 3.43 (2H, ddd, J=36.3, 13.8, 7.8 Hz), 4.07-4.16 (2H, m).

Reference Example 10 tert-Butyl methyl{[1-(7-oxabicyclo[2.2.1]hept-2-ylmethyl)-5-oxo-4,5-dihydro-1H-pyrazol-3-yl]methyl}carbamate

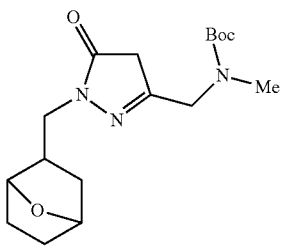 [SMILES: CN(CC1=NN(CC2CC3CCC2O3)C(=O)C1)C(=O)OC(C)(C)C]

¹H-NMR (300 MHz, CDCl₃) δ: 1.34-1.74 (15H, m), 2.13-2.22 (1H, m), 2.88 (3H, br s), 3.23 (2H, s), 3.53 (2H, br ddd, J=38.7, 13.8, 7.5 Hz), 4.11 (2H, br s), 4.41 (1H, d, J=4.4 Hz), 4.58 (1H, t, J=4.6 Hz).

Reference Example 11 tert-Butyl methyl{[1-(2-oxabicyclo[2.2.2]oct-3-ylmethyl)-5-oxo-4,5-dihydro-1H-pyrazol-3-yl]methyl}carbamate

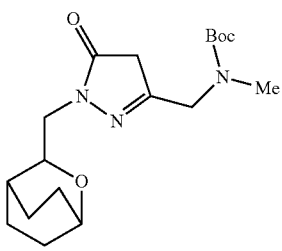 [SMILES: CN(CC1=NN(CC2OC3CCC2CC3)C(=O)C1)C(=O)OC(C)(C)C]

¹H-NMR (300 MHz, CDCl₃) δ: 1.43-1.76 (15H, m), 1.94-2.04 (3H, m), 2.86 (3H, br s), 3.23 (2H, br s), 3.64-3.92 (3H, m), 4.02-4.24 (3H, m).

Reference Example 12 tert-Butyl ({1-[(4,4-difluorocyclohexyl)methyl]-5-oxo-4,5-dihydro-1H-pyrazol-3-yl}methyl)methylcarbamate

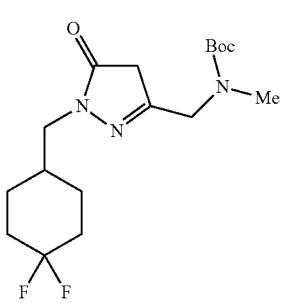 [SMILES: CN(CC1=NN(CC2CCC(F)(F)CC2)C(=O)C1)C(=O)OC(C)(C)C]

¹H-NMR (300 MHz, CDCl₃) δ: 1.39 (2H, m), 1.47 (9H, s), 1.59-1.90 (5H, m), 2.09 (2H, m), 2.87 (3H, s), 3.24 (2H, s), 3.56 (2H, d, J=6.8 Hz), 4.11 (2H, br s).

Reference Example 13 tert-Butyl ({1-[(1-fluorocyclohexyl)methyl]-5-oxo-4,5-dihydro-1H-pyrazol-3-yl}methyl)methylcarbamate

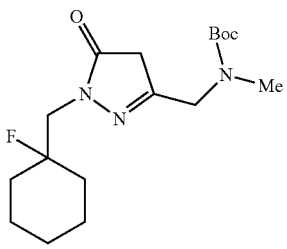 [SMILES: CN(CC1=NN(CC2(F)CCCCC2)C(=O)C1)C(=O)OC(C)(C)C]

¹H-NMR (400 MHz, CDCl₃) δ: 1.15-1.69 (17H, m), 1.74-1.88 (2H, m), 2.86 (3H, brs), 3.25 (2H, s), 3.79 (2H, d, J=19.5 Hz), 4.13 (2H, brs).

Reference Example 14 tert-Butyl {[1-(2-cyclopentylethyl)-5-oxo-4,5-dihydro-1H-pyrazol-3-yl]methyl}methylcarbamate

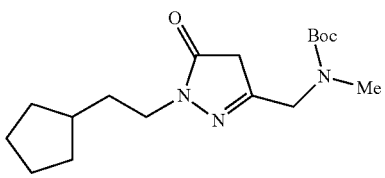 [SMILES: CN(CC1=NN(CCC2CCCC2)C(=O)C1)C(=O)OC(C)(C)C]

¹H-NMR (300 MHz, CDCl₃) δ: 1.12 (2H, m), 1.47 (9H, s), 1.47-1.88 (9H, m), 2.87 (3H, s), 3.22 (2H, s), 3.65 (2H, t, J=7.2 Hz), 4.12 (2H, s).

Reference Example 15 tert-Butyl [(1-butyl-5-oxo-4,5-dihydro-1H-pyrazol-3-yl)-methyl] methylcarbamate

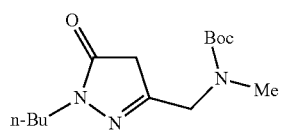

¹H-NMR (400 MHz, CDCl₃) δ: 0.94 (3H, t, J=7.3 Hz), 1.34 (2H, m), 1.47 (9H, s), 1.66 (2H, quin, J=7.3 Hz), 2.87 (3H, s), 3.22 (2H, s), 3.64 (2H, t, J=7.2 Hz), 4.12 (2H, s).

Reference Example 16 tert-Butyl methyl[(5-oxo-1-pentyl-4,5-dihydro-1H-pyrazol-3-yl)methyl]carbamate

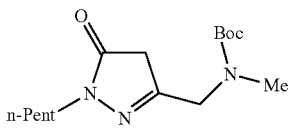

¹H-NMR (300 MHz, CDCl₃) δ: 0.89 (3H, t, J=7.0 Hz), 1.24-1.40 (4H, m), 1.47 (9H, s), 1.67 (2H, quin, J=7.2 Hz), 2.87 (3H, s), 3.22 (2H, s), 3.63 (2H, t, J=7.2 Hz), 4.12 (2H, s).

Reference Example 17 tert-Butyl [(1-hexyl-5-oxo-4,5-dihydro-1H-pyrazol-3-yl)-methyl] methylcarbamate

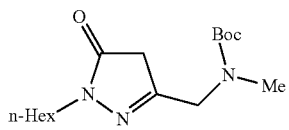

¹H-NMR (300 MHz, CDCl₃) δ: 0.88 (3H, t, J=6.7 Hz), 1.22-1.36 (6H, m), 1.47 (9H, s), 1.61-1.73 (2H, m), 2.87 (3H, br s), 3.22 (2H, s), 3.63 (2H, t, J=7.2 Hz), 4.07-4.17 (2H, m).

Reference Example 18 tert-Butyl [(1-heptyl-5-oxo-4,5-dihydro-1H-pyrazol-3-yl)-methyl]methylcarbamate

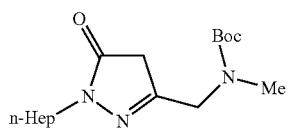

¹H-NMR (300 MHz, CDCl₃) δ: 0.88 (3H, t, J=7.2 Hz), 1.24-1.35 (8H, m), 1.47 (9H, s), 1.66 (2H, m), 2.87 (3H, s), 3.22 (2H, s), 3.63 (2H, t, J=7.2 Hz), 4.12 (2H, s).

Reference Example 19 tert-Butyl methyl{[5-oxo-1-(pentan-3-yl)-4,5-dihydro-1H-pyrazol-3-yl]methyl}carbamate

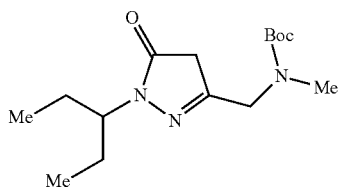 [SMILES: CCC(CC)N1N=C(CN(C)C(=O)OC(C)(C)C)CC1=O]

¹H-NMR (300 MHz, CDCl₃) δ: 0.83 (6H, t, J=7.3 Hz), 1.47 (9H, s), 1.68 (4H, m), 2.86 (3H, br s), 3.27 (2H, s), 3.91 (1H, tt, J=8.8, 4.0 Hz), 4.12 (2H, br s).

Reference Example 20 tert-Butyl methyl{[1-(2-methylpropyl)-5-oxo-4,5-dihydro-1H-pyrazol-3-yl]methyl}carbamate

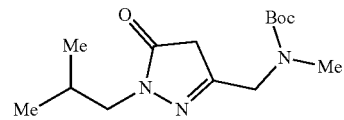

¹H-NMR (300 MHz, CDCl₃) δ: 0.92 (6H, d, J=6.8 Hz), 1.47 (9H, s), 2.03-2.12 (1H, m), 2.87 (3H, br s), 3.24 (2H, s), 3.46 (2H, d, J=7.2 Hz), 4.07-4.16 (2H, m).

Reference Example 21 tert-Butyl {[1-(2,2-dimethylpropyl)-5-oxo-4,5-dihydro-1H-pyrazol-3-yl]methyl}methylcarbamate

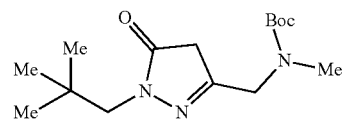 [SMILES: CN(CC1=NN(CC(C)(C)C)C(=O)C1)C(=O)OC(C)(C)C]

¹H-NMR (400 MHz, CDCl₃) δ: 0.96 (9H, s), 1.47 (9H, s), 2.87 (3H, br s), 3.22 (2H, s), 3.45 (2H, s), 4.07-4.14 (2H, m).

Reference Example 22 tert-Butyl {[1-(3,3-dimethylbutyl)-5-oxo-4,5-dihydro-1H-pyrazol-3-yl]methyl}methylcarbamate

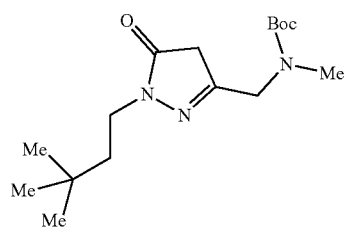 [SMILES: CN(CC1=NN(CCC(C)(C)C)C(=O)C1)C(=O)OC(C)(C)C]

¹H-NMR (300 MHz, CDCl₃) δ: 0.96 (9H, s), 1.47 (9H, s), 1.56-1.61 (2H, m), 2.87 (3H, br s), 3.20 (2H, br s), 3.63-3.69 (2H, m), 4.12 (2H, br s).

Reference Example 23 tert-Butyl {[1-(2-ethylbutyl)-5-oxo-4,5-dihydro-1H-pyrazol-3-yl]methyl}methylcarbamate

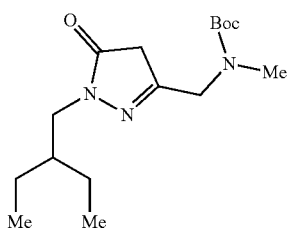 [SMILES: CCC(CC)CN1N=C(CN(C)C(=O)OC(C)(C)C)CC1=O]

$^1$H-NMR (300 MHz, CDCl$_3$) δ: 0.89 (6H, t, J=7.5 Hz), 1.26-1.38 (4H, m), 1.47 (9H, s), 1.67-1.77 (1H, m), 2.86 (3H, br s), 3.22 (2H, br s), 3.54 (2H, d, J=7.0 Hz), 4.11 (2H, br s).

Reference Example 24 tert-Butyl methyl{[1-(3-methylbutyl)-5-oxo-4,5-dihydro-1H-pyrazol-3-yl]methyl}carbamate

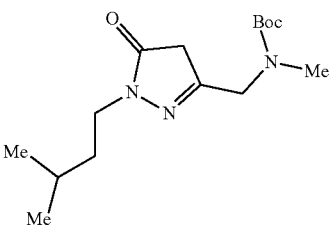 [SMILES: CC(C)CCN1N=C(CN(C)C(=O)OC(C)(C)C)CC1=O]

$^1$H-NMR (300 MHz, CDCl$_3$) δ: 0.94 (6H, d, J=6.1 Hz), 1.47 (9H, s), 1.53-1.68 (3H, m), 2.87 (3H, br s), 3.22 (2H, br s), 3.66 (2H, br t, J=7.2 Hz), 4.11 (2H, br s).

Reference Example 25 tert-Butyl methyl{[5-oxo-1-(4,4,4-trifluorobutyl)-4,5-dihydro-1H-pyrazol-3-yl]methyl}carbamate

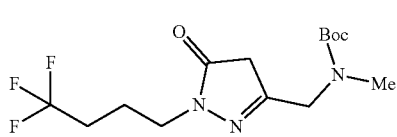 [SMILES: CN(CC1=NN(CCCC(F)(F)F)C(=O)C1)C(=O)OC(C)(C)C]

$^1$H-NMR (300 MHz, CDCl$_3$) δ: 1.47 (9H, s), 1.90-2.23 (4H, m), 2.88 (3H, s), 3.25 (2H, s), 3.72 (2H, t, J=6.8 Hz), 4.12 (2H, s).

Reference Example 26 tert-Butyl {[1-(3-methoxy-3-methylbutyl)-5-oxo-4,5-dihydro-1H-pyrazol-3-yl]methyl}methylcarbamate

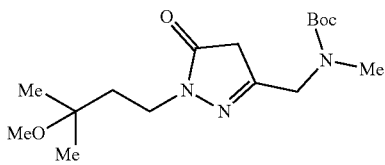 [SMILES: COC(C)(C)CCN1N=C(CN(C)C(=O)OC(C)(C)C)CC1=O]

$^1$H-NMR (300 MHz, CDCl$_3$) δ: 1.20 (6H, s), 1.47 (9H, s), 1.82-1.88 (2H, m), 2.86 (3H, br s), 3.17-3.26 (5H, m), 3.68-3.77 (2H, m), 4.08-4.14 (2H, m).

Reference Example 27 tert-Butyl methyl({1-[(1-methylcyclohexyl)methyl]-5-oxo-4,5-dihydro-1H-pyrazol-3-yl}methyl)carbamate

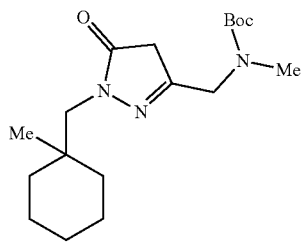

$^1$H-NMR (300 MHz, CDCl$_3$) δ: 0.94 (3H, s), 1.24-1.56 (19H, m), 2.87 (3H, s), 3.21 (2H, s), 3.48 (2H, s), 4.11 (2H, s).

Reference Example 28 tert-Butyl methyl({1-[(2-methylcyclohexyl)methyl]-5-oxo-4,5-dihydro-1H-pyrazol-3-yl}methyl)carbamate

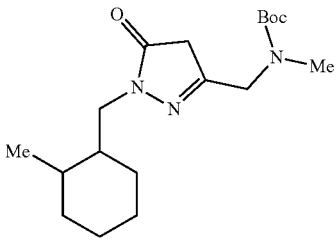

$^1$H-NMR (300 MHz, CDCl$_3$) δ: 0.93 (3H, d, J=7.2 Hz), 1.14-1.45 (7H, m), 1.47 (9H, s), 1.65 (1H, m), 1.81 (1H, m), 2.01 (1H, m), 2.86 (3H, s), 3.22 (2H, s), 3.49 (1H, dd, J=12.3, 5.9 Hz), 3.57 (1H, dd, J=12.3, 6.9 Hz), 4.11 (2H, s).

Reference Example 29 tert-Butyl methyl({1-[(3-methylcyclohexyl)methyl]-5-oxo-4,5-dihydro-1H-pyrazol-3-yl}methyl)carbamate

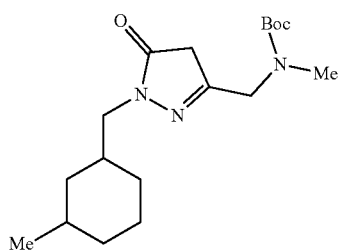 [SMILES: CC1CCCC(CN2N=C(CN(C)C(=O)OC(C)(C)C)CC2=O)C1]

$^1$H-NMR (300 MHz, CDCl$_3$) δ: 0.63 (1H, m), 0.74-0.95 (5H, m), 1.13-1.42 (2H, m), 1.47 (9H, s), 1.55-1.85 (5H, m), 2.87 (3H, s), 3.23 (2H, s), 3.47 (2H, d, J=7.2 Hz), 4.11 (2H, br s).

Reference Example 30 tert-Butyl methyl({1-[(4-methylcyclohexyl)methyl]-5-oxo-4,5-dihydro-1H-pyrazol-3-yl}methyl)carbamate

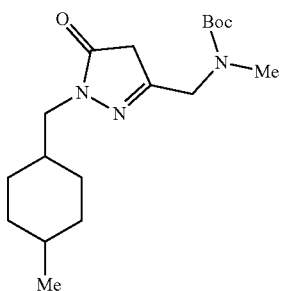 [SMILES: CC1CCC(CN2N=C(CN(C)C(=O)OC(C)(C)C)CC2=O)CC1]

$^1$H-NMR (300 MHz, CDCl$_3$) δ: 0.92 (3H, d, J=7.0 Hz), 1.24-1.73 (18H, m), 1.97 (1H, m), 2.86 (3H, s), 3.23 (2H, s), 3.59 (2H, d, J=7.7 Hz), 4.12 (2H, br s).

Reference Example 31 tert-Butyl {1-[1-(cyclopentylmethyl)-5-oxo-4,5-dihydro-1H-pyrazol-3-yl] ethyl}methylcarbamate

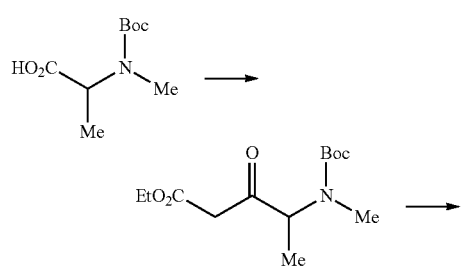

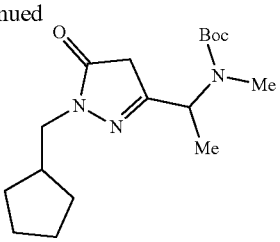

The title compound was prepared in the same manner as in Reference Example 1 except that N-tert-butoxycarbonyl-N-methylalanine was used.

$^1$H-NMR (300 MHz, CDCl$_3$) δ: 1.14-1.87 (20H, m), 2.32 (1H, m), 2.68 (3H, s), 3.17 (2H, m), 3.58 (2H, d, J=7.5 Hz), 5.11 (1H, br s).

The compounds of Reference Examples 32 to 35 were prepared in the same manner as in Reference Example 31.

Reference Example 32 tert-Butyl {1-[1-(cyclohexylmethyl)-5-oxo-4,5-dihydro-1H-pyrazol-3-yl]ethyl}methylcarbamate

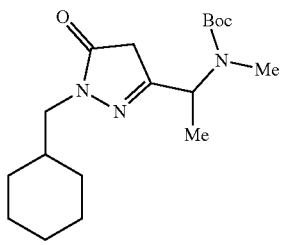 [SMILES: CC(C1=NN(CC2CCCCC2)C(=O)C1)N(C)C(=O)OC(C)(C)C]

$^1$H-NMR (300 MHz, CDCl$_3$) δ: 0.97 (2H, m), 1.20 (4H, m), 1.39 (3H, d, 7.0 Hz), 1.47 (9H, s), 1.68 (5H, m), 2.69 (3H, s), 3.17 (2H, m), 3.45 (1H, dd, J=14.0, 7.1 Hz), 3.51 (1H, dd, J=14.0, 7.4 Hz), 5.09 (1H, br s).

Reference Example 33 tert-Butyl {1-[1-(2-cyclopentylethyl)-5-oxo-4,5-dihydro-1H-pyrazol-3-yl]ethyl}methylcarbamate

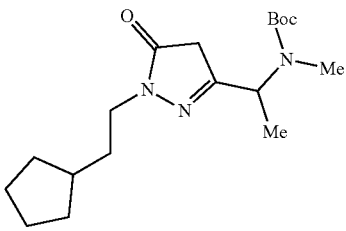 [SMILES: CC(C1=NN(CCC2CCCC2)C(=O)C1)N(C)C(=O)OC(C)(C)C]

$^1$H-NMR (300 MHz, CDCl$_3$) δ: 1.12 (2H, m), 1.40 (3H, d, J=7.0 HZ), 1.47-1.87 (18H, m), 2.69 (3H, s), 3.16 (2H, m), 3.62 (1H, dt, J=14.3, 7.1 Hz), 3.68 (1H, dt, J=14.3, 7.1 Hz), 4.95 (1H, br s).

Reference Example 34 tert-Butyl {1-[1-(2-cyclohexylethyl)-5-oxo-4,5-dihydro-1H-pyrazol-3-yl]ethyl}methylcarbamate

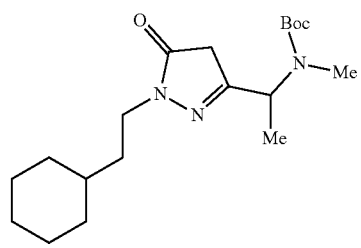 [SMILES: CC(C1=NN(CCC2CCCCC2)C(=O)C1)N(C)C(=O)OC(C)(C)C]

¹H-NMR (300 MHz, CDCl₃) δ: 0.81-1.81 (25H, m), 2.68 (3H, s), 3.16 (2H, m), 3.64 (1H, dt, J=14.5, 7.2 Hz), 3.70 (1H, dt, J=14.5, 7.5 Hz), 4.96 (1H, br s).

Reference Example 35 tert-Butyl {1-[1-(2-ethylbutyl)-5-oxo-4,5-dihydro-1H-pyrazol-3-yl]ethyl}methylcarbamate

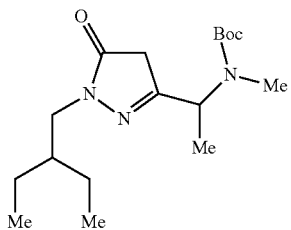 [SMILES: CCC(CC)CN1N=C(C(C)N(C)C(=O)OC(C)(C)C)CC1=O]

¹H-NMR (300 MHz, CDCl₃) δ: 0.87 (6H, t, J=7.4 Hz), 1.29 (4H, m), 1.36 (3H, d, J=7.2 Hz), 1.45 (9H, s), 1.71 (1H, m), 2.66 (3H, s), 3.14 (2H, m), 3.53 (2H, d, J=7.0 Hz), 5.05 (1H, br s).

Reference Example 36 tert-Butyl [(1-benzyl-5-oxo-4,5-dihydro-1H-pyrazol-3-yl)methyl]methylcarbamate

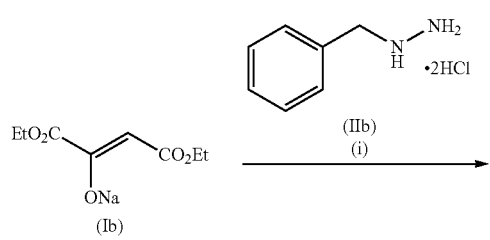

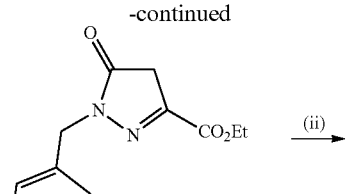

(IIIb)

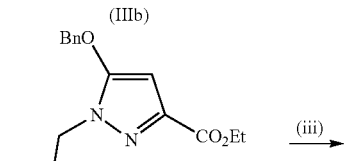

(IVb)

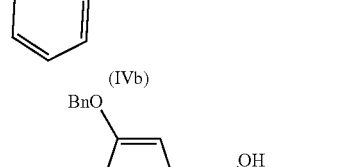

(Vb)

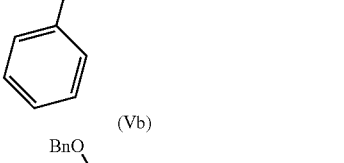

(VIb)

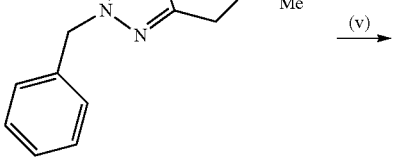

(VIIb)

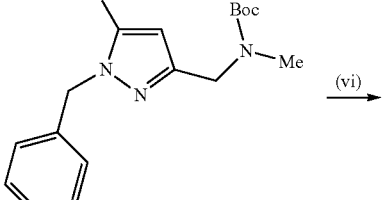

(VIIIb)

Step (i)

To a solution of Compound (Ib) (1.32 g, 6.3 mmol) in a mixture of acetic acid (13 mL) and toluene (6.3 mL) was added a solution of Compound (IIb) (1.00 g, 6.3 mmol) in water (6.3 mL). The reaction mixture was stirred at 80° C. for 4 hours, at 120° C. for 3 hours, and then at 130° C. for 3 hours. The solvent was evaporated under reduced pressure and water (3 mL) was added to the concentrated residue. The resulting solid was collected by filtration and toluene (5 mL) was added thereto. The mixture was heated under reflux for 1 hour, slowly cooled to 0° C., and stirred at 0° C. for 1 hour. The solid was collected by filtration and dried under reduced pressure to give Compound (IIIb) (919 mg, 59%).

Steps (ii) to (iii)

To a solution of the Compound (IIIb) (710 mg, 2.9 mmol) and K$_2$CO$_3$ (418 mg, 3.0 mmol) in dimethylformamide (8.6 mL) was added benzyl bromide (360 μL, 3.0 mmol) at room temperature, and the reaction mixture was stirred at room temperature for 1 hour. The salt was filtered off, the solvent was evaporated under reduced pressure, and the concentrated residue was purified by silica gel column chromatography (n-hexane/ethyl acetate) to give a crude product of Compound (IVb), which was used in the next step without further purification. The resulting Compound (IVb) was dissolved in tetrahydrofuran (14 mL), lithium aluminum hydride (131 mg, 3.4 mmol) was added thereto in small portions at room temperature, and the reaction mixture was stirred for 30 minutes. To the reaction solution were added water (150 μL), 2 mol/L aq. NaOH (150 μL) and water (450 μL). The mixture was stirred at room temperature for 20 minutes, the resulting precipitate was filtered off through Celite, the filtrate was concentrated, and the concentrated residue was purified by silica gel column chromatography (n-hexane:ethyl acetate=1:1→ethyl acetate) to give Compound (Vb) (608 mg, 72%).

Steps (iv) to (v)

To a solution of the Compound (Vb) (607 mg, 2.1 mmol) and triethylamine (282 μL, 4.2 mmol) in dichloromethane (6.2 mL) was added methanesulfonyl chloride (239 μL, 3.1 mmol) at 0° C., and the reaction mixture was stirred at the same condition for 30 minutes. To the mixture was added 40% methylamine-methanol (6.2 mL) in small portions, and the reaction mixture was stirred overnight with slowly warming to room temperature. To the resultant was added sat. aq. NaHCO$_3$, the mixture was extracted with 10% methanol-chloroform, the organic layer was dried over anhydrous Na$_2$SO$_4$, and the solvent was evaporated under reduced pressure to give a crude product of Compound (VIb), which was used in the next step without further purification. The resulting Compound (VIb) and triethylamine (282 μL, 4.2 mmol) were dissolved in dichloromethane (10 mL), di-tert-butyl dicarbonate (900 mg, 4.1 mmol) was added thereto at room temperature, and the reaction mixture was stirred at room temperature for 30 minutes. To the mixture was added sat. aq. NaHCO$_3$, and the mixture was extracted with chloroform. The organic layer was dried over anhydrous Na$_2$SO$_4$, the solvent was evaporated under reduced pressure, and the concentrated residue was purified by silica gel column chromatography (n-hexane:ethyl acetate=95:5→60:40) to give Compound (VIIb) (643 mg, 76%).

Step (vi)

The Compound (VIIb) (300 mg, 0.74 mmol) was hydrogenated in methanol (2 mL) with 10% palladium carbon (30 mg) at room temperature over 1 hour at ambient pressure. The catalyst was filtered off through Celite and the filtrate was concentrated to give the title Compound (VIIIb) (243 mg, quantitative).

$^1$H-NMR (300 MHz, CDCl$_3$) δ: 1.45 (9H, s), 2.84 (3H, br s), 3.25 (2H, br s), 4.09 (2H, br s), 4.82 (2H, s), 7.27-7.37 (5H, m).

Reference Example 37 tert-Butyl {[5-oxo-1-(2-phenylethyl)-4,5-dihydro-1H-pyrazol-3-yl]methyl}methylcarbamate

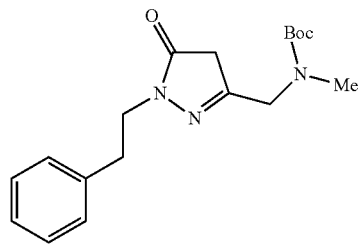 [SMILES: CN(CC1=NN(CCc2ccccc2)C(=O)C1)C(=O)OC(C)(C)C]

The title compound was prepared in the same manner as in Reference Example 36.

$^1$H-NMR (300 MHz, CDCl$_3$) δ: 1.47 (9H, s), 2.85 (3H, br s), 2.99 (2H, br t, J=7.6 Hz), 3.17 (2H, br s), 3.87-3.92 (2H, m), 4.12 (2H, br s), 7.18-7.32 (5H, m).

Preparation of Hydrazine Compounds:

Reference Example 38

(Cyclohexylmethyl)hydrazine dihydrochloride

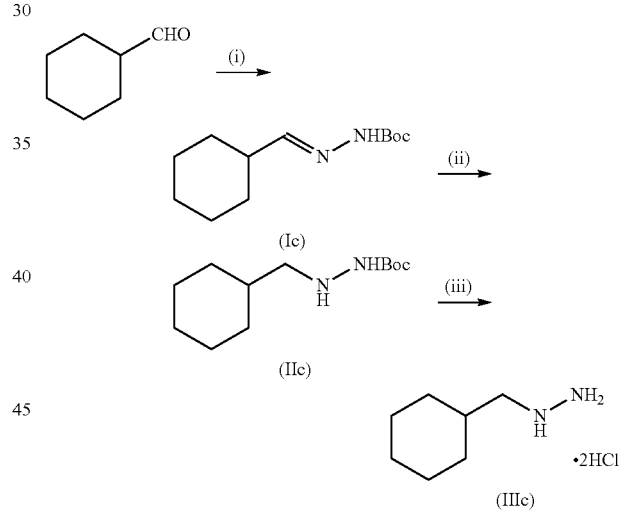

Step (i)

To a solution of cyclohexylaldehyde (38 g, 339 mmol) in methanol (677 mL) was added N-Boc-hydrazine (44.8 g, 339 mmol) at room temperature, and the reaction mixture was stirred at room temperature for 3 hours. The solvent was evaporated under reduced pressure, to the concentrated residue was added hexane (100 mL), and the mixture was suspended. The resulting precipitate was collected by filtration to give Compound (Ic) (55.9 g) as a white solid. The filtrate was concentrated, to the concentrated residue was added n-hexane (30 mL), and the resulting precipitate was collected by filtration and washed with n-hexane (15 mL) to give Compound (Ic) (14.3 g, 70.2 g in total, 91%) as a white solid.

Steps (ii) to (iii)

To a solution of sodium cyanoborohydride (12.5 g, 189 mmol) in a mixture of methanol (430 mL) and acetic acid (40 mL) was added the Compound (Ic) (42.8 g, 189 mmol) over 10 minutes with cooling in an ice bath to keep the internal temperature below 15° C. The reaction mixture was stirred for 30 minutes, and then for further 30 minutes with slowly warming to room temperature. The mixture was adjusted to pH 8 with 2 mol/L aq. NaOH (50 mL) with cooling in the ice bath again, and extracted with chloroform (×2, 300 mL and 50 mL). The combined organic layers were washed with sat. aq. $NaHCO_3$ (200 mL) and brine (200 mL), and dried over anhydrous $Na_2SO_4$. The solvent was evaporated under reduced pressure to give a crude product of Compound (IIc) (46.3 g) as an oil, which was used in the next step without further purification. The resulting Compound (IIc) was dissolved in methanol (400 mL), and conc. HCl (100 mL) was added dropwise to the solution at 55° C. over 30 minutes. The reaction mixture was stirred at 55° C. to 60° C. for 1 hour and cooled to room temperature, and the solvent was evaporated under reduced pressure. To the concentrated residue was added methanol (200 mL), and the solvent was evaporated under reduced pressure twice. To the concentrated residue was added ethyl acetate (200 mL), the mixture was stirred at room temperature, and the resulting precipitate was collected by filtration to give the title Compound (IIIc) (39.4 g) as a white powder.

$^1$H-NMR (300 MHz, DMSO-$d_6$) δ: 0.90 (2H, br dd, J=22.6, 11.7 Hz), 1.09-1.26 (3H, m), 1.55-1.78 (6H, m), 2.72 (2H, br d, J=4.4 Hz).

The following hydrazine compounds were prepared in the same manner as in Reference Example 38 except that a corresponding ketone compound was used.

Reference Example 39

(1-Cyclohexylethyl)hydrazine dihydrochloride

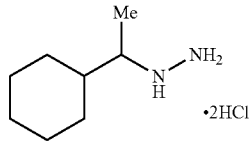

$^1$H-NMR (300 MHz, DMSO-$d_6$) δ: 0.85-1.32 (8H, m), 1.53-1.80 (6H, m), 2.92 (1H, dq, J=6.8, 5.4 Hz), 8.37 (5H, br s).

Reference Example 40

(1-Cyclohexylpropyl)hydrazine dihydrochloride

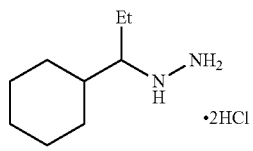 [SMILES: CCC(NN)C1CCCCC1]

$^1$H-NMR (300 MHz, DMSO-$d_6$) δ: 0.90 (3H, t, J=7.4 Hz), 0.96-1.28 (5H, m), 1.50 (2H, m), 1.55-1.76 (6H, m), 2.64 (1H, dt, J=5.6, 5.6 Hz), 7.06 (5H, br s).

Reference Example 41

Pentan-3-ylhydrazine dihydrochloride

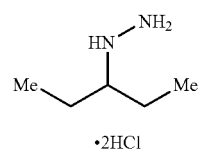

$^1$H-NMR (300 MHz, DMSO-$d_6$) δ: 0.85 (6H, t, J=7.1 Hz), 1.54 (4H, m), 2.81 (1H, quin, J=5.9 Hz).

Reference Example 42

Ethyl cyclohexyl(hydrazinyl)acetate dihydrochloride

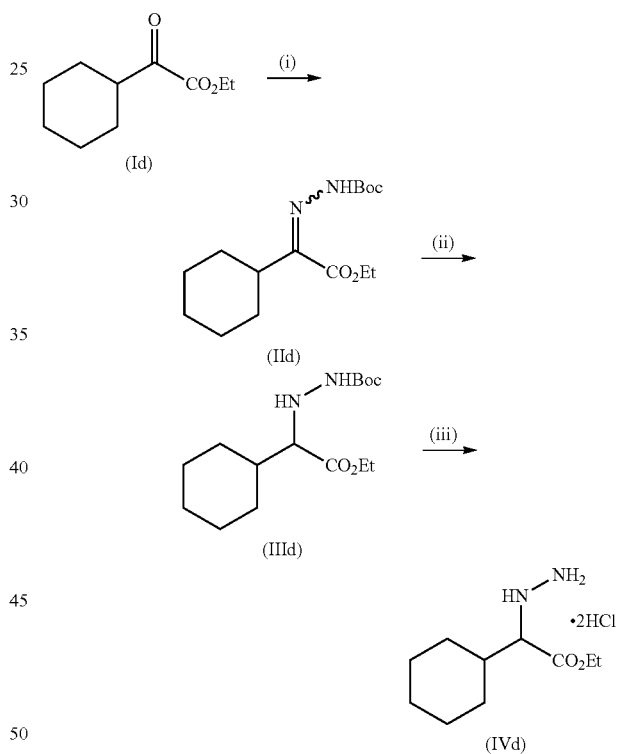

Steps (i) to (ii)

A solution of α-Ketoester (Id) (887 mg, 4.8 mmol) prepared according to the method disclosed in Tetrahedron, 1996, 52 (42), 13513 and tert-butyl carbazate (636 mg, 4.8 mmol) in toluene (5 mL) was heated under reflux for 1 day. The mixture was cooled to room temperature, and the solvent was evaporated under reduced pressure to give a crude product of Compound (IId), which was used in the next step without further purification. The resulting Compound (IId) was dissolved in methanol (24 mL) and acetic acid (2.4 mL), to the solution was added sodium cyanohydride (603 mg, 9.6 mmol) in a water bath to keep the temperature at room temperature, and the reaction mixture was heated under reflux overnight. To the reaction solution was added water (10 mL) with cooling in an ice bath, sat. aq.

NaHCO$_3$ was added thereto, and the mixture was extracted with chloroform. The organic layer was dried over anhydrous Na$_2$SO$_4$, the solvent was evaporated under reduced pressure, and the concentrated residue was purified by silica gel column chromatography (n-hexane:ethyl acetate=4:1) to give Compound (IIId) (482 mg, 33%) as a colorless oil.

Step (iii)

To a solution of the Compound (IIId) (377 mg, 1.3 mmol) in ethanol (2.5 mL) was added 4 mol/L HCl/1,4-dioxane (1.9 mL) at room temperature, and the reaction solution was stirred at 50° C. for 35 minutes. To the mixture was further added 4 mol/L HCl/1,4-dioxane (0.3 mL), and the reaction solution was stirred at 50° C. for 30 minutes. The reaction solution was cooled to room temperature, and the solvent was evaporated under reduced pressure. The concentrated residue was purified by adding diethyl ether and removing the supernatant by decantation to give the title Compound (IVd) (238 mg, 80%) as a white solid.

Reference Example 43

(Cyclopentylmethyl)hydrazine dihydrochloride

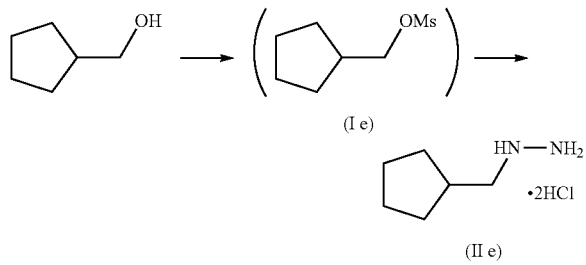

To a solution of cyclopentylmethyl alcohol (51.1 g, 0.51 mol) and triethylamine (82.6 g, 0.82 mol) in tetrahydrofuran (510 mL) was added dropwise methanesulfonyl chloride (67.2 g, 0.59 mmol) over 55 minutes with keeping the temperature below 10° C., and the reaction mixture was stirred for 1 hour. To the mixture was added water (380 mL) with keeping the internal temperature below 10° C., and the mixture was extracted with toluene (765 mL). The organic layer was dried over anhydrous MgSO$_4$, and the solvent was evaporated under reduced pressure to give a crude product of Compound (Ie) (86.9 g). The crude product of Compound (Ie) (50 g, equivalent to 0.28 mol) and hydrazine monohydrate (84.3 g, 1.7 mol) were dissolved in ethanol (281 mL), and the reaction mixture was stirred at 45° C. to 55° C. for 7 hours and then cooled to room temperature. To the resultant was added water (94 mL), and the mixture was extracted with chloroform (562 mL). The organic layer was washed with water (94 mL) twice, and dried over anhydrous Na$_2$SO$_4$. To the solution was added conc. HCl (85 g) at an internal temperature below 10° C., methanol (190 mL) was added thereto to dissolve the solid, and the solvent was evaporated under reduced pressure. To the concentrated residue was added 2-propanol (234 mL), and the solvent was evaporated under reduced pressure four times. To the concentrated residue was added 2-propanol (85 mL). The mixture was heated to 40° C., n-hexane (170 mL) was added dropwise thereto at 40° C. over 30 minutes, and the mixture was stirred at 40° C. for 1 hour. Then, the mixture was cooled to 10° C. over 1 hour and stirred at an internal temperature below 10° C. for 1 hour. The resulting precipitate was collected by filtration, washed with a mixed solution of cooled n-hexane/2-propanol (2:1) (36 mL), and dried under reduced pressure to give the title compound (33.6 g, 64%) as a white powder.

$^1$H-NMR (300 MHz, DMSO-d$_6$) δ: 1.12-1.26 (2H, m), 1.42-1.65 (4H, m), 1.67-1.81 (2H, m), 2.02-2.17 (1H, m), 2.84 (2H, d, J=7.3 Hz), 7.16 (5H, br s).

The compounds in Reference Examples 44 to 60 were prepared in the same manner as in Reference Example 43 except that a corresponding alkyl chloride, alkyl bromide, alkyl iodide or alkyl methanesulfonate was used.

Reference Example 44

(Cyclopropylmethyl)hydrazine dihydrochloride

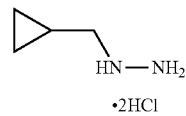

$^1$H-NMR (300 MHz, DMSO-d$_6$) δ: 0.32 (2H, br dt, J=8.1, 3.1 Hz), 0.53 (2H, br ddd, J=9.4, 5.0, 3.1 Hz), 0.94-1.09 (1H, m), 2.81 (2H, d, J=7.2 Hz), 8.21 (5H, br s).

Reference Example 45

(Cyclobutylmethyl)hydrazine dihydrochloride

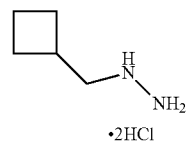

$^1$H-NMR (300 MHz, DMSO-d$_6$) δ: 1.67-1.92 (4H, m), 1.98-2.07 (2H, m), 2.52-2.61 (1H, m), 2.94 (2H, d, J=7.3 Hz), 7.68 (5H, br s).

Reference Example 46

(Cycloheptylmethyl)hydrazine dihydrochloride

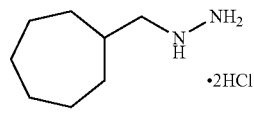

$^1$H-NMR (300 MHz, DMSO-d$_6$) δ: 1.11-1.23 (2H, m), 1.33-1.82 (11H, m), 2.73 (2H, d, J=6.8 Hz), 7.51 (5H, br s).

Reference Example 47

(2-Cyclohexylethyl)hydrazine dihydrochloride

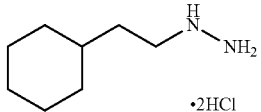

$^1$H-NMR (300 MHz, CD$_3$OD) δ: 0.99 (2H, m), 1.15-1.40 (4H, m), 1.52 (2H, m), 1.63-1.79 (5H, m), 3.06 (2H, m).

Reference Example 48

(2-Cyclopentylethyl)hydrazine dihydrochloride

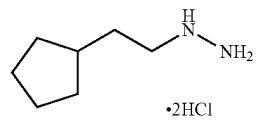

$^1$H-NMR (300 MHz, DMSO-d$_6$) δ: 1.05 (2H, m), 1.38-1.63 (6H, m), 1.65-1.82 (3H, m), 2.87 (2H, t, J=8.0 Hz), 5.73 (5H, br s).

Reference Example 49

[(4-Methylcyclohexyl)methyl]hydrazine dihydrochloride

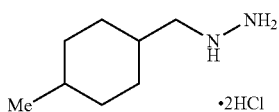

$^1$H-NMR (300 MHz, DMSO-d$_6$) δ: 0.87 (3H, d, J=7.7 Hz), 0.85-1.85 (10H, m), 2.83 (2H, d, J=7.0 Hz), 746 (3H, br s).

Reference Example 50

[(1-Methylcyclohexyl)methyl]hydrazine dihydrochloride

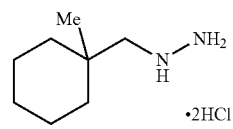

$^1$H-NMR (300 MHz, DMSO-d$_6$) δ: 0.91 (3H, s), 1.16-1.50 (10H, m), 2.72 (2H, s), 7.62 (3H, br s).

Reference Example 51

[(2-Methylcyclohexyl)methyl]hydrazine dihydrochloride

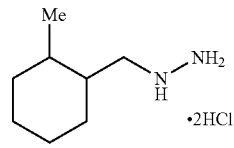

$^1$H-NMR (300 MHz, CDCl$_3$) δ: 0.95 (3H, d, J=7.0 Hz), 1.30-1.74 (8H, m), 2.02 (1H, m), 2.22 (1H, m), 3.52 (2H, m), 4.75 (5H, br s).

Reference Example 52

[(4,4-Difluorocyclohexyl)methyl]hydrazine dihydrochloride

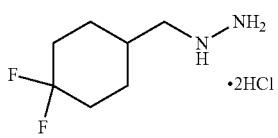 [SMILES: NNCC1CCC(F)(F)CC1]

$^1$H-NMR (300 MHz, CD$_3$OD) δ: 1.34 (2H, m), 1.66-1.93 (5H, m), 2.06 (2H, m) 2.90 (2H, d, J=6.8 Hz).

Reference Example 53

[(1-Fluorocyclohexyl)methyl]hydrazine dihydrochloride

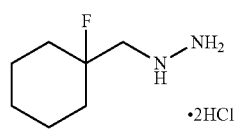

$^1$H-NMR (300 MHz, DMSO-d$_6$) δ: 1.14-1.86 (10H, m), 3.00 (2H, d, J=21.1 Hz).

Reference Example 54

(3,3-Dimethylbutyl)hydrazine dihydrochloride

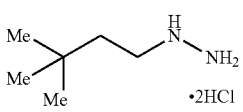

$^1$H-NMR (400 MHz, DMSO-d$_6$) δ: 0.87 (9H, s), 1.47 (2H, br dd, J=10.4, 7.0 Hz), 2.86-2.93 (2H, m), 8.95 (5H, br s).

Reference Example 55

(2,2-Dimethylpropyl)hydrazine dihydrochloride

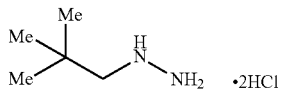

¹H-NMR (300 MHz, DMSO-d₆) δ: 0.90 (9H, s), 2.65 (2H, s), 7.43 (5H, br s).

Reference Example 56

(2-Ethylbutyl)hydrazine dihydrochloride

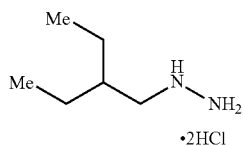

¹H-NMR (400 MHz, DMSO-d₆) δ: 0.83 (6H, t, J=7.4 Hz), 1.24-1.40 (4H, m), 1.52 (1H, dq, J=25.6, 6.5 Hz), 2.80 (2H, d, J=6.6 Hz), 8.54 (5H, br s).

Reference Example 57

(3-Methylbutyl)hydrazine dihydrochloride

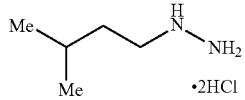

¹H-NMR (300 MHz, DMSO-d₆) δ: 0.87 (6H, d, J=6.6 Hz), 1.46 (2H, tt, J=6.5, 3.0 Hz), 1.61 (1H, dq, J=26.8, 6.6 Hz), 2.89-2.94 (2H, m), 6.47 (5H, s).

Reference Example 58

(Bicyclo[2.2.1]hept-2-ylmethyl)hydrazine dihydrochloride

¹H-NMR (300 MHz, DMSO-d₆) δ: 1.00-1.18 (4H, m), 1.21-1.53 (4H, m), 1.64-1.75 (1H, m), 2.18 (2H, br s), 2.58-2.90 (2H, m), 6.98 (3H, br s).

Reference Example 59

(4,4,4-Trifluorobutyl)hydrazine dihydrochloride

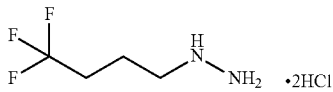

¹H-NMR (300 MHz, DMSO-d₆) δ: 1.76 (2H, m), 2.34 (2H, m), 2.93 (2H, t, J=7.4 Hz), 8.80 (5H, br s).

Reference Example 60

(3-Methoxy-3-methylbutyl)hydrazine dihydrochloride

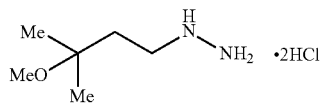

¹H-NMR (300 MHz, DMSO-d₆) δ: 1.10 (6H, s), 1.72-1.80 (2H, m), 2.91-2.99 (2H, m), 3.09 (3H, s), 5.18 (5H, br s).

Reference Example 61: Hydrazine 3-bicyclo (7-Oxabicyclo[2.2.1]hept-2-ylmethyl)hydrazine dihydrochloride

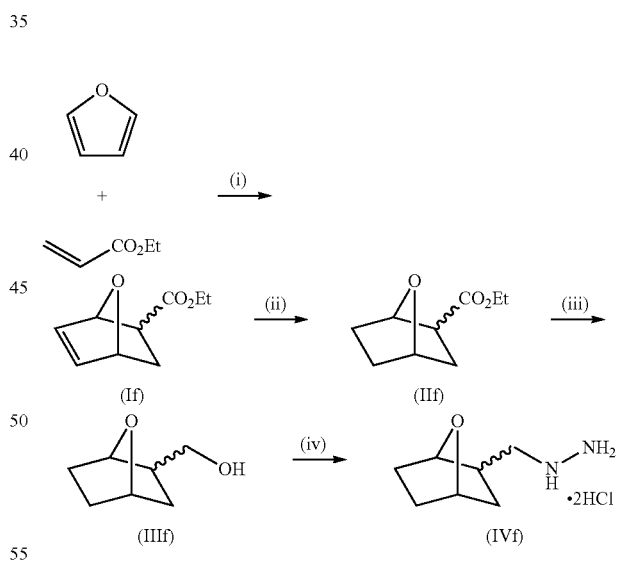

Steps (i) to (iii)

The compounds were prepared according to the methods disclosed in Teterahedron Letters, 23 (50), 5299. A mixed solution of furan (3.0 mL, 41 mmol), ethyl acrylate (3.00 g, 30 mmol) and zinc iodide (2.87 g, 9.0 mmol) was stirred at 40° C. for 1 day. The mixture was extracted with ethyl acetate, and filtered through a mixture of silica gel and Celite. The filtrate was concentrated to give a crude product of Compound (If) (6.34 g), which was used in the next step without further purification. The resulting Compound (If) was hydrogenated in methanol (30 mL) with 5% palladium carbon (700 mg) overnight at ambient pressure. The catalyst was filtered off through Celite, and the filtrate was concentrated under reduced pressure to give a crude product of Compound (IIf) (3.70 g), which was used in the next step without further purification. The resulting Compound (IIf) was dissolved in tetrahydrofuran (90 mL), to the solution was added lithium aluminum hydride (1.20 g, 32 mmol) in small portions at 0° C., and the reaction mixture was stirred at 0° C. for 30 minutes. To the reaction solution were subsequently added water, 2 mol/L aq. NaOH and then water, the mixture was stirred at room temperature, and the resulting precipitate was filtered off through Celite. The filtrate was concentrated, and the concentrated residue was purified by silica gel column chromatography (n-hexane: ethyl acetate) to give Compound (IIIf) (2.40 g, 63%).

Step (iv)

To a solution of the Compound (IIIf) (2.40 g, 19 mmol) and triethylamine (5.2 mL, 38 mmol) in dichloromethane (30 mL) was added methanesulfonyl chloride (2.2 mL, 28 mmol) at 0° C., and the reaction solution was stirred at 0° C. for 30 minutes. To the solution was added sat. aq. NaHCO$_3$, the mixture was extracted with chloroform, the combined organic layers were dried over anhydrous Na$_2$SO$_4$, and the solvent was concentrated under reduced pressure. The concentrated residue was dissolved in ethanol (19 mL), to the solution was added hydrazine monohydrate (5.63 g, 113 mmol), and the reaction mixture was stirred at room temperature for 5 days and then at 60° C. for 8 hours. The mixture was cooled to room temperature and the solvent was evaporated under reduced pressure. To the concentrated residue was added sat. aq. NaHCO$_3$, the mixture was extracted with chloroform, the combined organic layers were dried over anhydrous Na$_2$SO$_4$, and the solvent was evaporated under reduced pressure. The concentrated residue was dissolved in tetrahydrofuran (16 mL), to the solution was added 4 mol/L HCl/1,4-dioxane (16 mL) at room temperature, and the mixture was stirred at room temperature overnight. The resulting precipitate was collected by filtration and dried under reduced pressure to give the title Compound (IVf) (2.91 g, 87%) as a white powder.

$^1$H-NMR (400 MHz, DMSO-d$_6$) δ: 1.15-2.07 (7H, m), 2.59-2.82 (1H, m), 2.92-3.72 (1H, m), 4.44-4.49 (2H, m), 5.74 (5H, s)

Reference Example 62: Hydrazine 4-bicyclo (2-Oxabicyclo[2.2.2]oct-3-ylmethyl)hydrazine dihydrochloride

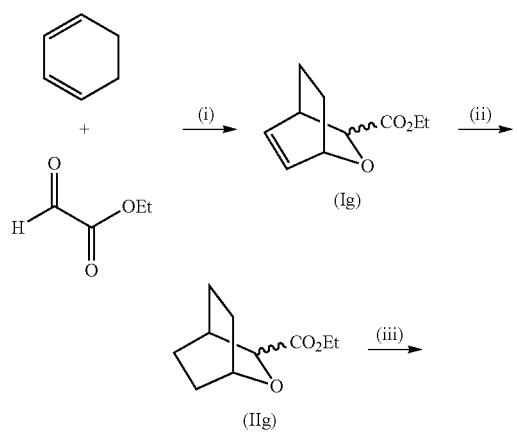

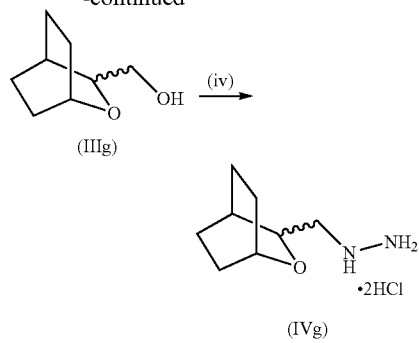

Steps (i) to (ii)

The compounds were prepared according to the methods disclosed in Teterahedron, 52(21), 7321. To a solution of copper (II) triflate (88 mg, 0.24 mmol) and 2,2'-iso-propy-lidenebis[(4S)-4-tert-butyl-2-oxazoline] (108 mg, 0.37 mmol) in dichloromethane (5 mL) was subsequently added at room temperature a solution of cyclohexadiene (4.7 mL, 49 mmol) in dichloromethane (10 mL) and then freshly prepared ethyl glyoxylate monomer (5.0 g, 49 mmol), and the reaction mixture was stirred at room temperature overnight. The mixture was diluted with diethyl ether and filtered through silica gel, and the filtrate was concentrated to give a crude product of Compound (Ig) (2.65 g), which was used in the next step without further purification. The resulting Compound (Ig) (1.58 g) was hydrogenated with 10% palladium carbon (158 mg) in methanol (10 mL) at room temperature over 2.5 hours at ambient pressure. The catalyst was filtered off through Celite, the filtrate was concentrated, and the concentrated residue was purified by silica gel column chromatography (n-hexane:ethyl acetate=90: 10→75:25) to give Compound (IIg) (460 mg, 9%).

Step (iii)

To a solution of the Compound (IIg) (199 mg, 1.1 mmol) in tetrahydrofuran (10 mL) was added lithium borohydride (70 mg, 3.2 mmol) at room temperature, and the reaction mixture was stirred at room temperature for 1 hour. To the reaction solution was added dropwise aq. NH$_4$Cl at 0° C., and the mixture was extracted with ethyl acetate. The combined organic layers were dried over anhydrous Na$_2$SO$_4$, the solvent was evaporated under reduced pressure, and the concentrated residue was purified by silica gel column chromatography (n-hexane:ethyl acetate=70: 30→30:70) to give Compound (IIIg) (120 mg, 78%).

Step (iv)

To a solution of the Compound (IIIg) (440 mg, 3.0 mmol) and triethylamine (878 μL, 6.3 mmol) in dichloromethane (9 mL) was added methanesulfonyl chloride (366 μL, 4.7 mmol) at 0° C., and the reaction solution was stirred at 0° C. for 30 minutes. To the solution was added sat. aq. NaHCO$_3$, the mixture was extracted with chloroform, the combined organic layers were dried over anhydrous Na$_2$SO$_4$, and the solvent was concentrated under reduced pressure. The concentrated residue was dissolved in ethanol (3 mL), to the solution was added hydrazine monohydrate (946 mg, 19 mmol), and the reaction mixture was stirred at room temperature overnight and then at 100° C. for 4 hours. The mixture was cooled to room temperature and the solvent was evaporated under reduced pressure. To the concentrated residue was added sat. aq. NaHCO$_3$, the mixture was extracted with chloroform, the combined organic layers were dried over anhydrous Na$_2$SO$_4$, and the solvent was evaporated under reduced pressure. The concentrated residue was dissolved in tetrahydrofuran (5 mL), to the solution was added 4 mol/L HCl/dioxane (3.5 mL) at room temperature, and the mixture was stirred at room temperature for 30 minutes and then at 0° C. for 30 minutes. The resulting precipitate was collected by filtration and dried under reduced pressure to give the title Compound (IVg) (220 mg, 31%) as a white powder.

$^1$H-NMR (300 MHz, DMSO-$d_6$) δ: 1.45-1.92 (9H, m), 2.91 (1H, dd, J=12.0, 4.7 Hz), 3.07 (1H, dd, J=11.9, 8.6 Hz), 3.53 (5H, br s), 3.68-3.74 (1H, m), 3.93-3.99 (1H, m).

Reference Example 63

(Tetrahydro-2H-pyran-2-ylmethyl)hydrazine dihydrochloride

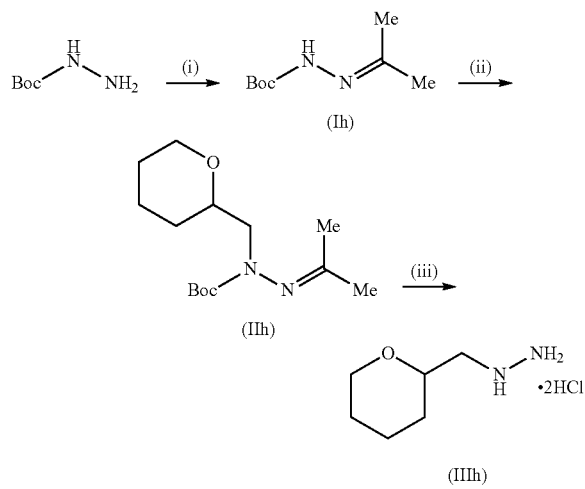

Step (i)

The compound was prepared according to the method disclosed in Synlett, 2004, 13, 2355. A solution of N-Boc-hydrazine (50 g, 378 mmol), anhydrous MgSO$_4$ (10 g) and acetic acid (25 drops) in acetone (375 mL) was heated under reflux for 2 hours. The mixture was cooled to room temperature, the resulting precipitate was filtered off, and the filtrate was concentrated under reduced pressure to give Compound (Ih) (65.1 g, quantitative) as a white solid.

Steps (ii) to (iii)

A solution of the Compound (Ih) (10 g, 58 mmol), 2-(tetrahydropyranyl)methylbromide (10 mL, 81 mmol), potassium hydroxide (4.89 g, 87 mmol) and tetrabutylammonium sulfate (1.97 g, 5.8 mmol) in toluene (200 mL) was heated under reflux for 9 hours. To the reaction mixture was added water (200 mL), and the aqueous layer was extracted with ethyl acetate (200 mL). The combined organic layers were dried over anhydrous MgSO$_4$ and the solvent was evaporated under reduced pressure. The concentrated residue was purified by silica gel column chromatography (n-hexane/ethyl acetate) to give Compound (IIh) (9.30 g). The Compound (IIh) was dissolved in a mixed solvent of methanol (65 mL) and chloroform (30 mL), to the solution was added 4 mol/L HCl/1,4-dioxane (65 mL) at room temperature, and the reaction mixture was stirred at 50° C. for 1 hour. The solvent was evaporated under reduced pressure, to the concentrated residue was added ethyl acetate (100 mL), and the mixture was stirred for 1 hour at room temperature. The resulting precipitate was collected by filtration, washed with ethyl acetate (5 mL) twice, and dried under reduced pressure to give the title Compound (IIIh) (6.79 g, 70%) as a white solid.

$^1$H-NMR (300 MHz, DMSO-$d_6$) δ: 1.12-1.28 (1H, m), 1.37-1.59 (4H, m), 1.70-1.85 (1H, m), 2.83-2.94 (2H, m), 3.30-3.42 (1H, m), 3.49-3.60 (1H, m), 3.84-3.94 (1H, m), 7.69 (5H, brs).

The following hydrazine compounds were prepared in the same manner as in Reference Example 63 except that a corresponding alkyl chloride, alkyl bromide, alkyl iodide, methanesulfonate and the like were used.

Reference Example 64

[(3-Methylcyclohexyl)methyl]hydrazine dihydrochloride

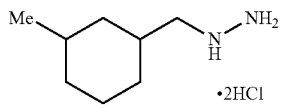

$^1$H-NMR (300 MHz, CDCl$_3$) δ: 0.90 (3H, d, J=6.6 Hz), 1.05-2.05 (10H, m), 3.13 (2H, d, J=6.8 Hz), 5.86 (3H, br s).

Reference Example 65

(Cyclopentylmethyl)hydrazine phosphate

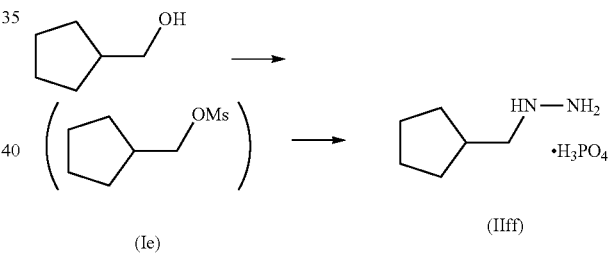

To a solution of cyclopentyl methanol (22.3 g, 0.22 mol) and triethylamine (33.8 g, 0.33 mol) in tetrahydrofuran was added dropwise methanesulfonyl chloride (29.3 g, 0.26 mol) with keeping the temperature below 15° C. over 50 minutes, and the reaction mixture was stirred at the same condition for 1 hour. To the mixture was added dropwise water (134 g) with keeping the internal temperature below 15° C. over 10 minutes. To the resultant was further added toluene (232 g), and the mixture was extracted. The organic layer was washed with water (134 g), and the solvent was evaporated under reduced pressure to give a crude product of Compound (Ie) (40.0 g), which was used in the next step without further purification. The resulting Compound (Ie) and hydrazine monohydrate (66.9 g, 1.34 mol) were dissolved in ethanol (178 g), and the reaction mixture was stirred at 60° C. to 65° C. (internal temperature) for 7 hours. The mixture was cooled to room temperature, and partitioned between chloroform (674 g) and water (71.5 g). The chloroform layer was washed with water (71.5 mL, ×2) to give a solution of a free base of Compound (IIff) in chloroform (808 g). To the solution (202 g, equivalent to 55 mmol) were added at room temperature 85% phosphoric acid (6.42 g, 60 mmol) and then 2-propanol (30 g), and the solvent was evaporated under reduced pressure. To the concentrated residue was added 2-propanol (36.7 g), and the solvent was evaporated under reduced pressure (×4). To the concentrated residue (24 g) was added 2-propanol to adjust the total weight to 45 g, and the mixture was stirred at 40° C. for 1 hour. The mixture was cooled to 5° C. over 1.5 hours, and then stirred at 5° C. for 1 hour. The precipitate was collected by filtration, washed with a mixed solution of 2-propanol (1.98 g) and n-hexane (3.47 g), and dried under reduced pressure to give Compound (IIff) (9.33 g, 80%) as a white crystalline solid.

$^1$H-NMR (400 MHz, DMSO-$d_6$) δ: 1.14-1.19 (2H, m), 1.40-1.55 (4H, m), 1.70-1.75 (2H, m), 2.00-2.10 (1H, m), 2.74 (2H, d, J=8.0 Hz), 7.15 (6H, br).

Reference Example 66

(Cyclopentylmethyl)hydrazine sulfate

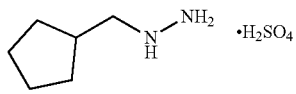

To the solution of the free base of Compound (IIff) in Reference Example 65 in chloroform (202 g, equivalent to 55 mmol) were added at room temperature conc. $H_2SO_4$ (98% r 5.57 g, 60 mmol) and then 2-propanol (30 g). The solvent was evaporated under reduced pressure. To the concentrated residue was added 2-propanol (36.7 g), and the solvent was evaporated under reduced pressure (×4). To the concentrated residue (24.9 g) was added 2-propanol to adjust the total weight to 45 g, and the mixture was stirred at 40° C. for 1 hour. The mixture was cooled to 5° C. over 1.5 hours and then stirred at 5° C. for 1 hour. The precipitate was collected by filtration, washed with a mixed solution of 2-propanol (1.98 g) and n-hexane (3.47 g), and dried under reduced pressure to give the title compound (8.77 g, 75%) as a white crystalline solid.

$^1$H-NMR (400 MHz, DMSO-$d_6$) δ: 1.14-1.21 (2H, m), 1.46-1.58 (4H, m), 1.68-1.75 (2H, m), 1.99-2.07 (1H, m), 2.82 (2H, d, J=8.0 Hz), 7.95 (5H, br).

Reference Example 67

(3-Methylbutyl)hydrazine phosphate

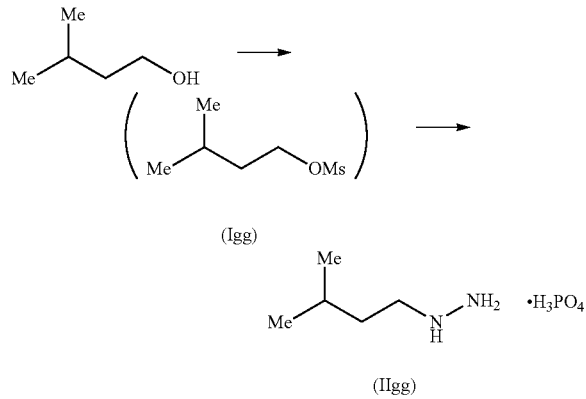

To a solution of isoamyl alcohol (100 g, 1.13 mol) and triethylamine (173 mL, 1.25 mol) in tetrahydrofuran (1.13 L) was added dropwise methanesulfonyl chloride (136 g, 1.19 mol) with keeping the internal temperature below 17° C. over 1 hour, and the reaction mixture was stirred at the same condition for 1 hour. To the resultant was added dropwise water (1.0 L) with keeping the internal temperature below 13° C., and the mixture was extracted with toluene (1.7 L) The organic layer was dried over anhydrous $MgSO_4$ and the solvent was evaporated under reduced pressure to give a crude product of Compound (Igg) (198 g), which was used in the next step without further purification. The resulting Compound (Igg) and hydrazine monohydrate (339 g, 6.77 mol) were dissolved in ethanol (1.13 L), and the reaction mixture was stirred at 50° C. (internal temperature) for 2 hours. The mixture was cooled to room temperature, and partitioned between chloroform (2.26 L) and water (339 mL). The chloroform layer was washed with water (339 mL, ×2) To the solution of chloroform was added phosphoric acid (85%, 130 g, 1.13 mol) at room temperature, and the solvent was evaporated under reduced pressure. To the obtained white-solid was added 2-propanol (300 mL), and the solvent was evaporated under reduced pressure (×3). To the concentrated residue was added 2-propanol (1.13 L). The mixture was stirred for 1.5 hours at 45° C. (internal temperature) and then stirred overnight with slowly cooling to room temperature. The resulting precipitate was collected by filtration, washed with cold 2-propanol (100 mL, ×2), and dried under reduced pressure to give the title Compound (IIgg) (181 g, 80%) as a white powder.

$^1$H-NMR (300 MHz, DMSO) δ: 0.85 (d, J=6.6 Hz, 6H), 1.39 (dd, J=15.2, 7.2 Hz, 2H), 1.59 (sept, J=6.6 Hz, 1H), 2.68-2.84 (m, 2H), 7.13 (br s, 6H).

Reference Example 68

(3-Methylbutyl)hydrazine sulfate

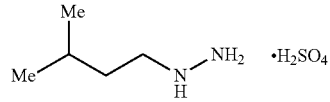

To the compound of Reference Example 57 (3.50 g, 20 mmol) was added 10% aq. $K_2CO_3$, and the mixture was extracted with chloroform (30 mL×2+10 mL). The chloroform layer was washed with brine and dried over anhydrous $Na_2SO_4$, and the solvent was evaporated under reduced pressure to give a free form of hydrazine (470 mg) as a yellow oil. Then 235 mg of the product (equivalent to 4.60 mmol) was dissolved in 2-propanol (5 g). To the solution were added at room temperature conc. $H_2SO_4$ (230 mg, 2.3 mmol) and then n-hexane (5 mL), and the resulting precipitate was collected by filtration and dried under reduced pressure to give the title compound (81 mg) as a white solid.

$^1$H-NMR (400 MHz, DMSO-$d_6$) δ: 0.87 (6H, d, J=6.6 Hz), 1.36-1.42 (2H, m), 1.55-1.63 (1H, m), 2.88 (2H, t, J=8.0 Hz), 7.85 (5H, br).

Reference Example 69

[(1-Methoxycyclopentyl)methyl]hydrazine dihydrochloride

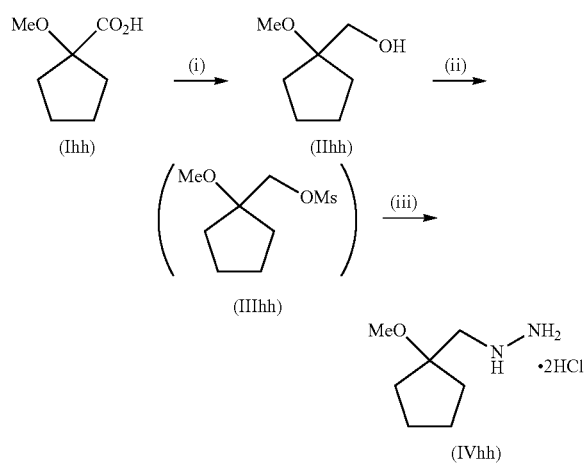

Step (i)

To a solution of Compound (Ihh) prepared according to the method disclosed in Organometallics, 6(10), 1987, 2079 (637 mg, 3.8 mmol) in tetrahydrofuran (8.7 mL) was added borane tetrahydrofuran complex (1.1 mol/L, 8.7 mL, 9.6 mmol) at room temperature, the reaction mixture was stirred at room temperature overnight, and methanol (5 mL) was added thereto. After the gas evolution ceased, the solvent was evaporated under reduced pressure, the concentrated residue was dissolved in a mixed solution of chloroform and methanol (9:1), the mixture was filtered through silica gel, and the filtrate was concentrated. The concentrated residue was purified by silica gel column chromatography (chloroform:methanol=99:1→90:10) to give Compound (IIhh) (420 mg, 84%) as a colorless oil.

Steps (ii) to (iii)

Compound (IVhh) was prepared in the same manner as in Reference Example 43.

$^1$H-NMR (300 MHz, CD$_3$OD) δ: 1.51-1.80 (6H, m), 1.93 (2H, m), 3.16 (2H, m), 3.23 (3H, s). 5H unditected (NH, NH$_2$, 2HCl)

Reference Example 70

[(1-Methoxycyclohexyl)methyl]hydrazine dihydrochloride

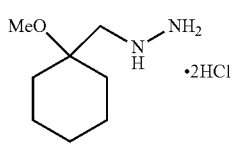

The title compound was prepared in the same manner as in Reference Example 69.

$^1$H-NMR (300 MHz, CD$_3$OD) δ: 1.36-1.61 (8H, m), 1.79 (2H, m), 3.07 (2H, s), 3.22 (3H, s). 5H unditected (NH, NH$_2$, 2HCl)

The compounds in Reference Examples 71 and 72 were prepared in the same manner as in Reference Example 43 except that a corresponding alkyl chloride, alkyl bromide, alkyl iodide or alkyl methanesulfonate was used.

Reference Example 71

(3-Methoxybutyl)hydrazine dihydrochloride

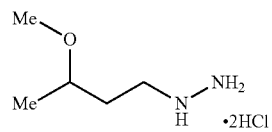

$^1$H-NMR (300 MHz, DMSO) δ: 1.05 (d, J=6.1 Hz, 3H), 1.52-1.94 (m, 2H), 2.80-3.05 (m, 2H), 3.19 (s, 3H), 3.28-3.45 (m, 1H), 6.59 (br s, 5H).

Reference Example 72

(2-Cyclopropylethyl)hydrazine dihydrochloride

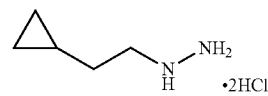

$^1$H-NMR (300 MHz, DMSO-d$_6$) δ: 0.05 (2H, m), 0.41 (2H, m), 0.71 (1H, m), 1.43 (2H, q, J=7.3 Hz), 2.94 (2H, t, J=7.6 Hz). 5H unditected (NH, NH$_2$, 2HCl)

Reference Example 73: 3-Et-amylhydrazine (3-Ethylpentyl)hydrazine dihydrochloride

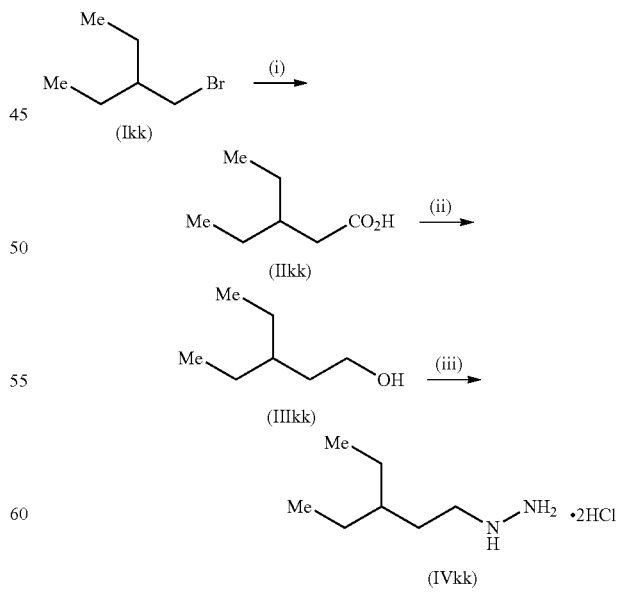

Step (i)

To a suspension of magnesium (729 mg, 33 mmol) in tetrahydrofuran (3 mL) was added Compound (Ikk) (1.5 g)

To the resultant was further added dropwise a solution of Compound (Ikk) (3.45 g) in anhydrous tetrahydrofuran (40 mL), and the mixture was stirred for 40 minutes. To the reaction mixture was added dry ice (5 g), and the reaction mixture was stirred for 3 hours with slowly warming to room temperature. To the resultant was added 1 N HCl, the mixture was extracted with ethyl acetate, the organic layer was washed with brine and dried over anhydrous MgSO$_4$, and the solvent was evaporated under reduced pressure to give a crude product of Compound (IIkk) (3.80 g) as a colorless oil.

Steps (ii) to (iii)

The crude product of Compound (IIkk) (2.6 g, equivalent to 20 mmol) was dissolved in tetrahydrofuran (40 mL), to the solution was added borane tetrahydrofuran complex (in 0.9 N tetrahydrofuran, equivalent to 60 mmol) with ice-cooling, and the reaction mixture was stirred at the same condition for 1 hour. To the mixture was added 1 N HCl, the tetrahydrofuran was evaporated under reduced pressure, and the concentrated residue was extracted with ethyl acetate. The organic layer was subsequently washed with sat. aq. NaHCO$_3$ and brine, and dried over anhydrous MgSO$_4$. The solvent was evaporated under reduced pressure to give a crude product of Compound (IIIkk) (2.96 g), which was used in the next step without further purification. The resulting Compound (IIIkk) and triethylamine (3.5 mL, 25 mmol) were dissolved in tetrahydrofuran (40 mL), to the solution was added methanesulfonyl chloride (1.7 mL, 22 mmol) with ice-cooling, and the reaction mixture was stirred for 30 minutes. To the resultant was added water, the mixture was extracted with ethyl acetate, the organic layer was dried over anhydrous MgSO$_4$, and the solvent was evaporated under reduced pressure. The concentrated residue (4.35 g) and hydrazine monohydrate (6.0 g, 120 mmol) were dissolved in ethanol (20 mL), and the mixture was stirred at 50° C. for 3 hours. The reaction mixture was cooled to room temperature, water was added thereto, and the mixture was extracted with chloroform. The organic layer was washed with water and dried over anhydrous Na$_2$SO$_4$. To the organic layer was added 4 N HCl/1,4-dioxane solution, and the solvent was evaporated under reduced pressure. To the concentrated residue were added 2-propanol (10 mL) and n-hexane (100 mL), and the mixture was insonated. The resulting precipitate was collected by filtration to give Compound (IVkk) (612 mg, 10%) as a white powder.

$^1$H-NMR (300 MHz, DMSO-d$_6$) δ: 0.80 (6H, t, J=7.5 Hz), 1.18-1.35 (5H, m), 1.45-1.55 (2H, m), 2.86 (2H, d, J=7.5 Hz), 7.00 (5H, br).

The compounds in Reference Examples 74 to 78 were prepared in the same manner as in Reference Example 1 except that the compounds in Reference Examples 69 to 73 were used.

Reference Example 74 tert-Butyl {[1-(2-cyclopropylethyl)-5-oxo-4,5-dihydro-1H-pyrazol-3-yl]methyl}methylcarbamate

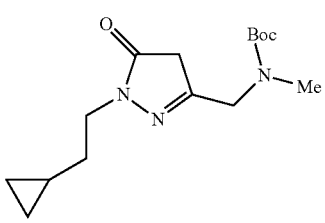 [SMILES: CN(CC1=NN(CCC2CC2)C(=O)C1)C(=O)OC(C)(C)C]

$^1$H-NMR (300 MHz, CDCl$_3$) δ: 0.04 (2H, m), 0.44 (2H, m), 0.67 (1H, m), 1.47 (9H, s), 1.57 (2H, m), 2.87 (3H, s), 3.22 (2H, s), 3.74 (2H, t, J=7.2 Hz), 4.11 (2H, s).

Reference Example 75 tert-Butyl ({1-[(1-methoxycyclopentyl)methyl]-5-oxo-4,5-dihydro-1H-pyrazol-3-yl}methyl)methylcarbamate

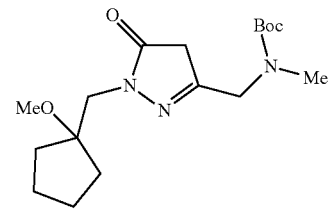 [SMILES: COC1(CN2N=C(CN(C)C(=O)OC(C)(C)C)CC2=O)CCCC1]

$^1$H-NMR (300 MHz, CDCl$_3$) δ: 1.47 (9H, s), 1.55-1.86 (8H, m), 2.87 (3H, s), 3.22 (2H, s), 3.27 (3H, s), 3.79 (2H, s), 4.11 (2H, br s).

Reference Example 76 tert-Butyl ({1-[(1-methoxycyclohexyl)methyl]-5-oxo-4,5-dihydro-1H-pyrazol-3-yl}methyl)methylcarbamate

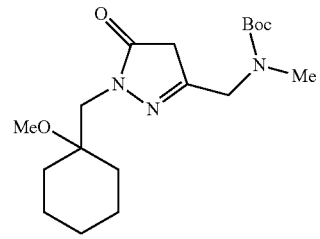 [SMILES: COC1(CN2N=C(CN(C)C(=O)OC(C)(C)C)CC2=O)CCCCC1]

$^1$H-NMR (300 MHz, CDCl$_3$) δ: 1.13-1.80 (10H, m), 1.46 (9H, s), 2.86 (3H, s), 3.21 (2H, s), 3.28 (3H, s), 3.64 (2H, s), 4.10 (2H, br s).

Reference Example 77 tert-Butyl {[1-(3-methoxybutyl)-5-oxo-4,5-dihydro-1H-pyrazol-3-yl]methyl}methylcarbamate

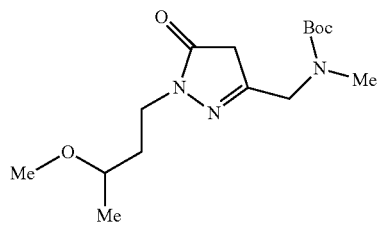 [SMILES: COC(C)CCN1N=C(CN(C)C(=O)OC(C)(C)C)CC1=O]

$^1$H-NMR (300 MHz, CDCl$_3$) δ: 1.17 (d, J=6.2 Hz, 3H), 1.47 (s, 9H), 1.71-1.92 (m, 2H), 2.87 (s, 3H), 3.22 (s, 2H), 3.28-3.40 (m, 4H), 3.75 (t, J=7.0 Hz, 2H), 4.12 (br s, 2H).

Reference Example 78 tert-Butyl {[1-(3-ethylpentyl)-5-oxo-4,5-dihydro-1H-pyrazol-3-yl]methyl}methylcarbamate

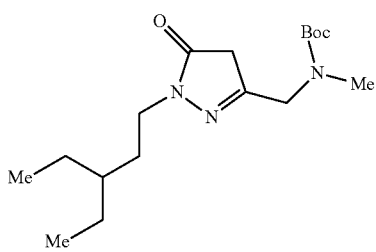 [SMILES: CCC(CC)CCN1N=C(CN(C)C(=O)OC(C)(C)C)CC1=O]

$^1$H-NMR (400 MHz, CDCl$_3$) δ: 0.83 (6H, t, J=8.0 Hz), 1.14-1.33 (5H, m), 1.44 (9H, s), 1.56-1.62 (2H, m), 2.83 (3H, s), 3.19 (2H, s), 3.62 (2H, t, J=8.0 Hz, 8.0 Hz), 4.07-4.10 (2H, m).

Reference Example 79 tert-Butyl ({1-[2-(1-hydroxycyclopentyl)ethyl]-5-oxo-4,5-dihydro-1H-pyrazol-3-yl}methyl)methylcarbamate

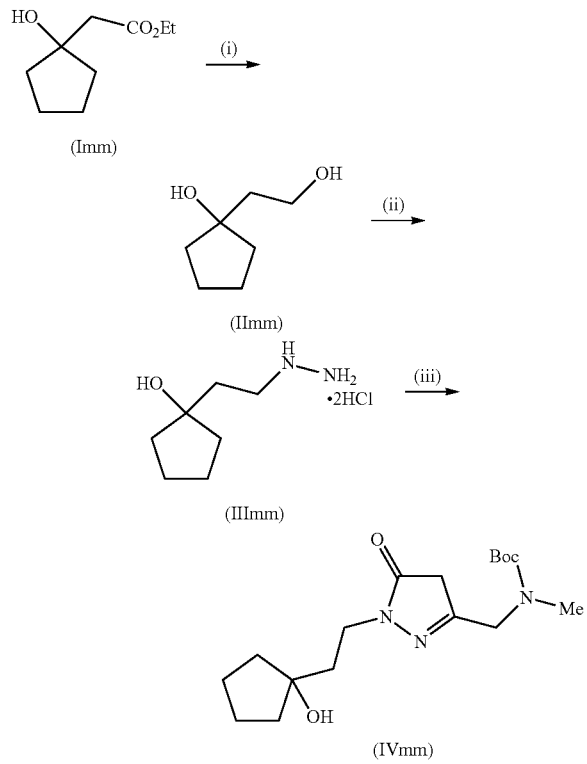

Step (i)

To a suspension of lithium aluminum hydride (1.83 g, 48 mmol) in anhydrous tetrahydrofuran (mL) was added dropwise a solution of Compound (Imm) prepared according to the method disclosed in Journal of Organic Chemistry, 69(3), 2004, 997 (4.16 g, 24 mmol) in anhydrous tetrahydrofuran (mL) with heating under reflux, and then the reaction mixture was heated under reflux for 1 hour. To the mixture was added sat. aq. Na$_2$SO$_4$ (7.3 mL) with cooling in an ice bath, and the mixture was stirred for 2 hours with slowly warming to room temperature. To the mixture was further added anhydrous Na$_2$SO$_4$, the solid was filtered off, and the filtrate was concentrated. The concentrated residue was purified by silica gel column chromatography (n-hexane:ethyl acetate=1:4→ethyl acetate→chloroform:methanol=10:1) to give Compound (IImm) (1.04 g, 66%) as a colorless oil.

Steps (ii) to (iii)

To a solution of the Compound (IImm) (0.97 g, 7.5 mmol) and triethylamine (1.56 g, 11 mmol) in dichloromethane (15 mL) was added methanesulfonyl chloride (692 µL, 8.9 mmol) over 5 minutes with ice-cooling, and the reaction mixture was stirred at ice temperature for 20 minutes. To the mixture was added water, the mixture was extracted with chloroform, the organic layer was washed with brine and dried over anhydrous Na$_2$SO$_4$, and the solvent was evaporated under reduced pressure to give a concentrated residue (1.59 g), which was used in the next step without further purification. The concentrated residue (1.59 g) and hydrazine monohydrate (2.2 mL, 45 mmol) were dissolved in ethanol (7.5 mL), and the mixture was stirred at 50° C. for 3 hours. The mixture was cooled to room temperature, water (1 mL) was added thereto, the mixture was extracted with chloroform, and the organic layer was washed with water and dried over anhydrous Na$_2$SO$_4$. To the organic layer was added 4 N HCl-1,4-dioxane (7.5 mL), and the solvent was evaporated under reduced pressure to give a crude product of Compound (IIImm) (2.05 g), which was used in the next step without further purification. The resulting Compound (IIImm) and triethylamine (1.3 mL, 9.0 mmol) were dissolved in ethanol (7 ml), and the mixture was stirred at 50° C. for 10 minutes. To the mixture was added the Compound (IIa) (1.35 g, 5.2 mmol) in Reference Example 1, and the reaction mixture was stirred at 70° C. for 30 minutes. The mixture was cooled to room temperature, 5% aq. KHSO$_4$ (50 mL) was added thereto, the mixture was extracted with ethyl acetate (100 mL), the organic layer was dried over anhydrous Na$_2$SO$_4$, and the solvent was evaporated under reduced pressure. The concentrated residue was purified by silica gel column chromatography to give the title Compound (IVmm) (217 mg, 37%) as a light brown solid.

$^1$H-NMR (CDCl$_3$) δ: 1.43-1.88 (8H, m), 1.47 (9H, s), 1.95 (2H, t, J=6.9 Hz), 2.87 (3H, s), 3.23 (2H, s), 3.87 (2H, t, J=6.9 Hz), 4.12 (2H, br s). 1H unditected (OH)

Reference Example 80 tert-Butyl methyl[(5-oxo-1-{[1-(trifluoromethyl)cyclopropyl]methyl}-4,5-dihydro-1H-pyrazol-3-yl)methyl]carbamate

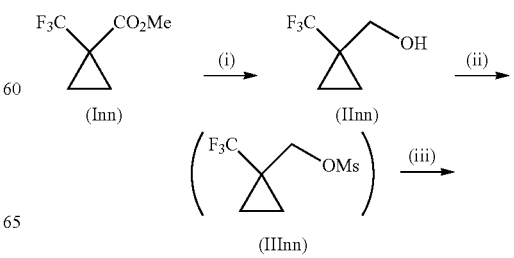

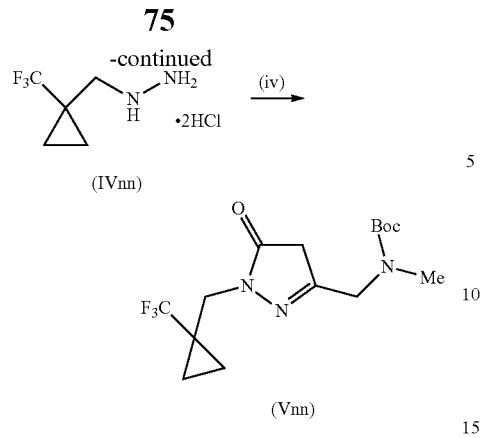

Steps (i) to (iii)

To a suspension of lithium aluminum hydride (903 mg, 23.8 mmol) in tetrahydrofuran (40 mL) was added dropwise Compound (Inn) (2.00 g, 11.9 mmol) with ice-cooling, and the reaction mixture was stirred with ice-cooling for 1 hour. To the reaction mixture were added water (0.9 mL) and 15% aq. NaOH (0.9 mL), and then water (4.5 mL) was further added thereto. The mixture was stirred with slowly warming to room temperature and the resulting precipitate was filtered off. The filtrate was dried over anhydrous $Na_2SO_4$, and the solvent was evaporated under reduced pressure to give a crude product of Compound (IInn) (1.31 g, equivalent to 9.4 mmol), which was used in the next step without further purification.

The resulting Compound (IInn) and triethylamine (2.0 mL, 14 mmol) were dissolved in tetrahydrofuran (19 mL), to the solution was added methanesulfonyl chloride (871 µL, 11 mmol) at ice temperature, and the reaction mixture was stirred at the same condition for 1.5 hours. The mixture was partitioned between ethyl acetate and water, and the organic layer was washed with brine and dried over anhydrous $Na_2SO_4$. The solvent was evaporated under reduced pressure to give a crude product of Compound (IIInn) (1.77 g), which was used in the next step without further purification.

The resulting Compound (IIInn) and hydrazine monohydrate (2.2 mL, 45 mmol) were dissolved in ethanol (7 mL), and the reaction mixture was stirred at ° C. for 3 hours. The mixture was cooled to room temperature, and partitioned between chloroform (40 mL) and water (2 mL). The chloroform layer was washed with water (2 mL) and dried over anhydrous $Na_2SO_4$. To the resultant was added 10% HCl-methanol (20 mL), and the solvent was evaporated under reduced pressure. To the concentrated residue was added diethyl ether (3 mL), and the resulting precipitate was collected by filtration and dried under reduced pressure to give Compound (IVnn) (1.00 g, 44%).

Step (iv)

Compound (Vnn) was prepared in the same manner as in Reference Example 1.

$^1$H-NMR (300 MHz, $CDCl_3$) δ: 0.87-0.95 (m, 2H), 1.00-1.08 (m, 2H), 1.47 (s, 9H), 2.86 (s, 3H), 3.22 (s, 2H), 3.87 (s, 2H), 4.11 (br s, 2H).

The compounds of Reference Examples 81 and 82 were prepared in the same manner as in Reference Example 80.

Reference Example 81 tert-Butyl methyl[(5-oxo-1-{[1-(trifluoromethyl)cyclobutyl]methyl}-4,5-dihydro-1H-pyrazol-3-yl)methyl]carbamate

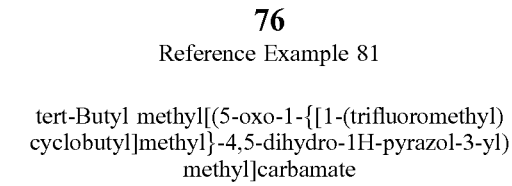

$^1$H-NMR (300 MHz, $CDCl_3$) δ: 1.47 (s, 9H), 1.81-2.04 (m, 2H), 2.14-2.39 (m, 4H), 2.86 (s, 3H), 3.25 (s, 2H), 3.93 (s, 2H), 4.12 (br s, 2H).

Reference Example 82 tert-Butyl methyl[(5-oxo-1-{[1-(trifluoromethyl)cyclopentyl]methyl}-4,5-dihydro-1H-pyrazol-3-yl)methyl]carbamate

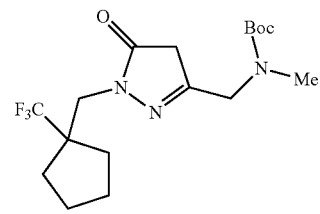 [SMILES: CN(CC1=NN(CC2(C(F)(F)F)CCCC2)C(=O)C1)C(=O)OC(C)(C)C]

$^1$H-NMR (300 MHz, $CDCl_3$) δ: 1.47 (s, 9H), 1.54-1.76 (m, 4H), 1.79-1.99 (m, 4H), 2.86 (s, 3H), 3.22 (s, 2H), 3.82 (s, 2H), 4.12 (br s, 2H).

The compounds of Reference Examples 83 and 84 were prepared in the same manner as in Reference Example 31.

Reference Example 83 tert-Butyl methyl{1-[1-(3-methylbutyl)-5-oxo-4,5-dihydro-1H-pyrazol-3-yl]-ethyl}carbamate

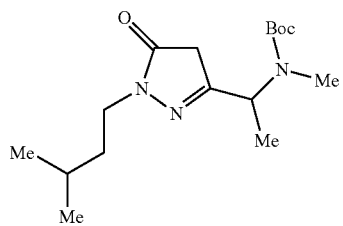 [SMILES: CC(C)CCN1N=C(C(C)N(C)C(=O)OC(C)(C)C)CC1=O]

$^1$H-NMR (400 MHz, $CDCl_3$) δ: 0.91 (6H, d, J=8.0 Hz), 1.37 (3H, d, J=8.0 Hz), 1.44 (9H, s), 1.51-1.60 (3H, m), 2.65 (3H, s), 3.13 (2H, br s), 3.60-3.66 (2H, m), 4.78 and 5.06 (1H, br s).

Reference Example 84 tert-Butyl methyl{1-[1-(4-methylpentyl)-5-oxo-4,5-dihydro-1H-pyrazol-3-yl]ethyl}carbamate

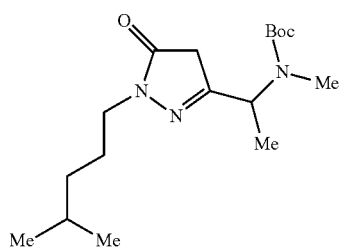 [SMILES: CC(C)CCCN1N=C(C(C)N(C)C(=O)OC(C)(C)C)CC1=O]

$^1$H-NMR (400 MHz, CDCl$_3$) δ: 0.85 (6H, t, J=6.6 Hz), 1.12-1.18 (2H, m), 1.37 (3H, d, J=8.0 Hz), 1.44 (9H, s), 1.50-1.57 (1H, m), 1.60-1.68 (2H, m), 2.65 (3H, s), 3.14 (2H, br s), 3.56-3.61 (2H, m), 4.78 and 5.07 (1H, br).

Reference Example 85

Ethyl 1-(cyclopentylmethyl)-5-hydroxy-1H-pyrazole-3-carboxylate

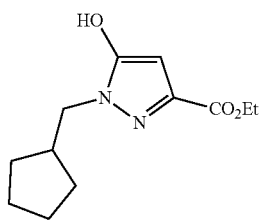 [SMILES: CCOC(=O)c1cc(O)n(CC2CCCC2)n1]

To a solution of the Compound (IIff) (77.6 g, 370 mmol) in Reference Example 65 in ethanol (504 g) was added dropwise triethylamine (92.5 g, 910 mmol) at room temperature over 10 minutes, to the mixture was added Compound (Ib) disclosed in Example 1 below (92.2 g, 440 mmol), and the reaction mixture was stirred at 30° C. for 5.5 hours. To the reaction mixture were added water (481 g) and conc. HCl (36%, 100 g) with keeping the internal temperature below 30° C., and the ethanol was evaporated under reduced pressure. To the concentrated residue was added t-butyl methyl ether (660 g), and the organic layer was washed with water (489 g) and then concentrated under reduced pressure. To the concentrated residue (123 g) was added acetonitrile (310 g), and the mixture was heated at 70° C. After the solid was dissolved, the mixture was cooled to 60° C. The resulting precipitate was stirred at 60° C. for 1 hour, cooled to 5° C. (internal temperature) over 2 hours, and then stirred at 5° C. for 1 hour. The resulting precipitate was collected by filtration and washed with cold acetonitrile (23 g×3) to give the title compound (52.2 g, 60%) as a light brown powder.

$^1$H-NMR (300 MHz, DMSO) δ: 1.16-1.37 (m, 5H), 1.39-1.68 (m, 6H), 2.22-2.43 (m, 1H), 3.82 (d, J=7.5 Hz, 2H), 4.19 (q, J=7.1 Hz, 2H), 5.74 (s, 1H), 11.34 (br s, 1H).

Reference Example 86 tert-Butyl methyl{[1-(3-methylbutyl)-5-oxo-4,5-dihydro-1H-pyrazol-3-yl]methyl}carbamate

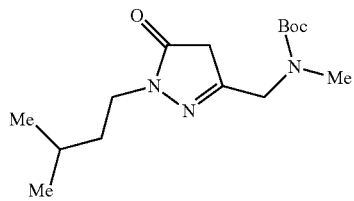 [SMILES: CC(C)CCN1N=C(CN(C)C(=O)OC(C)(C)C)CC1=O]

A solution of the title compound in Reference Example 67 (6.00 g, 30 mmol) and triethylamine (10.5 mL, 75 mmol) in ethanol (60 mL) was stirred at room temperature for 10 minutes, to the mixture was added the Compound (IIa) in Reference Example 1 (8.19 g, 30 mmol) at 60° C., and the reaction mixture was stirred at 70° C. for 1 hour. The mixture was cooled to room temperature, 5% KHSO$_4$ (140 mL) was added thereto to adjust the pH to around pH 4, and the ethanol was evaporated under reduced pressure to give a concentrated residue (160 g). To the residue was added ethyl acetate (120 mL), the aqueous layer was re-extracted with ethyl acetate (20 mL), the combined organic layers were dried over anhydrous MgSO$_4$, and the solvent was evaporated under reduced pressure. To the concentrated residue was added ethyl acetate (30 mL), and the mixture was heated to 70° C. After the solution was homogeneous, n-hexane (60 mL) was added dropwise to the solution at 70° C. The solution was slowly cooled to room temperature, and to the solution were added seed crystals (5 mg) of the title compound. The mixture was stirred at room temperature for 1 hour, and then at ice temperature for 1 hour. The resulting precipitate was collected by filtration, washed with a mixed solution of cooled ethyl acetate/n-hexane (1:2, 12 mL), and dried under reduced pressure to give the title compound (6.33 g, 71%) as a white solid.

Reference Example 87

Ethyl 5-hydroxy-1-(3-methylbutyl)-1H-pyrazole-3-carboxylate

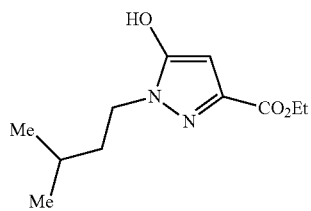 [SMILES: CCOC(=O)c1cc(O)n(CCC(C)C)n1]

A solution of the title compound in Reference Example 67 (50 g, 250 mmol) and triethylamine (87 mL, 620 mmol) in ethanol (500 mL) was stirred at room temperature, and then the solution was homogeneous. To the solution was added Compound (Ib) disclosed in Example 1 below (63 g, 300 mmol), and the reaction mixture was stirred at room temperature for 2 hours. At ice temperature, the reaction mixture was added dropwise to a mixed solution of 1 N HCl (600 mL) and water (500 mL) with keeping the internal temperature below 20° C. The mixture was stirred for 1 hour with keeping the internal temperature at 5° C., and the resulting precipitate was collected by filtration and washed with cold water (100 mL). The resulting solid was dried under reduced pressure at 50° C. to give a crude crystal of the title compound (44.8 g), and acetonitrile (200 mL) was added thereto. The mixture was stirred for 1 hour at 75° C., stirred for 3 hours with cooling to room temperature, and then ice-cooled for 1 hour. The resulting precipitate was collected on a filter and washed with cold acetonitrile (20 mL) to give the title compound (38.3 g, 68%) as a light brown powder.

$^1$H-NMR (300 MHz, DMSO) δ: 0.88 (d, J=6.2 Hz, 6H), 1.24 (t, J=7.1 Hz, 3H), 1.37-1.53 (m, 1H), 1.57 (dd, J=14.3, 7.2 Hz, 2H), 3.91 (t, J=7.2 Hz, 2H), 4.19 (q, J=7.1 Hz, 2H), 5.74 (s, 1H), 11.37 (br s, 1H).

Example 1

1-[1-Benzyl-5-(benzyloxy)-1H-pyrazol-3-yl]-N-methylmethanamine hydrochloride

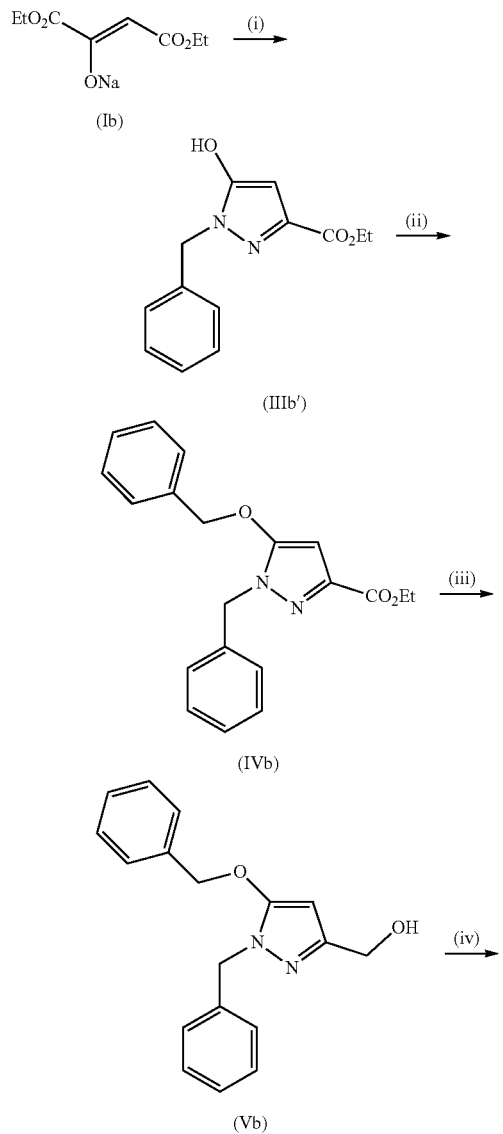

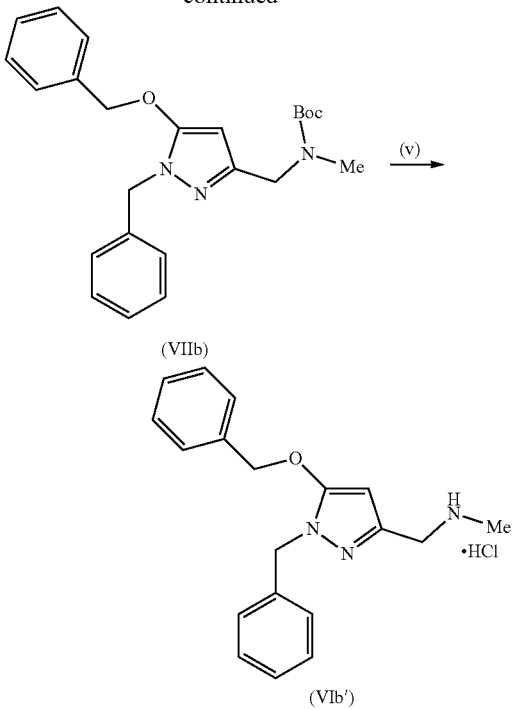

Steps (i) to (iii)

To a solution of Compound (IIIb') (710 mg, 2.9 mmol) prepared in the same manner as in Step (i) of Reference Example 31 except that benzylhydrazine and Compound (Ib) were used and K$_2$CO$_3$ (418 mg, 3.0 mmol) in DMF (8.6 mL) was added benzyl bromide (360 μL, 3.0 mmol) at room temperature, and the reaction mixture was stirred at room temperature overnight. The salt was filtered off, and the solvent was evaporated under reduced pressure to give a crude product of Compound (IVb), which was used in the next step without further purification. The resulting Compound (IVb) was dissolved in tetrahydrofuran (14 mL), to the solution was added lithium aluminum hydride (131 mg, 3.5 mmol) in small portions at 0° C., and the reaction mixture was stirred for 30 minutes. To the reaction solution were added water (150 μL), 2 mol/L aq. NaOH (150 μL) and water (450 μL), the mixture was stirred at room temperature, and the resulting precipitate was filtered off through Celite. The filtrate was concentrated, and the concentrated residue was purified by silica gel column chromatography (n-hexane:ethyl acetate=50:50→ethyl acetate) to give Compound (Vb) (608 mg, 72%).

Step (iv)

To a solution of the Compound (Vb) (607 mg, 2.1 mmol) and triethylamine (282 μL, 2.0 mmol) in dichloromethane (6.2 mL) was added methanesulfonyl chloride (239 μL, 3.1 mmol) at 0° C., and the reaction mixture was stirred at the same condition for 30 minutes. To the resultant was added 40% methylamine-methanol (6.2 mL) in small portions, and the reaction mixture was stirred overnight with slowly warming to room temperature. To the resultant was added sat. aq. NaHCO$_3$, the mixture was extracted with chloroform, the organic layer was dried over anhydrous Na$_2$SO$_4$, and the solvent was evaporated under reduced pressure to give a crude product, which was used in the next step without further purification. To a solution of the crude product and triethylamine (282 μL, 2.0 mmol) in dichloromethane (10 mL) was added di-tert-butyl dicarbonate (900 mg, 4.1 mmol) at room temperature, and the reaction mixture was stirred at room temperature for 30 minutes. To the resultant was added sat. aq. NaHCO₃, the mixture was extracted with chloroform, the organic layer was dried over anhydrous Na₂SO₄, and the solvent was evaporated under reduced pressure to give a concentrated residue. The residue was purified by silica gel column chromatography (n-hexane:ethyl acetate=95:5→60:40) to give Compound (VIIb) (643 mg, 76%).

Step (v)

To a solution of the Compound (VIIb) (120 mg, 0.29 mmol) in chloroform (0.3 mL) was added 4 mol/L HCl/1,4-dioxane (0.9 mL) at room temperature, and the reaction solution was stirred at room temperature for 1 hour. The solvent was evaporated under reduced pressure, the concentrated residue was purified by adding diethyl ether and removing the supernatant by decantation, and the resultant solid was evaporated under reduced pressure to give the title Compound (VIb') (102 mg, quantitative) as a white powder.

¹H-NMR (300 MHz, CD₃OD) δ: 2.67 (3H, s), 4.05 (2H, br s), 5.17 (2H, br s), 5.18 (2H, br s), 5.85 (1H, s), 7.17 (2H, dd, J=7.3, 2.2 Hz), 7.25-7.31 (3H, m), 7.33 (5H, br s). Obs MS [M+1]: 308.4

Examples 2 to 7

The compounds of Examples 2 to 7 as shown in Table 1 were prepared in the same manner as in Example 1.

TABLE 1

| Ex. | R | Salt |
|---|---|---|
| 2 | * —CH₂CH₂—phenyl | Free base |
| 3 | * —CH₂CH₂CH₂—phenyl | Free base |
| 4 | * —CH₂—cyclopentyl | Free base |
| 5 | * —CH₂—cyclohexyl | Free base |
| 6 | * —CH₂—cycloheptyl | Free base |

TABLE 1-continued

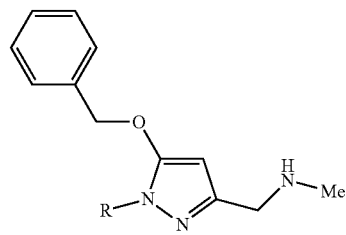

| Ex. | R | Salt |
|---|---|---|
| 7 | * —CH₂—tetrahydropyran-2-yl | Free base |

(* shows the bonding position)

Example 2

1-[5-(Benzyloxy)-1-(2-phenylethyl)-1H-pyrazol-3-yl]-N-methylmethanamine

¹H-NMR (400 MHz, CDCl₃) δ: 2.47 (3H, s), 3.06 (2H, t, J=7.4 Hz), 3.67 (2H, s), 4.15 (2H, t, J=7.4 Hz), 4.88 (2H, s), 5.49 (1H, s), 7.08 (2H, dt, J=7.1, 2.3 Hz), 7.17-7.28 (4H, m), 7.32-7.41 (4H, m).

Obs MS [M+1]: 322.4

Example 3

1-[5-(Benzyloxy)-1-(3-phenylpropyl)-1H-pyrazol-3-yl]-N-methylmethanamine

¹H-NMR (400 MHz, CDCl₃) δ: 2.04-2.14 (2H, m), 2.46 (3H, s), 2.56-2.62 (2H, m), 3.65 (2H, s), 3.96 (2H, t, J=7.1 Hz), 5.05 (2H, s), 5.55 (1H, s), 7.12-7.44 (10H, m).

Example 4

1-[5-(Benzyloxy)-1-(cyclopentylmethyl)-1H-pyrazol-3-yl]-N-methylmethanamine

¹H-NMR (400 MHz, CDCl₃) δ: 1.20-1.29 (2H, m), 1.47-1.69 (6H, m), 2.35-2.44 (1H, m), 2.45 (3H, br s), 3.64 (2H, s), 3.84 (2H, d, J=7.6 Hz), 5.05 (2H, s), 5.53 (1H, s), 0.7.34-7.42 (5H, m).

Obs MS [M+1]: 300.3

Example 5

1-[5-(Benzyloxy)-1-(cyclohexylmethyl)-1H-pyrazol-3-yl]-N-methylmethanamine

¹H-NMR (300 MHz, CDCl₃) δ: 0.94 (2H, dd, J=23.6, 11.5 Hz), 1.13-1.20 (3H, m), 1.53-1.72 (5H, m), 1.79-1.91 (1H, m), 2.46 (3H, s), 3.64 (2H, s), 3.75 (2H, d, J=7.3 Hz), 5.05 (2H, s), 5.52 (1H, s), 7.35-7.40 (5H, m).

Obs MS [M+1]: 314.3

Example 6

1-[5-(Benzyloxy)-1-(cycloheptylmethyl)-1H-pyrazol-3-yl]-N-methylmethanamine $^1$H-NMR (300 MHz, CDCl$_3$) δ: 1.12-1.21 (2H, m), 1.41-1.57 (10H, m), 2.06-2.10 (1H, m), 2.45 (3H, s), 3.64 (2H, s), 3.73 (2H, d, J=7.5 Hz), 5.05 (2H, s), 5.52 (1H, s), 7.35-7.41 (5H, m).
Obs MS [M+1]: 328.6

Example 7

1-[5-(Benzyloxy)-1-(tetrahydro-2H-pyran-2-ylmethyl)-1H-pyrazol-3-yl]-N-methylmethanamine $^1$H-NMR (400 MHz, CDCl$_3$) δ: 1.21-1.34 (1H, m), 1.37-1.61 (4H, m), 1.81 (1H, br d, J=10.1 Hz), 2.45 (3H, br s), 3.39 (1H, td, J=11.4, 2.6 Hz), 3.64 (2H, s), 3.66-3.78 (1H, m), 3.85 (1H, dd, J=13.9, 5.9 Hz), 3.93-4.00 (1H, m), 4.06 (1H, dd, J=13.8, 6.9 Hz), 5.07 (2H, s), 5.52 (1H, s), 7.33-7.41 (5H, m).

Example 8

1-{1-Benzyl-5-[(2-chlorobenzyl)oxy]-1H-pyrazol-3-yl}-N-methylmethanamine hydrochloride

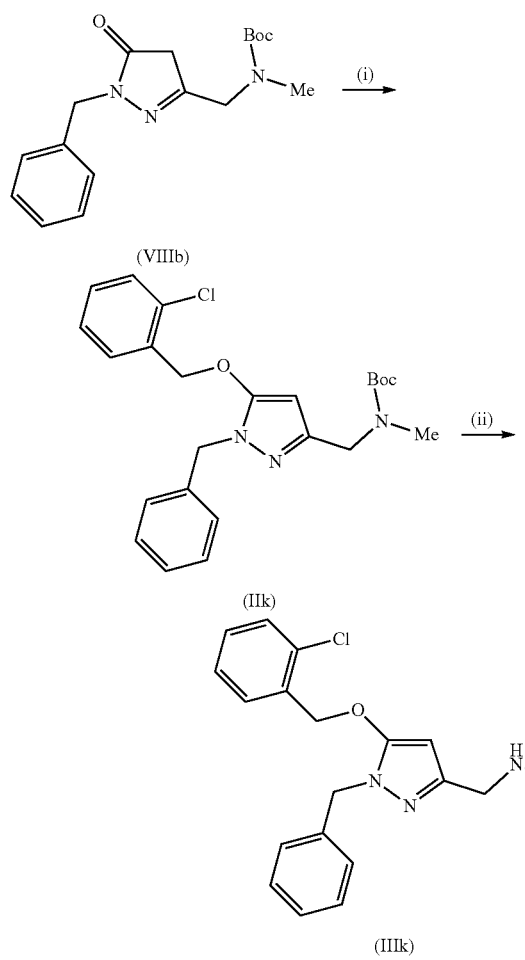

Step (i)

To a solution of the Compound (VIIIb) prepared in Reference Example 36 (20 mg, 0.063 mmol) and cesium carbonate (31 mg, 0.95 mmol) in DMF (0.2 mL) was added 2-chlorobenzyl chloride (12 µL, 0.095 mmol) at 0° C., and the reaction mixture was stirred overnight with slowly warming to room temperature. The salt was filtered off, the filtrate was concentrated, and the concentrated residue was purified by PTLC (toluene:ethyl acetate=30:70) to give the title Compound (IIk) (24 mg, 85%).

Step (ii)

To a solution of the Compound (IIk) (24 mg, 0.054 mmol) in chloroform (0.5 mL) was added 4 mol/L HCl/1,4-dioxane (0.5 mL) at room temperature, and the reaction solution was stirred at room temperature for 30 minutes. The solvent was evaporated under reduced pressure, the concentrated residue was purified by adding diethyl ether and removing the supernatant by decantation, and the resultant solid was evaporated under reduced pressure to give the title Compound (IIIk) (20 mg, 97%) as a white powder.

$^1$H-NMR (300 MHz, DMSO-d$_6$) δ: 2.54 (3H, br s), 4.00 (2H, s), 5.15 (2H, s), 5.26 (2H, s), 6.00 (1H, s), 7.15 (2H, td, 3.9, 2.0 Hz), 7.24-7.45 (5H, m), 7.53 (2H, dt, J=7.5, 1.7 Hz), 8.91 (2H, br s).
Obs MS [M+1]: 342.3

Examples 9 to 13

The compounds of Examples 9 to 13 as shown in Table 2 were prepared in the same manner as in Example 8 except that a corresponding benzyl bromide or benzyl chloride was used.

TABLE 2

| Ex. | X | Obs MS [M + 1] |
|-----|------|----------------|
| 9   | 3-Cl | 342.3 |
| 10  | 4-Cl | 342.3 |
| 11  | 2-Me | 322.4 |
| 12  | 3-Me | 322.4 |
| 13  | 4-Me | 322.4 |

Examples 14 to 19

The compounds of Examples 14 to 19 as shown in Table 3 were prepared in the same manner as in Example 8 except that the compound obtained in Reference Example 37 and a corresponding benzyl bromide or benzyl chloride were used.

TABLE 3

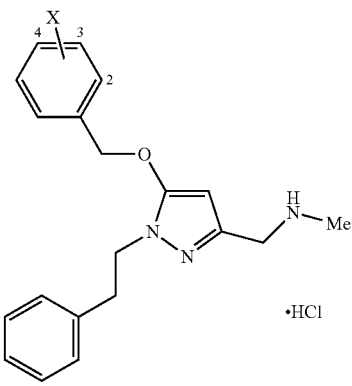

| Ex. | X | Obs MS [M + 1] |
|---|---|---|
| 14 | 2-Cl | 356.3 |
| 15 | 3-Cl | 356.3 |
| 16 | 4-Cl | 356.3 |
| 17 | 2-Me | 336.4 |
| 18 | 3-Me | 336.4 |
| 19 | 4-Me | 336.4 |

Examples 20 to 40

According to the general process below, the compounds of Examples 20 to 40 as shown in Table 4 were prepared.

General Process of Compound (IIIm)

Compound (Im) prepared in Reference Example 4 and a corresponding benzyl bromide or benzyl chloride were used to prepare Compound (IIIm). Step (i) was carried out by any of the following Method A, B or C.

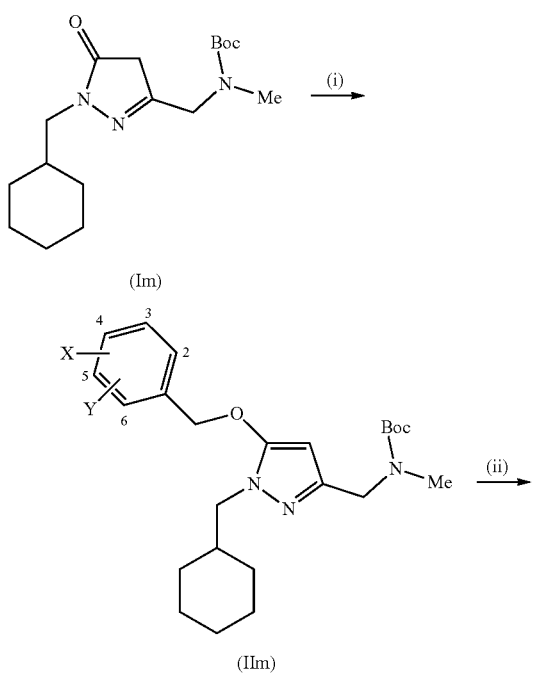

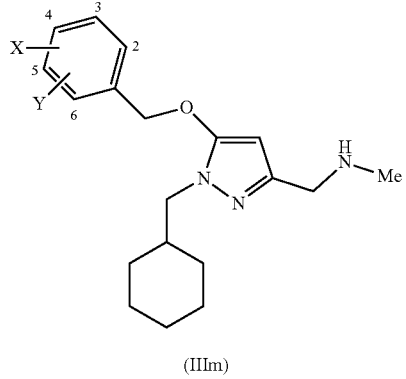

(IIIm)

Step (i): Alkylation Reaction

Method A:

To a solution of Compound (Im) prepared in Reference Example 4 (20 mg, 0.063 mmol) and cesium carbonate (1.5 equivalent, 31 mg, 0.095 mmol) in dimethylformamide (0.2 mL) was added a corresponding benzyl chloride (1.5 equivalent, 0.095 mmol) at 0° C., and the reaction mixture was stirred for 2 days with slowly warming to room temperature. The salt was filtered off, and the solvent was evaporated under reduced pressure to give a crude product of Compound (IIm). If necessary, the crude product of Compound (IIm) was purified by silica gel column chromatography (n-hexane:ethyl acetate=50:50) or PTLC (toluene:ethyl acetate=70:30).

Method B:

To a solution of Compound (Im) (100 mg, 0.31 mmol) and silver oxide (79 mg, 0.34 mmol) in acetonitrile (1 mL) was added a solution of a corresponding benzyl bromide (1.5 equivalent, 0.46 mmol) in acetonitrile (2 mL) at room temperature, and the reaction mixture was stirred at room temperature for 2 hours. To the solution was added ethyl acetate, the salt was filtered off, and the filtrate was concentrated to give a crude product of Compound (IIm). If necessary, the crude product of Compound (IIm) was purified by silica gel column chromatography (n-hexane ethyl acetate=50:50) or PTLC (toluene:ethyl acetate=70:30).

Method C:

To a solution of Compound (Im) (100 mg, 0.31 mmol) and cesium carbonate (1.5 equivalent, 151 mg, 0.46 mmol) in acetonitrile (1 mL) was added a solution of a corresponding benzyl bromide (1.5 equivalent, 0.46 mmol) in acetonitrile (2 mL) at room temperature, and the reaction mixture was stirred at room temperature for 18 hours. To the solution was added ethyl acetate, the salt was filtered off, and the filtrate was concentrated to give a crude product of Compound (IIm). If necessary, the crude product of Compound (IIm) was purified by silica gel column chromatography (n-hexane:ethyl acetate=50:50) or PTLC (toluene:ethyl acetate=70:30).

Step (ii): Deprotection of N-Boc Group

The Compound (IIm) was dissolved in chloroform (1 mL), 4 mol/L HCl/1,4-dioxane (2 mL) was added to the solution at room temperature, the reaction mixture was stirred for 2 hours, and the solvent was evaporated under reduced pressure. The residue was purified by adding diethyl ether and removing the supernatant by decantation, and the resulting solid was dried under reduced pressure to give a hydrochloride of Compound (IIIm). If necessary, the concentrated residue was purified by reversed-phase liquid chromatography (0.05% trifluoroacetic acid→acetonitrile/0.05% trifluoroacetic acid/water) to give a fraction of Compound (IIIm), and the compound in the fraction was converted to a free base of Compound (IIIm) by a typical method.

The reversed-phase liquid chromatography can be carried out under, for example, the following conditions:
Apparatus: Parallex Flex (trademark) (Biotage, Inc)
Column: YMC Combiprep ODS-A 50×30 mm I.D.
Moving bed:
Solution A; 0.07% trifluoroacetic acid-acetonitrile
Solution B; 0.1% trifluoroacetic acid-$H_2O$
Gradient program: The mixture ratio of Solution A and Solution B was initially A:B=1:99, and the proportion of Solution A was increased 8.55% per 1 minute so that the ratio can be A:B=95:5 after 11 minutes.

Flow rate of the moving bed: 40 mL/min

TABLE 4

(IIIm)

| Ex. | X | Y | Benzylation method | Salt | Obs MS [M + 1] |
|---|---|---|---|---|---|
| 20 | 2-F | H | C | Free base | 332.5 |
| 21 | 3-F | H | C | Free base | 332.5 |
| 22 | 4-F | H | C | Free base | 332.5 |
| 23 | 2-Cl | H | A | Hydrochloride | 348.5 |
| 24 | 3-Cl | H | A | Hydrochloride | 348.5 |
| 25 | 4-Cl | H | A | Hydrochloride | 348.5 |
| 26 | 2-Me | H | A | Hydrochloride | 328.3 |
| 27 | 3-Me | H | A | Hydrochloride | 328.6 |
| 28 | 4-Me | H | A | Hydrochloride | 328.6 |
| 29 | 2-F | 4-F | C | Free base | 350.2 |
| 30 | 2-Cl | 4-F | C | Free base | 366.2 |
| 31 | 2-Me | 4-F | C | Free base | 346.2 |
| 32 | 2-CN | 4-F | C | Hydrochloride | 357.4 |
| 33 | 2-F | 5-F | B | Hydrochloride | 350.7 |
| 34 | 2-F | 5-Cl | B | Hydrochloride | 366.1 |
| 35 | 2-F | 5-Me | B | Hydrochloride | 346.2 |
| 36 | 2-F | 5-MeO | B | Hydrochloride | 362.5 |
| 37 | 2-Cl | 5-F | B | Hydrochloride | 366.1 |
| 38 | 2-Cl | 5-Cl | B | Hydrochloride | 382.4 |
| 39 | 2-Cl | 5-Me | C | Free base | 362.5 |
| 40 | 2-Cl | 5-MeO | C | Free base | 378.5 |

Example 20

1-{1-(Cyclohexylmethyl)-5-[(2-fluorobenzyl)oxy]-1H-pyrazol-3-yl}-N-methylmethanamine $^1$H-NMR (300 MHz, $CDCl_3$) δ: 7.43 (ddd, 1H, J=7.5, 7.5, 1.7 Hz), 7.39-7.30 (m, 1H), 7.17 (ddd, 1H, J=7.5, 7.5, 1.1 Hz), 7.10 (ddd, 1H, J=9.7, 8.4, 1.1 Hz), 5.60 (s, 1H), 5.12 (s, 2H), 3.74 (d, 2H, J=7.2 Hz), 3.67 (s, 2H), 2.46 (s, 3H), 2.06 (brs, 1H), 1.92-1.75 (m, 1H), 1.75-1.51 (m, 5H), 1.29-1.04 (m, 3H), 1.02-0.84 (m, 2H).

Example 21

1-{1-(Cyclohexylmethyl)-5-[(3-fluorobenzyl)oxy]-1H-pyrazol-3-yl}-N-methylmethanamine $^1$H-NMR (300 MHz, $CDCl_3$) δ:7.36 (ddd, 1H, J=7.9, 7.9, 5.8 Hz), 7.18-7.00 (m, 3H), 5.56 (s, 1H), 5.05 (s, 2H), 3.76 (d, 2H, J=7.3 Hz), 3.68 (s, 2H), 2.46 (s, 3H), 1.94-1.76 (m, 1H), 1.75-1.54 (m, 5H), 1.30-1.05 (m, 3H), 1.03-0.86 (m, 2H).

Example 22

1-{1-(Cyclohexylmethyl)-5-[(4-fluorobenzyl)oxy]-1H-pyrazol-3-yl}-N-methylmethanamine $^1$H-NMR (300 MHz, $CDCl_3$) δ:7.36 (dd, 2H, J=8.8, 5.3 Hz), 7.09 (dd, 2H, J=8.8, 8.8 Hz), 5.56 (s, 1H), 5.01 (s, 2H), 3.73 (d, 2H, J=7.2 Hz), 3.67 (s, 2H), 2.46 (s, 3H), 2.27 (brs, 1H), 1.92-1.75 (m, 1H), 1.75-1.52 (m, 5H), 1.28-1.04 (m, 3H), 1.01-0.84 (m, 2H).

Example 23

1-{5-[(2-Chlorobenzyl)oxy]-1-(cyclohexylmethyl)-1H-pyrazol-3-yl}-N-methylmethanamine hydrochloride $^1$H-NMR (400 MHz, DMSO-$d_6$) δ: 0.89 (2H, br dd, J=23.2, 12.0 Hz), 1.06-1.15 (3H, m), 1.47 (2H, d, J=12.7 Hz), 1.60 (3H, t, J=10.4 Hz), 1.71-1.74 (1H, m), 2.52 (3H, br s), 3.71 (2H, d, J=7.1 Hz), 3.96 (2H, br s), 5.21 (2H, s), 5.93 (1H, s), 7.38-7.45 (2H, m), 7.54 (1H, dd, J=7.3, 1.5 Hz), 7.60 (1H, dd, J=6.8, 2.4 Hz), 8.92 (2H, s).

Example 24

1-{5-[(3-Chlorobenzyl)oxy]-1-(cyclohexylmethyl)-1H-pyrazol-3-yl}-N-methylmethanamine hydrochloride $^1$H-NMR (400 MHz, DMSO-$d_6$) δ: 0.92 (2H, br q, J=11.5 Hz), 1.06-1.19 (3H, m), 1.49 (2H, d, J=12.4 Hz), 1.56-1.68 (3H, m), 1.69-1.79 (1H, m), 2.51 (3H, br s), 3.75 (2H, d, J=7.1 Hz), 3.95 (2H, br s), 5.19 (2H, s), 5.89 (1H, s), 7.42-7.46 (3H, m), 7.52 (1H, br s), 9.04 (2H, br s).

Example 25

1-{5-[(4-Chlorobenzyl)oxy]-1-(cyclohexylmethyl)-1H-pyrazol-3-yl}-N-methylmethanamine hydrochloride $^1$H-NMR (400 MHz, DMSO-$d_6$) δ: 0.89 (2H, br dd, J=22.0, 12.2 Hz), 1.05-1.18 (3H, m), 1.47 (2H, br d, J=11.5 Hz), 1.53-1.76 (4H, m), 2.51 (3H, br s), 3.72 (2H, d, J=6.8

Hz), 3.95 (2H, br s), 5.15 (2H, s), 5.85 (1H, s), 7.47 (4H, br d, J=1.0 Hz), 8.92 (2H, br s).

Example 26

1-{1-(Cyclohexylmethyl)-5-[(2-methylbenzyl)oxy]-1H-pyrazol-3-yl}-N-methylmethanamine hydrochloride ¹H-NMR (300 MHz, DMSO-d₆) δ: 0.90 (2H, br q, J=10.9 Hz), 1.03-1.19 (3H, m), 1.49 (2H, br d, J=13.2 Hz), 1.54-1.78 (4H, m), 2.35 (3H, s), 2.53 (3H, br s), 3.71 (2H, d, J=7.2 Hz), 3.97 (2H, s), 5.15 (2H, s), 5.96 (1H, s), 7.19-7.33 (3H, m), 7.40 (1H, br d, J=7.3 Hz), 9.01 (2H, br s).

Example 27

1-{1-(Cyclohexylmethyl)-5-[(3-methylbenzyl)oxy]-1H-pyrazol-3-yl}-N-methylmethanamine hydrochloride ¹H-NMR (300 MHz, DMSO-d₆) δ: 0.92 (2H, br q, J=11.2 Hz), 1.08-1.21 (3H, m), 1.49 (2H, br d, J=13.2 Hz), 1.56-1.80 (4H, m), 2.32 (3H, s), 2.50 (3H, br s), 3.73 (2H, d, J=7.2 Hz), 3.95 (2H, br t, J=5.0 Hz), 5.12 (2H, s), 5.87 (1H, s), 7.16-7.32 (4H, m), 8.97 (2H, br s).

Example 28

1-{1-(Cyclohexylmethyl)-5-[(4-methylbenzyl)oxy]-1H-pyrazol-3-yl}-N-methylmethanamine hydrochloride ¹H-NMR (300 MHz, DMSO-d₆) δ: 0.90 (2H, br dd, J=23.0, 11.6 Hz), 1.05-1.17 (3H, m), 1.48 (2H, br d, J=12.7 Hz), 1.55-1.75 (4H, m), 2.31 (3H, s), 2.51 (3H, br s), 3.71 (2H, d, J=7.1 Hz), 3.95 (2H, br s), 5.10 (2H, s), 5.89 (1H, s), 7.22 (2H, d, J=7.8 Hz), 7.33 (2H, d, J=8.0 Hz), 9.01 (2H, br s).

Example 29

1-{1-(Cyclohexylmethyl)-5-[(2,4-difluorobenzyl)oxy]-1H-pyrazol-3-yl}-N-methylmethanamine ¹H-NMR (300 MHz, CDCl₃) δ: 0.83-1.02 (2H, m), 1.05-1.29 (3H, m), 1.49-1.91 (6H, m), 2.46 (3H, s), 3.66 (2H, s), 3.72 (2H, d, J=7.3 Hz), 5.06 (2H, s), 5.57 (1H, s), 6.80-6.96 (2H, m), 7.34-7.46 (1H, m).

Example 30

1-{5-[(2-Chloro-4-fluorobenzyl)oxy]-1-(cyclohexylmethyl)-1H-pyrazol-3-yl}-N-methylmethanamine ¹H-NMR (400 MHz, CDCl₃) δ: 0.87-1.01 (2H, m), 1.07-1.28 (3H, m), 1.53-1.94 (6H, m), 2.48 (3H, s), 3.69 (2H, s), 3.75 (2H, d, J=7.3 Hz), 5.10 (2H, s), 5.60 (1H, s), 7.00-7.07 (1H, m), 7.16-7.1 (1H, m), 7.42-7.48 (1H, m).

Example 31

1-{1-(Cyclohexylmethyl)-5-[(4-fluoro-2-methylbenzyl)oxy]-1H-pyrazol-3-yl}-N-methylmethanamine ¹H-NMR (400 MHz, CDCl₃) δ: 0.84-0.99 (2H, m), 1.05-1.27 (3H, m), 1.50-1.90 (6H, m), 2.36 (3H, s), 2.48 (3H, s), 3.67 (2H, s), 3.71 (2H, d, J=7.3 Hz), 4.98 (2H, s), 5.58 (1H, s), 6.87-6.99 (2H, m), 7.28-7.34 (1H, m).

Example 32

2-[({1-(Cyclohexylmethyl)-3-[(methylamino)methyl]-1H-pyrazol-5-yl}oxy)methyl]-5-fluorobenzonitrile hydrochloride ¹H-NMR (300 MHz, DMSO-d₆) δ: 0.77-1.00 (2H, m), 1.01-1.22 (3H, m), 1.41-1.53 (2H, m), 1.53-1.68 (3H, m), 1.68-1.82 (1H, m), 2.54 (3H, t, J=5.3 Hz), 3.73 (2H, d, J=7.0 Hz), 3.98 (2H, t, J=5.7 Hz), 5.30 (2H, s), 5.97 (1H, s), 7.68 (1H, ddd, J=8.6, 8.6, 2.8 Hz), 7.83 (1H, dd, J=8.6, 5.5 Hz), 8.00 (1H, dd, J=8.6, 2.8 Hz), 8.95 (2H, brs).

Example 33

1-{1-(Cyclohexylmethyl)-5-[(2,5-difluorobenzyl)oxy]-1H-pyrazol-3-yl}-N-methylmethanamine hydrochloride ¹H-NMR (300 MHz, DMSO-d₆) δ: 0.80-0.98 (2H, m), 1.03-1.21 (3H, m), 1.42-1.52 (2H, m), 1.54-1.80 (4H, m), 2.52 (3H, t, J=5.3 Hz), 3.72 (2H, d, J=7.2 Hz), 3.97 (2H, t, J=5.6 Hz), 5.20 (2H, s), 5.96 (1H, s), 7.26-7.48 (3H, m), 9.03 (2H, brs).

Example 34

1-{5-[(5-Chloro-2-fluorobenzyl)oxy]-1-(cyclohexylmethyl)-1H-pyrazol-3-yl}-N-methylmethanamine hydrochloride ¹H-NMR (300 MHz, DMSO-d₆) δ: 0.81-1.00 (2H, m), 1.04-1.22 (3H, m), 1.41-1.53 (2H, m), 1.54-1.80 (4H, m), 2.52-2.56 (3H, m), 3.72 (2H, d, J=7.2 Hz), 3.94-4.03 (2H, m), 5.22 (2H, s), 5.93 (1H, s), 7.36 (1H, t, J=9.2 Hz), 7.49-7.57 (1H, m), 7.62-7.68 (1H, m), 8.92 (2H, br s).

Example 35

1-{1-(Cyclohexylmethyl)-5-[(2-fluoro-5-methylbenzyl)oxy]-1H-pyrazol-3-yl}-N-methylmethanamine hydrochloride ¹H-NMR (300 MHz, DMSO-d₆) δ: 0.79-0.99 (2H, m), 1.02-1.21 (3H, m), 1.40-1.52 (2H, m), 1.52-1.79 (4H, m), 2.29 (3H, s), 2.53 (3H, brs), 3.70 (2H, d, J=7.0 Hz), 3.96 (2H, t, J=5.5 Hz), 5.15 (2H, s), 5.96 (1H, s), 7.15 (1H, dd, J=10.0, 8.5 Hz), 7.21-7.28 (1H, m), 7.35 (1H, dd, J=7.2, 1.8 Hz), 9.06 (2H, brs).

Example 36

1-{1-(Cyclohexylmethyl)-5-[(2-fluoro-5-methoxybenzyl)oxy]-1H-pyrazol-3-yl}-N-methylmethanamine hydrochloride ¹H-NMR (400 MHz, DMSO-d₆) δ: 0.83-0.97 (2H, m), 1.03-1.19 (3H, m), 1.43-1.52 (2H, m), 1.53-1.78 (4H, m), 2.53 (3H, brs), 3.71 (2H, d, J=7.1 Hz), 3.75 (3H, s), 3.97 (2H, t, J=5.6 Hz), 5.17 (2H, s), 5.94 (1H, s), 6.98 (1H, ddd, J=8.9, 8.9, 3.7 Hz), 7.09 (1H, dd, J=6.0, 3.3 Hz), 7.21 (1H, dd, J=9.3, 9.3 Hz), 8.99 (2H, brs).

Example 37

1-{5-[(2-Chloro-5-fluorobenzyl)oxy]-1-(cyclohexyl-methyl)-1H-pyrazol-3-yl}-N-methylmethanamine hydrochloride $^1$H-NMR (300 MHz, DMSO-$d_6$) δ: 0.84-1.01 (2H, m), 1.04-1.22 (3H, m), 1.43-1.54 (2H, m), 1.55-1.83 (4H, m), 2.53 (3H, brs), 3.75 (2H, d, J=7.2 Hz), 3.97 (2H, t, J=5.0 Hz), 5.22 (2H, s), 5.95 (1H, s), 7.33 (1H, ddd, J=8.5, 8.5, 3.0 Hz), 7.49 (1H, dd, J=9.1, 3.0 Hz), 7.61 (1H, dd, J=8.9, 5.0 Hz), 8.97 (2H, brs).

Example 38

1-{1-(Cyclohexylmethyl)-5-[(2,5-dichlorobenzyl) oxy]-1H-pyrazol-3-yl}-N-methylmethanamine hydrochloride $^1$H-NMR (300 MHz, DMSO-$d_6$) δ: 0.83-1.00 (2H, m), 1.05-1.22 (3H, m), 1.43-1.54 (2H, m), 1.54-1.83 (4H, m), 2.53 (3H, brs), 3.74 (2H, d, J=7.2 Hz), 3.98 (2H, t, J=5.6 Hz), 5.22 (2H, s), 5.95 (1H, s), 7.52 (1H, dd, J=8.6, 2.6 Hz), 7.60 (1H, d, J=8.6 Hz), 7.68 (1H, d, J=2.6 Hz), 8.98 (2H, brs).

Example 39

1-{5-[(2-Chloro-5-methylbenzyl)oxy]-1-(cyclohex-ylmethyl)-1H-pyrazol-3-yl}-N-methylmethanamine $^1$H-NMR (300 MHz, CDCl$_3$) δ: 7.28 (d, 1H, J=8.3 Hz), 7.26 (s, 1H), 7.10 (dd, 1H, J=8.3, 1.7 Hz), 5.59 (s, 1H), 5.11 (s, 2H), 3.77 (d, 2H, J=7.3 Hz), 3.68 (s, 2H), 2.47 (s, 3H), 2.34 (s, 3H), 1.99 (brs, 1H), 1.96-1.80 (m, 1H), 1.75-1.55 (m, 5H), 1.29-1.05 (m, 3H), 1.05-0.88 (m, 2H).

Example 40

1-{5-[(2-Chloro-5-methylbenzyl)oxy]-1-(cyclohex-ylmethyl)-1H-pyrazol-3-yl}-N-methylmethanamine $^1$H-NMR (400 MHz, CDCl$_3$) δ: 0.91-1.02 (2H, m), 1.08-1.27 (3H, m), 1.59-1.74 (5H, m), 1.82-1.95 (1H, m), 2.46 (3H, s), 3.65 (2H, s), 3.78 (2H, d, J=7.3 Hz), 3.80 (3H, s), 5.11 (2H, s), 5.56 (1H, s), 6.83 (1H, dd, J=8.8, 3.1 Hz), 7.02 (1H, d, J=3.1 Hz), 7.30 (1H, d, J=8.8 Hz).

Examples 41 to 91

The compounds of Examples 41 to 91 as shown in Table 5 were prepared in the same manner as in Examples 20 to 40 by using the compound obtained in Reference Example 4 and a corresponding benzyl bromide or benzyl chloride.

TABLE 5

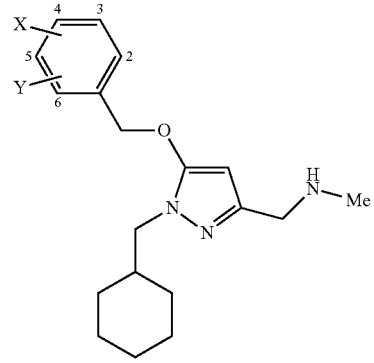

| Ex. | X | Y | Benzylation method | Salt | Obs MS [M + 1] |
|---|---|---|---|---|---|
| 41 | 2-MeO | H | A | Hydrochloride | 344.3 |
| 42 | 3-MeO | H | A | Hydrochloride | 344.3 |
| 43 | 4-MeO | H | A | Hydrochloride | 344.3 |
| 44 | 2-CF$_3$ | H | A | Hydrochloride | 382.4 |
| 45 | 3-CF$_3$ | H | A | Hydrochloride | 382.4 |
| 46 | 4-CF$_3$ | H | A | Hydrochloride | 382.4 |
| 47 | 2-CN | H | C | Hydrochloride | 339.2 |
| 48 | 3-CN | H | C | Free base | 339.2 |
| 49 | 4-CN | H | C | Free base | 339.2 |
| 50 | 2-F | 3-F | B | Hydrochloride | 350.4 |
| 51 | 2-F | 3-Cl | B | Hydrochloride | 366.1 |
| 52 | 2-F | 3-Me | B | Hydrochloride | 346.5 |
| 53 | 2-F | 3-MeO | B | Hydrochloride | 362.5 |
| 54 | 2-Cl | 3-F | B | Hydrochloride | 366.1 |
| 55 | 2-Cl | 3-Cl | C | Free base | 382.4 |
| 56 | 2-Cl | 3-Me | B | Hydrochloride | 362.2 |
| 57 | 2-Cl | 3-MeO | B | Hydrochloride | 378.5 |
| 58 | 2-Me | 3-F | B | Hydrochloride | 346.2 |
| 59 | 2-Me | 3-Cl | B | Hydrochloride | 362.2 |
| 60 | 2-Me | 3-Me | B | Hydrochloride | 342.3 |
| 61 | 2-MeO | 3-F | B | Hydrochloride | 362.5 |
| 62 | 2-MeO | 3-Cl | B | Hydrochloride | 378.5 |
| 63 | 2-Me | 5-F | B | Hydrochloride | 346.2 |
| 64 | 2-Me | 5-Cl | C | Free base | 362.2 |
| 65 | 2-Me | 5-Me | C | Free base | 342.3 |
| 66 | 2-MeO | 5-F | B | Hydrochloride | 362.2 |
| 67 | 2-MeO | 5-Cl | C | Free base | 378.5 |
| 68 | 2-F | 5-CN | C | Free base | 357.2 |
| 69 | 2-CN | 5-F | C | Free base | 357.4 |
| 70 | 2-F | 6-F | B | Hydrochloride | 350.4 |
| 71 | 2-F | 6-Cl | C | Free base | 367.5 |
| 72 | 2-Cl | 6-Cl | B | Hydrochloride | 382.4 |
| 73 | 2-Me | 6-F | C | Free base | 346.5 |
| 74 | 2-Me | 6-Cl | C | Free base | 362.2 |
| 75 | 2-Me | 6-Me | C | Hydrochloride | 342.3 |
| 76 | 2-MeO | 6-F | B | Hydrochloride | 363.6 |
| 77 | 2-MeO | 6-Cl | B | Hydrochloride | 378.5 |
| 78 | 3-F | 4-F | C | Free base | 350.4 |
| 79 | 3-Cl | 4-F | C | Free base | 342.3 |
| 80 | 3-Me | 4-F | C | Free base | 346.2 |
| 81 | 3-MeO | 4-F | C | Free base | 362.5 |
| 82 | 3-CN | 4-F | C | Free base | 357.4 |
| 83 | 3-F | 5-F | C | Free base | 350.2 |
| 84 | 3-F | 5-Cl | C | Free base | 367.0 |
| 85 | 3-Cl | 5-Cl | C | Free base | 384.3 |
| 86 | 3-Me | 5-F | C | Free base | 346.5 |
| 87 | 3-Me | 5-Cl | B | Hydrochloride | 362.2 |
| 88 | 3-Me | 5-Me | C | Free base | 342.3 |
| 89 | 3-MeO | 5-F | C | Free base | 362.2 |
| 90 | 3-MeO | 5-Cl | C | Free base | 378.5 |
| 91 | 3-MeO | 5-MeO | C | Free base | 374.3 |

Examples 92 to 114

The compounds of Examples 92 to 114 as shown in Table 6 were prepared in the same manner as in Examples 20 to 40 except that the compound obtained in Reference Example 5 and a corresponding benzyl bromide or benzyl chloride were used.

TABLE 6

[Structure: benzyl ether of pyrazole with X,Y substituents on phenyl ring (positions 2-6), pyrazole N substituted with CH2-tetrahydropyran-2-yl, other position with CH2-NHMe]

| Ex. | X | Y | Benzylation method | Salt | Obs MS [M + 1] |
|---|---|---|---|---|---|
| 92 | 2-F | H | C | Free base | 334.5 |
| 93 | 3-F | H | C | Free base | 334.5 |
| 94 | 4-F | H | C | Free base | 334.5 |
| 95 | 2-Cl | H | A | Hydrochloride | 350.4 |
| 96 | 3-Cl | H | A | Hydrochloride | 350.4 |
| 97 | 4-Cl | H | A | Hydrochloride | 350.4 |
| 98 | 2-Br | H | A | Free base | 394.1 |
| 99 | 3-Br | H | A | Free base | 394.1 |
| 100 | 2-Me | H | A | Hydrochloride | 330.3 |
| 101 | 3-Me | H | A | Hydrochloride | 330.3 |
| 102 | 4-Me | H | A | Hydrochloride | 330.3 |
| 103 | 2-CF$_3$ | H | A | Hydrochloride | 384.3 |
| 104 | 3-CF$_3$ | H | A | Hydrochloride | 384.3 |
| 105 | 4-CF$_3$ | H | A | Hydrochloride | 384.3 |
| 106 | 2-F | 4-F | C | Free base | 352.1 |
| 107 | 2-Cl | 4-F | C | Free base | 368.1 |
| 108 | 2-Me | 4-F | C | Free base | 348.2 |
| 109 | 2-F | 5-F | C | Free base | 352.1 |
| 110 | 2-F | 5-Cl | C | Free base | 368.1 |
| 111 | 2-F | 5-Me | C | Free base | 348.2 |
| 112 | 2-Cl | 5-F | C | Hydrochloride | 368.4 |
| 113 | 2-Cl | 5-Cl | C | Hydrochloride | 384.3 |
| 114 | 2-Cl | 5-Me | C | Free base | 364.2 |

Examples 115 to 134

The compounds of Examples 115 to 134 as shown in Table 7 were prepared in the same manner as in Examples 20 to 40 except that the compound obtained in Reference Example 2, 3 or 9 to 13 and a corresponding benzyl bromide or benzyl chloride were used.

TABLE 7

[Structure: benzyl ether of pyrazole, X,Y on phenyl (positions 2-6); pyrazole N-CH2-Q substituent; other position CH2-NHMe·HCl]

| Ex. | Q | X | Y | Benzylation method | Obs MS [M + 1] |
|---|---|---|---|---|---|
| 115 | norbornyl* | H | H | B | 326.4 |
| 116 | norbornyl* | 3-Cl | H | B | 360.5 |
| 117 | norbornyl* | 2-F | 5-F | B | 362.5 |
| 118 | norbornyl* | 2-F | 5-Cl | B | 378.5 |
| 119 | oxanorbornyl* | H | H | C | 328.3 |
| 120 | oxanorbornyl* | 3-Cl | H | C | 362.5 |
| 121 | oxanorbornyl* | 2-F | 5-Cl | C | 380.4 |
| 122 | oxabicyclic* | 3-Cl | H | C | 376.5 |
| 123 | 4,4-difluorocyclohexyl* | H | H | C | 350.4 |
| 124 | 4,4-difluorocyclohexyl* | 2-F | 5-F | C | 386.6 |

TABLE 7-continued

| Ex. | Q | X | Y | Benzylation method | Obs MS [M + 1] |
|---|---|---|---|---|---|
| 125 | 4,4-difluorocyclohexyl | 2-F | 5-Cl | C | 402.5 |
| 126 | 1-fluorocyclohexyl | H | H | C | 332.5 |
| 127 | 1-fluorocyclohexyl | 2-F | 5-F | C | 368.4 |
| 128 | 1-fluorocyclohexyl | 2-F | 5-Cl | C | 384.3 |
| 129 | cyclopropyl | H | H | C | 272.3 |
| 130 | cyclopropyl | 2-F | 5-F | C | 308.4 |
| 131 | cyclopropyl | 2-F | 5-Cl | C | 324.4 |
| 132 | cyclobutyl | H | H | C | 286.3 |
| 133 | cyclobutyl | 2-F | 5-F | C | 322.4 |
| 134 | cyclobutyl | 2-F | 5-Cl | C | 338.4 |

(* shows the bonding position)

Example 129

1-[5-(Benzyloxy)-1-(cyclopropylmethyl)-1H-pyrazol-3-yl]-N-methylmethanamine hydrochloride $^1$H-NMR (300 MHz, CDCl$_3$) δ: 0.28-0.34 (2H, m), 0.47-0.54 (2H, m), 1.15-1.27 (1H, m), 2.63 (3H, br s), 3.81 (2H, d, J=7.0 Hz), 4.09 (2H, br s), 5.09 (2H, s), 6.11 (1H, s), 7.35-7.42 (5H, m), 9.77 (2H, br s).

Example 130

1-{1-(Cyclopropylmethyl)-5-[(2,5-difluorobenzyl)oxy]-1H-pyrazol-3-yl}-N-methylmethanamine hydrochloride $^1$H-NMR (300 MHz, CDCl$_3$) δ: 0.28-0.34 (2H, m), 0.49-0.55 (2H, m), 1.15-1.28 (1H, m), 2.64 (3H, br s), 3.81 (2H, d, J=7.0 Hz), 4.10 (2H, br s), 5.12 (2H, s), 6.14 (1H, s), 7.02-7.10 (2H, m), 7.11-7.18 (1H, m), 9.78 (2H, br s).

Example 131

1-{5-[(5-Chloro-2-fluorobenzyl)oxy]-1-(cyclopropylmethyl)-1H-pyrazol-3-yl}-N-methylmethanamine hydrochloride $^1$H-NMR (300 MHz, CDCl$_3$) δ: 0.28-0.35 (2H, m), 0.48-0.56 (2H, m), 1.14-1.27 (1H, m), 2.64 (3H, br s), 3.81 (2H, d, J=7.0 Hz), 4.10 (2H, br s), 5.11 (2H, s), 6.15 (1H, s), 7.06 (1H, br t, J=9.0 Hz), 7.32 (1H, br ddd, J=8.7, 4.5, 2.7 Hz), 7.41 (1H, br dd, J=6.1, 2.7 Hz), 9.79 (2H, br s).

Example 132

1-[5-(Benzyloxy)-1-(cyclobutylmethyl)-1H-pyrazol-3-yl]-N-methylmethanamine hydrochloride $^1$H-NMR (300 MHz, DMSO-d$_6$) δ: 1.67-1.84 (4H, m), 1.86-1.95 (2H, m), 2.50 (3H, br s), 2.59-2.72 (1H, m), 3.91 (2H, br d, J=7.2 Hz), 3.93 (2H, br t, J=5.6 Hz), 5.14 (2H, s), 5.91 (1H, s), 7.33-7.48 (5H, m), 9.10 (2H, br s).

Example 133

1-{1-(Cyclobutylmethyl)-5-[(2,5-difluorobenzyl)oxy]-1H-pyrazol-3-yl}-N-methylmethanamine hydrochloride $^1$H-NMR (300 MHz, CDCl$_3$) δ: 1.70-1.92 (4H, m), 1.92-2.06 (2H, m), 2.61 (3H, br s), 2.73 (1H, br td, J=14.8, 7.3 Hz), 3.95 (2H, d, J=7.3 Hz), 4.09 (2H, br s), 5.11 (2H, s), 6.13 (1H, s), 7.01-7.11 (2H, m), 7.11-7.19 (1H, m), 9.79 (2H, s).

Example 134

1-{5-[(5-Chloro-2-fluorobenzyl)oxy]-1-(cyclobutylmethyl)-1H-pyrazol-3-yl}-N-methylmethanamine hydrochloride $^1$H-NMR (300 MHz, CDCl$_3$) δ: 1.70-1.92 (4H, m), 1.94-2.04 (2H, m), 2.61 (3H, br s), 2.69-2.78 (1H, m), 3.95 (2H, d, J=7.2 Hz), 4.09 (2H, br s), 5.10 (2H, s), 6.13 (1H, s), 7.06 (1H, t, J=9.0 Hz), 7.33 (1H, ddd, J=8.8, 4.5, 2.7 Hz), 7.42 (1H, dd, J=6.2, 2.6 Hz), 9.79 (2H, br s).

Examples 135 to 191

The compounds of Examples 135 to 191 as shown in Table 8 were prepared in the same manner as in Examples 20 to 40 except that the Compound (IIIa) in Reference Example 1 and a corresponding benzyl bromide or benzyl chloride were used.

TABLE 8

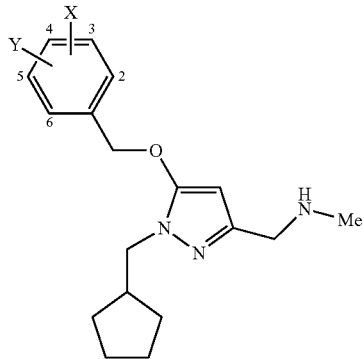

| Ex. | X | Y | Benzylation method | Salt | Obs MS [M + 1] |
|---|---|---|---|---|---|
| 135 | 2-F | H | C | TFA salt | 317.9 |
| 136 | 3-F | H | A | Hydrochloride | 318.2 |
| 137 | 4-F | H | C | TFA salt | 318.0 |
| 138 | 2-Cl | H | C | TFA salt | 333.9 |
| 139 | 3-Cl | H | A | Hydrochloride | 334.2 |
| 140 | 4-Cl | H | C | Free base | 333.9 |
| 141 | 2-Me | H | C | TFA salt | 313.9 |
| 142 | 3-Me | H | A | Hydrochloride | 314.3 |
| 143 | 4-Me | H | C | TFA salt | 313.9 |
| 144 | 2-F | 4-F | C | TFA salt | 335.9 |
| 145 | 2-Cl | 4-F | C | TFA salt | 351.8 |
| 146 | 2-Me | 4-F | C | TFA salt | 331.8 |
| 147 | 2-F | 5-F | B | Hydrochloride | 336.4 |
| 148 | 2-F | 5-Cl | B | Hydrochloride | 352.4 |
| 149 | 2-F | 5-Me | C | TFA salt | 331.9 |
| 150 | 2-Cl | 5-F | C | TFA salt | 351.9 |
| 151 | 2-Cl | 5-Cl | C | TFA salt | 367.7 |
| 152 | 2-Cl | 5-Me | C | TFA salt | 348.1 |
| 153 | 2-Br | H | C | TFA salt | 379.6 |
| 154 | 3-Br | H | C | TFA salt | 377.8 |
| 155 | 4-Br | H | C | Free base | 379.6 |
| 156 | 2-CF$_3$ | H | C | TFA salt | 367.8 |
| 157 | 3-CF$_3$ | H | C | TFA salt | 367.8 |
| 158 | 4-CF$_3$ | H | C | Free base | 368.2 |
| 159 | 2-CF$_3$O | H | C | TFA salt | 383.7 |
| 160 | 3-CF$_3$O | H | C | TFA salt | 383.8 |
| 161 | 4-CF$_3$O | H | C | TFA salt | 383.8 |
| 162 | 2-CN | H | C | TFA salt | 324.8 |
| 163 | 3-CN | H | C | TFA salt | 324.8 |
| 164 | 4-CN | H | C | TFA salt | 325.1 |
| 165 | 2-F | 3-F | C | TFA salt | 335.9 |
| 166 | 2-F | 3-Cl | C | Free base | 351.9 |
| 167 | 2-F | 3-Me | C | TFA salt | 331.9 |
| 168 | 2-Cl | 3-F | C | TFA salt | 351.8 |
| 169 | 2-Cl | 3-Cl | C | TFA salt | 367.8 |
| 170 | 2-Cl | 3-Me | C | TFA salt | 348.0 |
| 171 | 2-Me | 3-F | C | TFA salt | 331.9 |
| 172 | 2-Me | 3-Cl | C | TFA salt | 348.0 |
| 173 | 2-Me | 3-Me | C | TFA salt | 328.1 |
| 174 | 2-Me | 5-F | C | TFA salt | 332.1 |
| 175 | 2-Me | 5-Cl | C | TFA salt | 348.0 |
| 176 | 2-Me | 5-Me | C | TFA salt | 328.1 |
| 177 | 2-F | 6-F | C | TFA salt | 335.9 |
| 178 | 2-F | 6-Cl | C | TFA salt | 351.9 |
| 179 | 2-Cl | 6-Cl | C | TFA salt | 367.7 |
| 180 | 2-Me | 6-F | C | TFA salt | 332.0 |
| 181 | 2-Me | 6-Cl | C | TFA salt | 347.8 |
| 182 | 2-Me | 6-Me | C | TFA salt | 327.9 |
| 183 | 3-F | 4-F | C | TFA salt | 335.7 |
| 184 | 3-Cl | 4-F | C | Free base | 351.9 |
| 185 | 3-Me | 4-F | C | TFA salt | 331.8 |
| 186 | 3-F | 5-F | C | TFA salt | 336.1 |
| 187 | 3-F | 5-Cl | C | TFA salt | 352.0 |
| 188 | 3-Cl | 5-Cl | C | TFA salt | 368.0 |
| 189 | 3-Me | 5-F | C | TFA salt | 332.0 |
| 190 | 3-Me | 5-Cl | C | TFA salt | 348.0 |
| 191 | 3-Me | 5-Me | C | TFA salt | 328.0 |

Example 135

1-{1-(Cyclopentylmethyl)-5-[(2-fluorobenzyl)oxy]-1H-pyrazol-3-yl}-N-methylmethanamine trifluoroacetate $^1$H-NMR (400 MHz, CDCl$_3$) δ: 1.11-1.26 (2H, m), 1.46-1.68 (6H, m), 2.24-2.37 (1H, m), 2.70 (3H, s), 3.86 (2H, d, J=7.6 Hz), 4.14 (2H, s), 5.15 (2H, s), 5.91 (1H, s), 7.10 (1H, dd, J=9.2, 9.2 Hz), 7.17 (1H, dd, J=7.6, 7.6 Hz), 7.33-7.44 (2H, m), 9.15 (2H, brs).

Example 136

1-{1-(Cyclopentylmethyl)-5-[(3-fluorobenzyl)oxy]-1H-pyrazol-3-yl}-N-methylmethanamine hydrochloride $^1$H-NMR (300 MHz, DMSO-d$_6$) δ: 1.16-1.27 (2H, m), 1.44-1.61 (6H, m), 2.22-2.34 (1H, m), 2.51 (3H, s), 3.82 (2H, d, J=7.5 Hz), 3.95 (2H, br t, J=5.7 Hz), 5.18 (2H, s), 5.85 (1H, s), 7.19 (1H, ddt, J=12.5, 6.9, 2.3 Hz), 7.26-7.31 (2H, m), 7.42-7.50 (1H, m), 8.94 (2H, br s).

Example 137

1-{1-(Cyclopentylmethyl)-5-[(4-fluorobenzyl)oxy]-1H-pyrazol-3-yl}-N-methylmethanamine trifluoroacetate $^1$H-NMR (400 MHz, CDCl$_3$) δ: 1.12-1.28 (2H, m), 1.44-1.70 (6H, m), 2.25-2.39 (1H, m), 2.67 (3H, s), 3.86 (2H, d, J=7.6 Hz), 4.10 (2H, s), 5.03 (2H, s), 5.85 (1H, s), 7.08 (2H, dd, J=8.8, 8.8 Hz), 7.35 (2H, dd, J=8.8, 3.2 Hz), 9.58 (2H, brs).

Example 138

1-{5-[(2-Chlorobenzyl)oxy]-1-(cyclopentylmethyl)-1H-pyrazol-3-yl}-N-methylmethanamine trifluoroacetate $^1$H-NMR (400 MHz, CDCl$_3$) δ: 1.13-1.30 (2H, m), 1.44-1.71 (6H, m), 2.27-2.40 (1H, m), 2.68 (3H, s), 3.88 (2H, d, J=7.6 Hz), 4.12 (2H, s), 5.16 (2H, s), 5.90 (1H, s), 7.24-7.37 (2H, m), 7.38-7.48 (2H, m), 9.42 (2H, brs).

Example 139

1-{5-[(3-Chlorobenzyl)oxy]-1-(cyclopentylmethyl)-1H-pyrazol-3-yl}-N-methylmethanamine hydrochloride $^1$H-NMR (300 MHz, DMSO-d$_6$) δ: 1.17-1.27 (2H, m), 1.44-1.61 (6H, m), 2.25-2.34 (1H, m), 2.51 (3H, br s), 3.82 (2H, d, J=7.5 Hz), 3.96 (2H, br t, J=5.7 Hz), 5.18 (2H, s), 5.84 (1H, s), 7.39-7.45 (3H, m), 7.51 (1H, br s), 8.89 (2H, br s).

Example 140

1-{5-[(4-Chlorobenzyl)oxy]-1-(cyclopentylmethyl)-1H-pyrazol-3-yl}-N-methylmethanamine $^1$H-NMR (400 MHz, CDCl$_3$) δ: 1.11-1.29 (2H, m), 1.40-1.68 (6H, m), 2.26-2.42 (1H, m), 2.58 (3H, s), 3.82 (2H, d, J=7.6 Hz), 4.03 (2H, s), 5.03 (2H, s), 6.02 (1H, s), 7.32 (2H, d, J=8.4 Hz), 7.35 (2H, d, J=8.4 Hz).

Example 141

1-{1-(Cyclopentylmethyl)-5-[(2-methylbenzyl)oxy]-1H-pyrazol-3-yl}-N-methylmethanamine trifluoroacetate $^1$H-NMR (400 MHz, CDCl$_3$) δ: 1.11-1.28 (2H, m), 1.46-1.71 (6H, m), 2.25-2.43 (1H, m), 2.34 (3H, s), 2.72 (3H, s), 3.88 (2H, d, J=7.6 Hz), 4.16 (2H, s), 5.09 (2H, s), 5.93 (1H, s), 7.17-7.37 (4H, m), 9.23 (2H, brs).

Example 142

1-{1-(Cyclopentylmethyl)-5-[(3-methylbenzyl)oxy]-1H-pyrazol-3-yl}-N-methylmethanamine hydrochloride $^1$H-NMR (300 MHz, DMSO-d$_6$) δ: 1.17-1.27 (2H, m), 1.44-1.61 (6H, m), 2.24-2.34 (4H, m), 2.51 (3H, s), 3.80 (2H, d, J=7.3 Hz), 3.95 (2H, br t, J=5.7 Hz), 5.11 (2H, s), 5.86 (1H, s), 7.15-7.31 (4H, m), 8.95 (2H, br s).

Example 143

1-{1-(Cyclopentylmethyl)-5-[(4-methylbenzyl)oxy]-1H-pyrazol-3-yl}-N-methylmethanamine trifluoroacetate $^1$H-NMR (400 MHz, CDCl$_3$) δ: 1.11-1.27 (2H, m), 1.44-1.71 (6H, m), 2.25-2.42 (1H, m), 2.34 (3H, s), 2.70 (3H, s), 3.88 (2H, d, J=7.6 Hz), 4.13 (2H, s), 5.05 (2H, s), 5.87 (1H, s), 7.20 (2H, d, J=7.8 Hz), 7.26 (2H, d, J=7.8 Hz), 9.18 (2H, brs).

Example 144

1-{1-(Cyclopentylmethyl)-5-[(2,4-difluorobenzyl)oxy]-1H-pyrazol-3-yl}-N-methylmethanamine trifluoroacetate $^1$H-NMR (400 MHz, CDCl$_3$) δ: 1.04-1.22 (2H, m), 1.36-1.60 (6H, m), 2.17-2.32 (1H, m), 2.59 (3H, s), 3.76 (2H, d, J=6.8 Hz), 4.01 (2H, s), 5.00 (2H, s), 5.80 (1H, s), 6.76-6.90 (2H, m), 7.32 (1H, dd, J=14.4, 8.4 Hz), 9.36 (2H, brs).

Example 145

1-{5-[(2-Chloro-4-fluorobenzyl)oxy]-1-(cyclopentylmethyl)-1H-pyrazol-3-yl}-N-methylmethanamine trifluoroacetate $^1$H-NMR (400 MHz, CDCl$_3$) δ: 1.07-1.23 (2H, m), 1.38-1.63 (6H, m), 2.21-2.35 (1H, m), 2.59 (3H, s), 3.78 (2H, d, J=7.6 Hz), 4.01 (2H, s), 5.04 (2H, s), 5.79 (1H, s), 6.96 (1H, ddd, J=8.6, 8.6, 2.6 Hz), 7.12 (1H, dd, J=8.6, 2.6 Hz), 7.36 (1H, dd, J=8.6, 6.0 Hz), 9.43 (2H, brs).

Example 146

1-{1-(Cyclopentylmethyl)-5-[(4-fluoro-2-methylbenzyl)oxy]-1H-pyrazol-3-yl}-N-methylmethanamine trifluoroacetate $^1$H-NMR (400 MHz, CDCl$_3$) δ: 1.05-1.23 (2H, m), 1.37-1.61 (6H, m), 2.20-2.37 (1H, m), 2.27 (3H, s), 2.57 (3H, s), 3.75 (2H, d, J=7.6 Hz), 3.99 (2H, s), 4.93 (2H, s), 5.78 (1H, s), 6.78-6.91 (2H, m), 7.23 (1H, dd, J=8.4, 6.0 Hz), 9.46 (2H, brs).

Example 147

1-{1-(Cyclopentylmethyl)-5-[(2,5-difluorobenzyl)oxy]-1H-pyrazol-3-yl}-N-methylmethanamine hydrochloride $^1$H-NMR (300 MHz, DMSO-d$_6$) δ: 1.10-1.30 (2H, m), 1.45-1.72 (6H, m), 2.20-2.35 (1H, m), 2.51 (3H, t, J=5.5 Hz), 3.79 (2H, d, J=7.3 Hz), 3.96 (2H, t, J=5.7 Hz), 5.19 (2H, s), 5.94 (1H, s), 7.24-7.48 (3H, m), 9.00 (2H, br s).

Example 148

1-{5-[(5-Chloro-2-fluorobenzyl)oxy]-1-(cyclopentylmethyl)-1H-pyrazol-3-yl}-N-methylmethanamine hydrochloride $^1$H-NMR (300 MHz, DMSO-d$_6$) δ: 1.15-1.27 (2H, m), 1.46-1.59 (6H, m), 2.27 (1H, q, J=7.0 Hz), 2.54 (3H, br t, J=5.6 Hz), 3.80 (2H, d, J=7.5 Hz), 3.99 (2H, t, J=5.5 Hz), 5.22 (2H, s), 5.91 (1H, s), 7.36 (1H, t, J=9.2 Hz), 7.51-7.56 (1H, m), 7.65 (1H, dd, J=6.5, 2.7 Hz), 8.81 (2H, br s).

Example 149

1-{1-(Cyclopentylmethyl)-5-[(2-fluoro-5-methylbenzyl)oxy]-1H-pyrazol-3-yl}-N-methylmethanamine trifluoroacetate $^1$H-NMR (300 MHz, CDCl$_3$) δ: 1.10-1.30 (2H, m), 1.42-1.71 (6H, m), 2.20-2.42 (1H, m), 2.32 (3H, s), 2.67 (3H, s), 3.85 (2H, d, J=7.8 Hz), 4.10 (2H, s), 5.08 (2H, s), 5.88 (1H, s), 6.97 (1H, dd, J=9.6, 9.6 Hz), 7.11-7.23 (2H, m), 9.30 (2H, brs).

Example 150

1-{5-[(2-Chloro-5-fluorobenzyl)oxy]-1-(cyclopentylmethyl)-1H-pyrazol-3-yl}-N-methylmethanamine trifluoroacetate $^1$H-NMR (300 MHz, CDCl$_3$) δ: 1.12-1.33 (2H, m), 1.43-1.71 (6H, m), 2.27-2.45 (1H, m), 2.61 (3H, s), 3.87 (2H, d, J=7.5 Hz), 4.10 (2H, s), 5.10 (2H, s), 5.81 (1H, s), 7.00 (1H, ddd, J=8.5, 8.5, 3.0 Hz), 7.16 (1H, dd, J=9.0, 3.0 Hz), 7.36 (1H, dd, J=8.5, 4.8 Hz), 9.55 (2H, brs).

Example 151

1-{1-(Cyclopentylmethyl)-5-[(2,5-dichlorobenzyl)oxy]-1H-pyrazol-3-yl}-N-methylmethanamine trifluoroacetate $^1$H-NMR (300 MHz, CDCl$_3$) δ: 1.11-1.33 (2H, m), 1.40-1.72 (6H, m), 2.27-2.45 (1H, m), 2.60 (3H, s), 3.86 (2H, d, J=7.5 Hz), 4.03 (2H, s), 5.08 (2H, s), 5.83 (1H, s), 7.26 (1H, dd, J=8.4, 2.2 Hz), 7.33 (1H, d, J=8.4 Hz), 7.42 (1H, d, J=2.2 Hz), 9.57 (2H, brs).

Example 152

1-{5-[(2-Chloro-5-methylbenzyl)oxy]-1-(cyclopentylmethyl)-1H-pyrazol-3-yl}-N-methylmethanamine trifluoroacetate ¹H-NMR (400 MHz, CDCl₃) δ: 1.16-1.31 (2H, m), 1.50-1.73 (6H, m), 2.28-2.43 (1H, m), 2.33 (3H, s), 2.72 (3H, s), 3.89 (2H, d, J=7.6 Hz), 4.13 (2H, s), 5.04 (2H, s), 5.87 (1H, s), 7.18 (1H, d, J=8.0 Hz), 7.27 (1H, dd, J=8.0, 2.0 Hz), 7.35 (1H, d, J=2.0 Hz), 9.33 (2H, brs).

Example 192

1-[5-(Benzyloxy)-1-(2-cyclopentylethyl)-1H-pyrazol-3-yl]-N-methylmethanamine

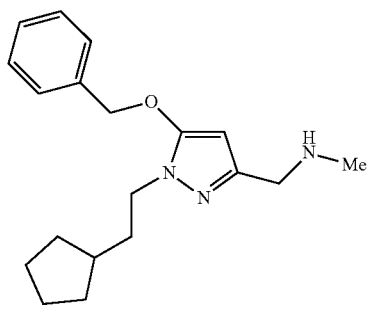 [SMILES: CNCc1cc(OCc2ccccc2)n(CCC2CCCC2)n1]

The title compound was prepared in the same manner as in Examples 20 to 40 except that the compound obtained in Reference Example 14 was used. The benzylation reaction of Step (i) was carried out by Method B described as a general process in Examples 20 to 40.

¹H-NMR (300 MHz, CDCl₃) δ: 1.09 (2H, m), 1.41-1.89 (9H, m), 2.67 (3H, s), 4.04 (2H, t, J=7.2 Hz), 4.20 (2H, s), 5.17 (2H, s), 6.43 (1H, s), 7.42-7.39 (5H, m), 10.06 (2H, s).

Obs MS [M+1]: 314.3

Example 193

1-{1-(2-Cyclopentylethyl)-5-[(2,5-difluorobenzyl)oxy]-1H-pyrazol-3-yl}-N-methylmethanamine

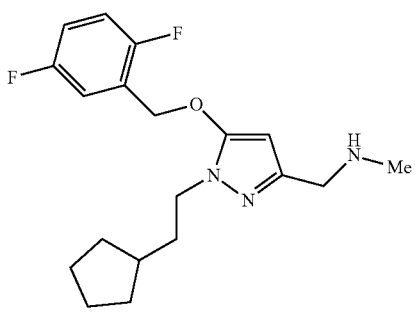 [SMILES: CNCc1cc(OCc2cc(F)ccc2F)n(CCC2CCCC2)n1]

The title compound was prepared in the same manner as in Example 192.

¹H-NMR (300 MHz, CDCl₃) δ: 1.07 (2H, m), 1.42-1.84 (9H, m), 2.63 (3H, br s), 3.96 (2H, t, J=7.2 Hz), 4.11 (2H, br s), 5.13 (2H, s), 6.20 (1H, s), 7.05 (2H, m), 7.15 (1H, m), 9.85 (br s).

Obs MS [M+1]: 350.4

Example 194

1-{1-(2-Cyclopentylethyl)-5-[(2,4-difluorobenzyl)oxy]-1H-pyrazol-3-yl}-N-methylmethanamine

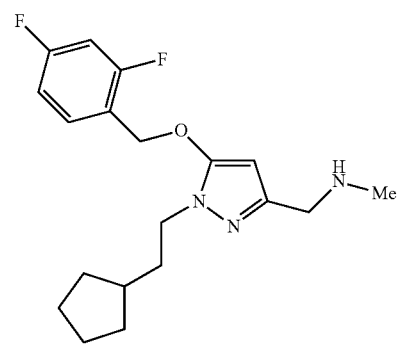 [SMILES: CNCc1cc(OCc2ccc(F)cc2F)n(CCC2CCCC2)n1]

The title compound was prepared in the same manner as in Example 192.

¹H-NMR (300 MHz, CDCl₃) δ: 1.07 (2H, s), 1.37-1.80 (7H, m), 1.88 (2H, m), 2.78 (3H, s), 4.15 (2H, t, J=7.2 Hz), 4.40 (2H, s), 5.30 (2H, s), 6.92 (3H, m), 7.49 (1H, dd, J=14.7, 8.4 Hz), 10.38 (2H, br s).

Obs MS [M+1]: 350.4

Examples 195 to 197

The compounds of Examples 195 to 197 as shown in Table 9 were prepared in the same manner as in Examples 20 to 40 except that the compound obtained in Reference Example 36 and a corresponding benzyl bromide were used. The benzylation reaction of Step (i) was carried out by Method B described as a general process in Examples 20 to 40.

TABLE 9

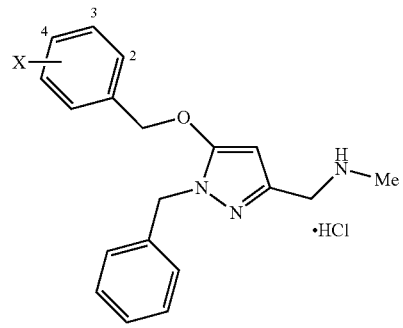

| Ex. | X | Obs MS [M + 1] |
|---|---|---|
| 195 | 2-F | 326.4 |
| 196 | 3-F | 326.4 |
| 197 | 4-F | 326.4 |

Example 198

1-[5-(Benzyloxy)-1-(2-fluorobenzyl)-1H-pyrazol-3-yl]-N-methylmethanamine hydrochloride

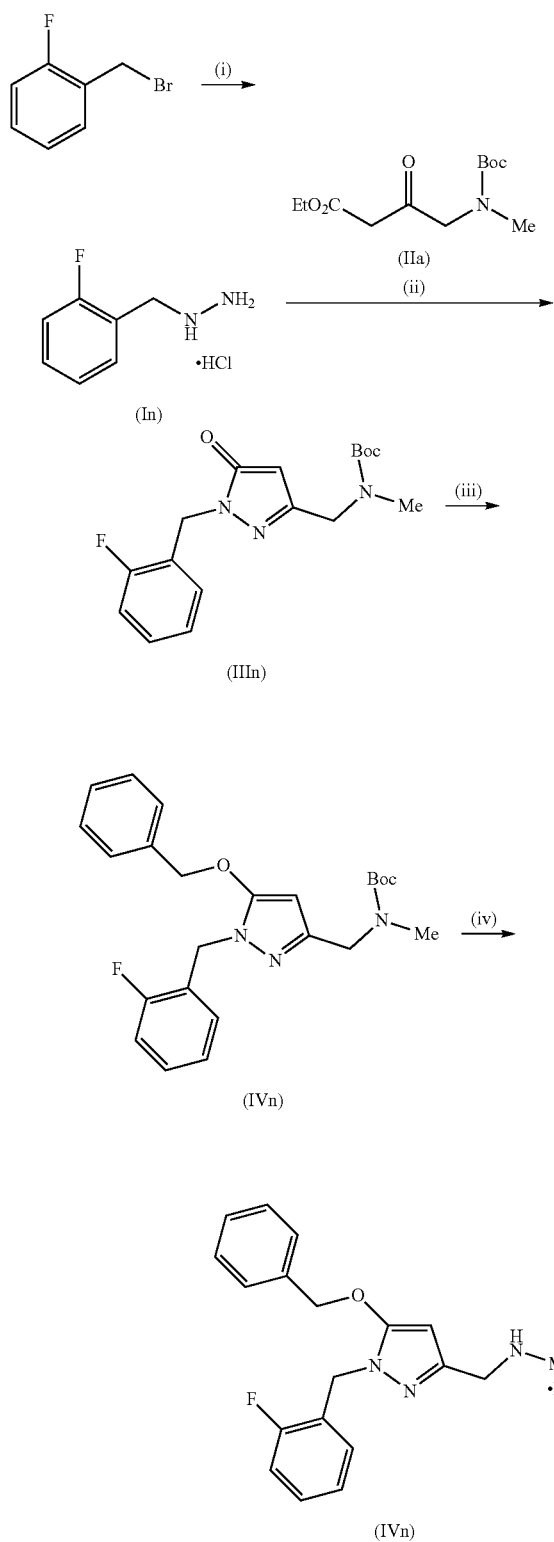

Step (i)

A solution of 2-fluorobenzylbromide (2.0 g, 11 mmol) and hydrazine monohydrate (3.1 mL, 63 mmol) in ethanol (10 mL) was stirred at 60° C. for 18 hours. The solvent was evaporated under reduced pressure, and the concentrated residue was diluted with chloroform (40 mL) and washed with water (6 mL) twice. The organic layer was dried over anhydrous MgSO$_4$, and the solvent was evaporated under reduced pressure. The concentrated residue was dissolved in chloroform (6 mL), to the solution was added 4 mol/L HCl/1,4-dioxane (12 mL) at room temperature, the solution was stirred at room temperature for 30 minutes, and the solvent was evaporated under reduced pressure. To the concentrated residue was added a mixed solution of ethyl acetate:n-hexane (2:1) (20 mL), the mixture was suspended, and the resulting precipitate was collected by filtration and dried under reduced pressure to give Compound (In) (1.68 g, 75%).

Step (ii)

A solution of the Compound (In) (1.0 g, 4.7 mmol), the Compound (IIa) prepared in Step (i) of Reference Example 1 (1.22 g, 4.7 mmol) and triethylamine (1.6 mL, 11 mmol) in ethanol (9 mL) was stirred at 80° C. for 5 hours. The reaction mixture was cooled to room temperature, to the concentrated residue was added 5% aq. KHSO$_4$, and the mixture was extracted with ethyl acetate. The combined organic layers were washed with brine and dried over anhydrous MgSO$_4$, and the solvent was evaporated under reduced pressure. The concentrated residue was purified by silica gel column chromatography (n-hexane:ethyl acetate=50:50) to give Compound (IIIn) (970 mg, 62%) as a light-brown oil.

Steps (iii) to (iv)

To a solution of the Compound (IIIn) (100 mg, 0.30 mmol) and cesium carbonate (146 mg, 0.45 mmol) in acetonitrile (1.5 mL) was added benzyl chloride (41 mg, 0.33 mmol) at room temperature, and the reaction mixture was stirred at room temperature for 17 hours. The reaction mixture was diluted with ethyl acetate, the salt was filtered off, and the filtrate was evaporated under reduced pressure to give a concentrated residue, which was used in the next step without further purification. The residue was dissolved in chloroform (1 mL), to the solution was added 4 mol/L HCl/1,4-dioxane (4 mL) at room temperature, the solution was stirred at room temperature for 30 minutes, and the solvent was evaporated under reduced pressure. To the concentrated residue was added a mixed solution of ethyl acetate:n-hexane (5:1), the mixture was suspended, and the resulting precipitate was collected by filtration and dried under reduced pressure to give the title compound (62 mg, 59% yield in 2 steps) as a light brown powder.

Obs MS [M+1]: 350.4

Examples 199 to 240

The compounds of Examples 199 to 240 as shown in Table 10 were prepared in the same manner as in Example 198 except that a corresponding benzyl chloride or benzyl bromide was used.

TABLE 10

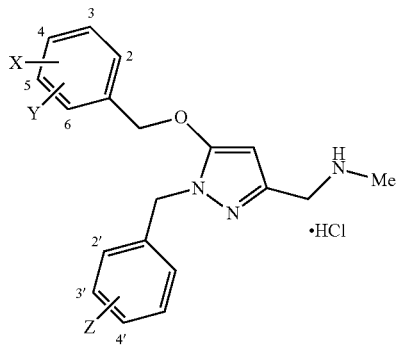

| Ex. | X | Y | Z | Obs MS [M + 1] |
|---|---|---|---|---|
| 199 | H | H | 3'-F | 326.2 |
| 200 | H | H | 4'-F | 326.2 |
| 201 | H | H | 2'-Cl | 342.3 |
| 202 | H | H | 3'-Cl | 342.3 |
| 203 | H | H | 4'-Cl | 342.3 |
| 204 | H | H | 2'-Me | 322.2 |
| 205 | H | H | 3'-Me | 322.2 |
| 206 | H | H | 4'-Me | 322.2 |
| 207 | H | H | 2'-CF$_3$ | 376.5 |
| 208 | H | H | 4'-CF$_3$ | 376.5 |
| 209 | H | H | 2'-CN | 333.4 |
| 210 | H | H | 3'-CN | 333.4 |
| 211 | H | H | 4'-CN | 333.4 |
| 212 | H | H | 4'-MeO | 338.4 |
| 213 | H | H | 2'-CF$_3$O | 392.2 |
| 214 | H | H | 3'-CF$_3$O | 392.2 |
| 215 | H | H | 4'-CF$_3$O | 392.2 |
| 216 | 2-F | H | 2'-F | 344.1 |
| 217 | 2-F | 5-F | 2'-F | 362.1 |
| 218 | 2-F | H | 4'-F | 344.1 |
| 219 | 2-F | 5-F | 4'-F | 362.1 |
| 220 | 2-F | H | 2'-Cl | 360.3 |
| 221 | 2-F | 5-F | 2'-Cl | 378.5 |
| 222 | 2-F | H | 4'-Cl | 360.3 |
| 223 | 3-Me | H | 4'-Cl | 356.3 |
| 224 | 2-F | 5-F | 4'-Cl | 378.5 |
| 225 | 2-F | 5-Me | 4'-Cl | 374.3 |
| 226 | 2-F | H | 2'-Me | 340.4 |
| 227 | 2-F | 5-F | 2'-Me | 358.6 |
| 228 | 2-F | H | 4'-Me | 340.4 |
| 229 | 3-Me | H | 4'-Me | 336.4 |
| 230 | 2-F | 5-F | 4'-Me | 358.3 |
| 231 | 2-F | 5-Me | 4'-Me | 354.4 |
| 232 | 2-F | H | 2'-CN | 351.6 |
| 233 | 4-F | H | 2'-CN | 351.6 |
| 234 | 2-F | 5-F | 2'-CN | 369.2 |
| 235 | 2-F | 5-Cl | 2'-CN | 385.2 |
| 236 | 2-F | 5-Me | 2'-CN | 365.3 |
| 237 | 2-F | 5-F | 4'-CN | 369.2 |
| 238 | 2-F | 5-Cl | 4'-CN | 385.2 |
| 239 | 2-F | H | 4'-CF$_3$O | 410.4 |
| 240 | 2-F | 5-F | 4'-CF$_3$O | 428.3 |

Examples 241 to 275

The compounds of Examples 241 to 275 as shown in Table 11 were prepared in the same manner as in Examples 20 to 40 except that the compound obtained in Reference Examples 15 to 26 and a corresponding benzyl chloride or benzyl bromide were used. The benzylation in Step (i) was carried out by Method B or C described as a general process in Examples 20 to 40.

TABLE 11

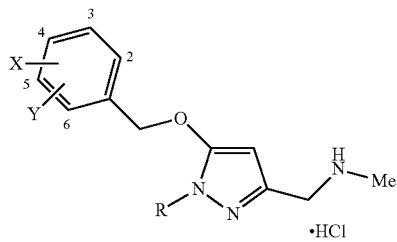

| Ex. | R | X | Y | Benzylation method |
|---|---|---|---|---|
| 241 | n-Bu | H | H | C |
| 242 | n-Bu | 2-F | 5-F | C |
| 243 | n-Pent | H | H | C |
| 244 | n-Pent | 2-F | 5-F | C |
| 245 | n-Hex | H | H | C |
| 246 | n-Hex | 2-F | 5-F | C |
| 247 | n-Hex | 2-F | 5-Cl | C |
| 248 | n-Hep | H | H | C |
| 249 | n-Hep | 2-F | 5-F | C |
| 250 | isobutyl-CH(Me)CH$_2$Me | H | H | C |
| 251 | isobutyl-CH(Me)CH$_2$Me | 2-F | 5-F | C |
| 252 | isobutyl-CH(Me)CH$_2$Me | 2-F | 4-F | C |
| 253 | isobutyl-CH(Me)CH$_2$Me | 2-Cl | 4-F | C |
| 254 | iso-Bu | H | H | C |
| 255 | iso-Bu | 2-F | 5-F | C |
| 256 | iso-Bu | 2-F | 5-Cl | C |
| 257 | neopentyl | H | H | C |
| 258 | neopentyl | 2-F | 5-F | C |
| 259 | neopentyl | 2-F | 5-Cl | C |

TABLE 11-continued

[Structure: benzyl ether of pyrazole with R on N, CH2NHMe substituent, ·HCl salt; X at position 5, Y at position 6 of phenyl]

| Ex. | R | X | Y | Benzylation method |
|---|---|---|---|---|
| 260 | Me-CH(CH2Me)-CH2-* (isobutyl-like, 2-methylbutyl) | H | H | B |
| 261 | Me-CH(CH2Me)-CH2-* | 3-Cl | H | C |
| 262 | Me-CH(CH2Me)-CH2-* | 2-F | 5-F | C |
| 263 | Me-CH(CH2Me)-CH2-* | 2-F | 5-Cl | C |
| 264 | Me3C-CH2-* (neopentyl) | H | H | B |
| 265 | Me3C-CH2-* | 3-Cl | H | C |
| 266 | Me3C-CH2-* | 2-F | 5-F | C |
| 267 | Me3C-CH2-* | 2-F | 5-Cl | C |
| 268 | Me2CH-CH2-CH2-* (isoamyl) | H | H | C |
| 269 | Me2CH-CH2-CH2-* | 2-F | 5-F | C |
| 270 | Me2CH-CH2-CH2-* | 2-F | 5-Cl | C |
| 271 | CF3-CH2-CH2-CH2-* | H | H | C |
| 272 | CF3-CH2-CH2-CH2-* | 2-F | 5-F | C |
| 273 | Me-O-C(Me)2-CH2-CH2-* | H | H | C |
| 274 | Me-O-C(Me)2-CH2-CH2-* | 2-F | 5-F | C |
| 275 | Me-O-C(Me)2-CH2-CH2-* | 2-F | 5-Cl | C |

(*shows the bonding position)

Example 241

Obs MS [M+1]: 274.5

Example 242

Obs MS [M+1]: 310.4

Example 243

Obs MS [M+1]: 288.3

Example 244

Obs MS [M+1]: 324.4

Example 245

$^1$H-NMR (300 MHz, DMSO-$d_6$) δ: 0.77-0.84 (3H, m), 1.14-1.25 (6H, m), 1.59-1.69 (2H, m), 2.53 (3H, br t, J=5.3 Hz), 3.88 (2H, br t, J=7.0 Hz), 3.96 (2H, br t, J=5.9 Hz), 5.16 (2H, s), 5.85 (1H, s), 7.35-7.47 (5H, m), 8.84 (2H, br s).
Obs MS [M+1]: 302.5

Example 246

$^1$H-NMR (300 MHz, DMSO-$d_6$) δ: 0.76-0.83 (3H, m), 1.12-1.23 (6H, m), 1.57-1.68 (2H, m), 2.53 (3H, br t, J=5.3 Hz), 3.87 (2H, br t, J=6.8 Hz), 3.97 (2H, br t, J=5.5 Hz), 5.20 (2H, s), 5.92 (1H, s), 7.26-7.39 (2H, m), 7.40-7.47 (1H, m), 8.91 (2H, br s).
Obs MS [M+1]: 338.4

Example 247

¹H-NMR (300 MHz, DMSO-d₆) δ:0.75-0.83 (3H, m), 1.10-1.24 (6H, m), 1.57-1.68 (2H, m), 2.52 (3H, br s), 3.86 (4H, br t, J=6.8 Hz), 3.97 (4H, br s), 5.20 (2H, s), 5.92 (1H, s), 7.35 (1H, t, J=9.2 Hz), 7.49-7.56 (1H, m), 7.65 (1H, dd, J=6.2, 2.6 Hz), 8.90 (2H, br s).
Obs MS [M+1]: 354.5

Example 248

Obs MS [M+1]: 316.6

Example 249

Obs MS [M+1]: 352.4

Example 250

¹H-NMR (300 MHz, CDCl₃) δ: 0.73 (6H, t, J=7.3 Hz), 1.75 (2H, m), 1.88 (2H, m), 2.62 (3H, s), 4.06 (1H, m), 4.17 (2H, s), 5.13 (2H, s), 6.25 (1H, s), 7.39 (5H, m), 9.89 (2H, br s).

Example 251

Obs MS [M+1]: 324.4

Example 252

Obs MS [M+1]: 324.7

Example 253

Obs MS [M+1]: 340.4

Example 254

1-[5-(Benzyloxy)-1-(2-methylpropyl)-1H-pyrazol-3-yl]-N-methylmethanamine hydrochloride ¹H-NMR (300 MHz, DMSO-d₆) δ: 0.82 (6H, d, J=6.8 Hz), 1.98-2.09 (1H, m), 2.52 (3H, br s), 3.71 (2H, d, J=7.2 Hz), 3.96 (2H, br s), 5.14 (2H, d, J=12.5 Hz), 5.84 (1H, s), 7.35-7.46 (5H, m), 8.80 (2H, s).
Obs MS [M+1]: 274.5

Example 255

1-{5-[(2,5-Difluorobenzyl)oxy]-1-(2-methylpropyl)-1H-pyrazol-3-yl}-N-methylmethanamine hydrochloride ¹H-NMR (300 MHz, DMSO-d₆) δ: 0.79 (7H, d, J=6.6 Hz), 1.96-2.09 (1H, m), 2.52 (3H, br t, J=5.3 Hz), 3.69 (2H, d, J=7.3 Hz), 3.97 (2H, br t, J=5.5 Hz), 5.19 (2H, s), 5.94 (1H, s), 7.26-7.39 (2H, m), 7.40-7.47 (1H, m), 8.95 (2H, s).
Obs MS [M+1]: 310.4

Example 256

1-{5-[(5-Chloro-2-fluorobenzyl)oxy]-1-(2-methylpropyl)-1H-pyrazol-3-yl}-N-methylmethanamine hydrochloride ¹H-NMR (300 MHz, DMSO-d₆) δ: 0.79 (6H, d, J=6.6 Hz), 1.97-2.08 (1H, m), 2.54 (3H, br t, J=5.1 Hz), 3.69 (2H, d, J=7.2 Hz), 3.98 (2H, br t, J=5.0 Hz), 5.20 (2H, s), 5.91 (1H, s), 7.35 (1H, t, J=9.4 Hz), 7.49-7.56 (1H, m), 7.65 (1H, dd, J=6.4, 2.9 Hz), 8.83 (2H, br s).
Obs MS [M+1]: 326.4

Example 257

1-[5-(Benzyloxy)-1-(2,2-dimethylpropyl)-1H-pyrazol-3-yl]-N-methylmethanamine hydrochloride ¹H-NMR (300 MHz, DMSO-d₆) δ: 0.89 (9H, s), 2.52 (3H, br t, J=5.0 Hz), 3.68 (2H, br s), 3.96 (2H, br t, J=4.7 Hz), 5.14 (2H, s), 5.90 (1H, s), 7.32-7.48 (5H, m), 8.99 (2H, br s).
Obs MS [M+1]: 288.3

Example 258

1-{5-[(2,5-Difluorobenzyl)oxy]-1-(2,2-dimethylpropyl)-1H-pyrazol-3-yl}-N-methylmethanamine hydrochloride ¹H-NMR (300 MHz, DMSO-dG) δ: 0.86 (9H, s), 2.52 (3H, br t, J=5.1 Hz), 3.67 (2H, s), 3.96 (2H, br t, J=5.1 Hz), 5.17 (2H, s), 5.98 (1H, s), 7.26-7.39 (2H, m), 7.41-7.47 (1H, m), 9.07 (2H, br s).
Obs MS [M+1]: 324.4

Example 259

1-{5-[(5-Chloro-2-fluorobenzyl)oxy]-1-(2,2-dimethylpropyl)-1H-pyrazol-3-yl}-N-methylmethanamine hydrochloride ¹H-NMR (300 MHz, DMSO-d₆) δ: 0.86 (9H, s), 2.52 (3H, br d, J=5.1 Hz), 3.66 (2H, s), 3.96 (2H, br t, J=5.3 Hz), 5.18 (2H, s), 5.98 (1H, s), 7.35 (1H, t, J=9.2 Hz), 7.49-7.55 (1H, m), 7.66 (1H, dd, J=6.1, 2.6 Hz), 9.06 (2H, br s).
Obs MS [M+1]: 340.4

Example 260

1-[5-(Benzyloxy)-1-(2-ethylbutyl)-1H-pyrazol-3-yl]-N-methylmethanamine hydrochloride ¹H-NMR (300 MHz, DMSO-d₆) δ: 0.81 (6H, t, J=7.4 Hz), 1.14-1.28 (4H, m), 1.65-1.79 (1H, m), 2.53 (3H, br s), 3.79 (2H, br d, J=6.8 Hz), 3.97 (2H, br t, J=5.8 Hz), 5.16 (2H, s), 5.87 (1H, s), 7.36-7.47 (5H, m), 8.87 (2H, br s).
Obs MS [M+1]: 302.5

Example 261

1-{5-[(3-Chlorobenzyl)oxy]-1-(2-ethylbutyl)-1H-pyrazol-3-yl}-N-methylmethanamine hydrochloride Obs MS [M+1]: 336.4

Example 262

1-{5-[(2,5-Difluorobenzyl)oxy]-1-(2-ethylbutyl)-1H-pyrazol-3-yl}-N-methylmethanamine hydrochloride Obs MS [M+1]: 338.4

Example 263

1-{5-[(5-Chloro-2-fluorobenzyl)oxy]-1-(2-ethylbutyl)-1H-pyrazol-3-yl}-N-methylmethanamine hydrochloride Obs MS [M+1]: 354.4

Example 264

1-[5-(Benzyloxy)-1-(3,3-dimethylbutyl)-1H-pyrazol-3-yl]-N-methylmethanamine hydrochloride $^1$H-NMR (300 MHz, DMSO-d$_6$) δ: 0.88 (9H, s), 1.53-1.58 (2H, m), 2.52 (3H, br s), 3.88-3.98 (4H, m), 5.18 (2H, s), 5.89 (1H, s), 7.37-7.48 (5H, m), 8.94 (2H, br s).
Obs MS [M+1]: 302.5

Example 265

1-{5-[(3-Chlorobenzyl)oxy]-1-(3,3-dimethylbutyl)-1H-pyrazol-3-yl}-N-methylmethanamine hydrochloride $^1$H-NMR (300 MHz, DMSO-d$_6$) δ: 0.90 (9H, s), 1.53-1.59 (2H, m), 2.52 (3H, br s), 3.90-3.97 (4H, m), 5.20 (2H, s), 5.90 (1H, br s), 7.40-7.47 (3H, m), 7.53 (1H, s), 9.04 (2H, br s).
Obs MS [M+1]: 336.4

Example 266

1-{5-[(2,5-Difluorobenzyl)oxy]-1-(3,3-dimethylbutyl)-1H-pyrazol-3-yl}-N-methylmethanamine hydrochloride $^1$H-NMR (300 MHz, DMSO-d$_6$) δ: 0.87 (9H, s), 1.51-1.56 (2H, m), 2.52 (3H, br s), 3.86-3.92 (2H, m), 3.96 (2H, br t, J=5.1 Hz), 5.22 (2H, s), 5.96 (1H, br s), 7.27-7.39 (2H, m), 7.40-7.47 (1H, m), 9.01 (2H, br s).
Obs MS [M+1]: 338.4

Example 267

1-{5-[(5-Chloro-2-fluorobenzyl)oxy]-1-(3,3-dimethylbutyl)-1H-pyrazol-3-yl}-N-methylmethanamine hydrochloride $^1$H-NMR (300 MHz, DMSO-d$_6$) δ: 0.87 (9H, s), 1.51-1.56 (2H, m), 2.53 (3H, t, J=4.5 Hz), 3.87-3.92 (2H, m), 3.97 (2H, br t, J=5.7 Hz), 5.23 (2H, s), 5.95 (1H, s), 7.37 (1H, t, J=9.3 Hz), 7.50-7.56 (1H, m), 7.66 (1H, dd, J=6.3, 2.7 Hz), 8.95 (2H, br s).
Obs MS [M+1]: 354.3

Example 268

1-[5-(Benzyloxy)-1-(3-methylbutyl)-1H-pyrazol-3-yl]-N-methylmethanamine hydrochloride $^1$H-NMR (300 MHz, CDCl$_3$) δ: 0.90 (6H, d, J=6.4 Hz), 1.44-1.57 (1H, m), 1.59-1.65 (2H, m), 2.61 (3H, br s), 3.95 (2H, t, J=7.3 Hz), 4.09 (2H, br s), 5.09 (2H, s), 6.11 (1H, s), 7.34-7.41 (5H, m), 9.78 (2H, br s).
Obs MS [M+1]: 288.3

Example 269

1-{5-[(2,5-Difluorobenzyl)oxy]-1-(3-methylbutyl)-1H-pyrazol-3-yl}-N-methylmethanamine hydrochloride $^1$H-NMR (300 MHz, CDCl$_3$) δ: 0.91 (6H, d, J=6.6 Hz), 1.45-1.68 (3H, m), 2.63 (3H, br s), 3.96 (2H, br t, J=7.3 Hz), 4.10 (2H, br s), 5.13 (2H, s), 6.15 (1H, s), 7.02-7.10 (2H, m), 7.12-7.18 (1H, m), 9.80 (2H, s).
Obs MS [M+1]: 324.4

Example 270

1-{5-[(5-Chloro-2-fluorobenzyl)oxy]-1-(3-methylbutyl)-1H-pyrazol-3-yl}-N-methylmethanamine hydrochloride $^1$H-NMR (300 MHz, CDCl$_3$) δ: 0.91 (6H, d, J=6.4 Hz), 1.47-1.67 (3H, m), 2.63 (3H, br s), 3.95 (2H, br t, J=7.2 Hz), 4.10 (2H, br s), 5.11 (2H, s), 6.11 (1H, d, J=7.0 Hz), 7.03-7.09 (1H, m), 7.28-7.35 (1H, m), 7.42 (1H, dd, J=6.2, 2.4 Hz), 9.77 (2H, d, J=0.9 Hz).
Obs MS [M+1]: 340.4

Example 271

1-[5-(Benzyloxy)-1-(4,4,4-trifluorobutyl)-1H-pyrazol-3-yl]-N-methylmethanamine hydrochloride $^1$H-NMR (300 MHz, CDCl$_3$) δ: 2.04 (4H, m), 2.62 (3H, s), 4.01 (2H, m), 4.09 (2H, br s), 5.10 (2H, s), 6.15 (1H, s), 7.39 (5H, m), 9.81 (2H, br s).
Obs MS [M+1]: 328.3

Example 272

1-{5-[(2,5-Difluorobenzyl)oxy]-1-(4,4,4-trifluorobutyl)-1H-pyrazol-3-yl}-N-methylmethanamine hydrochloride $^1$H-NMR (300 MHz, CDCl$_3$) δ: 2.04 (4H, m), 2.62 (3H, s), 4.01 (2H, m), 4.09 (2H, br s), 5.13 (2H, s), 6.18 (1H, br s), 7.03-7.09 (2H, m), 7.14 (1H, m), 9.86 (2H, br s)
Obs MS [M+1]: 364.2

Example 273

1-[5-(Benzyloxy)-1-(3-methoxy-3-methylbutyl)-1H-pyrazol-3-yl]-N-methylmethanamine hydrochloride $^1$H-NMR (300 MHz, DMSO-d$_6$) δ: 1.08 (6H, s), 1.76-1.83 (2H, m), 2.52 (3H, br t, J=5.5 Hz), 3.05 (3H, s), 3.88-3.97 (4H, m), 5.16 (2H, s), 5.87 (1H, s), 7.35-7.47 (5H, m), 8.93 (2H, br s).
Obs MS [M+1]: 318.2

Example 274

1-{5-[(2,5-Difluorobenzyl)oxy]-1-(3-methoxy-3-methylbutyl)-1H-pyrazol-3-yl}-N-methylmethanamine hydrochloride $^1$H-NMR (300 MHz, DMSO-d$_6$) δ: 1.07 (6H, s), 1.75-1.83 (2H, m), 2.53 (3H, br t, J=4.4 Hz), 3.04 (3H, s), 3.87-3.99 (4H, m), 5.21 (2H, s), 5.93 (1H, s), 7.29-7.38 (2H, m), 7.44 (1H, dd, J=8.7, 5.6 Hz), 8.94 (2H, s).
Obs MS [M+1]: 354.4

Example 275

1-{5-[(5-Chloro-2-fluorobenzyl)oxy]-1-(3-methoxy-3-methyl-butyl)-1H-pyrazol-3-yl}-N-methylmethanamine hydrochloride $^1$H-NMR (300 MHz, DMSO-$d_6$) δ: 1.08 (6H, s), 1.75-1.82 (2H, m), 2.53 (3H, br t, J=5.1 Hz), 3.04 (3H, s), 3.86-3.99 (4H, m), 5.21 (2H, s), 5.93 (1H, s), 7.35 (1H, t, J=9.3 Hz), 7.49-7.56 (1H, m), 7.66 (1H, dd, J=6.3, 2.7 Hz), 8.94 (2H, s).

Obs MS [M+1]: 370.3

Examples 276 to 282

The compounds of Examples 276 to 282 as shown in Table 12 were prepared in the same manner as in Examples 20 to 40 except that the compound obtained in Reference Example 1 and a corresponding benzyl chloride or benzyl bromide were used. Step (i) was carried out by Method C described as a general process in Examples 20 to 40.

TABLE 12

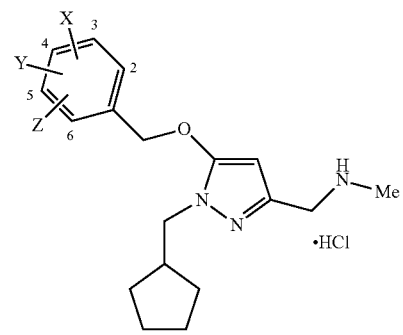

| Ex. | X | Y | Z | Obs MS [M + 1] |
|---|---|---|---|---|
| 276 | 2-F | 3-F | 4-F | 354.4 |
| 277 | 2-F | 3-F | 5-F | 354.4 |
| 278 | 2-F | 3-F | 6-F | 354.4 |
| 279 | 2-F | 3-Me | 6-F | 350.4 |
| 280 | 2-F | 4-F | 5-F | 354.4 |
| 281 | 2-F | 4-F | 6-F | 354.4 |
| 282 | 2-Cl | 4-F | 5-F | 370.3 |

Example 276

1-{1-(Cyclopentylmethyl)-5-[(2,3,4-trifluorobenzyl)oxy]-1H-pyrazol-3-yl}-N-methylmethanamine hydrochloride $^1$H-NMR (400 MHz, CDCl$_3$) δ: 1.19 (2H, m), 1.60-1.75 (6H, m), 2.41 (1H, m), 2.69 (3H, s), 3.95 (2H, d, J=8.0 Hz), 4.24 (2H, s), 5.22 (2H, s), 6.60 (1H, s), 7.05 (1H, m), 7.25 (1H, m), 10.14 (2H, br s).

Example 277

1-{1-(Cyclopentylmethyl)-5-[(2,3,5-trifluorobenzyl)oxy]-1H-pyrazol-3-yl}-N-methylmethanamine hydrochloride $^1$H-NMR (400 MHz, CDCl$_3$) δ: 1.20 (2H, m), 1.45-1.70 (6H, m), 2.36 (1H, m), 2.61 (3H, s), 3.86 (2H, d, J=8.0 Hz), 4.11 (2H, s), 5.15 (2H, s), 6.22 (1H, s), 6.90-7.00 (2H, m), 9.82 (2H, br s).

Example 278

1-{1-(Cyclopentylmethyl)-5-[(2,3,6-trifluorobenzyl)oxy]-1H-pyrazol-3-yl}-N-methylmethanamine hydrochloride $^1$H-NMR (400 MHz, CDCl$_3$) δ: 1.16 (2H, m), 1.44-1.65 (6H, m), 2.31 (1H, m), 2.60 (3H, s), 3.78 (2H, d, J=8.0 Hz), 4.09 (2H, s), 5.16 (2H, s), 6.19 (1H, s), 6.89 (1H, m), 7.18 (1H, m), 9.78 (2H, br s).

Example 279

1-{1-(Cyclopentylmethyl)-5-[(2,6-difluoro-3-methylbenzyl)-oxy]-1H-pyrazol-3-yl}-N-methylmethanamine hydrochloride $^1$H-NMR (400 MHz, CDCl$_3$) δ: 1.16 (2H, m), 1.40-1.65 (6H, m), 2.23 (3H, s), 2.31 (1H, m), 2.61 (3H, s), 3.78 (2H, d, J=8.0 Hz), 4.10 (2H, s), 5.14 (2H, s), 6.20 (1H, s), 6.79-6.85 (1H, m), 7.13-7.22 (1H, m), 9.82 (2H, br s).

Example 280

1-{1-(Cyclopentylmethyl)-5-[(2,4,5-trifluorobenzyl)oxy]-1H-pyrazol-3-yl}-N-methylmethanamine hydrochloride $^1$H-NMR (400 MHz, CDCl$_3$) δ: 1.19 (2H, m), 1.50-1.70 (6H, m), 2.38 (1H, m), 2.63 (3H, s), 3.88 (2H, d, J=8.0 Hz), 4.15 (2H, s), 5.11 (2H, s), 6.35 (1H, s), 6.94-7.02 (1H, m), 7.24-7.32 (1H, m), 9.97 (2H, br s).

Example 281

1-{1-(Cyclopentylmethyl)-5-[(2,4,6-trifluorobenzyl)oxy]-1H-pyrazol-3-yl}-N-methylmethanamine hydrochloride $^1$H-NMR (400 MHz, CDCl$_3$) δ: 1.16 (2H, m), 1.45-1.70 (6H, m), 2.30 (1H, m), 2.60 (3H, s), 3.77 (2H, d, J=8.0 Hz), 4.08 (2H, s), 5.09 (2H, s), 6.15 (1H, s), 6.71 (2H, dd, J=8.0, 8.0 Hz), 9.76 (2H, br s).

Example 282

1-{5-[(2-Chloro-4,5-difluorobenzyl)oxy]-1-(cyclopentyl-methyl)-1H-pyrazol-3-yl}-N-methylmethanamine hydrochloride $^1$H-NMR (400 MHz, CDCl$_3$) δ: 1.20 (2H, m), 1.45-1.70 (6H, m), 2.32 (1H, m), 2.63 (3H, s), 3.88 (2H, d, J=8.0 Hz), 4.12 (2H, s), 5.12 (2H, s), 6.24 (1H, s), 7.24-7.38 (2H, m), 9.89 (2H, br s).

Example 283

N-Methyl-1-{1-(3-methylbutyl)-5-[(2,4,5-trifluorobenzyl)-oxy]-1H-pyrazol-3-yl}methanamine hydrochloride

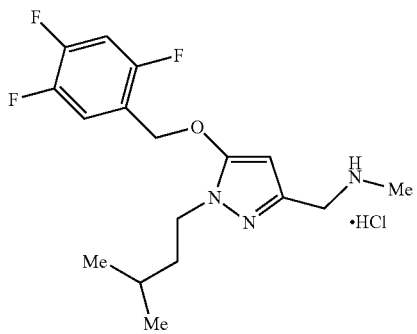 [SMILES: CNCc1cc(OCc2cc(F)c(F)cc2F)n(CCC(C)C)n1 ; Cl]

The title compound was prepared in the same manner as in Example 280 except that the compound in Reference Example 24 was used.

$^1$H-NMR (400 MHz, CDCl$_3$) δ: 0.88 (6H, d, J=6.0 Hz), 1.40-1.70 (5H, m), 2.59 (3H, s), 3.91 (2H, d, J=6.0 Hz), 4.06 (2H, s), 5.06 (2H, s), 6.11 (1H, s), 6.93-7.01 (1H, m), 7.22-7.35 (1H, m).

Example 284

1-{1-(3,3-Dimethylbutyl)-5-[(2,4,5-trifluorobenzyl)oxy]-1H-pyrazol-3-yl}-N-methylmethanamine hydrochloride

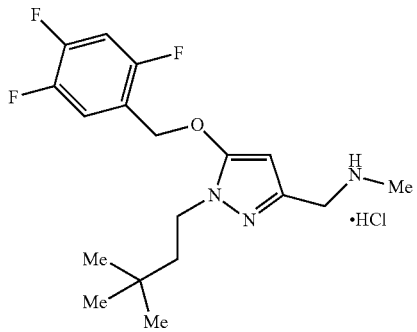 [SMILES: CNCc1cc(OCc2cc(F)c(F)cc2F)n(CCC(C)(C)C)n1 ; Cl]

The title compound was prepared in the same manner as in Example 280 except that the compound obtained in Reference Example 22 was used.

$^1$H-NMR (400 MHz, CDCl$_3$) δ: 0.90 (9H, s), 1.60-1.65 (2H, m), 2.59 (3H, s), 3.89-3.94 (2H, m), 4.07 (2H, s), 5.07 (2H, s), 6.13 (1H, s), 6.93-7.02 (1H, m), 7.25-7.35 (1H, m), 9.77 (2H, br s).

Example 285

1-{1-(4-Methoxybenzyl)-5-[(2,4,5-trifluorobenzyl)oxy]-1H-pyrazol-3-yl}-N-methylmethanamine hydrochloride

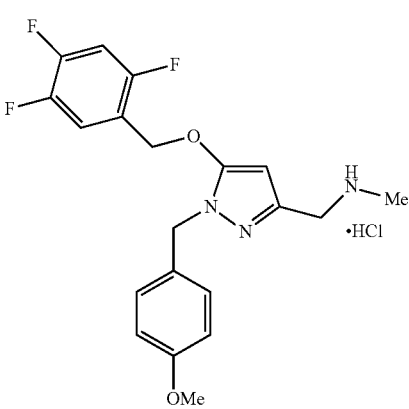 [SMILES: CNCc1cc(OCc2cc(F)c(F)cc2F)n(Cc2ccc(OC)cc2)n1 ; Cl]

The title compound was prepared in the same manner as in Example 198.

$^1$H-NMR (400 MHz, CDCl$_3$) δ: 2.58 (3H, s), 3.76 (3H, s), 4.06 (2H, s), 5.03 (2H, s), 5.03 (2H, s), 6.13 (1H, s), 6.80 (2H, d, J=8.0 Hz), 6.90-6.96 (1H, m), 7.08 (2H, d, J=8.0 Hz), 7.23-7.29 (1H, m), 9.79 (2H, br s).

Example 286

N-Methyl-1-{1-(4-methylbenzyl)-5-[(2,4,5-trifluorobenzyl)-oxy]-1H-pyrazol-3-yl}methanamine hydrochloride

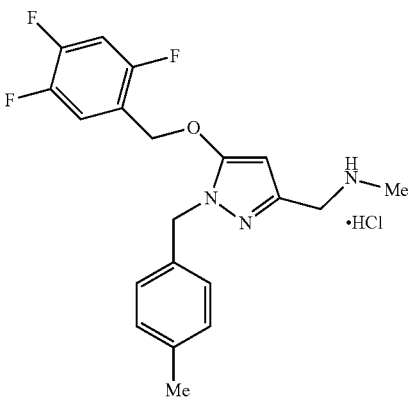 [SMILES: CNCc1cc(OCc2cc(F)c(F)cc2F)n(Cc2ccc(C)cc2)n1 ; Cl]

The title compound was prepared in the same manner as in Example 198.

$^1$H-NMR (400 MHz, CDCl$_3$) δ: 2.29 (3H, s), 2.58 (3H, s), 4.06 (2H, s), 5.03 (2H, s), 5.05 (2H, s), 6.14 (1H, s), 6.88-6.96 (1H, m), 7.01 (2H, d, J=8.0 Hz), 7.08 (2H, d, J=8.0 Hz), 7.21-7.26 (1H, m), 9.80 (2H, br s).

Example 287

2-({3-[(Methylamino)methyl]-5-[(2,4,5-trifluorobenzyl)oxy]-1H-pyrazol-1-yl}methyl)benzonitrile hydrochloride

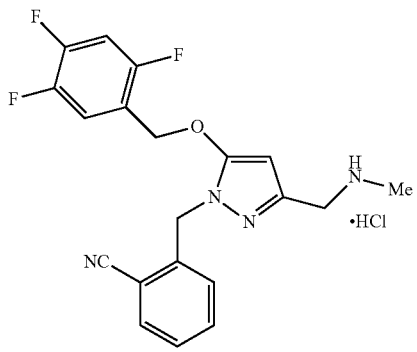 [SMILES: CNCc1cc(OCc2cc(F)c(F)cc2F)n(Cc2ccccc2C#N)n1 ; Cl]

The title compound was prepared in the same manner as in Example 198.

¹H-NMR (400 MHz, CDCl₃) δ: 2.61 (3H, s), 4.07 (2H, s), 5.07 (2H, s), 5.32 (2H, s), 6.19 (1H, s), 6.88-6.96 (1H, m), 7.06-7.16 (2H, m), 7.38 (1H, dd, J=8.0, 8.0 Hz), 7.52 (1H, dd, J=8.0, 8.0 Hz), 7.64 (1H, d, J=8.0 Hz), 9.85 (2H, br s).

Example 288

1-[5-(Benzyloxy)-1-(1-cyclopentylethyl)-1H-pyrazol-3-yl]-N-methylmethanamine hydrochloride

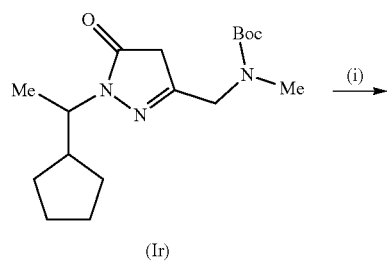

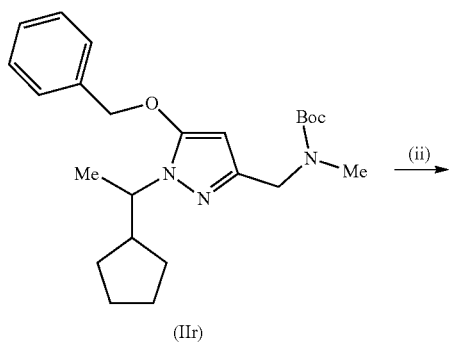

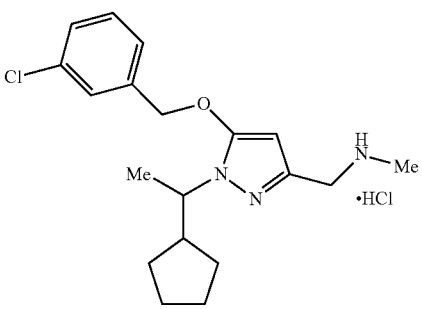 [SMILES: CNCc1cc(OCc2cccc(Cl)c2)n(C(C)C2CCCC2)n1 ; Cl]

Step (i)

To a solution of Compound (Ir) obtained in Reference Example 6 (40 mg, 0.12 mmol) and cesium carbonate (81 mg, 0.25 mmol) in acetonitrile (0.6 mL) was added a corresponding benzyl chloride (21 μL, 0.19 mmol) at room temperature, and the reaction mixture was stirred at room temperature for 3 hours. The salt was filtered off, the filtrate was concentrated, and the concentrated residue was purified by PTLC (n-hexane:ethyl acetate=70:30) to give Compound (IIr) (33 mg, 64%)

Step (ii)

The Compound (IIr) was dissolved in chloroform (0.6 mL), to the solution was added 4 mol/L HCl/1,4-dioxane (0.6 mL) at room temperature, the reaction mixture was stirred at room temperature for 30 minutes, and the solvent was evaporated under reduced pressure. The residue was purified by adding diethyl ether and removing the supernatant by decantation, and the resultant solid was dried under reduced pressure to give the title Compound (IIIr) (26 mg, 95%) as a light brown powder.

¹H-NMR (300 MHz, DMSO-d₆) δ: 0.90-1.03 (1H, m), 1.14-1.27 (2H, m), 1.31 (3H, d, J=6.6 Hz), 1.34-1.63 (4H, m), 1.67-1.80 (1H, m), 2.16-2.30 (1H, m), 2.50 (3H, br s), 3.95 (2H, br, J=5.6 Hz), 3.99-4.08 (1H, m), 5.14 (2H, s), 5.86 (1H, s), 7.32-7.46 (5H, m), 8.92 (2H, br s).

Examples 289 to 291

The compounds of Examples 289 to 291 were prepared in the same manner as in Example 288 except that the ketone compound obtained in Reference Example 6 and a corresponding benzyl chloride were used.

Example 289

1-{5-[(3-Chlorobenzyl)oxy]-1-(1-cyclopentylethyl)-1H-pyrazol-3-yl}-N-methylmethanamine hydrochloride ¹H-NMR (300 MHz, DMSO-d₆) δ: 0.90-1.02 (1H, m), 1.17-1.27 (2H, m), 1.32 (3H, d, J=6.8 Hz), 1.35-1.65 (4H, m), 1.69-1.80 (1H, m), 2.16-2.30 (1H, m), 2.50 (3H, br s), 3.94 (2H, br t, J=5.6 Hz), 3.99-4.09 (1H, m), 5.17 (2H, s), 5.87 (1H, s), 7.39-7.47 (3H, m), 7.50 (1H, br s), 9.03 (2H, br s).

Example 290

1-{1-(1-Cyclopentylethyl)-5-[(2,5-difluorobenzyl)oxy]-1H-pyrazol-3-yl}-N-methylmethanamine hydrochloride

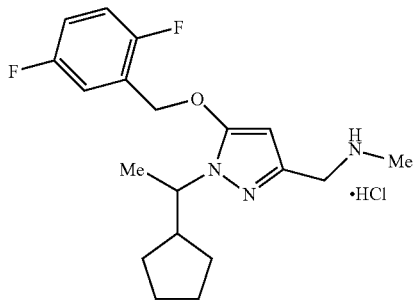 [SMILES: CNCc1cc(OCc2cc(F)ccc2F)n(C(C)C2CCCC2)n1 ; Cl]

¹H-NMR (300 MHz, DMSO-d₆) δ: 0.87-0.99 (1H, m), 1.12-1.27 (2H, m), 1.30 (3H, d, J=6.6 Hz), 1.34-1.60 (4H, m), 1.66-1.80 (1H, m), 2.21 (1H, br dt, J=25.6, 8.2 Hz), 2.50 (3H, br s), 3.94-4.05 (3H, m), 5.18 (2H, s), 5.93 (1H, s), 7.25-7.38 (2H, m), 7.40-7.46 (1H, m), 8.98 (2H, br s).

Example 291

1-{5-[(5-Chloro-2-fluorobenzyl)oxy]-1-(1-cyclopentylethyl)-1H-pyrazol-3-yl}-N-methylmethanamine hydrochloride

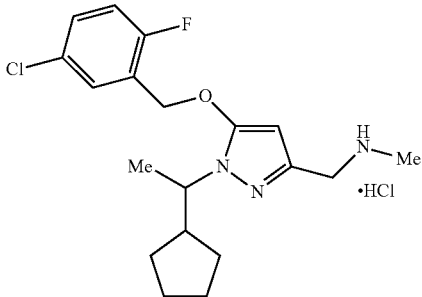 [SMILES: CNCc1cc(OCc2cc(Cl)ccc2F)n(C(C)C2CCCC2)n1 ; Cl]

¹H-NMR (300 MHz, DMSO-d₆) δ: 0.86-0.98 (1H, m), 1.12-1.26 (2H, m), 1.29 (3H, d, J=6.6 Hz), 1.33-1.60 (4H, m), 1.65-1.77 (1H, m), 2.20 (1H, br td, J=17.1, 8.9 Hz), 2.50 (3H, br s), 3.91-4.03 (3H, m), 5.18 (2H, s), 5.93 (1H, s), 7.34 (1H, t, J=9.2 Hz), 7.51 (1H, ddd, J=8.8, 4.4, 2.8 Hz), 7.63 (1H, br dd, J=6.2, 2.8 Hz), 8.99 (2H, br s).

Examples 292 to 295

The compounds of Examples 292 to 295 were prepared in the same manner as in Example 288 except that the compound obtained in Reference Example 7 and a corresponding benzyl chloride or benzyl bromide were used.

Example 292

1-[5-(Benzyloxy)-1-(1-cyclohexylethyl)-1H-pyrazol-3-yl]-N-methylmethanamine hydrochloride

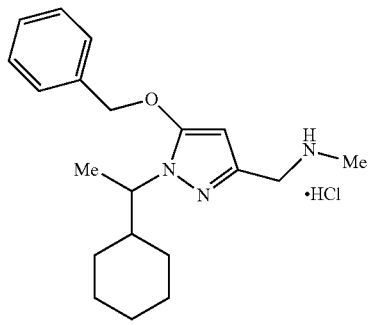 [SMILES: CNCc1cc(OCc2ccccc2)n(C(C)C2CCCCC2)n1 ; Cl]

¹H-NMR (300 MHz, DMSO-d₆) δ: 0.71-1.23 (6H, m), 1.30 (3H, d, J=6.8 Hz), 1.55-1.80 (5H, m), 2.51 (3H, br s), 3.93-4.04 (2H, m), 4.12-4.25 (1H, m), 5.15 (2H, br s), 5.84-5.93 (1H, m), 7.34-7.46 (5H, m), 8.83-9.13 (2H, m).

Obs MS [M+1]: 328.3

Example 293

1-{1-(1-Cyclohexylethyl)-5-[(2-fluorobenzyl)oxy]-1H-pyrazol-3-yl}-N-methylmethanamine hydrochloride

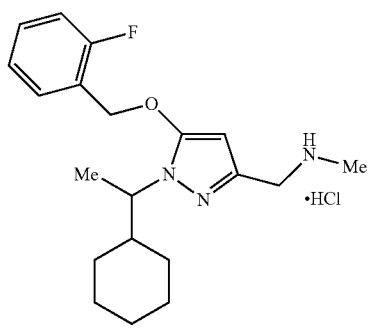 [SMILES: CNCc1cc(OCc2ccccc2F)n(C(C)C2CCCCC2)n1 ; Cl]

¹H-NMR (300 MHz, CDCl₃) δ: 0.74-1.00 (2H, m), 1.03-1.28 (4H, m), 1.39 (3H, d, J=7.0 Hz), 1.61-1.88 (5H, m), 2.45 (3H, s), 3.65 (2H, s), 3.91-4.02 (1H, m), 5.12 (2H, s), 5.56 (1H, s), 7.06-7.13 (1H, m), 7.17 (1H, ddd, J=7.5, 7.5, 1.1 Hz), 7.31-7.39 (1H, m), 7.43 (1H, ddd, J=7.5, 7.5, 1.8 Hz)

Obs MS [M+1]: 346.5

Example 294

1-{1-(1-Cyclohexylethyl)-5-[(3-fluorobenzyl)oxy]-1H-pyrazol-3-yl}-N-methylmethanamine hydrochloride

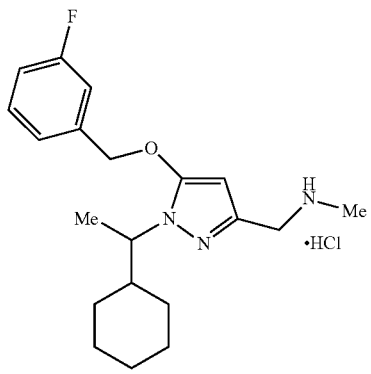 [SMILES: CNCc1cc(OCc2cccc(F)c2)n(C(C)C2CCCCC2)n1 ; Cl]

$^1$H-NMR (300 MHz, CDCl$_3$) δ: 0.73-1.32 (6H, m), 1.40 (3H, d, J=6.6 Hz), 1.56-1.90 (5H, m), 2.61 (3H, s), 3.97-4.23 (3H, m), 5.09 (2H, s), 6.13 (1H, s), 7.01-7.21 (3H, m), 7.31-7.42 (1H, m), 9.75 (2H, br s).

Obs MS [M+1]: 346.2

Example 295

1-{1-(1-Cyclohexylethyl)-5-[(4-fluorobenzyl)oxy]-1H-pyrazol-3-yl}-N-methylmethanamine hydrochloride

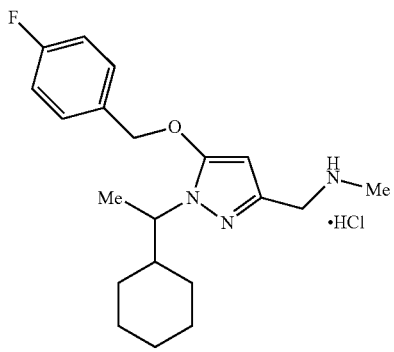 [SMILES: CNCc1cc(OCc2ccc(F)cc2)n(C(C)C2CCCCC2)n1 ; Cl]

$^1$H-NMR (300 MHz, CDCl$_3$) δ: 0.69-1.35 (6H, m), 1.43 (3H, d, J=5.3 Hz), 1.53-1.89 (5H, m), 2.65 (3H, s), 3.98-4.35 (3H, m), 5.12 (2H, s), 6.34 (1H, s), 7.03-7.17 (2H, m), 7.31-7.50 (2H, m), 9.92 (2H, br s).

Obs MS [M+1]: 346.2

Examples 296 to 308

The compounds of Examples 296 to 308 as shown in Table 13 were prepared in the same manner as in Examples 20 to 40 except that the compound obtained in Reference Example 7 and a corresponding benzyl bromide or benzyl chloride were used.

TABLE 13

| Ex. | X | Y | Benzylation method | Salt | Obs MS [M + 1] |
|---|---|---|---|---|---|
| 296 | 2-Cl | H | C | Free base | 362.2 |
| 297 | 3-Cl | H | C | Hydrochloride | 362.5 |
| 298 | 2-Me | H | C | Free base | 342.3 |
| 299 | 3-Me | H | B | Hydrochloride | 342.3 |
| 300 | 2-F | 4-F | B | Hydrochloride | 364.5 |
| 301 | 2-Cl | 4-F | B | Hydrochloride | 380.2 |
| 302 | 2-Me | 4-F | B | Hydrochloride | 360.5 |
| 303 | 2-F | 5-F | C | Free base | 364.2 |
| 304 | 2-F | 5-Cl | C | Free base | 380.4 |
| 305 | 2-F | 5-Me | C | Free base | 360.2 |
| 306 | 2-Cl | 5-F | C | Free base | 380.2 |
| 307 | 2-Me | 5-F | C | Free base | 360.5 |
| 308 | 3-Me | 5-Me | B | Hydrochloride | 356.2 |

Examples 309 and 310

The compounds of Examples 309 and 310 were prepared in the same manner as in Example 288.

Example 309

1-[5-(Benzyloxy)-1-(1-cyclohexylpropyl)-1H-pyrazol-3-yl]-N-methylmethanamine hydrochloride

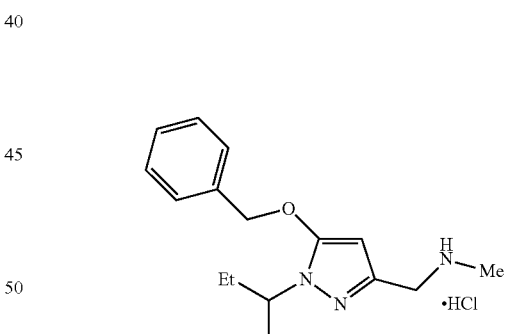

$^1$H-NMR (300 MHz, CDCl$_3$) δ: 0.64 (3H, t, J=7.3 Hz), 0.74-1.00 (2H, m), 1.04-1.31 (4H, m), 1.62 (2H, m), 1.68-1.93 (5H, m), 2.62 (3H, s), 3.84 (1H, dt, J=7.8, 7.8 Hz), 4.16 (2H, s), 5.12 (2H, s), 6.23 (1H, s), 7.40 (5H, m), 9.90 (2H, br s).

Obs MS [M+1]: 342.3

Example 310

1-{1-(1-Cyclohexylpropyl)-5-[(2,5-difluorobenzyl)oxy]-1H-pyrazol-3-yl}-N-methylmethanamine hydrochloride

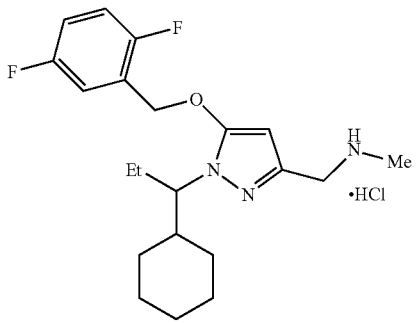 [SMILES: CCC(C1CCCCC1)n1nc(CNC)cc1OCc1cc(F)ccc1F ; Cl]

¹H-NMR (300 MHz, CDCl₃) δ: 0.63 (3H, t, J=7.2 Hz), 0.73-1.00 (2H, m), 1.04-1.32 (4H, m), 1.56-1.91 (7H, m), 2.59 (3H, s), 3.77 (1H, dt, J=8.0, 8.0 Hz), 4.12 (2H, s), 5.12 (2H, s), 6.14 (1H, s), 7.05 (2H, m), 7.14 (1H, m), 9.80 (2H, br s).
Obs MS [M+1]: 378.5

Examples 311 to 327

The compounds of Examples 311 to 327 as shown in Table 14 were prepared in the same manner as in Examples 20 to 40 except that the compounds obtained in Reference Examples 31 to 35 and a corresponding benzyl chloride or benzyl bromide were used. The benzylation in Step (i) was carried out by Method C described as a general process in Examples 20 to 40.

TABLE 14

| Ex. | R | X | Y | Salt | Obs MS [M + 1] |
|---|---|---|---|---|---|
| 311 | cyclopentylmethyl | 2-F | 5-F | Hydrochloride | 350.4 |
| 312 | cyclohexylmethyl | H | H | Hydrochloride | 328.6 |
| 313 | cyclohexylmethyl | 2-F | 5-F | Hydrochloride | 364.2 |
| 314 | cyclohexylmethyl | 2-F | 5-Cl | Hydrochloride | 380.4 |
| 315 | cyclopentylethyl | 2-F | 5-F | Hydrochloride | 364.5 |
| 316 | cyclohexylethyl | H | H | Hydrochloride | 342.3 |
| 317 | cyclohexylethyl | 2-Cl | H | Free base | 376.5 |
| 318 | cyclohexylethyl | 3-Cl | H | Free base | 376.5 |
| 319 | cyclohexylethyl | 4-Cl | H | Free base | 376.5 |
| 320 | cyclohexylethyl | 2-F | 3-F | Free base | 378.5 |
| 321 | cyclohexylethyl | 2-F | 4-F | Free base | 378.5 |
| 322 | cyclohexylethyl | 2-F | 5-F | Hydrochloride | 378.5 |
| 323 | cyclohexylethyl | 2-F | 6-F | Free base | 378.5 |
| 324 | cyclohexylethyl | 3-F | 4-F | Free base | 378.5 |

TABLE 14-continued

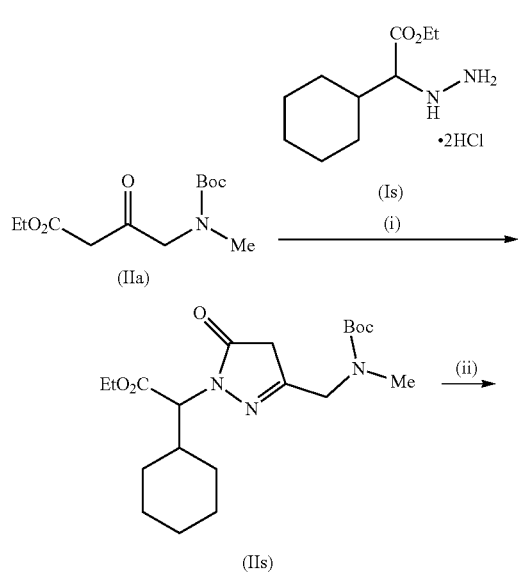

| Ex. | R | X | Y | Salt | Obs MS [M + 1] |
|---|---|---|---|---|---|
| 325 | cyclohexylethyl | 3-F | 5-F | Free base | 378.5 |
| 326 | Me-CH(CH2Me)-CH2- | H | H | Hydrochloride | 316.6 |
| 327 | Me-CH(CH2Me)-CH2- | 2-F | 5-F | Hydrochloride | 352.4 |

(*shows the bonding position)

Example 328

2-{5-(Benzyloxy)-3-[(methylamino)methyl]-H-pyrazol-1-yl}-2-cyclohexyl-ethanol hydrochloride

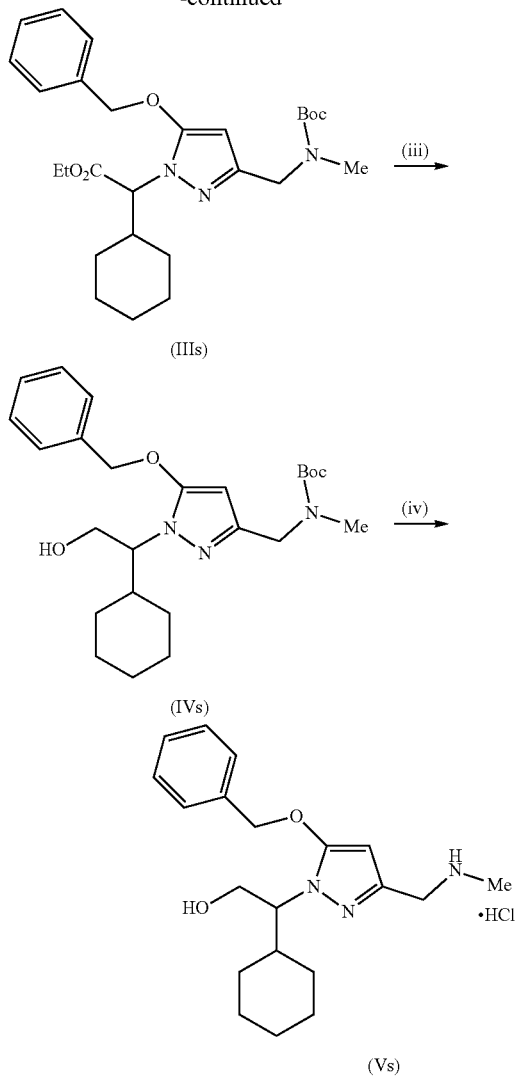

Step (i)

To a solution of Compound (Is) prepared in Reference Example 42 (238 mg, 1.0 mmol) and triethylamine (147 µL, 1.1 mmol) in ethanol (8 mL) was added the Compound (IIa) prepared in Step (i) of Reference Example 1 (262 mg, 1.0 mmol) at room temperature, and the reaction mixture was stirred at 80° C. for 16 hours. To the resultant was added triethylamine (147 µL, 1.1 mmol), and the reaction mixture was stirred at 80° C. for 3.5 hours. The mixture was cooled to room temperature, poured into 5% aq. KHSO4 (20 mL), and extracted with ethyl acetate. The organic layer was dried, the solvent was evaporated under reduced pressure, and the concentrated residue was purified by silica gel column chromatography (n-hexane:ethyl acetate=50:50) to give Compound (IIs) (189 mg, 47%) as a brown oil.

Step (ii)

To a solution of the Compound (IIs) (50 mg, 0.13 mmol) and cesium carbonate (82 mg, 0.25 mmol) in acetonitrile (0.65 mL) was added benzyl chloride (22 µL, 0.19 mmol) at room temperature, and the reaction mixture was stirred at room temperature for 2.5 hours. The resultant was diluted with ethyl acetate, the salt was filtered off, the filtrate was concentrated, and the concentrated residue was purified by PTLC (n-hexane:ethyl acetate=7:3) to give Compound (IIIs) (26 mg, 42%).

Step (iii)

To a solution of the Compound (IIIs) (26 mg, 0.054 mmol) in tetrahydrofuran (0.3 mL) was added lithium aluminum hydride (7 mg, 0.18 mmol) at 0° C., and the reaction mixture was stirred for 10 minutes. To the mixture was further added lithium aluminum hydride (12 mg, 0.32 mmol) at 0° C., and the reaction mixture was stirred for 10 minutes. To the mixture was added lithium aluminum hydride (10 mg, 0.31 mmol) at 0° C., and the reaction mixture was stirred for 40 minutes. To the mixture was added sat. aq. $Na_2SO_4$, the mixture was filtered, the filtrate was concentrated, and the concentrated residue was purified by silica gel column chromatography (ethyl acetate) to give Compound (IVs) (29 mg, quantitative)

Step (iv)

To a solution of the Compound (IVs) (29 mg, mmol) in chloroform (0.5 mL) was added 4 mol/L HCl/1,4-dioxane (0.5 mL) at room temperature, and the reaction solution was stirred at room temperature for 1 hour. The solvent was evaporated under reduced pressure to give the title Compound (Vs) (8.3 mg, 40%) as a brown oil.

$^1$H-NMR (300 MHz, DMSO-$d_6$) δ: 0.71-1.83 (11H, m), 2.53 (3H, br s), 3.76 (2H, m), 3.92-4.01 (3H, m), 4.58 (1H, br s), 5.14 (2H, s), 5.79 (1H, s), 7.35-7.45 (5H, m), 8.73 (2H, br s).

Example 329

2-Cyclohexyl-2-{5-[(2,5-difluorobenzyl)oxy]-3-[(methyl-amino)methyl]-1H-pyrazol-1-yl}ethanol hydrochloride

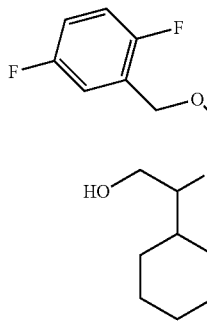

The title compound was prepared in the same manner as in Example 328.

$^1$H-NMR (300 MHz, CDCl$_3$) δ: 0.76-1.33 (6H, m), 1.55-1.99 (5H, m), 2.65 (3H, s), 3.82 (1H, m), 3.95-4.17 (4H, m), 5.12 (2H, s), 6.05 (1H, s), 7.05 (2H, m), 7.14 (1H, m), 9.57 (1H, br s), 9.81 (1H, br s).

Example 330

1-[5-(Benzyloxy)-1-(1-cyclohexyl-2-fluoroethyl)-1H-pyrazol-3-yl]-N-methylmethanamine hydrochloride

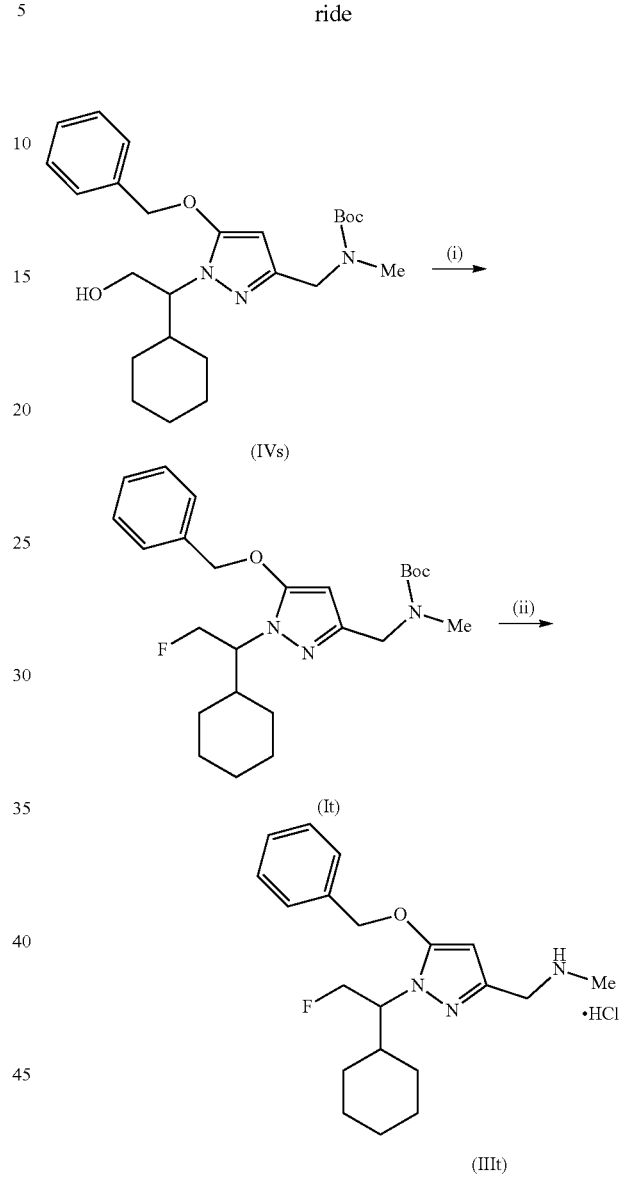

Step (i)

To a solution of the Compound (IVs) prepared in Step (iii) of Example 328 (40 mg, 0.090 mmol) in tetrahydrofuran (1 mL) was added perfluorobutane sulfonyl fluoride (32 μL, 0.18 mmol) at 0° C. To the mixture was added DBU (27 μL, 0.18 mmol) at 0° C., and the reaction mixture was stirred for 80 minutes at 0° C. and then for 3 hours with slowly warming to room temperature. To the mixture was added sat. aq. NaHCO$_3$, the mixture was extracted with ethyl acetate, the organic layer was washed with 5% KHSO$_4$, and the solvent was evaporated under reduced pressure. The concentrated residue was purified by silica gel column chromatography (n-hexane:ethyl acetate=4:1) to give Compound (It) (31 mg, 59%) as an oil.

Step (ii)

To a solution of the Compound (It) (31 mg, 0.070 mmol) in chloroform (0.4 mL) was added 4 mol/L HCl/1,4-dioxane (0.5 mL) at room temperature, and the reaction solution was stirred at room temperature for 1 hour. The solvent was evaporated under reduced pressure, the concentrated residue was purified by adding diethyl ether and removing the supernatant by decantation to give the title Compound (IIt) (24 mg, 90%) as a white powder.

$^1$H-NMR (300 MHz, CDCl$_3$) δ: 0.89 (1H, m), 0.96-1.33 (5H, m), 1.57-1.96 (5H, m), 2.59 (3H, s), 4.10 (2H, s), 4.27 (1H, m), 4.71 (1H, ddd, J=45.8, 9.7, 4.0 Hz), 4.82 (1H, ddd, J=48.2, 8.9, 8.9 Hz), 5.09 (2H, s), 6.10 (1H, s), 7.39 (5H, m), 9.77 (2H, br s).

Examples 331 to 339

The compounds of Examples 331 to 339 as shown in Table 15 were prepared in the same manner as in Examples 20 to 40 except that the compounds obtained in Reference Examples 27 to 30 and a corresponding benzyl bromide or benzyl chloride were used.

TABLE 15

| Ex. | Z | X | Y | Benzylation method | Obs MS [M + 1] |
|---|---|---|---|---|---|
| 331 | 1-Me | H | H | B | 328.6 |
| 332 | 1-Me | 3'-Cl | H | B | 362.5 |
| 333 | 1-Me | 2'-F | 5'-F | C | 364.5 |
| 334 | 2-Me | H | H | B | 328.3 |
| 335 | 2-Me | 3'-Cl | H | B | 362.2 |
| 336 | 3-Me | H | H | B | 328.3 |
| 337 | 3-Me | 3'-Cl | H | B | 362.5 |
| 338 | 4-Me | H | H | B | 328.6 |
| 339 | 4-Me | 3'-Cl | H | B | 362.5 |

Example 340

1-[5-(Benzyloxy)-1-(3,4-dihydro-2H-chromen-2-ylmethyl)-1H-pyrazol-3-yl]-N-methylmethanamine hydrochloride

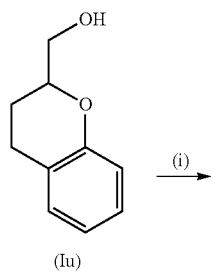

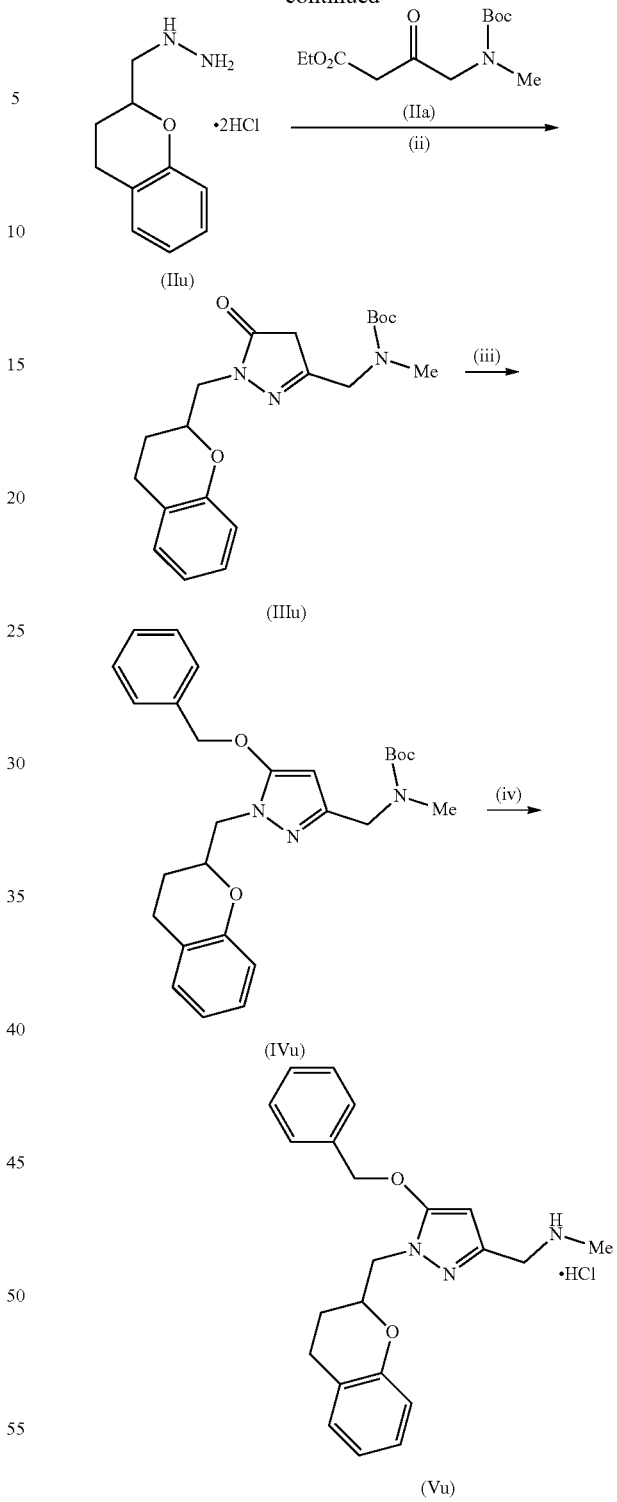

Step (i)

Compound (IIu) was prepared in the same manner as in Reference Example 42 except that Chroman-2-ylmethyl alcohol (Iu) was used.

Steps (ii) to (iv)

The desired Compound (Vu) was prepared in the same manner as in Steps (ii) to (iv) of Example 198.

¹H-NMR (400 MHz, DMSO-d₆) δ: 1.62-1.73 (1H, m), 1.94-2.02 (1H, m), 2.54 (3H, br t, J=5.2 Hz), 2.66-2.83 (2H, m), 3.99 (2H, br t, J=5.6 Hz), 4.13 (1H, dd, J=14.1, 5.1 Hz), 4.25 (1H, dd, J=14.3, 6.7 Hz), 4.32-4.39 (1H, m), 5.20 (2H, s), 5.91 (1H, s), 6.65 (1H, br d, J=8.0 Hz), 6.81 (1H, br t, J=7.0 Hz), 7.05 (2H, br t, J=7.6 Hz), 7.33-7.48 (5H, m), 8.96 (2H, br s).

Example 341

1-{5-[(3-Chlorobenzyl)oxy]-1-(3,4-dihydro-2H-chromen-2-yl-methyl)-1H-pyrazol-3-yl}-N-methyl-methanamine hydrochloride

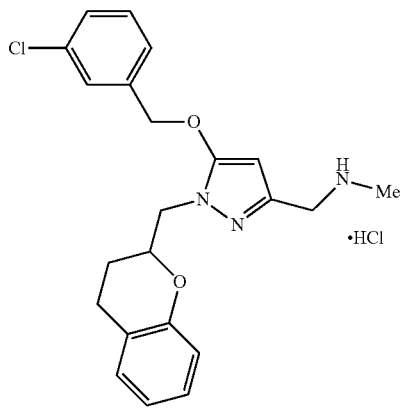 [SMILES: CNCc1cc(OCc2cccc(Cl)c2)n(CC2CCc3ccccc3O2)n1 ; Cl]

The title compound was prepared in the same manner as in Example 340.

¹H-NMR (400 MHz, DMSO-d₆) δ: 1.64-1.74 (1H, m), 1.96-2.03 (1H, m), 2.54 (3H, br t, J=4.3 Hz), 2.69-2.84 (2H, m), 3.98 (2H, br t, J=5.2 Hz), 4.16 (1H, dd, J=14.0, 5.0 Hz), 4.26 (1H, dd, J=14.4, 6.8 Hz), 4.33-4.40 (1H, m), 5.21 (2H, s), 5.90-5.96 (1H, m), 6.65 (1H, br d, J=8.0 Hz), 6.81 (1H, br t, J=7.4 Hz), 7.01-7.08 (2H, m), 7.41-7.47 (3H, m), 7.54 (1H, s), 9.01 (2H, br s).

Example 342

N-({1-(Cyclohexylmethyl)-5-[(2,5-difluorobenzyl)oxy]-1H-pyrazol-3-yl}methyl)cyclopropanamine

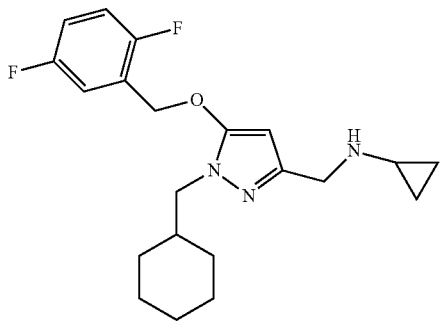 [SMILES: Fc1ccc(F)c(COc2cc(CNC3CC3)nn2CC2CCCCC2)c1]

The title compound (39 mg, 52%) was prepared in the same manner as in Steps (i) to (iv) of Reference Example 36 except that lithium borohydride was used instead of lithium aluminum hydride in Step (iii) of Reference Example 36.

¹H-NMR (300 MHz, CDCl₃) δ: 0.35-0.46 (4H, m), 0.87-1.04 (2H, m), 1.09-1.30 (3H, m), 1.54-1.94 (6H, m), 2.15-2.25 (1H, m), 3.73-3.79 (4H, m), 5.09 (2H, s), 5.53 (1H, s), 6.97-7.18 (3H, m).

The compounds in the following Examples 343 to 346 were prepared in the same manner as in Example 342.

Example 343

1-{1-(Cyclohexylmethyl)-5-[(2,5-difluorobenzyl)oxy]-1H-pyrazol-3-yl}-N,N-dimethylmethanamine

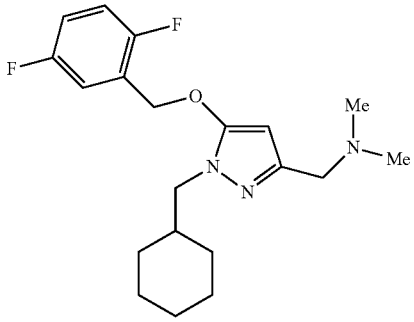 [SMILES: CN(C)Cc1cc(OCc2cc(F)ccc2F)n(CC2CCCCC2)n1]

¹H-NMR (300 MHz, CDCl₃) δ: 0.87-1.04 (2H, m), 1.09-1.30 (3H, m), 1.50-1.97 (6H, m), 2.27 (6H, s), 3.37 (2H, s), 3.77 (2H, d, J=7.2 Hz), 5.10 (2H, s), 5.59 (1H, s), 6.97-7.18 (3H, m).

Example 344

N-({1-(Cyclohexylmethyl)-5-[(2,5-difluorobenzyl)oxy]-1H-pyrazol-3-yl}methyl)ethanamine

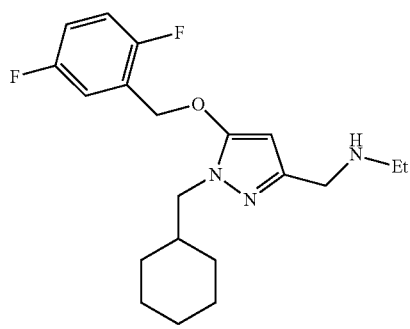 [SMILES: CCNCc1cc(OCc2cc(F)ccc2F)n(CC2CCCCC2)n1]

¹H-NMR (300 MHz, CDCl₃) δ: 0.86-1.02 (2H, m), 1.07-1.29 (6H, m), 1.44-1.94 (6H, m), 2.70 (2H, q, J=7.2 Hz), 3.69 (2H, s), 3.75 (2H, d, J=7.3 Hz), 5.10 (2H, s), 5.56 (1H, s), 6.97-7.18 (3H, m).

Example 345

N-({1-(Cyclohexylmethyl)-5-[(2,5-difluorobenzyl)oxy]-1H-pyrazol-3-yl}methyl)propan-1-amine

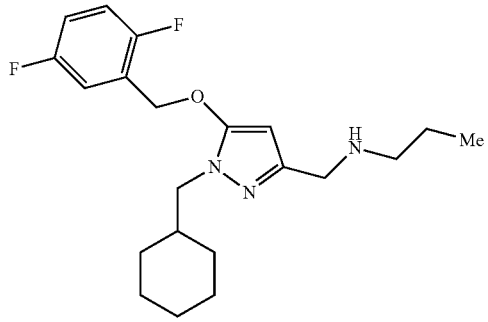 [SMILES: CCCNCc1cc(OCc2cc(F)ccc2F)n(CC2CCCCC2)n1]

$^1$H-NMR (300 MHz, CDCl$_3$) δ: 0.84-1.03 (5H, m), 1.08-1.30 (3H, m), 1.43-1.93 (8H, m), 2.61 (2H, q, J=7.3 Hz), 3.69 (2H, s), 3.75 (2H, d, J=7.2 Hz), 5.10 (2H, s), 5.55 (1H, s), 6.96-7.18 (3H, m).

Example 346

N-({1-(Cyclohexylmethyl)-5-[(2,5-difluorobenzyl)oxy]-1H-pyrazol-3-yl}methyl)propan-2-amine

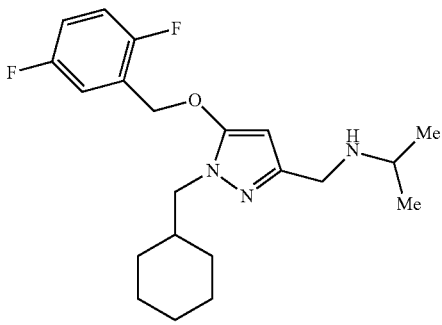 [SMILES: CC(C)NCc1cc(OCc2cc(F)ccc2F)n(CC2CCCCC2)n1]

$^1$H-NMR (300 MHz, CDCl$_3$) δ: 0.85-1.03 (2H, m), 1.09 (6H, d, J=6.2 Hz), 1.13-1.28 (3H, m), 1.48-1.93 (6H, m), 2.81-2.91 (1H, m), 3.68 (2H, s), 3.75 (2H, d, J=7.3 Hz), 5.09 (2H, s), 5.55 (1H, s), 6.97-7.18 (3H, m).

Example 347

1-{1-(Cyclopentylmethyl)-5-[(2,5-difluorobenzyl)oxy]-1H-pyrazol-3-yl}methanamine hydrochloride

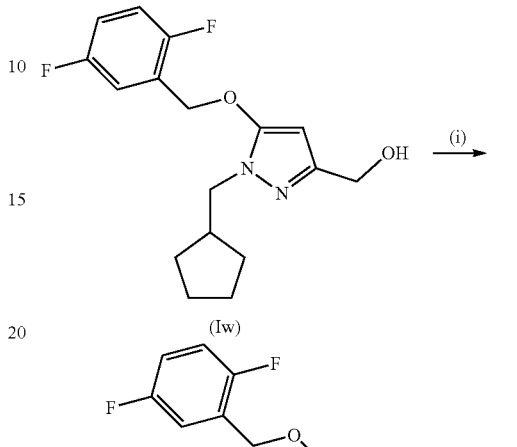

(Iw)

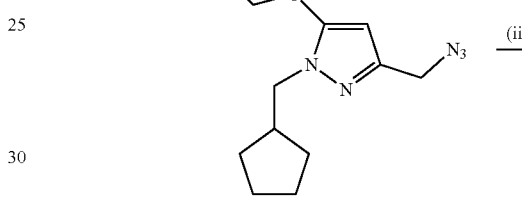

(IIw)

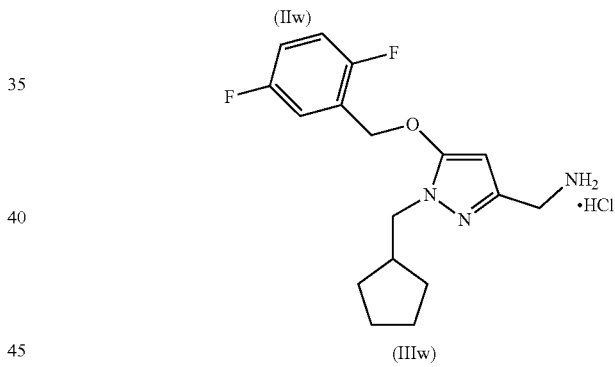

(IIIw)

Steps (i) to (iii)

To a solution of Compound (Iw) prepared in the same manner as in Steps (i) to (iii) of Example 1 (190 mg, 0.59 mmol) and triethylamine (164 μL, 1.2 mmol) in dichloromethane (3 mL) was added methanesulfonyl chloride (68 μL, 0.88 mmol) at 0° C., and the reaction mixture was stirred at 0° C. for 25 minutes. To the mixture was further added methanesulfonyl chloride (9 μL, 0.12 mmol), and the mixture was stirred at 0° C. for 5 minutes. To the reaction mixture was added sat. aq. NaHCO$_3$, and the mixture was extracted with ethyl acetate. The combined organic layers were dried over anhydrous Na$_2$SO$_4$, and the solvent was evaporated under reduced pressure to give a concentrated residue, which was used in the next step without further purification. The residue was dissolved in DMF (1.2 mL), sodium azide (77 mg, 1.2 mmol) was added to the solution at room temperature, and the reaction mixture was stirred at room temperature for 1.5 hours. To the reaction solution was added water (5 mL), the mixture was extracted with toluene, the combined organic layers were washed with water, and the solvent was evaporated under reduced pressure to give a crude product of Compound (IIw) (186 mg).

The Compound (IIw) was dissolved in tetrahydrofuran (3 mL), to the solution were added triphenylphosphine (186 mg, 0.71 mmol) and water (0.6 mL) at room temperature, and the reaction mixture was stirred at room temperature overnight. The solvent was evaporated under reduced pressure, the concentrated residue was purified by silica gel column chromatography (chloroform:methanol=99:1→10:1) to give a free base of Compound (IIIw) (61 mg). The product was dissolved in chloroform (0.4 mL), and 4 mol/L HCl/1,4-dioxane (0.4 mL) was added to the solution. The solvent was evaporated under reduced pressure, and to the concentrated residue was added diethyl ether. The resulting precipitate was collected by filtration, washed with diethyl ether (10 mL), and dried under reduced pressure to give the title Compound (IIIw) (70 mg, 33%) as a light brown solid.

$^1$H-NMR (300 MHz, CDCl$_3$) δ: 1.21 (2H, m), 1.45-1.77 (6H, m), 2.50 (1H, m), 4.10 (2H, d, J=8.1 Hz), 4.60 (2H, br s), 5.40 (2H, s), 6.97 (1H, s), 7.07 (2H, m), 7.26 (1H, m), 9.16 (3H, br s).

Obs MS [M+1]: 322.4

Example 348

1-{5-[(2,5-Difluorobenzyl)oxy]-1-(3-methylbutyl)-1H-pyrazol-3-yl}methanamine hydrochloride

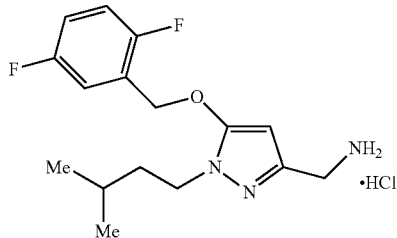 [SMILES: CC(C)CCn1nc(CN)cc1OCc1cc(F)ccc1F ; Cl]

The title compound was prepared in the same manner as in Example 347.

$^1$H-NMR (300 MHz, CDCl$_3$) δ: 0.88 (6H, d, J=6.6 Hz), 1.50 (1H, m), 1.67 (2H, m), 4.07 (2H, m), 4.43 (2H, s), 5.27 (2H, s), 6.59 (1H, s), 7.06 (2H, m), 7.26 (1H, m), 8.98 (3H, s).

Obs MS [M+1]: 310.4

Example 349

1-{1-(Cyclohexylmethyl)-5-[difluoro(phenyl)methoxy]-1H-pyrazol-3-yl}-N-methylmethanamine hydrochloride

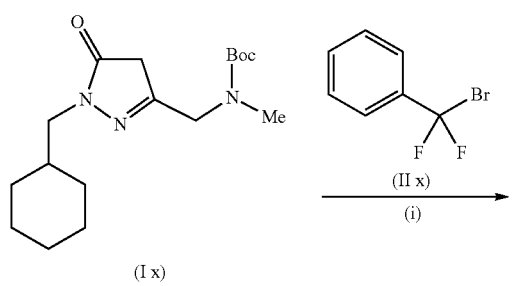

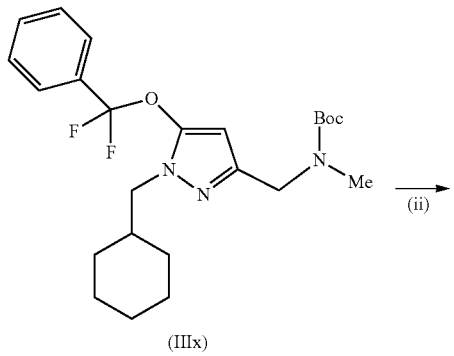

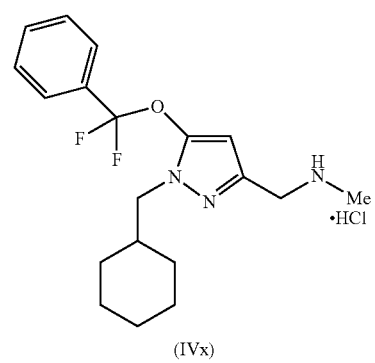

Step (i)

To a solution of Compound (Ix) prepared in Reference Example 4 (100 mg, 0.31 mmol) and cesium carbonate (151 mg, 0.46 mmol) in acetonitrile (2 mL) was added a solution of Compound (IIx) prepared according to the method disclosed in Synthetic Communications. 1999, 855-862. (96 mg, 0.46 mmol) in acetonitrile (1 mL), and the reaction solution was stirred at 50° C. for 1 day. The mixture was cooled to room temperature and diluted with ethyl acetate. The salt was filtered off, the filtrate was concentrated, and the concentrated residue was purified by silica gel column chromatography (n-hexane:ethyl acetate=94:6→73:27) to give Compound (IIIx) (49 mg, 36%) as a yellow oil.

Step (ii)

To a solution of Compound (IIIx) (47 mg, 0.11 mmol) in chloroform (1 mL) was added 4 mol/L HCl/1,4-dioxane (1 mL) at room temperature, and the reaction solution was stirred for 30 minutes. The solution was concentrated under reduced pressure to give the title Compound (IVx) (43 mg, quantitative) as a yellow oil.

$^1$H-NMR (300 MHz, CD$_3$OD) δ: 0.90-1.07 (2H, m), 1.13-1.27 (3H, m), 1.51-1.77 (5H, m), 1.81-1.96 (1H, m), 2.72 (3H, s), 3.88 (2H, d, J=7.2 Hz), 4.13 (2H, s), 6.19 (1H, t, J=1.8 Hz), 7.51-7.66 (3H, m), 7.68-7.76 (2H, m).

Obs MS [M+1]: 350.4

Example 350

1-{5-[1-(3-Chlorophenyl)ethoxy]-1-(cyclohexylmethyl)-1H-pyrazol-3-yl}-N-methylmethanamine hydrochloride

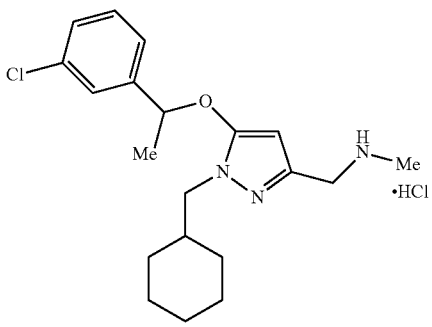 [SMILES: CNCc1cc(OC(C)c2cccc(Cl)c2)n(CC2CCCCC2)n1 ; Cl]

Step (i)

The title compound (55 mg, 45%) as a pale-yellow oil was prepared in the same manner as in the general processes of Examples 20 to 40 by using the compound prepared in Reference Example 4. The benzylation step was carried out by Method B described as a general process in Examples 20 to 40.

$^1$H-NMR (300 MHz, CD$_3$OD) δ: 0.93-1.10 (2H, m), 1.15-1.31 (3H, m), 1.49-1.93 (6H, m), 1.66 (3H, d, J=6.4 Hz), 2.63 (3H, s), 3.84 (2H, dd, J=7.3, 3.1 Hz), 3.97 (2H, s), 5.32 (1H, q, J=6.5 Hz), 5.58 (1H, s), 7.26-7.39 (3H, m), 7.40-7.43 (1H, m).

Obs MS [M+1]: 362.5

Example 351

1-{1-(Cyclohexylmethyl)-5-[(2,5-difluorobenzyl)oxy]-4-fluoro-1H-pyrazol-3-yl}-N-methylmethanamine hydrochloride

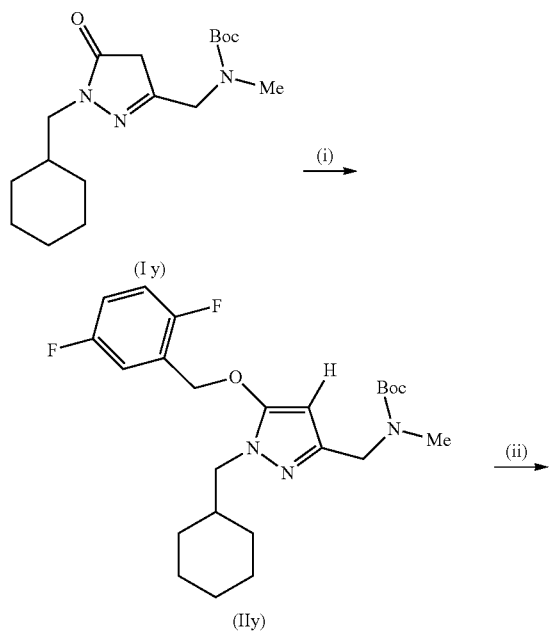

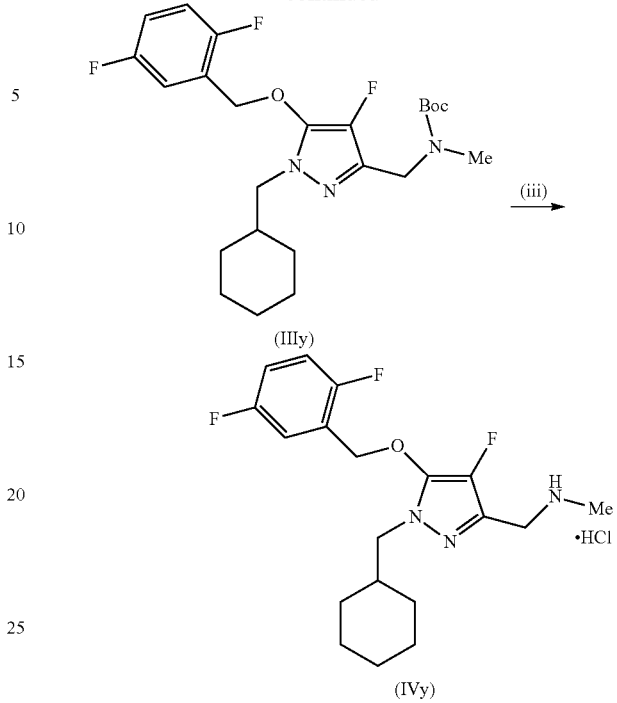

Step (i)

To a solution of Compound (Iy) prepared in Reference Example 4 (500 mg, 1.6 mmol) and cesium carbonate (756 mg, 2.3 mmol) in acetonitrile (3 mL) was added a solution of 2,5-difluorobenzylbromide (377 mg, 2.3 mmol) in acetonitrile (2 mL) at room temperature, and the reaction mixture was stirred at room temperature for 15 hours. To the solution was added ethyl acetate, the salt was filtered off, the filtrate was concentrated, and the concentrated residue was purified by silica gel column chromatography (n-hexane→n-hexane:ethyl acetate=80:20) to give Compound (IIy) (518 mg, 74%) as a pale-yellow oil.

Step (ii)

To a solution of the Compound (IIy) (40 mg, 0.089 mmol) in dimethylformamide (5 mL) was added a solution of Selectfluor (trademark) (38 mg, 0.11 mmol) in water (0.5 mL) with ice-cooling, and the reaction mixture was stirred for 1 hour at ice temperature and then stirred overnight with slowly warming to room temperature. To the mixture was added water (20 mL), the mixture was extracted with ethyl acetate, the combined organic layers were dried over anhydrous MgSO$_4$, and the solvent was evaporated under reduced pressure. The concentrated residue was purified by silica gel column chromatography (n-hexane:ethyl acetate=96:4→75:25) to give Compound (IIIy) (19 mg, 44%) as a colorless oil.

Step (iii)

To a solution of the Compound (IIIy) (19 mg, 0.040 mmol) in chloroform (0.5 mL) was added 4 mol/L HCl/1,4-dioxane (1 mL) at room temperature, and the reaction solution was stirred for 30 minutes. The solution was concentrated under reduced pressure to give the title compound (17 mg, quantitative) as a white solid.

$^1$H-NMR (300 MHz, CD$_3$OD) δ: 0.82-1.00 (2H, m), 1.07-1.25 (3H, m), 1.44-1.55 (2H, m), 1.59-1.82 (4H, m), 2.72 (3H, s), 3.71 (2H, d, J=7.3 Hz), 4.15 (2H, s), 5.36 (2H, s), 7.13-7.30 (3H, m).

Obs MS [M+1]: 368.4

Example 352

1-{4-Chloro-1-(cyclohexylmethyl)-5-[(2,5-difluorobenzyl)-oxy]-1H-pyrazol-3-yl}-N-methylmethanamine hydrochloride

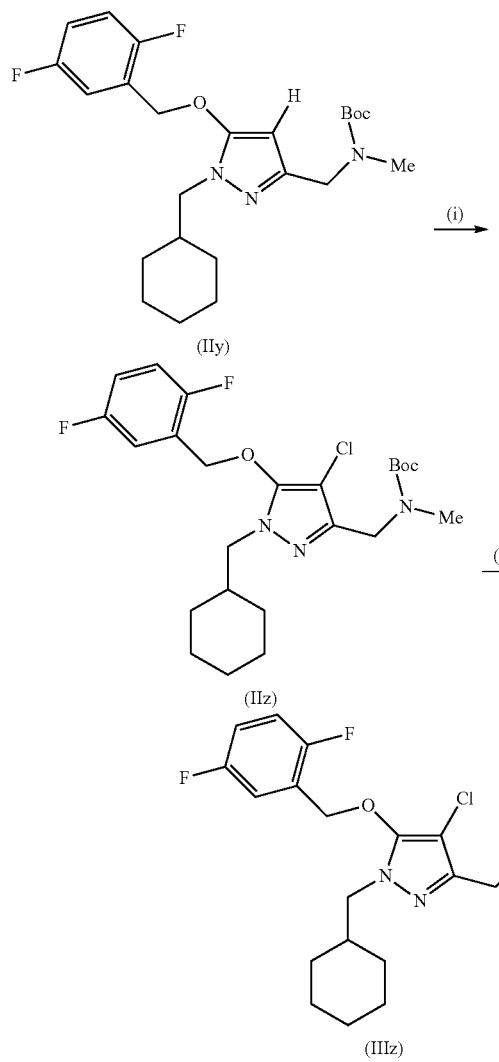

Step (i)

To a solution of the Compound (IIy) obtained in Step (i) of Example 351 (40 mg, 0.089 mmol) in DMF (0.5 mL) was added N-chlorosuccinimide (14 mg, 0.11 mmol) with ice-cooling, and the reaction mixture was stirred for 1 hour at ice temperature and then stirred overnight with slowly warming to room temperature. To the mixture was added water (20 mL), the mixture was extracted with ethyl acetate, the combined organic layers were dried over anhydrous MgSO$_4$, and the solvent was evaporated under reduced pressure. The concentrated residue was purified by silica gel column chromatography (n-hexane→n-hexane:ethyl acetate=83:17) to give Compound (IIz) (33 mg, 76%) as a colorless oil.

Step (ii)

To a solution of Compound (IIz) (33 mg, 0.067 mmol) in chloroform (0.5 mL) was added 4 mol/L HCl/1,4-dioxane (1 mL) at room temperature, and the reaction solution was stirred for 30 minutes. The solution was concentrated under reduced pressure to give the title Compound (IIIz) (28 mg, quantitative) as a colorless oil.

$^1$H-NMR (300 MHz, CD$_3$OD) δ: 0.73-0.90 (2H, m), 0.99-1.16 (3H, m), 1.36-1.47 (2H, m), 1.49-1.71 (4H, m), 2.66 (3H, s), 3.62 (2H, d, J=7.3 Hz), 4.05 (2H, s), 5.31 (2H, s), 7.06-7.20 (3H, m).

Obs MS [M+1]: 384.3

Example 353

1-{4-Bromo-1-(cyclohexylmethyl)-5-[(2,5-difluorobenzyl)-oxy]-1H-pyrazol-3-yl}-N-methylmethanamine hydrochloride

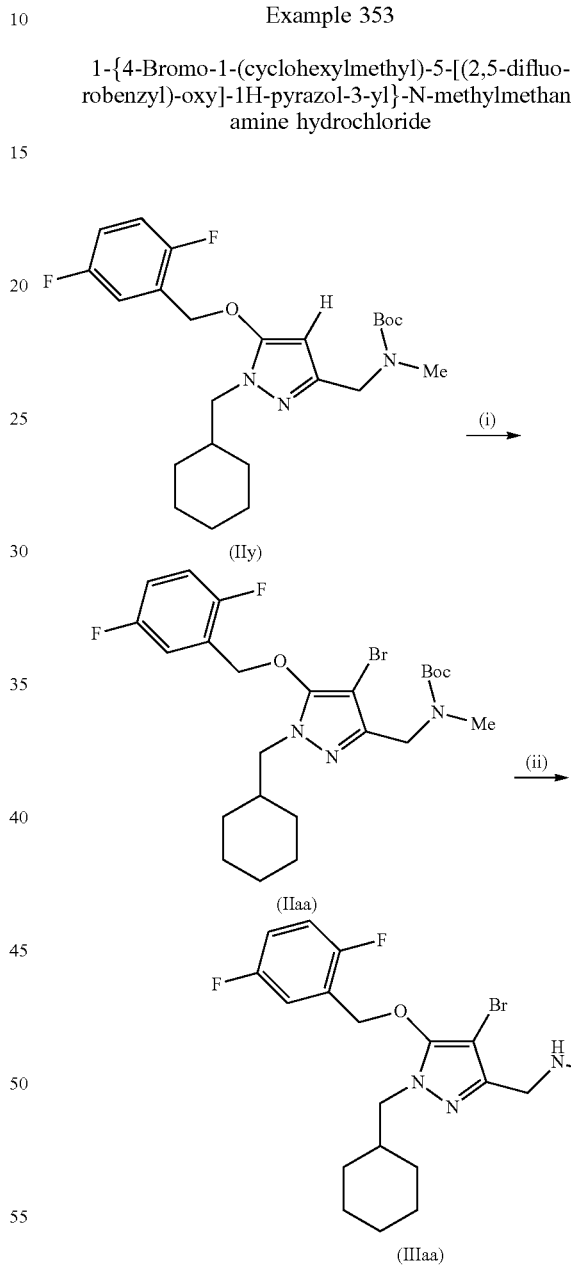

Step (i)

To a solution of the Compound (IIy) (400 mg, 0.89 mmol) in DMF (4 mL) was added N-bromosuccinimide (174 mg, 0.98 mmol) with ice-cooling, and the reaction mixture was stirred overnight with slowly warming to room temperature. To the mixture was added water (40 mL), the mixture was extracted with ethyl acetate, the combined organic layers were dried over anhydrous MgSO$_4$, and the solvent was evaporated under reduced pressure. The concentrated residue was purified by silica gel column chromatography (n-hexane→n-hexane:ethyl acetate=83:17) to give Compound (IIaa) (333 mg, 71%) as a colorless oil.

Step (ii)

To a solution of the Compound (IIaa) (25 mg, 0.047 mmol) in chloroform (0.5 mL) was added 4 mol/L HCl/1,4-dioxane (1 mL) at room temperature, and the reaction solution was stirred for 30 minutes. The solution was concentrated under reduced pressure to give the title Compound (IIIaa) (23 mg, quantitative) as a colorless oil.

$^1$H-NMR (300 MHz, CD$_3$OD) δ: 0.82-1.03 (2H, m), 1.09-1.26 (3H, m), 1.45-1.57 (2H, m), 1.59-1.82 (4H, m), 2.75 (3H, s), 3.73 (2H, d, J=7.2 Hz), 4.13 (2H, s), 5.39 (2H, d, J=1.1 Hz), 7.14-7.29 (3H, m).

Obs MS [M+1]: 428.3

Example 354

1-{1-(Cyclohexylmethyl)-5-[(2,5-difluorobenzyl)oxy]-4-methyl-1H-pyrazol-3-yl}-N-methylmethanamine hydrochloride

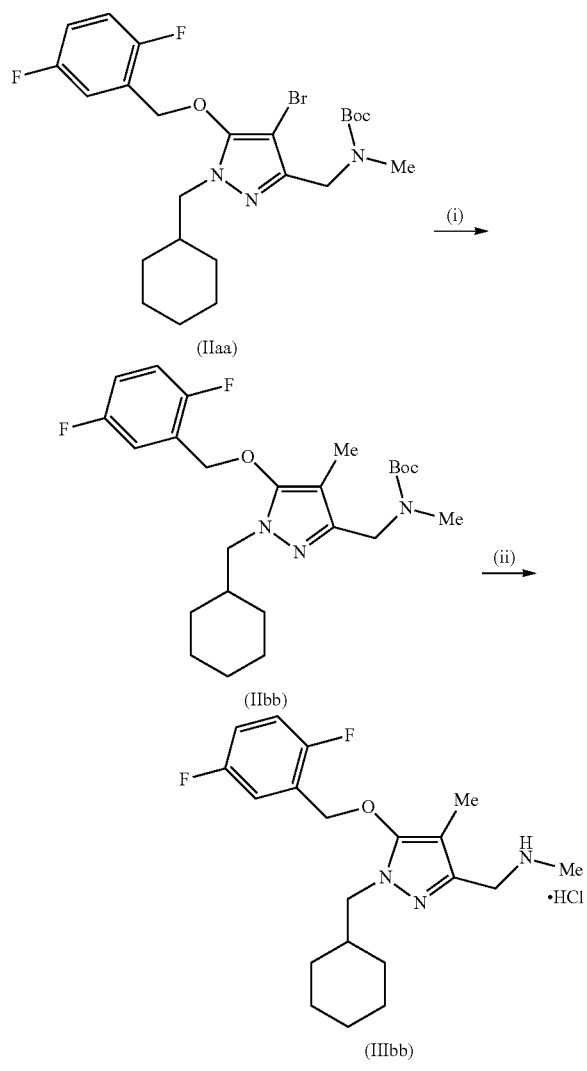

Step (i)

To a solution of the Compound (IIaa) prepared in Step (i) of Example 353 (50 mg, 0.095 mmol) and bis(tri-tert-butylphosphine)palladium (0) (9.7 mg, 0.019 mmol) in tetrahydrofuran (1 mL) was added methylzinc chloride (in 2.0 mol/L tetrahydrofuran, 62 μL, 0.12 mmol) at room temperature, and the reaction mixture was stirred at room temperature for 30 minutes. To the mixture were added water and sat. aq. NH$_4$Cl (10 mL), and the mixture was extracted with ethyl acetate. The combined organic layers were dried over anhydrous MgSO$_4$, the solvent was evaporated under reduced pressure, and the concentrated residue was purified by reversed-phase liquid chromatography to give Compound (IIbb) (23 mg, 51%) as a colorless oil. The conditions of the reversed-phase chromatography were the same as the conditions disclosed in Examples 20 to 40.

Step (ii)

To a solution of the Compound (IIbb) (23 mg, 0.049 mmol) in chloroform (0.5 mL) was added 4 mol/L HCl/1,4-dioxane (1 mL) at room temperature, and the reaction solution was stirred for 30 minutes. The solution was concentrated under reduced pressure to give the title Compound (IIIbb) (19 mg, 97%) as a white solid.

$^1$H-NMR (300 MHz, CD$_3$OD) δ: 0.82-1.01 (2H, m), 1.09-1.28 (3H, m), 1.46-1.57 (2H, m), 1.60-1.83 (4H, m), 2.02 (3H, s), 2.71 (3H, s), 3.69 (2H, d, J=7.3 Hz), 4.08 (2H, s), 5.17 (2H, d, J=1.1 Hz), 7.13-7.27 (3H, m).

Obs MS [M+1]: 364.5

Example 355

1-[1-Benzyl-5-(benzylsulfanyl)-1H-pyrazol-3-yl]-N-methylmethanamine hydrochloride

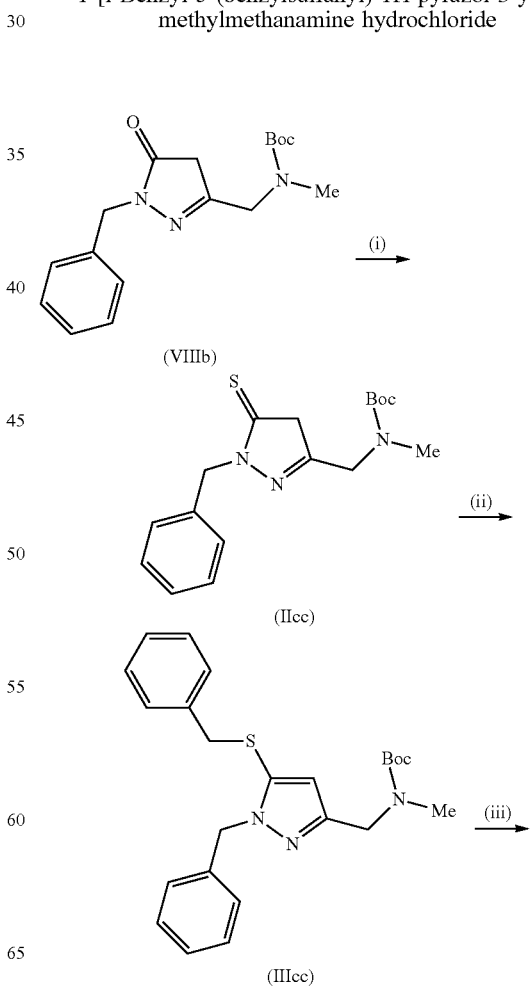

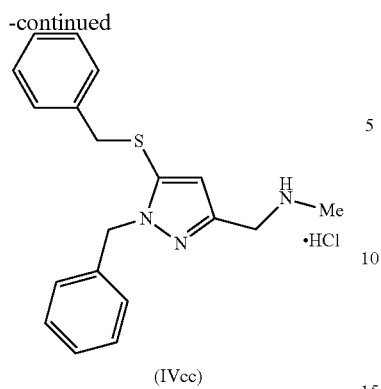

(IVcc)

Steps (i) to (ii)

A solution of the Compound (VIIIb) prepared in Reference Example 36 (100 mg, 0.32 mmol) and Lawesson's reagent [i.e. 2,4-bis(4-methoxyphenyl)-1,3-dithia-2,4-diphosphetane 2,4-disulfide] (127 mg, 0.32 mmol) in toluene (2 mL) was stirred at 100° C. for 30 minutes. To the solution were added benzyl bromide (56 μL, 0.47 mmol) and K₂CO₃ (131 mg, 0.95 mmol), and the reaction mixture was stirred at 100° C. for 1 hour. The mixture was cooled to room temperature, the salt was filtered off, the filtrate was concentrated, and the concentrated residue was purified by silica gel column chromatography (n-hexane ethyl acetate=4:1) to give Compound (IIIcc) (40 mg, 30%)

Step (iii)

To a solution of the Compound (IIIcc) (20 mg, 0.047 mmol) in chloroform (0.5 mL) was added 4 mol/L HCl/1,4-dioxane (1 mL) at room temperature, and the reaction mixture was stirred for 30 minutes. The solvent was evaporated under reduced pressure, the concentrated residue was purified by adding diethyl ether and removing the supernatant by decantation, and the resulting solid was dried under reduced pressure to give the title Compound (IVcc) (19 mg, quantitative) as a white solid.

¹H-NMR (300 MHz, DMSO-d₆) δ: 9.13 (brs, 2H), 7.37-7.23 (m, 6H), 7.14 (brd, 1H, J=6.4 Hz), 7.06 (brd, 2H, J=6.8 Hz), 6.59 (s, 1H), 5.24 (s, 2H), 4.06 (s, 2H), 4.02 (s, 2H), 2.53-2.47 (s, 3H).

Example 356

1-[5-(Benzylsulfanyl)-1-(3-phenylpropyl)-1H-pyrazol-3-yl]-N-methylmethanamine hydrochloride

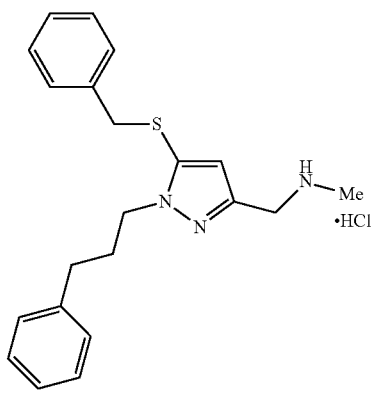 [SMILES: CNCc1cc(SCc2ccccc2)n(CCCc2ccccc2)n1 ; Cl]

The title compound was prepared in the same manner as in Example 355.

¹H-NMR (400 MHz, CDCl₃) δ 9.87 (brs, 2H), 7.32-7.16 (m, 6H), 7.15-7.08 (m, 4H), 6.78 (s, 1H), 4.14 (s, 2H), 3.91 (s, 2H), 3.85 (t, 2H, J=7.2 Hz), 2.58 (s, 3H), 2.49 (t, 2H, J=7.2 Hz), 1.94 (tt, 2H, J=7.2, 7.2 Hz).

Example 357

N-Benzyl-1-(cyclohexylmethyl)-3-[(methyl]-1H-pyrazol-5-amine dihydrochloride

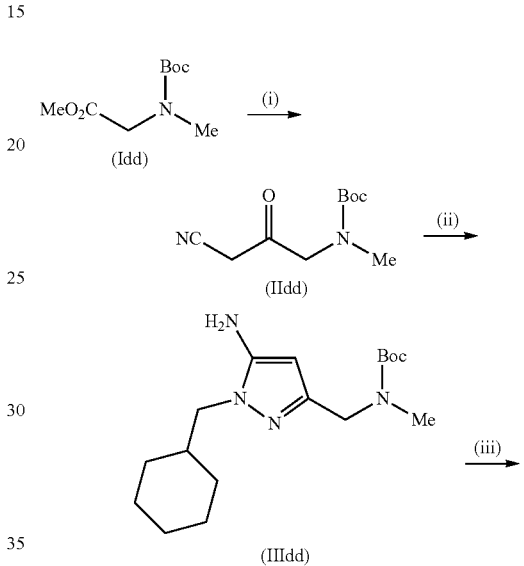

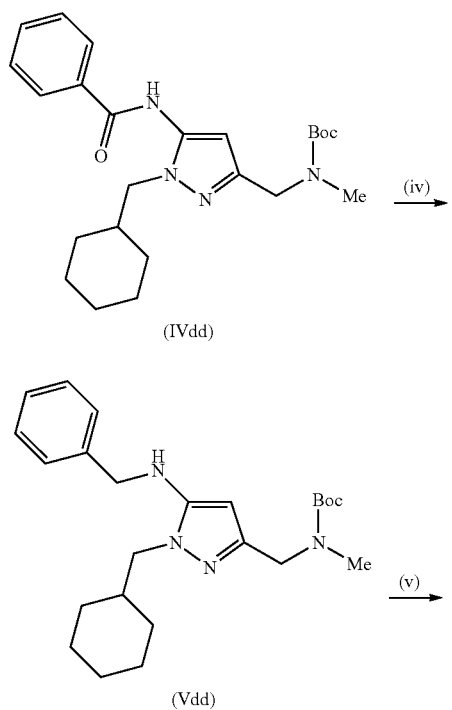

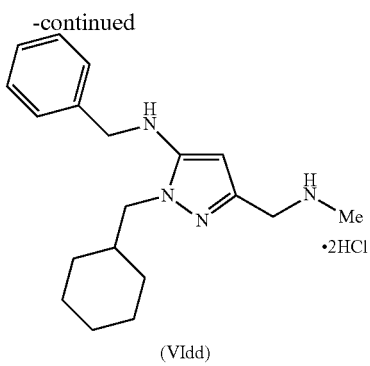

(VIdd)

Step (i)

To a suspension of potassium tert-butoxide (9.90 g, 88 mmol) in THF (170 mL) was added acetonitrile (3.62 g, 88 mmol) at 0° C., and the reaction solution was stirred for 30 minutes with slowly warming to room temperature. The mixture was cooled to 0° C. again, a solution of Compound (Idd) (13.8 g, 68 mmol) in tetrahydrofuran (50 mL) was added thereto, and the reaction mixture was stirred for 2 hours with slowly warming to room temperature. To the mixture was further added potassium tert-butoxide (2.28 g, 26 mmol), and the reaction mixture was stirred for 4 hours and then stirred at 50° C. for 30 minutes. The solution was cooled to 0° C., 5% aq. KHSO₄ (300 mL) was added to the solution, and the mixture was extracted with ethyl acetate and dried over anhydrous Na₂SO₄. The solvent was concentrated under reduced pressure, and the concentrated residue was purified by silica gel column chromatography (n-hexane/ethyl acetate) to give Compound (IIdd) (10.2 g, 72%) as a yellow oil.

Step (ii)

To a solution of cyclohexylmethyl hydrazine dihydrochloride (948 mg, 4.7 mmol) and K₂CO₃ (1.43 g, 19.4 mmol) in ethanol (10 mL) was added a solution of the Compound (IIdd): (1.00 g, 4.7 mmol) in ethanol (15 mL) at room temperature, and the reaction mixture was stirred at room temperature for 1 hour and then at 50° C. for 2 hours. The mixture was cooled to room temperature, water was added thereto, and the mixture was extracted with ethyl acetate. The organic layer was washed with sat. aq. NaHCO₃ and brine, and then dried over anhydrous Na₂SO₄. The solvent was evaporated under reduced pressure, and the concentrated residue was purified by silica gel column chromatography (n-hexane/ethyl acetate) to give Compound (IIIdd) (923 mg, 61%) as a pale-yellow solid.

Step (iii)

To a solution of Compound (IIIdd) (88 mg, 0.27 mmol) and pyridine (65 mg, 0.82 mmol) in dichloromethane (3 mL) was added benzoyl chloride (46 mg, 0.33 mmol) at room temperature, and the reaction mixture was stirred at room temperature overnight. The reaction solution was diluted with ethyl acetate, washed with 5% aq. KHSO₄, sat. aq. NaHCO₃ and brine, and dried over anhydrous Na₂SO₄. The solvent was evaporated under reduced pressure, and the concentrated residue was purified by silica gel column chromatography (n-hexane/ethyl acetate) to give Compound (IVdd) (105 mg, 90%) as a yellow oil.

Step (iv)

To a solution of the Compound (IVdd) (63 mg, 0.15 mmol) in THF (3 mL) was added borane-dimethyl sulfide complex (0.59 mmol) at 0° C., and the reaction solution was stirred at 70° C. for 3.5 hours. The reaction solution was cooled to 0° C., methanol was added thereto, and the mixture was heated under reflux for 30 minutes. The mixture was cooled to room temperature, the solvent was evaporated under reduced pressure, to the concentrated residue was added 5% aq. KHSO₄, and the mixture was extracted with ethyl acetate. The combined organic layers were subsequently washed with sat. aq. NaHCO₃ and brine, and then dried over anhydrous Na₂SO₄. The solvent was evaporated under reduced pressure, and the concentrated residue was purified by silica gel column chromatography (n-hexane/ethyl acetate) to give Compound (Vdd) (31 mg, 51%) as a colorless oil.

Step (v)

To a solution of the Compound (Vdd) (31 mg, 0.075 mmol) in chloroform (0.5 mL) was added 4 mol/L HCl/1,4-dioxane (1 mL) at room temperature, and the reaction solution was stirred at room temperature for 25 minutes. The solvent was evaporated under reduced pressure, and the concentrated residue was purified by adding a small amount of diethyl ether and removing the supernatant by decantation to give the title Compound (VIdd) (30 mg, quantitative) as a white powder.

¹H-NMR (300 MHz, DMSO-d₆) δ: 0.90-1.25 (5H, m), 1.50-1.90 (6H, m), 2.50 (3H, br s), 3.78 (2H, d, J=7.3 Hz), 3.82-3.90 (2H, m), 4.20 (2H, s), 5.39 (1H, s), 5.80 (2H, br s), 7.20-7.36 (5H, m), 8.87 (2H, br s).

Obs MS [M+1]: 313.8

Example 358

N-Benzyl-1-(cyclohexylmethyl)-N-methyl-3-[(methylamino)-methyl]-1H-pyrazol-5-amine dihydrochloride

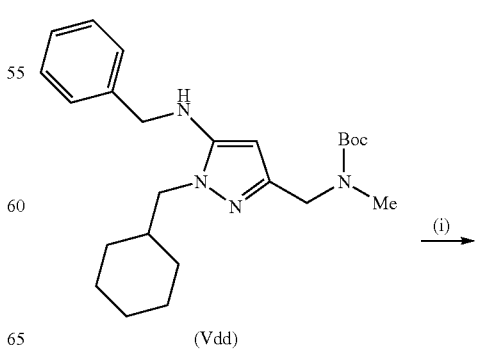

(Vdd)

-continued

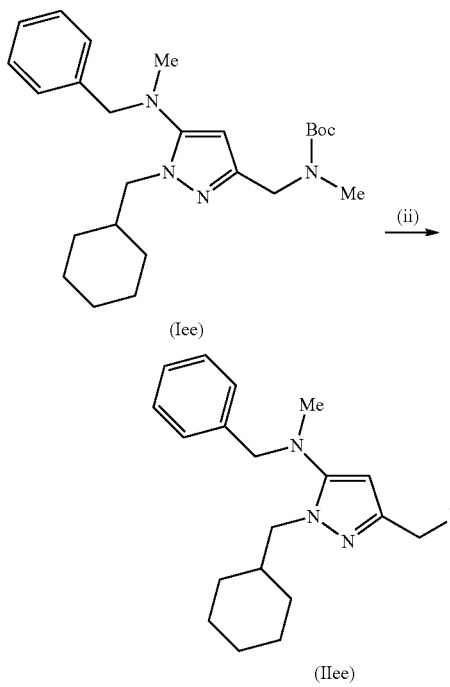

Step (i)

To a solution of the Compound (Vdd) prepared in Step (iv) of Example 357 (47 mg, 0.11 mmol) in DMF (1 mL) were added sodium hydride (60% oily suspension, 6.8 mg, 0.17 mmol) and methyl iodide (24 mg, 0.17 mmol) at room temperature, and the reaction solution was stirred at room temperature overnight. To the solution was added 5% aq. $KHSO_4$, and the mixture was extracted with ethyl acetate. The combined organic layers were washed with water and brine, and then dried over anhydrous $Na_2SO_4$. The solvent was evaporated under reduced pressure, and the concentrated residue was purified by silica gel column chromatography (n-hexane/ethyl acetate) to give Compound (Iee) (41 mg, 86%) as a colorless oil.

Step (ii)

To a solution of the Compound (Iee) (41 mg, 0.097 mmol) in chloroform (0.5 mL) was added 4 mol/L HCl/1,4-dioxane (1 mL) at room temperature, and the reaction solution was stirred at room temperature for 1 hour. The solvent was evaporated under reduced pressure to give the title Compound (IIee) (44 mg, quantitative) as a colorless oil.

$^1$H-NMR (300 MHz, $CDCl_3$) δ: 0.90-1.05 (2H, m), 1.10-1.30 (3H, m), 1.43-1.55 (2H, m), 1.60-1.80 (3H, m), 1.95-2.10 (1H, m), 2.67 (3H, br s), 2.73 (3H, s), 3.90 (2H, d, J=6.0 Hz), 4.13 (2H, s), 4.24 (2H, br s), 6.57 (1H, s), 7.23-7.40 (5H, m), 10.12 (2H, br s).

Obs MS [M+1]: 327.5

Examples 359 to 368

The compounds of Examples 359 to 368 as shown in Table 16 were prepared in the same manner as in Example 198 except that a corresponding benzyl chloride or benzyl bromide was used.

TABLE 16

| Ex. | X | Y | Obs MS [M + 1] |
|---|---|---|---|
| 359 | H | 4'-Et | 336.4 |
| 360 | H | 4'-i-Pr | 350.4 |
| 361 | H | 4'-tBu | 364.5 |
| 362 | H | 2'-F, 4'-Me | 340.4 |
| 363 | H | 4'-$CHF_2O$ | 374.3 |
| 364 | 2,5-F | 4'-Et | 372.3 |
| 365 | 2,5-F | 4'-i-Pr | 386.3 |
| 366 | 2,5-F | 4'-t-Bu | 400.3 |
| 367 | 2,5-F | 2'-F, 4'-Me | 376.5 |
| 368 | 2,5-F | 4'-$CHF_2O$ | 410.4 |

Examples 369 to 402

The compounds of Examples 369 to 402 as shown in Table 17 were prepared in the same manner as in Examples 20 to 40 except that the compounds of Reference Examples 20, 21, 22, 24, 78 and a corresponding benzyl chloride or benzyl bromide were used.

TABLE 17

| Ex. | R | X | Y | Z | Salt | Obs MS [M + 1] |
|---|---|---|---|---|---|---|
| 369 | a | 4-F | H | H | TFA salt | 292.3 |
| 370 | a | 2-F | 4-F | H | Free base | 310.5 |
| 371 | a | 2-Cl | 4-F | H | Free base | 326.4 |
| 372 | a | 2-Me | 4-F | H | Free base | 306.5 |
| 373 | a | 2-F | 5-Me | H | Free base | 306.5 |
| 374 | a | 2-F | 4-F | 5-F | Hydrochloride | 328.6 |
| 375 | b | 4-F | H | H | TFA salt | 306.5 |
| 376 | b | 2-F | 4-F | H | Free base | 324.6 |
| 377 | b | 2-Cl | 4-F | H | Free base | 340.4 |
| 378 | b | 2-Me | 4-F | H | TFA salt | 320.4 |
| 379 | b | 2-F | 5-Me | H | Free base | 320.4 |
| 380 | b | 2-F | 4-F | 5-F | Hydrochloride | 342.2 |
| 381 | c | 2-F | H | H | Hydrochloride | 306.4 |
| 382 | c | 3-F | H | H | Hydrochloride | 306.4 |
| 383 | c | 4-F | H | H | Free base | 306.4 |
| 384 | c | 2-Cl | H | H | Free base | 322.4 |
| 385 | c | 2-Me | H | H | Free base | 302.5 |
| 386 | c | 3-Me | H | H | Free base | 302.5 |

TABLE 17-continued

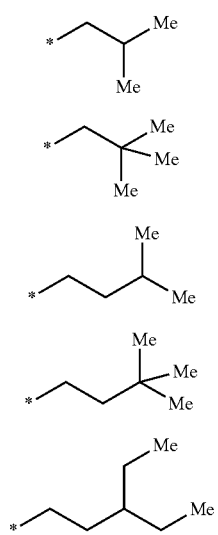

| Ex. | R | X | Y | Z | Salt | Obs MS [M + 1] |
|---|---|---|---|---|---|---|
| 387 | c | 4-Me | H | H | Free base | 302.5 |
| 388 | c | 2-CN | H | H | Free base | 313.5 |
| 389 | c | 2-F | 4-F | H | Free base | 324.4 |
| 390 | c | 2-Cl | 4-F | H | TFA salt | 340.4 |
| 391 | c | 2-Me | 4-F | H | Free base | 320.5 |
| 392 | c | 2-F | 5-Me | H | Free base | 320.5 |
| 393 | d | 4-F | H | H | TFA salt | 320.4 |
| 394 | d | 2-F | 4-F | H | TFA salt | 338.4 |
| 395 | d | 2-Cl | 4-F | H | TFA salt | 354.6 |
| 396 | e | 4-F | H | H | Hydrochloride | 334.5 |
| 397 | e | 2-F | 4-F | H | Hydrochloride | 352.6 |
| 398 | e | 2-Cl | 4-F | H | Hydrochloride | 368.1 |
| 399 | e | 2-Me | 4-F | H | Hydrochloride | 348.6 |
| 400 | e | 2-F | 5-F | H | Hydrochloride | 352.6 |
| 401 | e | 2-F | 5-Me | H | Hydrochloride | 348.6 |
| 402 | e | 2-F | 4-F | 5-F | Hydrochloride | 370.5 |

The variables "a" to "e" in Table 17 represent the groups below:

Example 375

1-{1-(2,2-Dimethylpropyl)-5-[(4-fluorobenzyl)oxy]-1H-pyrazol-3-yl}-N-methylmethanamine trifluoroacetate ¹H-NMR (300 MHz, CDCl₃) δ: 0.92 (9H, s), 2.67 (3H, s), 3.73 (2H, s), 4.08 (2H, s), 5.01 (2H, s), 5.82 (1H, s), 7.08 (2H, m), 7.35 (2H, m), 9.39 (2H, br s).

Example 376

1-{5-[(2,4-Difluorobenzyl)oxy]-1-(2,2-dimethylpropyl)-1H-pyrazol-3-yl}-N-methylmethanamine ¹H-NMR (300. MHz, CDCl₃) δ: 0.93 (9H, s), 1.92 (1H, br s), 2.46 (3H, s), 3.67 (2H, s), 3.69 (2H, s), 5.05 (2H, s), 5.60 (1H, s), 6.83-6.94 (2H, m), 7.40 (1H, m).

Example 377

1-{5-[(2-Chloro-4-fluorobenzyl)oxy]-1-(2,2-dimethylpropyl)-1H-pyrazol-3-yl}-N-methylmethanamine ¹H-NMR (300 MHz, CDCl₃) δ: 0.95 (9H, s), 2.47 (3H, s), 3.67 (2H, s), 3.73 (2H, s), 5.10 (2H, s), 5.59 (1H, s), 7.03 (1H, td, J=8.3, 2.6 Hz), 7.18 (1H, dd, J=8.4, 2.6 Hz), 7.45 (1H, dd, J=8.5, 6.0 Hz). 1H undetected (NH)

Example 378

1-{1-(2,2-Dimethylpropyl)-5-[(4-fluoro-2-methylbenzyl)oxy]-1H-pyrazol-3-yl}-N-methylmethanamine trifluoroacetate ¹H-NMR (300 MHz, CDCl₃) δ: 0.91 (9H, s), 2.35 (3H, s), 2.71 (3H, s), 3.70 (2H, s), 4.11 (2H, s), 5.00 (2H, s), 5.87 (1H, s), 6.87-6.96 (2H, m), 7.30 (1H, m), 9.48 (2H, s).

Example 379

1-{1-(2,2-Dimethylpropyl)-5-[(2-fluoro-5-methylbenzyl)oxy]-1H-pyrazol-3-yl}-N-methylmethanamine ¹H-NMR (CDCl₃) δ: 0.94 (9H, s), 2.33 (3H, s), 2.46 (3H, s), 3.66 (2H, s), 3.71 (2H, s), 5.06 (2H, s), 5.59 (1H, s), 6.97 (1H, t, J=9.0 Hz), 7.13 (1H, m), 7.21 (1H, m). 1H undetected (NH)

Example 380

1-{1-(2,2-Dimethylpropyl)-5-[(2,4,5-trifluorobenzyl)oxy]-1H-pyrazol-3-yl}-N-methylmethanamine ¹H-NMR (300 MHz, CDCl₃) δ: 0.93 (9H, s), 2.64 (3H, s), 3.74 (2H, s), 4.13 (2H, s), 5.08 (2H, s), 6.24 (1H, s), 7.00 (1H, m), 7.30 (1H, m), 9.88 (2H, br s).

Example 381

1-{5-[(2-Fluorobenzyl)oxy]-1-(3-methylbutyl)-1H-pyrazol-3-yl}-N-methylmethanamine hydrochloride ¹H-NMR (300 MHz, CDCl₃) δ: 0.90 (6H, d, J=6.6 Hz), 1.52 (1H, m), 1.72 (2H, q, J=7.2 Hz), 2.73 (3H, t, J=5.1 Hz), 4.10 (2H, t, J=7.4 Hz), 4.31 (2H, s), 5.29 (2H, s), 6.67 (1H, s), 7.13 (1H, t, J=9.3 Hz), 7.21 (1H, t, J=7.4 Hz), 7.38-7.49 (2H, m), 10.22 (2H, br s).

Example 382

1-{5-[(3-Fluorobenzyl)oxy]-1-(3-methylbutyl)-1H-pyrazol-3-yl}-N-methylmethanamine hydrochloride ¹H-NMR (300 MHz, CDCl₃) δ: 0.91 (6H, d, J=6.6 Hz), 1.52 (1H, m), 1.65 (2H, q, J=7.2 Hz), 2.62 (3H, s), 3.98 (2H, t, J=7.3 Hz), 4.11 (2H, s), 5.10 (2H, s), 6.18 (1H, s), 7.03-7.18 (3H, m), 7.36 (1H, m), 9.82 (2H, s).

Example 383

1-{5-[(4-Fluorobenzyl)oxy]-1-(3-methylbutyl)-1H-pyrazol-3-yl}-N-methylmethanamine $^1$H-NMR (400 MHz, CDCl$_3$) δ: 0.90 (6H, d, J=6.3 Hz), 1.53 (1H, m), 1.63 (2H, m), 2.46 (3H, s), 3.64 (2H, s), 3.92 (2H, t, J=7.4 Hz), 5.01 (2H, s), 5.52 (1H, s), 7.08 (2H, t, J=8.2 Hz), 7.36 (2H, m). 1H unditected (NH)

Example 389

1-{5-[(2,4-Difluorobenzyl)oxy]-1-(3-methylbutyl)-1H-pyrazol-3-yl}-N-methylmethanamine $^1$H-NMR (400 MHz, CDCl$_3$) δ: 0.89 (6H, d, J=6.6 Hz), 1.53 (1H, m), 1.63 (2H, m), 1.83 (1H, br s), 2.46 (3H, s), 3.66 (2H, s), 3.91 (2H, t, J=7.4 Hz), 5.07 (2H, s), 5.58 (1H, s), 6.84-6.93 (2H, m), 7.40 (1H, m).

Example 390

1-{5-[(2-chloro-4-fluorobenzyl)oxy]-1-(3-methylbutyl)-1H-pyrazol-3-yl}-N-methylmethanamine trifluoroacetate $^1$H-NMR (300 MHz, CDCl$_3$) δ: 0.89 (6H, d, J=6.4 Hz), 1.50 (1H, m), 1.62 (2H, dt, J=6.8, 6.8 Hz), 2.66 (3H, s), 3.94 (2H, t, J=7.4 Hz), 4.07 (2H, s), 5.11 (2H, s), 5.84 (1H, s), 7.02 (1H, td, J=8.3, 2.5 Hz), 7.19 (1H, dd, J=8.4, 2.6 Hz), 7.43 (1H, dd, J=8.6, 6.1 Hz), 9.46 (2H, br s).

Example 391

1-{5-[(4-fluoro-2-methylbenzyl)oxy]-1-(3-methylbutyl)-1H-pyrazol-3-yl}-N-methylmethanamine $^1$H-NMR (400 MHz, CDCl$_3$) δ: 0.89 (6H, d, J=6.6 Hz), 1.53 (1H, m), 1.62 (2H, m), 1.85 (1H, br s), 2.37 (3H, s), 2.48 (3H, s), 3.67 (2H, s), 3.90 (2H, t, J=7.4 Hz), 5.00 (2H, s), 5.59 (1H, s), 6.87-6.96 (2H, m), 7.31 (1H, dd, J=8.3, 5.9 Hz).

Example 392

1-{5-[(2-fluoro-5-methylbenzyl)oxy]-1-(3-methylbutyl)-1H-pyrazol-3-yl}-N-methylmethanamine $^1$H-NMR (400 NHz, CDCl$_3$) δ: 0.91 (6H, d, J=6.6 Hz), 1.55 (1H, m), 1.64 (2H, dt, J=6.8, 6.8 Hz), 1.75 (1H, br s), 2.35 (3H, s), 2.46 (3H, s), 3.65 (2H, s), 3.93 (2H, t, J=7.4 Hz), 5.08 (2H, s), 5.58 (1H, s), 6.97 (1H, t, J=9.0 Hz), 7.10-7.14 (1H, m), 7.21 (1H, dd, J=7.0, 1.8 Hz).

Examples 403 to 406

The compounds of Examples 403 to 406 as shown in Table 18 were prepared in the same manner as in Examples 20 to 40 except that the compound of Reference Example 77 and a corresponding benzyl chloride or benzyl bromide were used.

TABLE 18

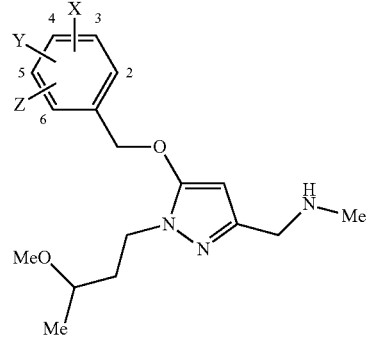

| Ex. | X | Y | Z | Salt | Obs MS [M + 1] |
|---|---|---|---|---|---|
| 403 | H | H | H | TFA salt | 304.0 |
| 404 | 2-F | 5-F | H | TFA salt | 339.9 |
| 405 | 2-F | 5-Cl | H | TFA salt | 356.0 |
| 406 | 2-F | 4-F | 5-F | Free base | 358.0 |

Examples 407 to 426

The compounds of Examples 407 to 426 as shown in Table 19 were prepared in the same manner as in Examples 20 to 40 except that the compounds of Reference Examples 2, 3, 74 and a corresponding benzyl chloride or benzyl bromide were used.

TABLE 19

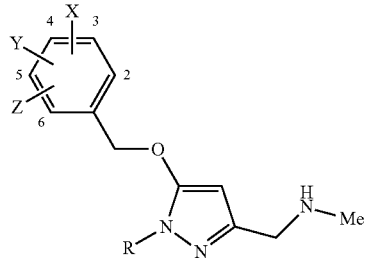

| Ex. | R | X | Y | Z | Salt | Obs MS [M + 1] |
|---|---|---|---|---|---|---|
| 407 | f | 4-F | H | H | TFA salt | 289.9 |
| 408 | f | 2-F | 4-F | H | TFA salt | 307.9 |
| 409 | f | 2-Cl | 4-F | H | TFA salt | 323.9 |
| 410 | f | 2-Me | 4-F | H | TFA salt | 303.9 |
| 411 | f | 4-F | 5-Me | H | TFA salt | 304.0 |
| 412 | f | 2-F | 4-F | 5-F | TFA salt | 325.9 |
| 413 | g | 4-F | H | H | Free base | 304.5 |
| 414 | g | 2-F | 4-F | H | Hydrochloride | 322.7 |
| 415 | g | 2-Cl | 4-F | H | Free base | 338.4 |
| 416 | g | 2-Me | 4-F | H | Hydrochloride | 318.4 |
| 417 | g | 2-F | 5-Me | H | Hydrochloride | 318.3 |
| 418 | g | 2-F | 4-F | 5-F | TFA salt | 340.4 |
| 419 | h | 4-F | H | H | Free base | 304.4 |
| 420 | h | 2-F | 4-F | H | Hydrochloride | 321.4 |
| 421 | h | 2-Cl | 4-F | H | TFA salt | 338.4 |
| 422 | h | 2-Me | 4-F | H | TFA salt | 318.4 |
| 423 | h | 2-F | 5-F | H | Hydrochloride | 322.5 |
| 424 | h | 2-F | 5-Cl | H | Hydrochloride | 338.4 |
| 425 | h | 2-F | 5-Me | H | Hydrochloride | 318.4 |
| 426 | h | 2-F | 4-F | 5-F | TFA salt | 340.4 |

The variables "f" to "h" in the table above represent the groups below:

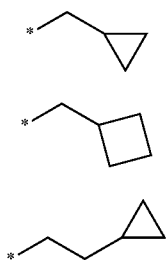

f g h

Example 423

¹H-NMR (300 MHz, CDCl₃) δ: −0.02 (2H, m), 0.38 (2H, m), 0.60 (1H, m), 1.63 (2H, m), 2.63 (3H, s), 4.00 (2H, t, J=6.7 Hz), 4.11 (2H, s), 5.13 (2H, s), 6.17 (1H, s), 7.02-7.10 (2H, m), 7.21 (1H, m), 9.81 (2H, br s).

Example 424

¹H-NMR (300 MHz, CDCl₃) δ: −0.02 (2H, m), 0.38 (2H, m), 0.60 (1H, m), 1.63 (2H, m), 2.63 (3H, s), 4.00 (2H, t, J=6.5 Hz), 4.11 (2H, s), 5.11 (2H, s), 6.16 (1H, s), 7.06 (1H, t, J=9.0 Hz), 7.32 (1H, m), 7.42 (1H, m), 9.78 (2H, br s).

Example 425

¹H-NMR (300 MHz, CDCl₃) δ: −0.03 (2H, m), 0.36 (2H, m), 0.59 (1H, m), 1.64 (2H, m), 2.34 (3H, s), 2.66 (3H, s), 4.05 (2H, t, J=6.3 Hz), 4.16 (2H, s), 5.13 (2H, s), 6.30 (1H, s), 6.98 (1H, t, J=9.0 Hz), 7.15 (1H, m), 7.23 (1H, m), 9.90 (2H, br s).

Example 426

¹H-NMR (CDCl₃) δ: −0.05 (2H, m), 0.38 (2H, m), 0.58 (1H, m), 1.62 (2H, m), 2.67 (3H, s), 4.01 (2H, t, J=7.0 Hz), 4.07 (2H, s), 5.05 (2H, s), 5.84 (1H, s), 6.99 (1H, td, J=9.6, 6.4 Hz), 7.26 (1H, m), 9.48 (2H, br s).

Examples 427 to 434

The compounds of Examples 427 to 434 as shown in Table 20 were prepared in the same manner as in Examples 20 to 40 except that the compounds of Reference Examples 69 and 70, and a corresponding benzyl chloride or benzyl bromide were used.

TABLE 20

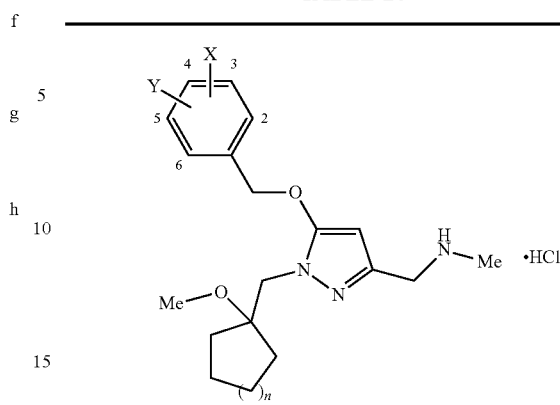

| Ex. | n | X | Y | Obs MS [M + 1] |
|---|---|---|---|---|
| 427 | 1 | 2-Cl | 4-F | 382.3 |
| 428 | 1 | 2-F | 5-F | 366.3 |
| 429 | 1 | 2-F | 4-Cl | 382.3 |
| 430 | 2 | H | H | 344.4 |
| 431 | 2 | 2-F | 4-F | 380.5 |
| 432 | 2 | 2-Cl | 4-F | 396.3 |
| 433 | 2 | 2-F | 5-F | 380.5 |
| 434 | 2 | 2-F | 5-Cl | 396.3 |

Example 435

1-(2-{5-[(5-Chloro-2-fluorobenzyl)oxy]-3-[(methyl-amino)-methyl]-1H-pyrazol-1-yl}ethyl)cyclopenta-nol hydrochloride

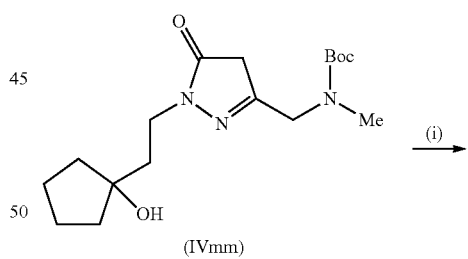

(IVmm)

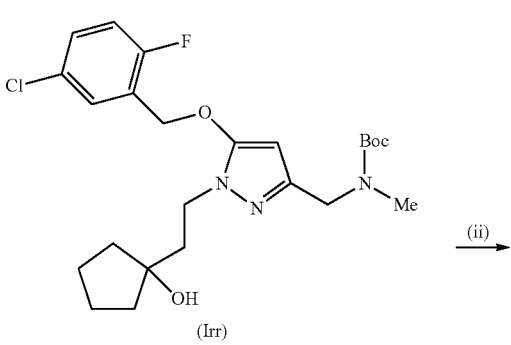

(Irr)

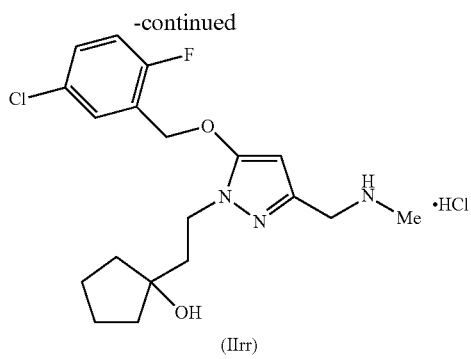

(IIrr)

Step (i)

To a solution of the Compound (IVmm) in Reference Example 79 (100 mg, 0.30 mmol) and cesium carbonate (163 mg, 0.50 mmol) in acetonitrile (1.2 mL) was added 2-fluoro-5-chlorobenzyl chloride (70 μL, 0.44 mmol) at room temperature, and the reaction mixture was stirred at room temperature for 4 days. The mixture was diluted with ethyl acetate, the salt was filtered off, the solvent was evaporated under reduced pressure, and the concentrated residue was purified by silica gel column chromatography (n-hexane:ethyl acetate=1:2) to give Compound (Irr) (53 mg, 37%) as a colorless oil.

Step (ii)

To a solution of the Compound (Irr) (21 mg, 0.044 mmol) in chloroform (0.4 mL) was added 4 N HCl-1,4-dioxane (0.6 mL) at room temperature, and the reaction mixture was stirred at room temperature for 50 minutes. The solvent was evaporated under reduced pressure, to the concentrated residue was added diethyl ether, and the precipitate was collected by filtration and dried under reduced pressure to give the title Compound (IIrr) (16 mg, 87%) as a light brown solid.

$^1$H-NMR (300 MHz, CDCl$_3$) δ: 1.47 (2H, m), 1.61 (2H, m), 1.80 (4H, m), 2.03 (2H, t, J=6.5 Hz), 2.64 (3H, s), 4.08 (2H, s), 4.14 (2H, t, J=6.7 Hz), 5.12 (2H, s), 6.15 (1H, s), 7.06 (1H, t, J=9.0 Hz), 7.32 (1H, m), 7.43 (1H, m), 9.79 (2H, br s). 1H unditected (OH)

Example 436

1-(2-{5-[(2,5-Difluorobenzyl)oxy]-3-[(methylamino)methyl]-1H-pyrazol-1-yl}ethyl)cyclopentanol hydrochloride

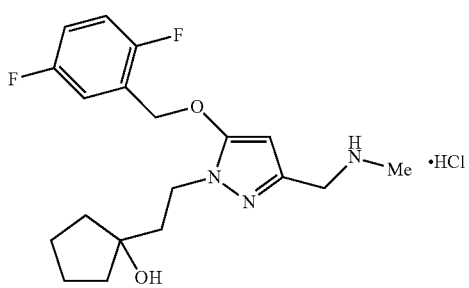 [SMILES: CNCc1cc(OCc2cc(F)ccc2F)n(CCC2(O)CCCC2)n1 ; Cl]

The above compound was prepared in the same manner as in Example 435.

$^1$H-NMR (300 MHz, CDCl$_3$) δ: 1.47 (2H, m), 1.61 (2H, m), 1.78 (2H, m), 2.04 (2H, m), 2.33 (2H, m), 2.64 (3H, s), 4.09 (2H, s), 4.16 (2H, m), 5.14 (2H, s), 6.18 (1H, s), 7.03-7.09 (2H, d, m), 7.18 (1H, m), 9.81 (2H, br s). 1H unditected (OH)

Example 437

1-{5-[(5-Chloro-2-fluorobenzyl)oxy]-1-[2-(1-methoxycyclo-pentyl)ethyl]-1H-pyrazol-3-yl}-N-methylmethanamine hydrochloride

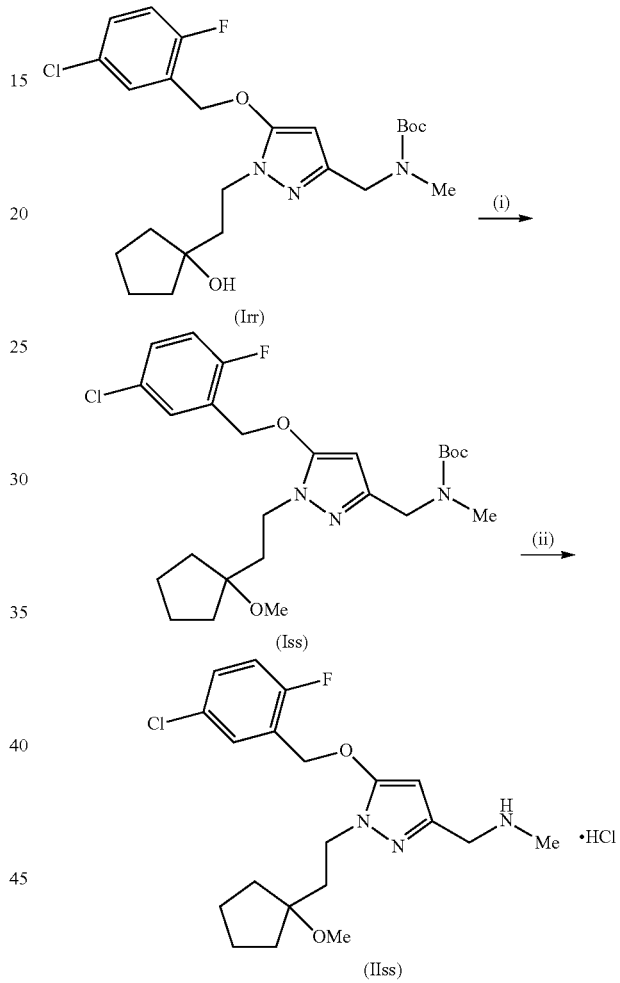

Step (i)

To a solution of the Compound (Irr) in Example 435 (38 mg, 0.079 mmol) in dimethylformamide (0.4 mL) was added sodium hydride (55% suspension, 12 mg, 0.28 mmol) at room temperature. To the solution was further added methyl iodide (20 μL, 0.31 mmol) at room temperature, and the reaction mixture was stirred at room temperature overnight. To the mixture was added 5% aq. KHSO$_4$, the mixture was extracted with ethyl acetate, the organic layer was dried over anhydrous Na$_2$SO$_4$, and the solvent was evaporated under reduced pressure. The concentrated residue was purified by silica gel column chromatography (n-hexane:ethyl acetate=1:2) to give Compound (Iss) (26 mg, 66%) as a pale-yellow oil.

Step (ii)

The title Compound (IIss) was prepared in the same manner as in Step (V) of Example 1.

¹H-NMR (300 MHz, CDCl₃) δ: 1.47 (2H, m), 1.55-1.74 (4H, m), 1.83 (2H, m), 2.02 (2H, m), 2.63 (3H, t, J=5.0 Hz), 3.13 (3H, s), 4.01 (2H, m), 4.09 (2H, s), 5.12 (2H, s), 6.15 (1H, s), 7.05 (1H, t, J=9.0 Hz), 7.29-7.34 (1H, m), 7.45 (1H, dd, J=6.2, 2.4 Hz), 9.82 (2H, br s).

Example 438

1-{5-[(2,5-Difluorobenzyl)oxy]-1-[2-(l-methoxycyclopentyl)-ethyl]-1H-pyrazol-3-yl}-N-methylmethanamine hydrochloride

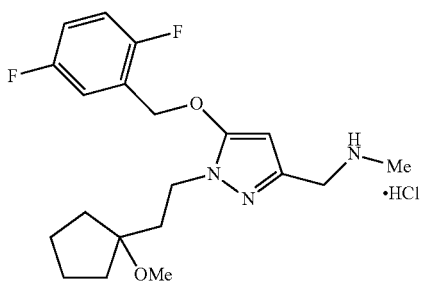 [SMILES: CNCc1cc(OCc2cc(F)ccc2F)n(CCC2(OC)CCCC2)n1 ; Cl]

The above compound was prepared in the same manner as in Example 437.

¹H-NMR (300 MHz, CDCl₃) δ: 1.39 (2H, m), 1.62 (2H, m), 1.67 (2H, m), 1.83 (2H, m), 2.02 (2H, m), 2.62 (3H, t, J=5.0 Hz), 3.12 (3H, s), 4.01 (2H, m), 4.09 (2H, s), 5.13 (2H, s), 6.15 (1H, s), 7.00-7.11 (2H, dd, m), 7.18 (1H, m), 9.82 (2H, br s).

Examples 439 to 449

The compounds of Examples 439 to 449 as shown in Table 21 were prepared in the same manner as in Examples 20 to 40 except that the compound of Reference Examples 80 to 82 and a corresponding benzyl chloride or benzyl bromide were used.

TABLE 21

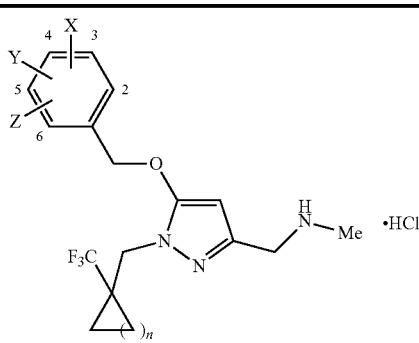

| Ex. | n | X | Y | Z | Salt | Obs MS [M + 1] |
|---|---|---|---|---|---|---|
| 439 | 1 | H | H | H | TFA salt | 339.9 |
| 440 | 1 | 4-F | H | H | TFA salt | 358.0 |
| 441 | 1 | 2-F | 5-F | H | TFA salt | 392.0 |
| 442 | 1 | 2-F | 5-Cl | H | TFA salt | 376.0 |
| 443 | 1 | 2-F | 4-F | 5-F | Hydrochloride | 394.0 |
| 444 | 2 | 2-F | 5-Cl | H | Hydrochloride | 406.0 |
| 445 | 3 | H | H | H | Hydrochloride | 368.2 |
| 446 | 3 | 4-F | H | H | Hydrochloride | 386.4 |

TABLE 21-continued

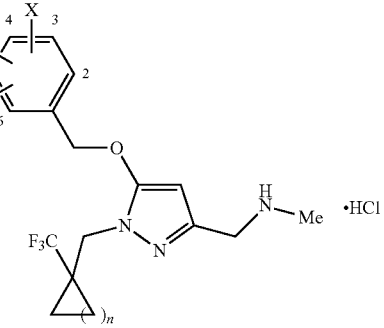

| Ex. | n | X | Y | Z | Salt | Obs MS [M + 1] |
|---|---|---|---|---|---|---|
| 447 | 3 | 2-F | 5-F | H | Hydrochloride | 404.6 |
| 448 | 3 | 2-F | 5-Cl | H | Hydrochloride | 420.2 |
| 449 | 3 | 2-F | 4-F | 5-F | Hydrochloride | 422.3 |

Example 439

1-[5-(Benzyloxy)-1-{[1-(trifluoromethyl)cyclopropyl]-methyl}-1H-pyrazol-3-yl]-N-methylmethanamine trifluoroacetate ¹H-NMR (300 MHz, CDCl₃) δ: 0.82-0.91 (m, 2H), 0.97-1.10 (m, 2H), 2.61 (s, 3H), 4.02 (s, 2H), 4.16 (s, 2H), 5.06 (s, 2H), 5.77 (s, 1H), 7.32-7.48 (m, 5H), 9.56 (br s, 2H).

Example 440

1-(5-[(4-Fluorobenzyl)oxy]-1-{[1-(trifluoromethyl)cyclopropyl]methyl}-1H-pyrazol-3-yl)-N-methylmethanamine trifluoroacetate ¹H-NMR (300 MHz, CDCl₃) δ: 0.82-0.92 (m, 2H), 0.97-1.08 (m, 2H), 2.62 (s, 3H), 4.03 (s, 2H), 4.15 (s, 2H), 5.02 (s, 2H), 5.77 (s, 1H), 7.08 (t, J=8.6 Hz, 2H), 7.37 (dd, J=8.6, 5.3 Hz, 2H), 9.51 (br s, 2H).

Example 441

1-(5-[(2,5-Difluorobenzyl)oxy]-1-{[1-(trifluoromethyl)-cyclopropyl]methyl}-1H-pyrazol-3-yl)-N-methylmethanamine trifluoroacetate ¹H-NMR (300 MHz, CDCl₃) δ: 0.83-0.93 (m, 2H), 0.97-1.06 (m, 2H), 2.63 (s, 3H), 4.04 (s, 2H), 4.17 (s, 2H), 5.10 (s, 2H), 5.81 (s, 1H), 6.99-7.19 (m, 3H), 9.51 (br s, 2H).

Example 442

1-(5-[(5-Chloro-2-fluorobenzyl)oxy]-1-{[1-(trifluoro-methyl)cyclopropyl]-methyl}-1H-pyrazol-3-yl)-N-methylmethanamine trifluoroacetate ¹H-NMR (300 MHz, CDCl₃) δ: 0.84-0.94 (m, 2H), 0.99-1.08 (m, 2H), 2.63 (s, 3H), 4.04 (s, 2H), 4.17 (s, 2H), 5.09

(s, 2H), 5.82 (s, 1H), 7.06 (t, J=9.1 Hz, 1H), 7.29-7.37 (m, 1H), 7.39-7.46 (m, 1H), 9.56 (br s, 2H).

Example 443

N-Methyl-1-(5-[(2,4,5-trifluorobenzyl)oxy]-1-{[1-(tri-fluoromethyl)cyclopropyl]methyl}-1H-pyrazol-3-yl)methanamine hydrochloride ¹H-NMR (300 MHz, CDCl₃) δ: 0.85-0.95 (m, 2H), 0.98-1.07 (m, 2H), 2.60 (t, J=5.4 Hz, 3H), 4.09 (br s, 2H), 4.16 (s, 2H), 5.09 (s, 2H), 6.14 (s, 1H), 7.00 (dt, J=9.5, 6.5 Hz, 1H), 7.28-7.37 (m, 1H), 9.84 (br s, 2H).

Example 444

N-methyl-1-(5-[(5-chloro-2-fluorobenzyl)oxy]-1-{[1-(tri-fluoromethyl)cyclobutyl]methyl}-1H-pyrazol-3-yl)methanamine hydrochloride ¹H-NMR (300 MHz, CDCl₃) δ: 1.53-2.01 (m, 2H), 2.19-2.37 (m, 4H), 2.62 (s, 3H), 4.12 (s, 2H), 4.19 (s, 2H), 5.12 (s, 2H), 6.18 (s, 1H), 7.06 (t, J=9.0 Hz, 1H), 7.32-7.41 (m, 2H), 9.83 (br s, 2H).

Example 445

1-[5-(Benzyloxy)-1-{[1-(trifluoromethyl)cyclopentyl]-methyl}-1H-pyrazol-3-yl]-N-methylmethanamine hydrochloride ¹H-NMR (300 MHz, CDCl₃) δ: 1.36-1.77 (m, 4H), 1.80-2.08 (m, 4H), 2.61 (s, 3H), 4.09 (s, 4H), 5.09 (s, 2H), 6.09 (s, 1H), 7.35-7.46 (m, 5H), 9.56 (br s, 2H).

Example 446

1-(5-[(4-Fluorobenzyl)oxy]-1-{[1-(trifluoromethyl)cyclopentyl]methyl}-1H-pyrazol-3-yl)-N-methyl-methanamine hydrochloride ¹H-NMR (300 MHz, CDCl₃) δ: 1.36-1.77 (m, 4H), 1.79-2.05 (m, 4H), 2.61 (s, 3H), 3.96-4.19 (m, 4H), 5.06 (s, 2H), 6.13 (s, 1H), 7.09 (t, J=8.3 Hz, 2H), 7.32-7.44 (m, 2H), 9.73 (br s, 2H).

Example 447

1-(5-[(2,5-Difluorobenzyl)oxy]-1-{[1-(trifluoromethyl)-cyclopentyl]methyl}-1H-pyrazol-3-yl)-N-methylmethanamine hydrochloride ¹H-NMR (300 MHz, CDCl₃) δ: 1.39-1.73 (m, 4H), 1.80-2.07 (m, 4H), 2.62 (s, 3H), 4.09 (s, 4H), 5.13 (s, 2H), 6.15 (s, 1H), 7.01-7.22 (m, 3H), 9.82 (br s, 2H).

Example 448

1-(5-[(5-Chloro-2-fluorobenzyl)oxy]-1-{[1-(trifluoro-methyl)cyclopentyl]-methyl}-1H-pyrazol-3-yl)-N-methylmethanamine hydrochloride ¹H-NMR (300 MHz, CDCl₃) δ: 1.38-1.71 (m, 4H), 1.78-2.03 (m, 4H), 2.61 (s, 3H), 4.09 (s, 4H), 5.12 (s, 2H), 6.15 (s, 1H), 7.06 (t, J=9.0 Hz, 1H), 7.29-7.37 (m, 1H), 7.39-7.47 (m, 1H), 9.73 (br s, 2H).

Example 449

N-Methyl-1-(5-[(2,4,5-trifluorobenzyl)oxy]-1-{[1-(tri-fluoromethyl)cyclopentyl]methyl}-1H-pyrazol-3-yl)methanamine hydrochloride ¹H-NMR (300 MHz, CDCl₃) δ: 1.40-1.73 (m, 4H), 1.81-2.01 (m, 4H), 2.61 (s, 3H), 4.07 (s, 2H), 4.10 (s, 2H), 5.08 (s, 2H), 6.15 (s, 1H), 6.88-7.08 (m, 2H), 9.78 (br s, 2H).

Examples 450 to 453

The compounds of Examples 450 to 453 as shown in Table 22 were prepared in the same manner as in Examples 20 to 40 except that the compound of Reference Example 11 and a corresponding benzyl chloride or benzyl bromide were used.

TABLE 22

| Ex. | X | Y | Z | Obs MS [M + 1] |
|---|---|---|---|---|
| 450 | 2-F | 4-F | H | 378.6 |
| 451 | 2-F | 5-F | H | 378.7 |
| 452 | 2-F | 5-Cl | H | 394.2 |
| 453 | 2-F | 4-F | 5-F | 396.3 |

Example 450

1-{5-[(2,4-Difluorobenzyl)oxy]-1-(2-oxabicyclo[2.2.2]oct-3-ylmethyl)-1H-pyrazol-3-yl}-N-methyl-methanamine ¹H-NMR (300 MHz, CDCl₃) δ: 1.43-1.68 (6H, m), 1.87-2.05 (3H, m), 2.46 (3H, brs), 3.65 (2H, brs), 3.76 (1H, brs), 3.94 (1H, dd, J=13.4, 7.0 Hz), 4.06-4.21 (2H, m), 5.08 (2H, s), 5.57 (1H, s), 6.81-6.95 (2H, m), 7.37-7.47 (1H, m).

Example 451

1-{5-[(2,5-Difluorobenzyl)oxy]-1-(2-oxabicyclo[2.2.2]oct-3-ylmethyl)-1H-pyrazol-3-yl}-N-methyl-methanamine hydrochloride ¹H-NMR (300 MHz, CD₃OD) δ: 1.48-1.81 (6H, m), 1.86-2.01 (3H, m), 2.70 (3H, brs), 3.71 (1H, brs), 4.00 (1H, dd, J=17.3, 9.8 Hz), 4.07 (2H, brs), 4.12-4.22 (2H, m), 5.24 (2H, s), 5.90 (1H, s), 7.10-7.24 (2H, m), 7.28-7.35 (1H, m).

Example 452

1-{5-[(5-Chloro-2-fluorobenzyl)oxy]-1-(2-oxabicyclo[2.2.2]-oct-3-ylmethyl)-1H-pyrazol-3-yl}-N-methylmethanamine hydrochloride $^1$H-NMR (300 MHz, CD$_3$OD) δ: 1.49-1.78 (6H, m), 1.87-2.03 (3H, m), 2.71 (3H, brs), 3.72 (1H, brs), 4.00 (1H, dd, J=17.6, 9.9 Hz), 4.06 (2H, brs), 4.11-4.22 (2H, m), 5.24 (2H, s), 5.89 (1H, s), 7.19 (1H, dd, J=9.2, 9.2 Hz), 7.38-7.45 (1H, m), 7.56 (1H, dd, J=6.2, 2.6 Hz).

Example 453

N-Methyl-1-{1-(2-oxabicyclo[2.2.2]oct-3-ylmethyl)-5-[(2,4,5-trifluorobenzyl)oxy]-1H-pyrazol-3-yl}methanamine hydrochloride $^1$H-NMR (300 MHz, CD$_3$OD) δ: 1.47-1.80 (6H, m), 1.85-2.02 (3H, m), 2.71 (3H, brs), 3.70 (1H, brs), 3.98 (1H, dd, J=17.3, 9.6 Hz), 4.06 (2H, brs), 4.10-4.21 (2H, m), 5.21 (2H, s), 5.90 (1H, s), 7.21-7.33 (1H, m), 7.48-7.58 (1H, m).

Examples 454 to 469

The compounds of Examples 454 to 469 as shown in Table 23 were prepared in the same manner as in Examples 20 to 40 except that the compounds of Reference Examples 33, 83 and 84, and a corresponding benzyl chloride or benzyl bromide were used.

TABLE 23

| Ex. | R | X | Y | Z | Salt | Obs MS [M + 1] |
|---|---|---|---|---|---|---|
| 454 | c | 2-Cl | H | H | Hydrochloride | 336.7 |
| 455 | c | 2-Me | H | H | Hydrochloride | 316.5 |
| 456 | c | 3-F | H | H | Hydrochloride | 320.5 |
| 457 | c | 2-F | 5-F | H | Hydrochloride | 338.4 |
| 458 | c | 2-Me | 5-F | H | Free base | 334.6 |
| 459 | c | 2-F | 5-MeO | H | Hydrochloride | 350.8 |
| 460 | c | 2-F | 4-F | 5-F | Hydrochloride | 356.3 |
| 461 | j | 2-F | 5-F | H | Hydrochloride | 352.7 |
| 462 | j | 2-F | 5-Cl | H | Hydrochloride | 368.1 |
| 463 | j | 2-F | 5-MeO | H | Hydrochloride | 364.6 |
| 464 | j | 2-F | 4-F | 5-F | Hydrochloride | 370.4 |
| 465 | k | 2-F | 4-F | H | Hydrochloride | 364.5 |
| 466 | k | 2-F | 5-Cl | H | Hydrochloride | 380.4 |
| 467 | k | 2-Me | 5-F | H | Hydrochloride | 360.5 |
| 468 | k | 2-MeO | 5-F | H | Free base | 376.6 |
| 469 | k | 2-F | 4-F | 5-F | Hydrochloride | 382.4 |

The variable "c" in Table 23 is the same as defined in Table 17, and the variables "j" and "k" in Table 23 represent the groups below:

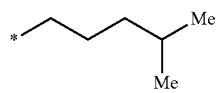 j

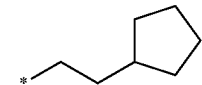 k

Example 470

(−)-1-{1-(1-Cyclohexylethyl)-5-[(2,5-difluorobenzyl)oxy]-1H-pyrazol-3-yl}-N-methylmethanamine

Example 471

(+)-1-{1-(1-Cyclohexylethyl)-5-[(2,5-difluorobenzyl)oxy]-1H-pyrazol-3-yl}-N-methylmethanamine

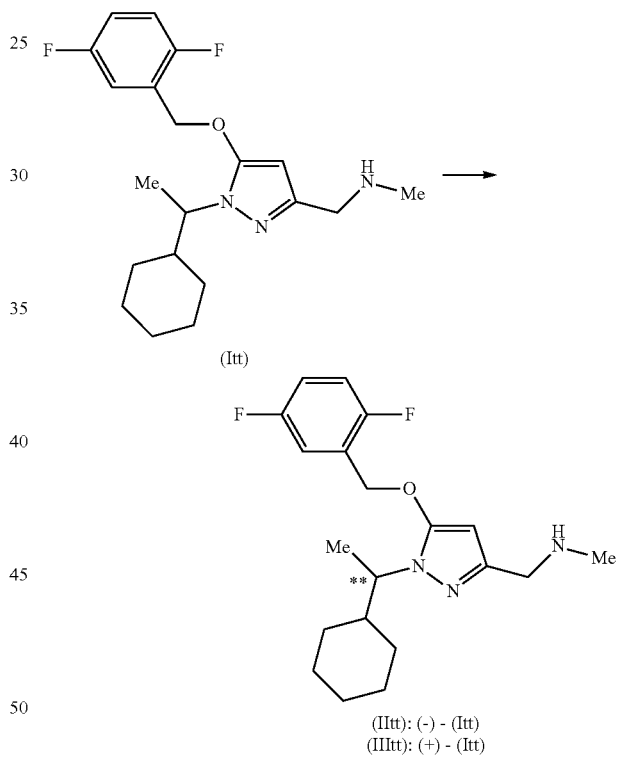

(IItt): (−) - (Itt)
(IIItt): (+) - (Itt)

wherein ** is an asymmetric carbon, and the compound containing it means an optically active substance.

Compound (Itt) in Example 303 was purified by liquid column chromatography under the following conditions. Compound (IItt) was eluted at a shorter retention time and then Compound (IIItt) was eluted later, which were both given as a light-brown oil. The conditions of the liquid column chromatography are as follows:

Column; CHIRALCEL (trademark) OZ-H 5 cm I.D.×25 cm

Mobile phase; acetonitrile:diisopropylamine=100:0.1 (v/v)

Flow rate; 47 mL/min

Temperature; 30° C.

Detected UV wavelength; 268 nm
Compound (IItt):
$^1$H-NMR (300 MHz, CDCl$_3$) δ: 0.83 (1H, m), 0.96 (1H, m), 1.06-1.33 (4H, m), 1.41 (3H, d, J=7.0 Hz), 1.57-1.90 (6H, m), 2.46 (3H, s), 3.66 (2H, s), 3.92-4.02 (1H, m), 5.09 (2H, s), 5.55 (1H, s), 6.98-7.17 (3H, m).
Specific rotation; [α]D$^{26}$−17.3 (c. 1.47, CHCl$_3$)
Compound (IIItt):
Specific rotation; [α]D$^{26}$+19.2 (c. 1.03, CHCl$_3$)

Example 472

(−)-1-{5-[(5-Chloro-2-fluorobenzyl)oxy]-1-(1-cyclohexyl-ethyl)-1H-pyrazol-3-yl}-N-methylmethanamine Example 473

(+)-1-{5-[(5-Chloro-2-fluorobenzyl)oxy]-1-(1-cyclohexyl-ethyl)-1H-pyrazol-3-yl}-N-methylmethanamine

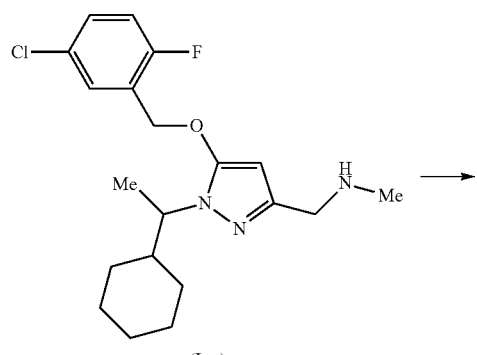

(Iuu)

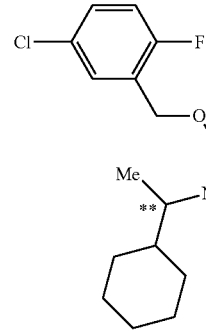

(IIuu): (−) - (Iuu)
(IIIuu): (+) - (Iuu)

wherein ** is as defined above.

Compound (Iuu) in Example 304 was purified by liquid column chromatography under the following conditions. Compound (IIuu) was eluted at a shorter retention time and then Compound (IIIuu) was eluted later, which were both given as a light-brown oil. The conditions of the liquid column chromatography are as follows:

Column; CHIRALCEL (trademark) OZ-H, 5 cm I.D.×25 cm
Mobile phase; acetonitrile:diisopropylamine=100:0.1 (v/v)
Flow rate; 47 mL/min
Temperature; 25° C.

Detected UV wavelength; 272 nm
Compound (IIuu):
$^1$H-NMR (300 MHz, CDCl$_3$) δ: 0.81 (1H, m), 0.96 (1H, m), 1.06-1.28 (4H, m), 1.41 (3H, d, J=6.8 Hz), 1.48-1.90 (6H, m), 2.46 (3H, s), 3.65 (2H, s), 3.96 (1H, m), 5.08 (2H, s), 5.54 (1H, s), 7.05 (1H, t, J=9.0 Hz), 7.29 (1H, m), 7.41 (1H, dd, J=6.2, 2.8 Hz).
Specific rotation; [α]D$^{26}$−13.1 (c. 1.13, CHCl$_3$)
Compound (IIIuu):
Specific rotation; [α]D$^{26}$+11.6 (c. 2.04, CHCl$_3$)

Example 474

(−)-1-{5-[(5-chloro-2-fluorobenzyl)oxy]-1-(tetrahydro-2H-pyran-2-ylmethyl)-1H-pyrazol-3-yl}-N-methylmethanamine hydrochloride

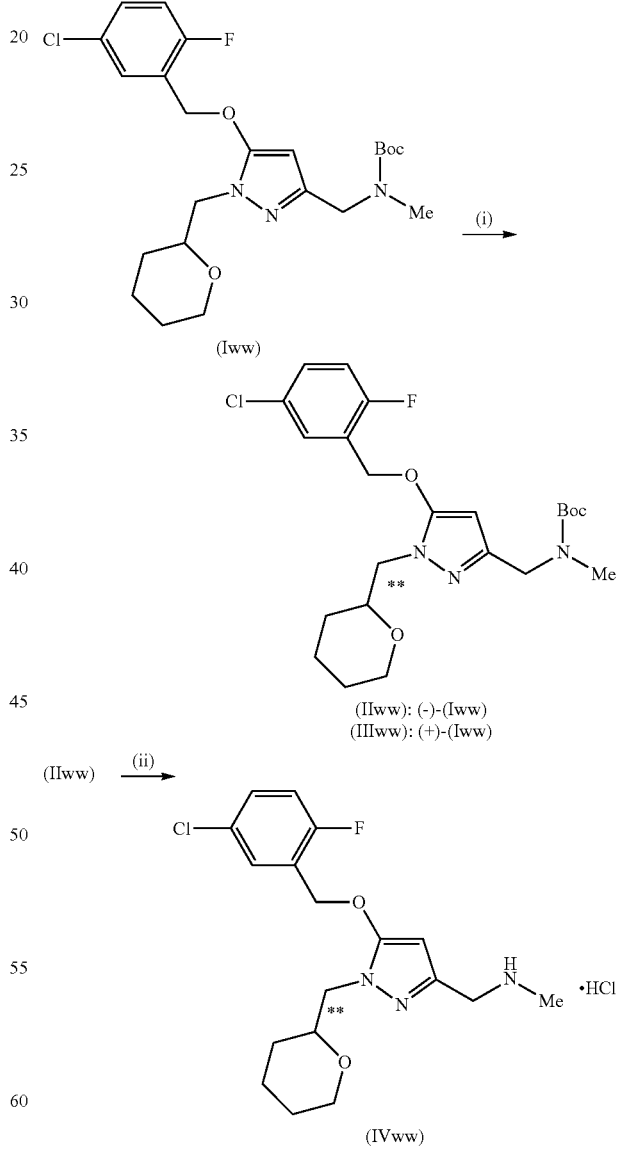

wherein ** is as defined above.
Step (i)
Compound (Iww) prepared in the same manner as in Examples 92 to 114 was purified by liquid column chromatography. Compound (IIww) was eluted at a shorter retention time and then Compound (IIIww) was eluted later, which were both given as a light-brown oil. The conditions of the liquid column chromatography are as follows:

Column; CHIRALCEL (trademark) OZ-H, 5 cm I.D.×25 cm

Mobile phase; acetonitrile

Flow rate; 47 mL/min

Temperature; 40° C.

Detected UV wavelength; 271 nm

Compound (IIww):

Specific rotation; $[\alpha]D^{26}$−5.0 (c. 1.04, CHCl$_3$)

Compound (IIIww):

Specific rotation; $[\alpha]D^{26}$+3.7 (c. 1.07, CHCl$_3$)

Step (ii)

Compound (IVww) was prepared in the same manner as in Step (V) of Example 1 except that the Compound (IIww) was used.

$^1$H-NMR (300 MHz, CDCl$_3$) δ: 1.29 (1H, m), 1.43-1.67 (4H, m), 1.84 (1H, m), 2.62 (3H, s), 3.36 (1H, t, J=10.8 Hz), 3.67 (1H, m), 3.88 (1H, dd, J=14.1, 4.4 Hz), 3.97 (1H, m), 4.05 (1H, m), 4.09 (2H, s), 5.13 (2H, s), 6.11 (1H, s), 7.04 (1H, t, J=9.0 Hz), 7.30 (1H, m), 7.47 (1H, dd, J=6.0, 2.5 Hz), 9.78 (2H, br s).

Specific rotation; $[\alpha]D^{26}$−6.6 (c. 1.21, CHCl$_3$)

Example 475

(+)-1-{5-[(5-Chloro-2-fluorobenzyl)oxy]-1-(tetrahydro-2H-pyran-2-ylmethyl)-1H-pyrazol-3-yl}-N-methylmethanamine hydrochloride

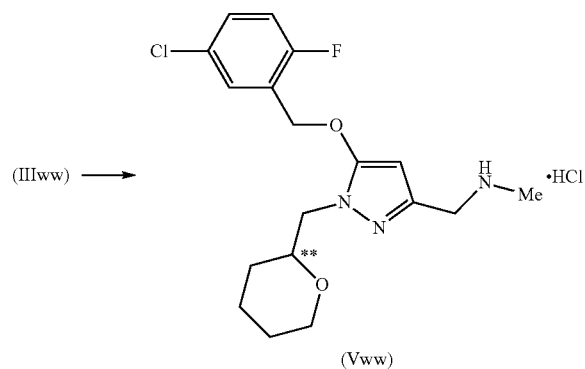 [SMILES: CNCc1cc(OCc2cc(Cl)ccc2F)n(CC2CCCCO2)n1 ; Cl]

wherein ** is as defined above.

Compound (Vww) was prepared in the same manner as in Step (V) of Example 1 except that the Compound (IIIww) was used.

$^1$H-NMR (300 MHz, CDCl$_3$) δ: 1.28 (1H, m), 1.41-1.65 (4H, m), 1.84 (1H, m), 2.61 (3H, s), 3.36 (1H, t, J=11.1 Hz), 3.66 (1H, m), 3.88 (1H, dd, J=13.9, 4.8 Hz), 3.97 (1H, m), 4.05 (1H, m), 4.09 (2H, s), 5.13 (2H, s), 6.11 (1H, s), 7.04 (1H, t, J=9.0 Hz), 7.29 (1H, m), 7.47 (1H, dd, J=6.1, 2.6 Hz), 9.79 (2H, br s).

Specific rotation; $[\alpha]D^{26}$+6.0 (c. 1.14, CHCl$_3$)

Example 476

(−)-1-{1-(2-Cyclopentylethyl)-5-[(2,5-difluorobenzyl)oxy]-1H-pyrazol-3-yl}-N-methylethanamine Example 477

(+)-1-{1-(2-Cyclopentylethyl)-5-[(2,5-difluorobenzyl)oxy]-1H-pyrazol-3-yl}-N-methylethanamine

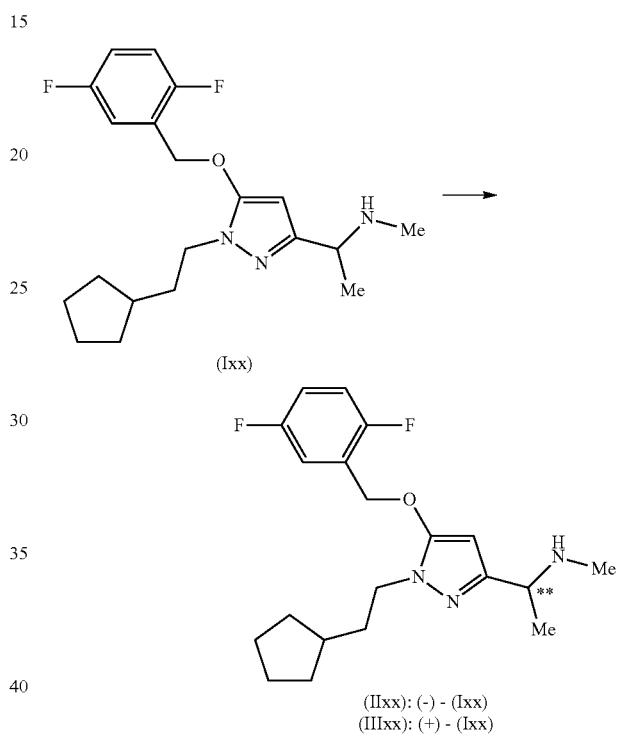

wherein ** is as defined above.

A free form of the Compound (Ixx) in Example 315 was purified by liquid column chromatography under the following conditions. Compound (IIxx) was eluted at a shorter retention time and then Compound (IIIxx) was eluted later, which were both given as a light-brown oil. The conditions of the liquid column chromatography are as follows:

Column; CHIRALPAK (trademark) AY-H, 5 cm I.D.×25 cm

Mobile phase; n-hexane:ethanol:diethylamine=95:5:0.1 (v/v)

Flow rate; 47 mL/min

Temperature; 40° C.

Detected UV wavelength; 268 nm

Compound (IIxx):

$^1$H-NMR (300 MHz, CDCl$_3$) δ: 1.09 (2H, m), 1.35 (3H, d, J=6.8 Hz), 1.44-1.63 (5H, m), 1.69-1.83 (5H, m), 2.37 (3H, s), 3.64 (1H, q, J=6.7 Hz), 3.94 (2H, t, J=7.2 Hz), 5.10 (2H, s), 5.52 (1H, s), 6.98-7.11 (2H, m), 7.15 (1H, m).

Specific rotation; $[\alpha]D^{26}$−25.4 (c. 1.42, CHCl$_3$)

Compound (IIIxx):

Specific rotation; [α]$D^{26}$+25.0 (c. 1.60, CHCl$_3$)

Example 478

1-{1-(3-Methylbutyl)-5-[(2,4,5-trifluorobenzyl)oxy]-1H-pyrazol-3-yl}methanamine hydrochloride

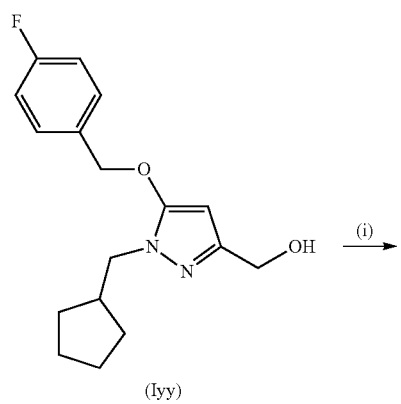

The title compound was prepared in the same manner as in Example 347.

$^1$H-NMR (400 MHz, CDCl$_3$) δ: 0.85 (6H, t, J=6.4 Hz), 1.42-1.52 (1H, m), 1.64-1.74 (2H, m), 4.15 (2H, br s), 4.60 (2H, br s), 5.37 (2H, br s), 6.90-7.00 (2H, m), 7.48-7.52 (1H, m), 9.06 (3H, br s).

Example 479

1-{1-(Cyclopentylmethyl)-5-[(4-fluorobenzyl)oxy]-1H-pyrazol-3-yl}methanamine

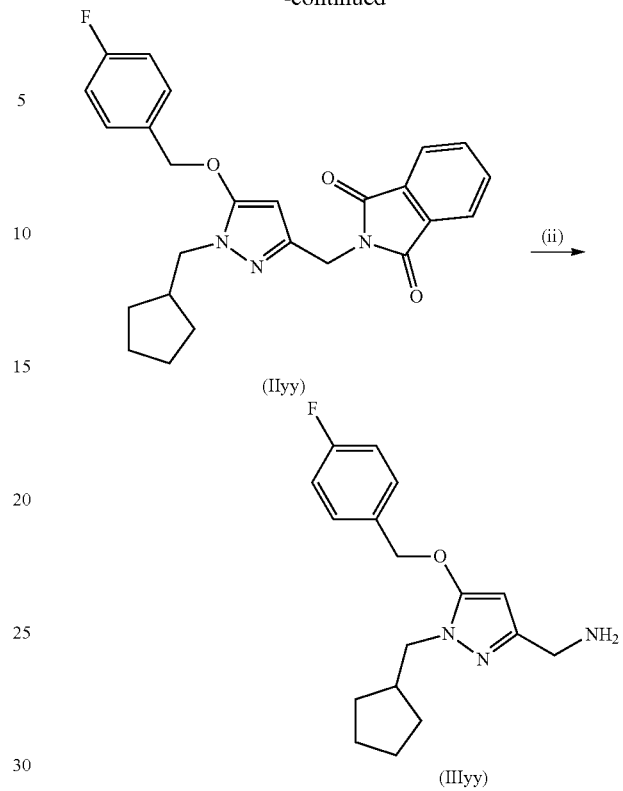

Step (i)

To a solution of Compound (Iyy) prepared in the same manner as in Steps (i) to (iii) of Example 1 (300 mg, 0.99 mmol), triphenylphosphine (310 mg, 1.2 mmol) and phthalimide (160 mg, 1.1 mmol) in tetrahydrofuran (5 mL) was added diisopropylazodicarboxylate (248 μL, 1.2 mmol) at room temperature, and the reaction mixture was stirred at room temperature overnight. The solvent was evaporated under reduced pressure, the concentrated residue was purified by silica gel column chromatography (n-hexane ethyl acetate=3:1) to give Compound (IIyy) (550 mg).

Step (ii)

To the Compound (IIyy) (550 mg, equivalent to 0.99 mmol) was added methylamine (in 40% methanol, 5 mL), and the reaction mixture was stirred at 40° C. for 30 minutes. The solvent was evaporated under reduced pressure, and the concentrated residue was purified by silica-gel chromatography (chloroform:methanol=10:1) to give Compound (IIIyy) (156 mg, 52% in 2 steps) as a light-brown oil.

$^1$H-NMR (300 MHz, CDCl$_3$) δ: 1.16-1.34 (m, 2H), 1.43-1.75 (m, 6H), 2.30-2.48 (m, 1H), 3.76 (s, 2H), 3.83 (d, J=7.5 Hz, 2H), 5.02 (s, 2H), 5.49 (s, 1H), 7.09 (t, J=8.6 Hz, 2H), 7.37 (dd, J=8.6, 5.5 Hz, 2H).

Example 480

1-{5-[(4-Fluorobenzyl)oxy]-1-(3-fluoro-3-methylbutyl)-1H-pyrazol-3-yl}-N-methylmethanamine hydrochloride

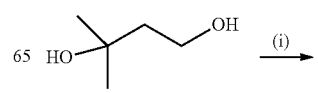

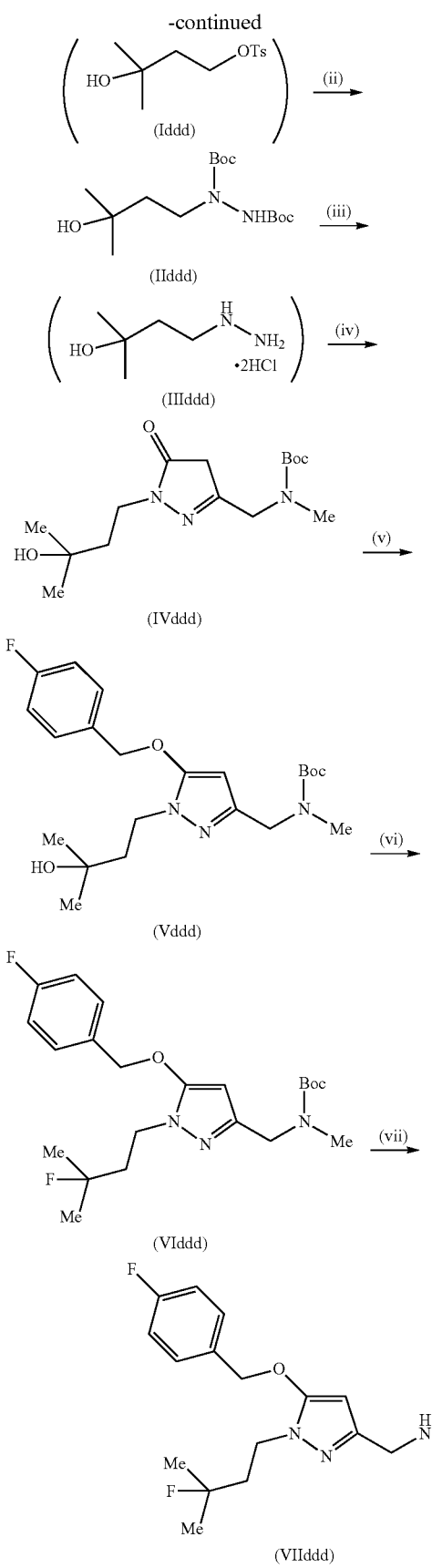

Steps (i) to (ii)

To a solution of 3-methyl-1,3-butanediol (2.5 g, 24 mmol) and 4-N,N-dimethylaminopyridine (3.08 g, 25 mmol) in dichloromethane (96 mL) was added dropwise a solution of p-toluene sulfonyl chloride (4.80 g, 25 mmol) in dichloromethane (32 mL) with cooling in a water bath, and the reaction mixture was stirred at room temperature for 22 hours. To the mixture was further added triethylamine (3.3 mL, 24 mmol), and the reaction mixture was stirred for 100 minutes. The mixture was partitioned between water (50 mL) and chloroform (30 mL). The organic layer was washed with water (50 mL×2) and brine (50 mL), and dried over anhydrous $Na_2SO_4$. The organic solvent was evaporated under reduced pressure to give a crude product of Compound (Iddd) (6.43 g), which was used in the next step without further purification.

The resulting Compound (Iddd), di-tert-butyl hydrazinedicarboxylate (5.57 g, 24 mmol) and cesium carbonate (9.38 g, 29 mmol) were dissolved in dimethylformamide (24 mL), and the reaction mixture was stirred at 60° C. for 3 hours. The mixture was cooled to room temperature and diluted with ethyl acetate (100 mL), the salt was filtered off, to the filtrate was added ethyl acetate (100 mL), and the resultant was washed with water (40 mL). The solvent was evaporated under reduced pressure, the concentrated residue was purified by silica gel column chromatography (n-hexane:ethyl acetate=1:1) to give Compound (IIddd) (3.40 g, 44%) as a colorless oil.

Steps (iii) to (iv)

To a solution of the Compound (IIddd) (3.40 g, 10.7 mmol) in methanol (11 mL) was added conc. HCl (5.3 mL), and the reaction mixture was stirred at room temperature for 3 hours. The methanol was evaporated under reduced pressure, to the concentrated residue was added toluene, and the solvent was evaporated under reduced pressure (×3) to give a crude product of Compound (IIIddd) (700 mg), which was used in the next step without further purification.

The resulting Compound (IIIddd) and triethylamine (1.2 mL, 8.7 mmol) were dissolved in ethanol (7.3 mL), and the mixture was stirred at 45° C. To the mixture was further added a solution of the Compound (IIa) in Reference Example 1 (863 mg, 3.3 mmol) in ethanol (2 mL), and the reaction mixture was stirred at 80° C. for 2 hours. The mixture was cooled to room temperature, 5% aq. $KHSO_4$ was added thereto, and the mixture was extracted with ethyl acetate. The organic layer was dried over anhydrous $MgSO_4$, the solvent was evaporated under reduced pressure, and the concentrated residue was purified by silica gel column chromatography (n-hexane:ethyl acetate=1:2→ethyl acetate→chloroform:methanol=10:1) to give Compound (IVddd) (474 mg, 45%) as a pale-yellow solid.

Step (V)

Compound (Vddd) as a pale-yellow oil was prepared in the same manner as in Examples 20 to 40 except that the Compound (IVddd) and 4-fluorobenzyl chloride were used.

Step (vi)

To a solution of the Compound (Vddd) (58 mg, 0.14 mmol) and DBU (62 μL, 0.41 mmol) in dichloromethane (0.7 mL) was added XtalFluor-E (trademark) (79 mg, 0.35 mmol) at ice temperature, and the reaction mixture was stirred at ice temperature for 20 minutes and then at room temperature for 30 minutes. To the mixture was added sat. aq. $NaHCO_3$, the mixture was extracted with chloroform, the organic layer was dried over anhydrous $Na_2SO_4$, and the solvent was evaporated under reduced pressure. The concentrated residue was purified by PTLC (n-hexane:ethyl acetate=1:1) to give Compound (VIddd) (17 mg, 29%) as a colorless oil.

Step (vii)

Compound (VIIddd) was prepared in the same manner as in Step (V) of Example 1 except that the Compound (VIddd) was used.

$^1$H-NMR (300 MHz, CDCl$_3$) δ: 1.35 (6H, d, J=21.3 Hz), 2.06 (2H, dt, J=19.5, 7.5 Hz), 2.61 (3H, s), 4.07 (4H, m), 5.06 (2H, s), 6.13 (1H, s), 7.08 (2H, t, J=8.4 Hz), 7.38 (2H, m), 9.77 (2H, br s).

Obs MS [M+1]: 324.6

Examples 481 to 483

The compounds of Examples 481 to 483 were prepared in the same manner as in Example 480.

Example 481

1-{5-[(2,5-Difluorobenzyl)oxy]-1-(3-fluoro-3-methylbutyl)-1H-pyrazol-3-yl}-N-methylmethanamine hydrochloride

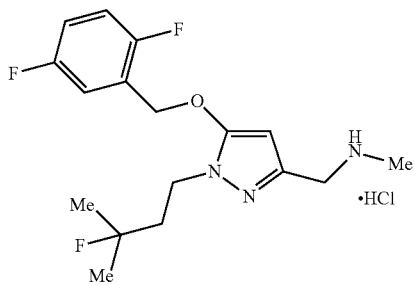 [SMILES: CNCc1cc(OCc2cc(F)ccc2F)n(CCC(C)(C)F)n1 ; Cl]

$^1$H-NMR (300 MHz, CDCl$_3$) δ: 1.36 (6H, d, J=21.3 Hz), 2.08 (2H, dt, J=19.5, 7.5 Hz), 2.62 (3H, s), 4.09 (4H, m), 5.13 (2H, s), 6.15 (1H, s), 7.06 (2H, m), 7.16 (1H, m), 9.80 (2H, br s).

Obs MS [M+1]: 342.3

Example 482

1-{5-[(5-Chloro-2-fluorobenzyl)oxy]-1-(3-fluoro-3-methyl-butyl)-1H-pyrazol-3-yl}-N-methylmethanamine hydrochloride

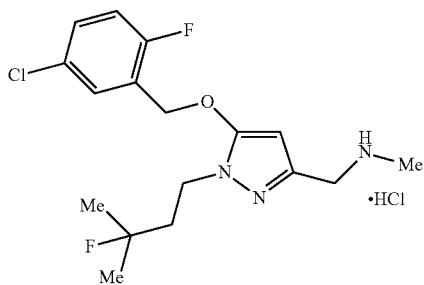 [SMILES: CNCc1cc(OCc2cc(Cl)ccc2F)n(CCC(C)(C)F)n1 ; Cl]

$^1$H-NMR (300 MHz, CDCl$_3$) δ: 1.36 (6H, d, J=21.5 Hz), 2.09 (2H, dt, J=19.5, 7.7 Hz), 2.62 (3H, s), 4.09 (4H, m), 5.12 (2H, s), 6.15 (1H, s), 7.06 (1H, t, J=9.0 Hz), 7.32 (1H, m), 7.44 (1H, m), 9.80 (2H, br s).

Obs MS [M+1]: 358.2

Example 483

1-{1-(3-Fluoro-3-methylbutyl)-5-[(2,4,5-trifluorobenzyl)-oxy]-1H-pyrazol-3-yl}-N-methylmethanamine hydrochloride

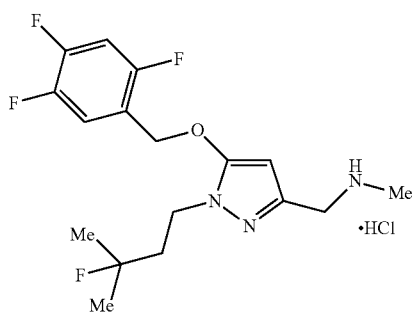 [SMILES: CNCc1cc(OCc2cc(F)c(F)cc2F)n(CCC(C)(C)F)n1 ; Cl]

$^1$H-NMR (300 MHz, CDCl$_3$) δ: 1.36 (6H, d, J=21.5 Hz), 2.08 (2H, dt, J=19.8, 7.7 Hz), 2.63 (3H, s), 4.08 (4H, m), 5.10 (2H, s), 6.15 (1H, s), 6.98 (1H, m), 7.31 (1H, m), 9.69 (2H, br s).

Obs MS [M+1]: 360.3

Example 484

1-{1-(Cyclopentylmethyl)-5-[(2,5-difluorobenzyl)oxy]-1H-pyrazol-3-yl}-N-methylmethanamine monophosphate

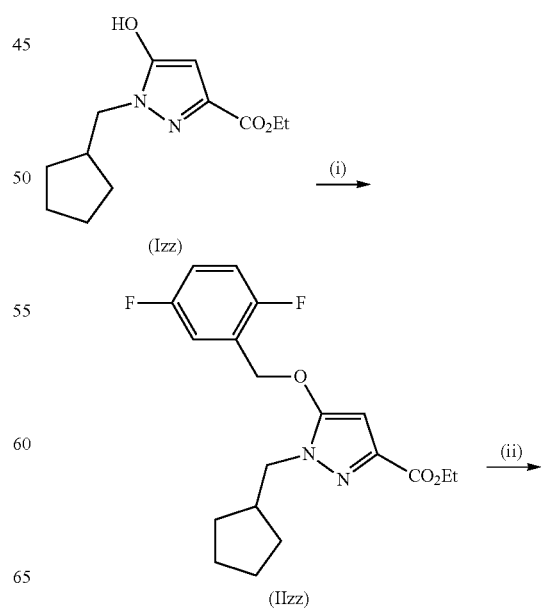

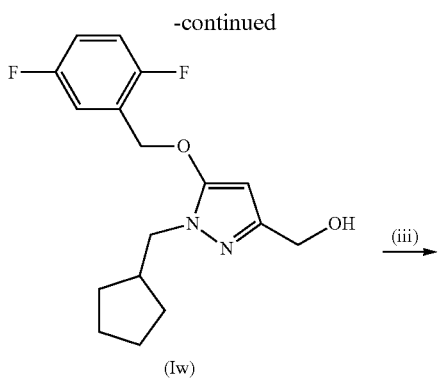

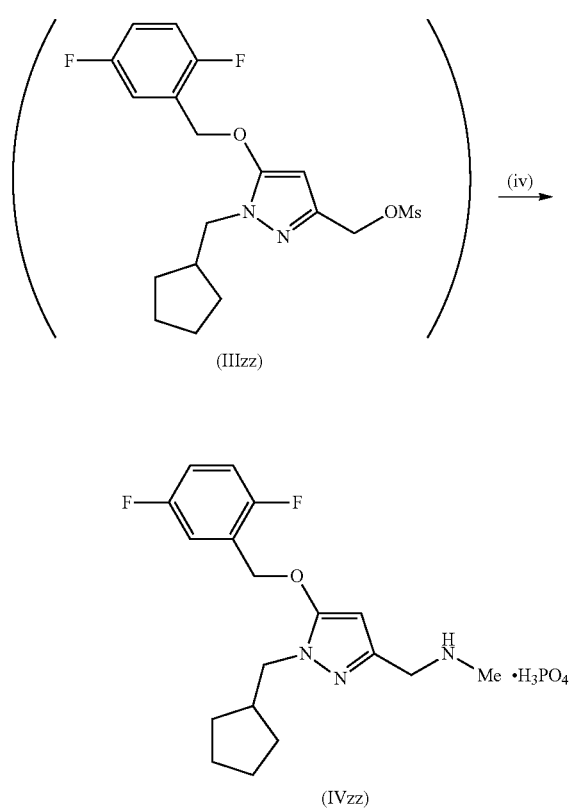

tetrahydrofuran (175 g) was added dropwise methanol (30.8 g) at 35° C. to 45° C. over 15 minutes, and the reaction mixture was stirred for 2 hours. The mixture was cooled to room temperature, and toluene (262.5 g) was added thereto. To the mixture was added dropwise 3.6% HCl (262.5 g) over 15 minutes with keeping the temperature below 40° C. The organic layer was washed with water (262.5 g×2) and concentrated under reduced pressure to give a crude product of Compound (Iw) (32.1 g).

Steps (iii) to (iv)

To a solution of the Compound (Iw) (5.00 g, 15.5 mmol) and triethylamine (2.35 g, 23 mmol) in tetrahydrofuran (45.5 g) was added dropwise methanesulfonyl chloride (2.13 g, 18.6 mmol) with keeping the temperature below 10° C., and the reaction mixture was stirred at around 5° C. for 1 hour and then slowly warmed to room temperature. The precipitate was filtered off to give a solution of Compound (IIIzz), which was used in the next step without further purification.

To 40% methylamine methanol solution (36 g) was added dropwise the solution of Compound (IIIzz) at ice temperature over 30 minutes, and the reaction mixture was stirred at the same condition for 1 hour. To the mixture were added toluene (50 g) and water (40 g), the mixture was slowly warmed to room temperature, and the organic layer was concentrated under reduced pressure. To the concentrated residue (5.09 g) were added 2-propanol (39 g) and phosphoric acid (75%, 2.10 g), the mixture was heated to 80° C., the solid was dissolved, and the solution was stirred at 60° C. to 65° C. After a solid was precipitated, the resultant was stirred at 60° C. to 65° C. for 1 hour. The solution was cooled to 3° C. over 6 hours and stirred at 3° C. for 7 hours. The resulting precipitate was collected by filtration, washed with cold 2-propanol (5 g), and dried under reduced pressure to give the title Compound (IVzz) (4.81 g, 72%) as a white crystalline solid.

$^1$H-NMR (300 MHz, DMSO-d$_6$) δ: 1.07-1.30 (m, 2H), 1.35-1.64 (m, 6H), 2.15-2.32 (m, 1H), 2.37 (s, 3H), 3.72 (s, 2H), 3.75 (s, 2H), 5.16 (s, 2H), 5.91 (s, 1H), 6.96 (br s, 4H), 7.22-7.51 (m, 3H).

Example 485

1-{1-(Cyclopentylmethyl)-5-[(2,5-difluorobenzyl)oxy]-1H-pyrazol-3-yl}-N-methylmethanamine monophosphate

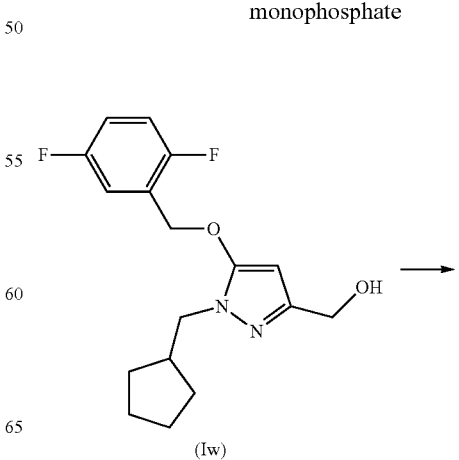

Step (i)

To a solution of Compound (Izz) in Reference Example 85 (48.0 g, 200 mmol) and K$_2$CO$_3$ (41.8 g, 300 mmol) in dimethylformamide (192 g) was added dropwise 2,5-difluorobenzyl chloride (36.0 g, 220 mmol) at room temperature. The reaction mixture was stirred at room temperature for 5.5 hours. The resultant salt was filtered off and washed with dimethylformamide (48 g). To 73.3 g (i.e. a quarter amount) of the resultant filtrate (293 g in total) was added dropwise water (180 g) at 35° C. over 1 hour, and the mixture was stirred for 1 hour at the same condition and then stirred for 1 hour with cooling to 15° C. The precipitate was collected by filtration, washed with a mixed solvent of dimethylformamide (8.4 g) and water (25 g), further washed with 2-propanol (15.6 g×2), and dried under reduced pressure to give Compound (IIzz) (16.6 g, 90%)

Step (ii)

To a suspension of the Compound (IIzz) (35.0 g, 100 mmol) and sodium borohydride (7.99 g, 210 mmol) in

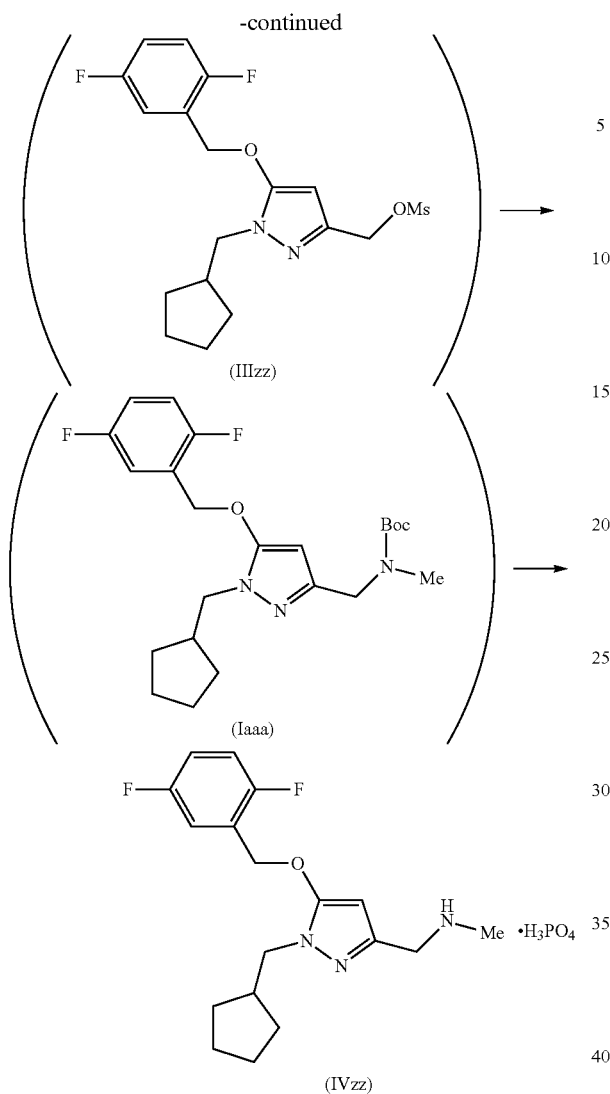

To a solution of Compound (Iw) in Example 480 (7.00 g, 21.7 mmol) and triethylamine (2.64 g, 36.0 mmol) in tetrahydrofuran (28 g) was added dropwise methanesulfonyl chloride (2.99 g, 26.1 mmol) with ice-cooling. The reaction mixture was stirred at around 5° C. for 1 hour, diluted with tetrahydrofuran (8.4 g), and slowly warmed to room temperature. The precipitate was filtered off, and the filtrate was used in the next step without further purification. To a suspension of potassium t-butoxide (4.39 g, 39.1 mmol) in tetrahydrofuran (28 g) was added dropwise N-Boc-methylamine (5.70 g, 43.5 mmol) at room temperature over 15 minutes. To the solution was added dropwise the above-obtained filtrate with keeping the internal temperature below 15° C. over 40 minutes, and the reaction mixture was stirred at below 15° C. for 0.1 hour. The mixture was slowly warmed to room temperature, to the mixture was added dropwise conc. HCl (36%, 21 g) at room temperature over 5 minutes, and the mixed solution was stirred at 40° C. for 4 hours. The mixture was cooled to room temperature, and partitioned between 27% aq. NaOH (11.9 g) and toluene (17.5 g). The organic layer was washed with water (31.5 g), and the solvent was evaporated under reduced pressure. To the concentrated residue (7.86 g) was added toluene to adjust the total weight to 32.5 g. To the mixture was further added 2-propanol (63 g). The mixed solution was heated to 50° C., and to the solution was added dropwise a solution of phosphoric acid (85%, 2.58 g) in 2-propanol (9.10 g) at 50° C. over 3 minutes (1.17 g out of the total). To the mixture were added seed crystals of the title compound (40 mg) at 50° C., and the remaining 10.52 g of the above-mentioned solution was added dropwise thereto over 1 hour. The mixture was stirred at 50° C. for 30 minutes, cooled at a rate of 20° C./hour, and stirred at 5° C. for 1 hour. The precipitate was collected by filtration, washed twice with a mixed solution of cold toluene (4 g) and 2-propanol (12 g), and dried under reduced pressure to give the title Compound (IVzz) (7.76 g, 83%) as a white powder.

Example 486

1-{1-(Cyclopentylmethyl)-5-[(2,5-difluorobenzyl)oxy]-1H-pyrazol-3-yl}-N-methylmethanamine hydrochloride

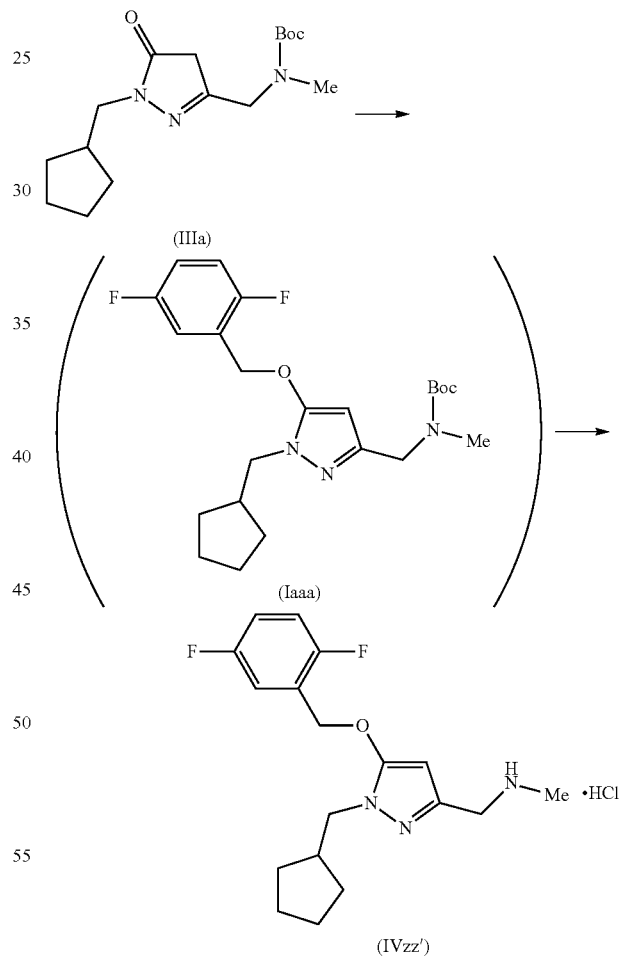

To a solution of a mixture of Compound (IIIa) in Reference Example 1 (108 g, 349 mmol) and cesium carbonate (171 g, 524 mmol) in dimethylformamide (1081 mL) was added dropwise a solution of 2,5-difluorobenzyl chloride (68.1 g, 419 mmol) in dimethylformamide (81 mL). The reaction mixture was stirred at room temperature for 14 hours, water (1729 mL) was added thereto with ice-cooling, and to the mixture was further added toluene (2579 mL). The organic layer was washed with water (562 mL) and the toluene was evaporated under reduced pressure to give a concentrated residue (146 g), which was used in the next step without further purification. The residue (146 g) was dissolved in methanol (394 mL), to the solution was added conc. HCl (36%, 120 g) at 50° C., and the reaction mixture was stirred at 50° C. for 1.5 hours. The mixture was cooled to room temperature, the solvent was evaporated under reduced pressure, to the concentrated residue was added 2-propanol (394 mL), and the solvent was evaporated under reduced pressure (×3) to give a concentrated residue (182 g) as a light brown solid. To the residue was added 2-propanol (591 mL). After the solid was dissolved, n-hexane (1183 mL) was added dropwise to the solution at room temperature over 1 hour. The mixture was stirred at room temperature overnight and then with ice-cooling for 3 hours. The precipitate was collected by filtration, washed with a mixed solution of cold 2-propanol (31 mL) and cold n-hexane (92 mL), and dried under reduced pressure to give the title Compound (IVzz') (68.7 g, 53%) as a white crystalline solid.

Example 487

1-{1-(Cyclopentylmethyl)-5-[(2,5-difluorobenzyl)oxy]-1H-pyrazol-3-yl}-N-methylmethanamine monocitrate

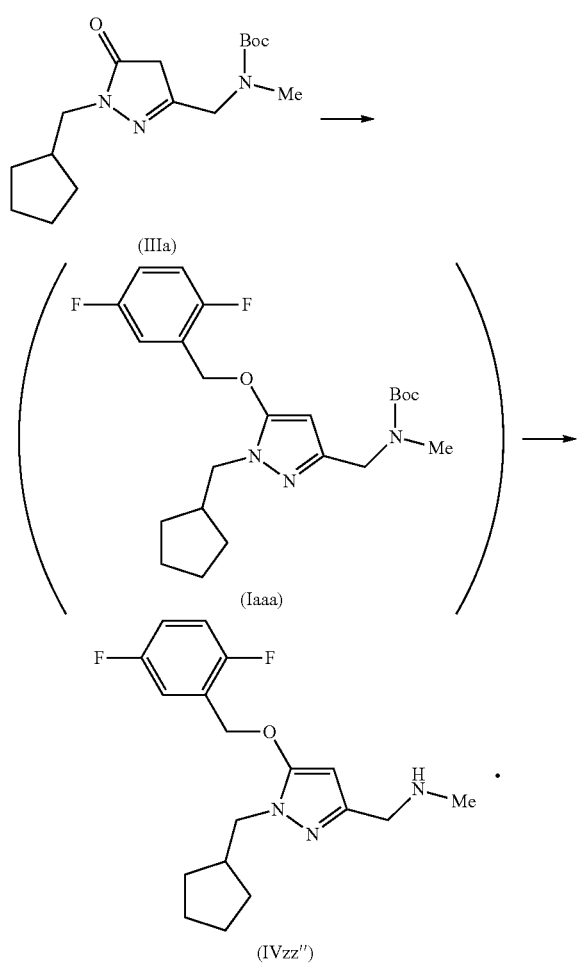

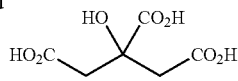

To a solution of a mixture of the Compound (IIIa) in Reference Example 1 (10 g, 32 mmol) and cesium carbonate (15.8 g, 48.5 mmol) in dimethylformamide (27 mL) was added dropwise a solution of 2,5-difluorobenzyl chloride (6.31 g, 38.8 mmol) in dimethylformamide (5 mL) at room temperature. The reaction mixture was stirred at room temperature for 17 hours, and to the mixture were added water (64 mL) and further toluene (96 mL). The organic layer was washed with water (32 mL), the toluene was evaporated under reduced pressure, methanol (20 mL) was added thereto, and the solvent was evaporated under reduced pressure (×3) to give a crude product of Compound (Iaaa) (14.8 g) as a brown oil, which was used in the next step without further purification.

The resulting Compound (Iaaa) was dissolved in methanol (32 mL), to the solution was added conc. HCl (36%, 9.8 g) at 50° C., and the reaction mixture was stirred at 50° C. for 1.5 hours. The mixture was cooled to room temperature, the solvent was evaporated under reduced pressure, and the mixture was partitioned between 20% aq. potassium bicarbonate (25 mL) and toluene (80 mL). The organic layer was washed with water (20 mL), the solvent was evaporated under reduced pressure, 2-propanol (20 mL) was added thereto, and the solvent was evaporated under reduced pressure (×2) to give a free base of the compound (14.5 g). A half amount of the compound (equivalent to 16.2 mmol) and anhydrous citric acid (3.10 g, 16.2 mmol) were added to 2-propanol (83 mL), and the mixture was heated to around 80° C. After the solid was dissolved, the solution was cooled to 50° C., seed crystals of the title Compound (IVzz") (5 mg) were added to the solution, and the mixture was stirred for 2 hours at around 45° C. and then stirred overnight with slowly cooling to room temperature. The mixture was cooled with ice for 2 hours, and the precipitate was collected by filtration and dried under reduced pressure to give the title Compound (IVzz") (6.17 g, 72%) as a white crystalline solid.

$^1$H-NMR (300 MHz, CD$_3$OD) δ: 1.17-1.35 (m, 2H), 1.46-1.69 (m, 6H), 2.29-2.47 (m, 1H), 2.68 (s, 3H), 2.72 (d, J=15.4 Hz, 2H), 2.81 (d, J=15.4 Hz, 2H), 3.88 (d, J=7.5 Hz, 2H), 4.06 (s, 2H), 5.22 (s, 2H), 5.90 (s, 1H), 7.09-7.32 (m, 3H).

Example 488

N-Methyl-1-{1-(3-methylbutyl)-5-[(2,4,5-trifluorobenzyl)-oxy]-1H-pyrazol-3-yl}methanamine hydrochloride

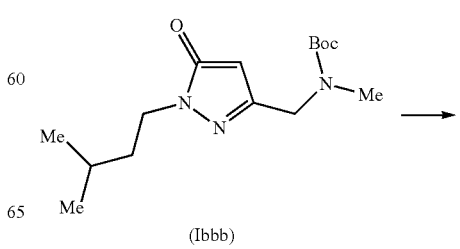

-continued

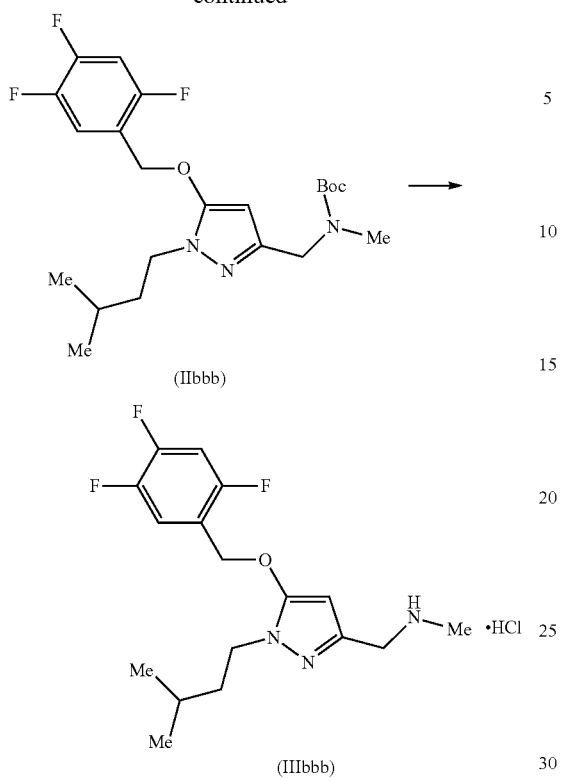

To a solution of the title Compound (Ibbb) of Reference Example 24 (11.9 g, 40 mmol) and cesium carbonate (1.95 g, 60 mmol) in dimethylformamide (123 mL) was added 2,4,5-trifluorobenzyl chloride (8.70 g, 48 mmol) at room temperature, and the reaction mixture was stirred at room temperature for 16 hours. The mixture was partitioned between water (190 mL) and toluene (190 mL), the organic layer was washed with water (62 mL) and dried over anhydrous MgSO$_4$, and the solvent was evaporated under reduced pressure. To the resultant was added toluene (39 mL) and the solvent was evaporated under reduced pressure. To the resultant was added methanol (39 mL) and the solvent was evaporated under reduced pressure (×2) to give a crude product of Compound (IIbbb) (18.0 g) as a brown oil (i.e. a concentrated residue), which was used in the next step without further purification.

The residue was dissolved in methanol (38 mL), to the solution was added conc. HCl (11.7 g) at 50° C., the reaction mixture was stirred at 50° C. for 2 hours, and the solvent was evaporated under reduced pressure. To the concentrated residue was added 2-propanol (40 mL), and the solvent was evaporated under reduced pressure (×2). To the resultant was further added 2-propanol (20 mL) and the solvent was evaporated under reduced pressure to give the concentrated residue (17.1 g) as a pale-yellow solid. To the residue was added 2-propanol (57 mL), the mixture was heated to 50° C., the solid was dissolved, and the solution was slowly cooled to around 30° C. After a solid was precipitated, n-hexane (114 mL) was added dropwise thereto at 25° C. to 30° C. over 1 hour. The mixture was stirred at 25° C. to 30° C. for 30 minutes, cooled to 5° C. over 1 hour, and stirred at ice temperature for 1 hour. The resulting precipitate was collected by filtration, washed with a mixed solution of cold 2-propanol and n-hexane (1:5, 12 mL), and dried under reduced pressure to give Compound (IIIbbb) as a white solid.

Example 489

N-Methyl-1-{1-(3-methylbutyl)-5-[(2,4,5-trifluorobenzyl)-oxy]-1H-pyrazol-3-yl}methanamine hydrochloride

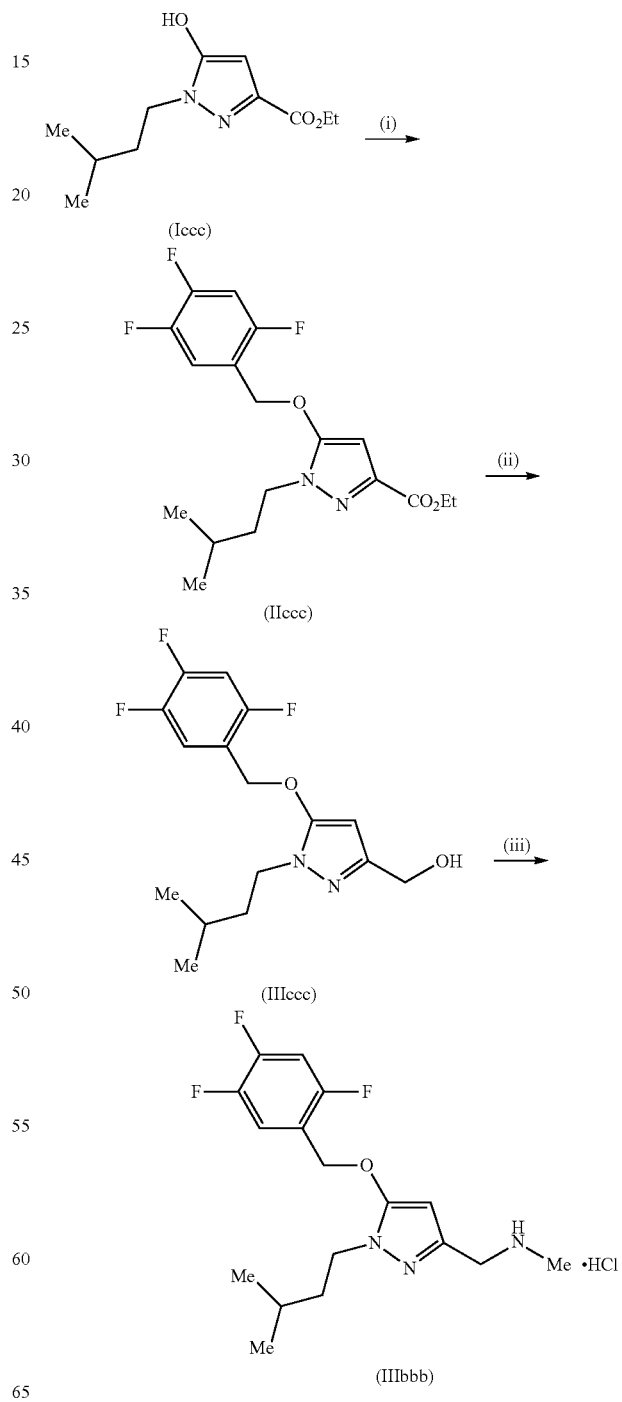

Step (i)

To a solution of a mixture of Compound (Iccc) in Reference Example 87 (5.00 g, 22 mmol) and $K_2CO_3$ (4.58 g, 33 mmol) in dimethylformamide (22 mL) was added 2,4,5-trifluorobenzyl chloride (4.79 g, 26.5 mmol) at room temperature, and the reaction mixture was stirred at room temperature for 15 hours. The salt was filtered off and washed with dimethylformamide (15 mL). The filtrate was added dropwise to water (111 mL) at 40° C. over 15 minutes. The mixture was stirred at 40° C. for 1 hour, cooled to 6° C. over 2 hours, and stirred for 1 hour. The precipitate was collected by filtration, and subsequently washed with a mixed solution of cold dimethylformamide and water (1:3, 10 mL), cold 2-propanol (10 mL), and then n-hexane (20 mL). The resultant was dried under reduced pressure to give Compound (IIccc) (6.56 g, 80%) as a light brown powder.

Step (ii)

To a suspension of lithium aluminum hydride (768 mg, 20 mmol) in tetrahydrofuran (20 mL) was added dropwise a solution of the above-obtained compound (5.00 g, 13.5 mmol) in tetrahydrofuran (12 mL) with keeping the internal temperature below 15° C. over 15 minutes, and the reaction mixture was stirred at the same condition for 1 hour. To the mixture was subsequently added water (0.77 mL), 15% NaOH (0.77 mL) and then water (2.31 mL). The precipitate was filtered off through Celite, the filtrate was concentrated under reduced pressure, to the concentrated residue (4.22 g) was added toluene (15 mL), and the solvent was evaporated under reduced pressure (×2). To the concentrated residue were added toluene (25 mL) and n-hexane (45 mL), the mixture was stirred for 1 hour at 40° C. (internal temperature), and a precipitate was formed. The resultant was cooled to ice temperature over 2 hours and stirred for 1 hour. The precipitate was collected by filtration, washed with a mixed solution of toluene and n-hexane (1:4, 4 mL), and dried under reduced pressure to give Compound (IIIccc) (3.76 g, 85%) as a white solid.

Step (iii)

To a solution of the Compound (IIIccc) (5.00 g, 15 mmol) and triethylamine (2.54 mL, 18 mmol) in tetrahydrofuran (30 mL) was added dropwise methanesulfonyl chloride (1.3 mL, 16.8 mmol) with keeping the internal temperature below 15° C. over 15 minutes. The reaction mixture was stirred for 2 hours with slowly warming to room temperature. The salt was filtered off and washed with tetrahydrofuran (5 mL, ×2). To the resultant filtrate was added dropwise 40% methylamine/methanol (40 mL) at 5° C. to 8° C. over 15 minutes, and the reaction mixture was stirred for 1 hour. To the mixture were added toluene (40 mL) and water (30 mL), the mixture was warmed to room temperature, and the organic layer was concentrated under reduced pressure. To the concentrated residue was added 2-propanol (15 mL), and the mixture was concentrated under reduced pressure (×2). The concentrated residue (5.54 g) was dissolved in 2-propanol (15 mL), to the solution was added 36% conc. HCl (3.08 g, 30.5 mmol) at room temperature, and the solvent was evaporated under reduced pressure. To the concentrated residue was added 2-propanol (15 mL), and the solvent was concentrated under reduced pressure (×2). To the concentrated residue (6.16 g) was added 2-propanol (20 mL), the resultant was heated to 50° C. (internal temperature), and the solid was dissolved. The solution was cooled to 35° C. to form a precipitate, and n-hexane (40 mL) was added dropwise thereto over 1 hour at around 35° C. (internal temperature). The mixture was stirred at 35° C. for 1 hour, cooled to 5° C. (internal temperature) over 2 hours, and stirred at the same condition for 1 hour. The precipitate was collected by filtration, washed with a mixed solution of cold 2-propanol and n-hexane (1:4, 5 mL), and dried under reduced pressure to give the title Compound (IIIbbb) (3.22 g, 56%) as a white crystalline solid.

Example 490

N-Methyl-1-{1-(3-methylbutyl)-5-[(2,4,5-trifluorobenzyl)-oxy]-1H-pyrazol-3-yl}methanamine monophosphate

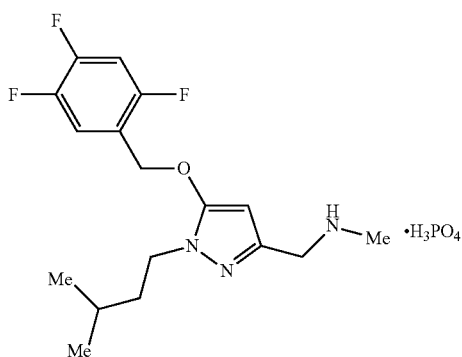

To the Compound (IIIbbb) in Example 488 (3.6 g, 9.5 mmol) was added 10% aq. $K_2CO_3$ (50 mL), and the mixture was extracted with chloroform (100 mL). The organic layer was dried over anhydrous $Na_2SO_4$, the solvent was evaporated under reduced pressure, and the concentrated residue was purified by silica gel column chromatography (chloroform methanol=10:1) to give a free base of Compound (IIIbbb) (3.02 g) as a light-brown oil. A solution of a mixture of the free base of Compound (IIIbbb) (200 mg, 0.59 mmol) and phosphoric acid (75%, 77 mg, 0.59 mmol) in 2-propanol (2 mL) was stirred at 80° C. for 30 minutes, and then stirred with slowly cooling to room temperature. The resulting precipitate was collected by filtration and dried under reduced pressure to give the title compound (219 mg, 84%) as a white crystalline solid.

$^1$H-NMR (400 MHz, DMSO-$d_6$) δ: 0.82 (6H, d, J=6.3 Hz), 1.38-1.42 (1H, m), 1.49 (2H, dt, J=7.1 Hz, J=7.1 Hz), 2.37 (3H, s), 3.72 (2H, s), 3.83 (2H, t, J=7.1 Hz), 5.14 (2H, s), 5.93 (1H, s), 6.13 (4H, br), 7.62-7.69 (1H, m), 7.74-7.78 (1H, m).

Example 491

N-Methyl-1-{1-(3-methylbutyl)-5-[(2,4,5-trifluorobenzyl)-oxy]-1H-pyrazol-3-yl}methanamine monocitrate

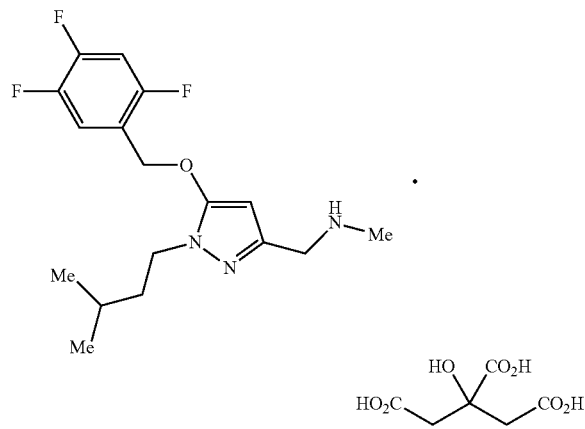

To a free base of Compound (IIIbbb) prepared in the same manner as in Example 490 (equivalent to 1.0 mmol) were added a solution of citric acid monohydrate (210 mg, 1.0 mmol) in water (1.5 mL), and further added 2-propanol (20 mL). The solvent was evaporated under reduced pressure (×2) to give a concentrated residue (546 mg). To the residue was added 2-propanol (4 mL), and the mixture was stirred at 50° C. After the solid was dissolved, the solution was slowly cooled to room temperature. To the solution was added dropwise n-hexane (8 mL) with ice-cooling, and the mixture was stirred at ice temperature for 30 minutes. The precipitate was collected by filtration, washed with a mixed solution of cold n-hexane/2-propanol (2:1, 5 mL), and dried under reduced pressure to give the title compound (325 mg) as a white crystalline solid.

$^1$H-NMR (400 MHz, DMSO-$d_6$) δ: 0.83 (6H, d, J=6.4 Hz), 1.38-1.45 (1H, m), 1.51 (2H, dt, J=6.8 Hz, J=6.8 Hz), 2.44-2.56 (7H, m), 3.31 (4H, br), 3.87 (2H, t, J=6.8 Hz), 3.96 (2H, s), 5.17 (2H, s), 5.89 (1H, s), 7.63-7.77 (2H, m), 10.62 (1H, br).

Test Example 1: [$^3$H] Citalopram Binding Assay to Evaluate Human Serotonin Reuptake Inhibitory Action 1-1. Preparation of the Cells and Membrane Preparations In the experiment, human serotonin transporter (h-SERT) was expressed in CHO cells (h-SERT/CHO). The cells were incubated with F12 containing 10% FCS, 500 μg/mL Geneticin and 100 U/mL penicillin—100 μg/mL streptmycin (all manufactured by Sigma Aldrich) in an incubator containing 5% $CO_2$; detached and collected using a SERT buffer [50 mmol/L Tris-HCl comprising 120 mmol/L NaCl and 5 mmol/L KCl (pH=7.4)]; homogenized with a homogenizer manufactured by Teflon (trademark); and then centrifuged (50,000×g, 30 min, 4° C.). The precipitate was suspended again in the appropriate amount of SERT buffer (to give a membrane preparation), and stored at −80° C. until used. The amount of protein in the membrane preparation was assayed by Dye Reagent Concentrate (manufactured by BIO-RAD) using bovine serum albumin (manufactured by Sigma Aldrich) as a standard.

1-2. h-SERT Binding Assay

The [$^3$H] citalopram binding was measured according to the method disclosed in Owens M. J. et al., J. Pharm. Exp. Ther., 283, 1305-1322 (1997). In specific, a solution of 200 μL in total was prepared by mixing 50 μL of [$^3$H] citalopram (manufactured by GE Healthcare) diluted with a SERT buffer (final concentration: about 2 nmol/L), 149 μL of the h-SERT/CHO membrane preparation (protein amount: 40 μg/well), and 1 μL of the test drug dissolved in dimethylsulfoxide. The solution was reacted at room temperature for 60 minutes, and then quickly suction-filtered under reduced pressure through a glass fiber filter coated with 0.05% aq. polyethyleneimine. The glass fiber filter was washed twice with 250 HL of the SERT buffer, placed in a plastic vial containing 4 mL of liquid scintillator (ACS-II, manufactured by Amersham) or Ecoscint A (manufactured by National Diagnostics), and the remaining radioactivity on the filter paper was assayed with a liquid scintillation counter. The non-specific binding of [$^3$H] citalopram was defined as a binding amount in the presence of 1 μmol/L clomipramine (manufactured by Sigma Aldrich) The $IC_{50}$ value was calculated according to Hill analysis [see, Hill A. V., J. Physiol., 40, 190-200 (1910)], and the binding inhibition constant (Ki) was calculated according to the following formula:

$$\text{Binding inhibition constant}(Ki) = IC_{50}/(1+S/Kd)$$

wherein S is a concentration of the added [$^3$H] citalopram, and Kd is a binding dissociation constant of [$^3$H] citalopram which was calculated from a saturated binding assay using the same cell membrane. A lower Ki value (i.e. a lower h-SERT binding inhibition constant) means that the test drug has a stronger human serotonin reuptake inhibitory action.

Test Example 2: [$^3$H] Mesulergine Binding Assay to Evaluate Affinity for Human 5-$HT_{2C}$ Receptor 2-1. Preparation of the Cells and Membrane Preparations In the experiment, human serotonin 2C receptor (h-5-$HT_{2C}$) was expressed in CHO cells (h-5-$HT_{2C}$/CHO). The cells were incubated with UltraCHO Lipuid (trademark) (manufactured by BioWhitakker) containing 1% FBS, 400 μg/mL Geneticin, 100 U/mL penicillin—100 μg/mL streptomycin (all manufactured by Sigma Aldrich) and 250 μg/mL Zeosin (manufactured by InvivoGen) in an incubator containing 5% $CO_2$; detached and collected using 50 mmol/L Tris-HCl (pH=7.4); homogenized with a homogenizer manufactured by Teflon (trademark); and then centrifuged (48,000×g, 25 min, 4° C.). The precipitate was suspended again in the appropriate amount of 50 mmol/L Tris-HCl (to give a membrane preparation), and stored at −80° C. until used. The amount of protein in the membrane preparation was assayed by Dye Reagent Concentrate (manufactured by BIO-RAD) using bovine serum albumin (manufactured by Sigma Aldrich) as a standard.

2-2. 5-$HT_{2C}$ Receptor Binding Assay

A solution of 200 μL in total was prepared by mixing 50 μL of [3H] mesulergine (manufactured by GE Healthcare) diluted with 50 mmol/L Tris-HCl (pH=7.4) (final concentration: about 2 nmol/L), 149 μL of the h-5-$HT_{2C}$/CHO membrane preparation (protein amount: 20 μg/well), and 1 μL of the test drug dissolved in dimethylsulfoxide. The solution was reacted at 37° C. for 30 minutes, and then quickly suction-filtered under reduced pressure through a glass fiber filter coated with 1% aq. bovine serum albumin. The glass fiber filter was washed twice with 250 μL of 50 mmol/L Tris-HCl (pH=7.4), placed in a plastic vial containing 4 mL of liquid scintillator (ACS-II, manufactured by Amersham) or Ecoscint A (manufactured by National Diagnostics), and the remaining radioactivity on the filter paper was assayed with a liquid scintillation counter. The non-specific binding of [$^3$H] mesulergine was defined as a binding amount in the presence of 10 μmol/L SB206553 (manufactured by Sigma Aldrich). The $IC_{50}$ value was calculated according to Hill analysis, and the binding inhibition constant (Ki) was calculated according to the following formula:

Binding inhibition constant$(Ki)=IC_{50}/(1+S/Kd)$ wherein S is a concentration of the added [$^3$H] mesulergine, and Kd is a binding dissociation constant of [$^3$H] mesulergine which was calculated from a saturated binding assay using the same cell membrane. A lower Ki value (i.e. a lower 5-$HT_{2C}$ binding inhibition constant) means that the test drug has a higher affinity for human serotonin reuptake inhibitory action.

Test Example 3: 5-$HT_{2C}$ Receptor Agonistic Action Assay 3-1. The Cells and Inoculation Thereof In the experiment, human serotonin 2C receptor (h-5-$HT_{2C}$) was expressed in CHO cells (h-5-$HT_{2C}$/CHO). The cells were incubated with UltraCHO Lipuid (trademark) (manufactured by BioWhitakker) containing 1% FBS, 400 μg/mL Geneticin, 100 U/mL penicillin—100 μg/mL streptomycin (all manufactured by Sigma Aldrich) and 250 μg/mL Zeosin (manufactured by InvivoGen) in an incubator containing 5% $CO_2$. On the day before using the cells, they were detached and collected using 250 μg/mL Trypsin solution (manufactured by Nacalai Tesque), then inoculated in a 96 well flat clear bottom black polystyrene TC-treated microplates (manufactured by Corning) at 40000 cells/well/60 μL in an incubator containing 5% $CO_2$ for 16 hours to 24 hours.

3-2. 5-$HT_{2C}$ Receptor Agonistic Action Assay

The 5-$HT_{2C}$ receptor agonistic action was evaluated with FLIPR Calcium 4 Assay kit (manufactured by Molecular Devices). In specific, to the cells inoculated in the plate were added Component A of FLIPR Calcium 4 Assay kit dissolved in 100 mL of HHBP buffer (1× Hanks buffer, 20 mmol/L HEPES, both manufactured by Gibco) at an amount of 40 μL/well, and the cells were incubated in an incubator containing 5% $CO_2$ for 1 hour. Then, the cells were set in FLIPR TETRA (trademark) (manufactured by Molecular Devices), to the cells was added the test material diluted with HHBP buffer, 2.5 mmol/L Probenecid (manufactured by Sigma) (concentration after dilution: 10 μmol/L) at an amount of 20 μL/well, and the fluorescence was measured. Then, in order to evaluate the antagonistic action of the test material, 20 μL/well of 5-HT solution (manufactured by Sigma, final concentration: 0.1 nmol/L) was further added to the cells, and the fluorescence was measured.

The 5-$HT_{2C}$ receptor agonistic action of each test material was calculated as a rate of fluorescence enhancement wherein 100% was defined as a value when the cells were given 10 μmol/L 5-HT. Furthermore, the 5-$HT_{2C}$ receptor inverse agonistic action was calculated as a rate of fluorescence decay wherein −100% was defined as a value when the cells were given 10 μmol/L SB206553 (manufactured by Sigma Aldrich). A lower value of the 5-$HT_{2C}$ receptor agonistic action of the test material means that the material has a higher antagonistic action. In particular, when the value of the 5-$HT_{2C}$ receptor agonistic action of the test material is below 0%, the material has an inverse agonistic action for 5-$HT_{2C}$ receptor.

The present-pyrazole compounds prepared in the Examples were tested by Test Examples 1, 2 and 3, and the results thereof are disclosed in Table 24. The test results clearly demonstrate that the present-pyrazole compound and a pharmaceutically acceptable salt thereof have both human serotonin reuptake inhibitory action and binding affinity for human 5-$HT_{2C}$ receptor, and in particular, an inverse agonistic action for human 5-$HT_{2C}$ receptor.

TABLE 24

| Compound (Ex. No.) | Test Ex. 1: h-SERT binding inhibition constant Ki [nM] | Test Ex. 2: 5-$HT_{2c}$ receptor binding inhibition constant Ki [nM] | Test Ex. 3: 5-$HT_{2c}$ receptor agonistic action [%] |
|---|---|---|---|
| 1 | 4.9 | 26 | −86 |
| 3 | 12 | 5.4 | −91 |
| 5 | 1.5 | 4.4 | −91 |
| 31 | 0.92 | 5.2 | −66 |
| 33 | 0.34 | 2.9 | −115 |
| 42 | 4.9 | 31 | −106 |
| 108 | 1.9 | 18 | −117 |
| 115 | 1.5 | 5.4 | −103 |
| 122 | 8.1 | 7.7 | −117 |
| 124 | 0.71 | 16 | −82 |
| 131 | 3.7 | 10 | −70 |
| 137 | 6.6 | 7.9 | −94 |
| 144 | 8.3 | 2.2 | −127 |
| 147 | 0.71 | 4.8 | −105 |
| 148 | 4.6 | 1.9 | −102 |
| 162 | 7.8 | 14 | −66 |
| 192 | 0.91 | 3.9 | −90 |
| 218 | 9.7 | 10 | −111 |
| 219 | 1.6 | 10 | −127 |
| 230 | 2.3 | 4.9 | −105 |
| 242 | 0.52 | 34 | −95 |
| 248 | 4.3 | 9.4 | −100 |
| 253 | 1.5 | 31 | −86 |
| 256 | 1.6 | 12 | −97 |
| 258 | 0.66 | 16 | −118 |
| 259 | 2.4 | 6.2 | −119 |
| 266 | 0.69 | 4.5 | −86 |
| 269 | 0.59 | 6.7 | −77 |
| 275 | 22 | 11 | −88 |
| 280 | 1.9 | 9.7 | −81 |
| 283 | 1.1 | 6.3 | −89 |
| 284 | 5.7 | 7.9 | −97 |
| 286 | 5.5 | 6.6 | −117 |
| 288 | 0.86 | 19 | −80 |
| 315 | 11 | 3.6 | −84 |
| 328 | 3.6 | 193 | −116 |
| 330 | 0.96 | 17 | −82 |
| 331 | 1.3 | 5.9 | −103 |
| 341 | 23 | 12 | −71 |
| 342 | 8.5 | 14 | −99 |
| 344 | 33 | 6.7 | −82 |
| 347 | 13 | 31 | −114 |
| 349 | 3.0 | 18 | −82 |
| 350 | 53 | 11 | −92 |
| 351 | 0.98 | 43 | −102 |
| 355 | 32 | 17 | −72 |
| 357 | 10 | 74 | −120 |
| 381 | 3.4 | 10 | −125 |
| 400 | 0.54 | 5.3 | −115 |
| 405 | 11 | 23 | −90 |
| 426 | 0.99 | 14 | −99 |
| 434 | 4.5 | 8.1 | −87 |
| 435 | 0.60 | 4.4 | −125 |
| 442 | 4.9 | 11 | −95 |
| 446 | 7.4 | 19 | −89 |
| 447 | 0.50 | 13 | −86 |
| 448 | 3.8 | 8.8 | −94 |

TABLE 24-continued

| Compound (Ex. No.) | Test Ex. 1: h-SERT binding inhibition constant Ki [nM] | Test Ex. 2: 5-HT$_{2C}$ receptor binding inhibition constant Ki [nM] | Test Ex. 3: 5-HT$_{2C}$ receptor agonistic action [%] |
|---|---|---|---|
| 458 | 5.1 | 21 | −87 |
| 474 | 11 | 16 | −111 |
| 475 | 9.2 | 19 | −95 |
| 476 | 14 | 2.3 | −72 |
| 477 | 9.9 | 3.1 | −94 |
| 481 | 0.85 | 22 | −109 |
| 482 | 2.9 | 2.6 | −116 |

The present compound is a novel serotonin reuptake inhibitor which also exhibits 5-HT$_{2C}$ antagonistic action, especially 5-HT$_{2C}$ inverse agonistic action, and thus it is expected that the present compound can exhibit therapeutic effects faster than conventional compounds which exhibit only either of the actions of the present compound.

INDUSTRIAL APPLICABILITY

The present compound is a serotonin reuptake inhibitor which also exhibits 5-HT$_{2C}$ antagonistic action, especially 5-HT$_{2C}$ inverse agonistic action, and shows potent antidepressive and anxiolytic effects; and thus the present compound is useful as a medicament for treating depression or anxiety, or preventing a relapse thereof.

The invention claimed is:

1. A process for preparing a compound of Formula (A-4):

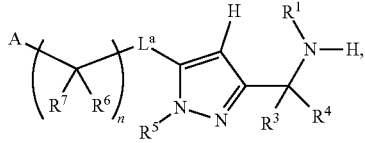
(A-4)

or a pharmaceutically acceptable salt thereof, wherein
$R^1$ is selected from the group consisting of a hydrogen atom, a $C_{1-6}$ alkyl group, and a $C_{3-8}$ cycloalkyl group,
$R^3$ and $R^4$ are independently selected from the group consisting of a hydrogen atom and a $C_{1-6}$ alkyl group,
$R^5$ is an optionally-substituted $C_{4-7}$ alkyl group or —$(CR^8R^9)_r$-E,
$R^6$, $R^7$, $R^8$, and $R^9$ are independently selected from the group consisting of a hydrogen atom, a fluorine atom, and an optionally-substituted $C_{1-6}$ alkyl group,
A is an optionally-substituted $C_{6-10}$ aryl group or an optionally-substituted 5- to 10-membered heteroaryl group,
r is 1, 2, 3, or 4,
E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms independently selected from the group consisting of an oxygen atom and a sulfur atom as a constituent atom of the ring, an optionally-substituted $C_{6-10}$ aryl group, or an optionally-substituted 5- to 10-membered heteroaryl group,
$L^a$ is an oxygen atom or a sulfur atom, and
n is 1, 2, or 3, which comprises the following Steps (i) and (ii):
Step (i): reacting a compound of Formula (A-1):

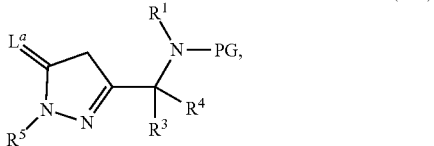
(A-1)

or a salt thereof, wherein $R^1$, $R^3$, $R^4$, $R^5$, and $L^a$ are the same as defined above and PG is a protecting group on amino groups,
with a compound of Formula (A-2):

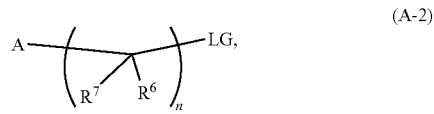
(A-2)

wherein $R^6$, $R^7$, and n are the same as defined above and LG is a leaving group,
to obtain a compound of Formula (A-3):

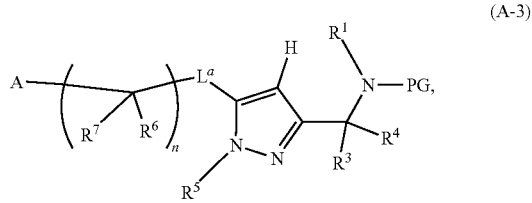
(A-3)

or a salt thereof, wherein $R^1$, $R^3$, $R^4$, $R^5$, $R^6$, $R^7$, $L^a$, n, and PG are the same as defined above, and
Step (ii): deprotecting the protecting group of the compound of Formula (A-3) to obtain the compound of Formula (A-4).

2. A process for preparing a compound of Formula (A-12):

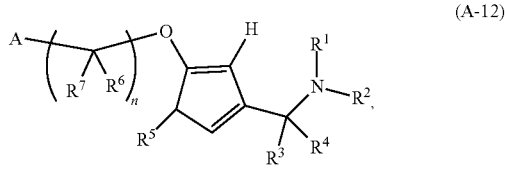
(A-12)

or a pharmaceutically acceptable salt thereof, which comprises the following Steps (i) to (v):
Step (i): reacting a compound of Formula (B-7):

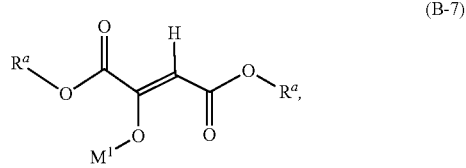
(B-7)

with a compound of Formula (B-4):

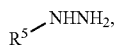
(B-4)

or a salt thereof,
to obtain a compound of Formula (B-8):

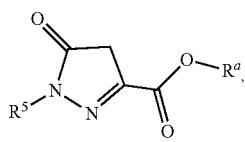
(B-8)

Step (ii): reacting the compound of Formula (B-8) with a compound of Formula (A-2):

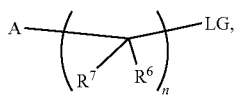
(A-2)

to obtain a compound of Formula (A-13):

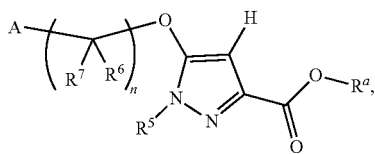
(A-13)

Step (iii): converting the compound of Formula (A-13) to a compound of Formula (B-9):

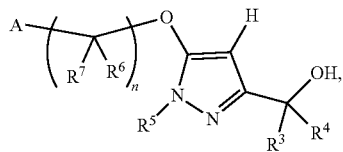
(B-9)

Step (iv): converting the compound of Formula (B-9) to a compound of Formula (A-10):

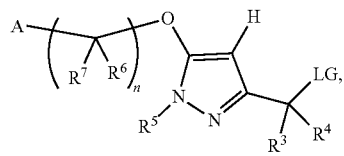
(A-10)

and

Step (v): reacting the compound of Formula (A-10) with a compound of Formula (A-11):

$$\underset{H}{\overset{R^1}{N}}-R^2$$
(A-11)

or a salt thereof,
to obtain the compound of Formula (A-12),
wherein
$R^1$ and $R^2$ are independently selected from the group consisting of a hydrogen atom and a $C_{1-6}$ alkyl group,
$R^3$ and $R^4$ are independently selected from the group consisting of a hydrogen atom and a methyl group,
$R^5$ is an optionally-substituted $C_{4-7}$ alkyl group or $-(CR^8R^9)_r$-E,
$R^6$ and $R^7$ are hydrogen atoms,
$R^8$ and $R^9$ are independently selected from the group consisting of a hydrogen atom, a fluorine atom, and an optionally-substituted $C_{1-6}$ alkyl group,
A is an optionally-substituted $C_{6-10}$ aryl group or an optionally-substituted 5- to 10-membered heteroaryl group,
r is 1 or 2,
E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms independently selected from the group consisting of an oxygen atom and a sulfur atom as a constituent atom of the ring, an optionally-substituted $C_{6-10}$ aryl group, or an optionally-substituted 5- to 10-membered heteroaryl group, and
n is 1,
$R^a$ is hydrogen atom or a $C_{1-6}$ alkyl group,
$M^1$ is hydrogen atom, an alkali metal, or an alkaline earth metal, and
LG is a leaving group.

* * * * *